US012806230B2

(12) United States Patent
Kenderian et al.

(10) Patent No.: US 12,806,230 B2
(45) Date of Patent: Nov. 24, 2026

(54) METHODS AND MATERIALS FOR USING ENGINEERED MESENCHYMAL STEM CELLS TO TREAT INFLAMMATORY CONDITIONS AND DEGENERATIVE DISEASES

(71) Applicant: Mayo Foundation for Medical Education and Research, Rochester, MN (US)

(72) Inventors: Saad J. Kenderian, Rochester, MN (US); Kendall J. Schick, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1116 days.

(21) Appl. No.: 17/774,658

(22) PCT Filed: Nov. 9, 2020

(86) PCT No.: PCT/US2020/059720
§ 371 (c)(1),
(2) Date: May 5, 2022

(87) PCT Pub. No.: WO2021/092577
PCT Pub. Date: May 14, 2021

(65) Prior Publication Data

US 2022/0401488 A1 Dec. 22, 2022

Related U.S. Application Data

(60) Provisional application No. 62/932,610, filed on Nov. 8, 2019.

(51) Int. Cl.

| | |
|---|---|
| ***A61K 35/28*** | (2015.01) |
| ***A61K 40/10*** | (2025.01) |
| ***A61K 40/11*** | (2025.01) |
| ***A61K 40/22*** | (2025.01) |
| ***A61K 40/31*** | (2025.01) |
| ***A61K 40/41*** | (2025.01) |
| ***A61K 40/42*** | (2025.01) |
| ***A61P 1/00*** | (2006.01) |

(52) U.S. Cl.
CPC .............. *A61K 35/28* (2013.01); *A61K 40/10* (2025.01); *A61K 40/11* (2025.01); *A61K 40/22* (2025.01); *A61K 40/31* (2025.01); *A61K 40/416* (2025.01); *A61K 40/4205* (2025.01); *A61K 40/4211* (2025.01); *A61K 40/4254* (2025.01); *A61P 1/00* (2018.01); *A61K 2239/31* (2023.05); *A61K 2239/38* (2023.05); *A61K 2239/49* (2023.05)

(58) Field of Classification Search
CPC .. A61K 35/28; A61K 40/4205; A61K 40/416; A61K 40/4254; A61P 1/00
See application file for complete search history.

(56) References Cited

U.S. PATENT DOCUMENTS

| | | | |
|---|---|---|---|
| 3,687,808 | A | 8/1972 | Merigan, Jr. et al. |
| 4,034,074 | A | 7/1977 | Miles |
| 4,036,945 | A | 7/1977 | Haber |
| 4,098,876 | A | 7/1978 | Piasio et al. |
| 4,233,402 | A | 11/1980 | Maggio et al. |
| 4,257,774 | A | 3/1981 | Richardson et al. |
| 4,272,398 | A | 6/1981 | Jaffe |
| 4,331,647 | A | 5/1982 | Goldenberg |
| 4,376,110 | A | 3/1983 | David et al. |
| 4,469,863 | A | 9/1984 | Ts'o et al. |
| 4,650,764 | A | 3/1987 | Temin et al. |
| 4,769,330 | A | 9/1988 | Paoletti et al. |
| 4,816,567 | A | 3/1989 | Cabilly et al. |
| 4,861,627 | A | 8/1989 | Mathiowitz et al. |
| 4,861,719 | A | 8/1989 | Miller |
| 4,925,673 | A | 5/1990 | Steiner et al. |
| 4,935,496 | A | 6/1990 | Kudo et al. |
| 4,946,778 | A | 8/1990 | Ladner et al. |
| 4,980,289 | A | 12/1990 | Temin et al. |
| 4,987,071 | A | 1/1991 | Cech et al. |
| 5,013,556 | A | 5/1991 | Woodle et al. |
| 5,124,263 | A | 6/1992 | Temin et al. |
| 5,155,020 | A | 10/1992 | Paoletti |
| 5,155,027 | A | 10/1992 | Sledziewski et al. |
| 5,175,099 | A | 12/1992 | Wills |
| 5,204,243 | A | 4/1993 | Paoletti |
| 5,214,136 | A | 5/1993 | Lin et al. |
| 5,218,105 | A | 6/1993 | Cook et al. |
| 5,225,336 | A | 7/1993 | Paoletti |
| 5,225,538 | A | 7/1993 | Capon et al. |
| 5,235,033 | A | 8/1993 | Summerton et al. |
| 5,240,846 | A | 8/1993 | Collins et al. |
| 5,254,678 | A | 10/1993 | Haseloff et al. |
| 5,278,056 | A | 1/1994 | Bank et al. |
| 5,284,656 | A | 2/1994 | Platz et al. |
| 5,296,347 | A | 3/1994 | LaMotte, III |

(Continued)

FOREIGN PATENT DOCUMENTS

| | | |
|---|---|---|
| CN | 103641917 | 3/2014 |
| CN | 105814074 | 7/2016 |

(Continued)

OTHER PUBLICATIONS

Schnoor (Dig Dis Sci. Apr. 2015;60(4):816-8. doi: 10.1007/s10620-015-3622-z.) (Year: 2015).*

(Continued)

*Primary Examiner* — Christopher M Babic
*Assistant Examiner* — Joel D Levin
(74) *Attorney, Agent, or Firm* — Fish & Richardson P.C.

(57) ABSTRACT

This document relates to methods and materials involved in treating a mammal (e.g., a human) having, or at risk of developing, a disease or a condition characterized by inflammation and/or degeneration of a tissue. For example, mesenchymal stem cells (MSCs) expressing an antigen receptor (e.g., a chimeric antigen receptor) targeting a tissue that can exert an immunosuppressive effect in the targeted tissue as well as methods for using such MSCs are provided herein.

3 Claims, 36 Drawing Sheets

Specification includes a Sequence Listing.

(56) References Cited

U.S. PATENT DOCUMENTS

| | | | |
|---|---|---|---|
| 5,391,682 | A | 2/1995 | Ogawa et al. |
| 5,451,569 | A | 9/1995 | Wong et al. |
| 5,502,167 | A | 3/1996 | Waldmann et al. |
| 5,521,288 | A | 5/1996 | Linsley et al. |
| 5,530,101 | A | 6/1996 | Queen et al. |
| 5,558,864 | A | 9/1996 | Bendig et al. |
| 5,565,332 | A | 10/1996 | Hoogenboom et al. |
| 5,567,584 | A | 10/1996 | Sledziewski et al. |
| 5,585,089 | A | 12/1996 | Queen et al. |
| 5,596,086 | A | 1/1997 | Matteucci et al. |
| 5,639,641 | A | 6/1997 | Pedersen et al. |
| 5,674,704 | A | 10/1997 | Goodwin et al. |
| 5,675,848 | A | 10/1997 | Kappel |
| 5,693,493 | A | 12/1997 | Robinson et al. |
| 5,693,761 | A | 12/1997 | Queen et al. |
| 5,693,762 | A | 12/1997 | Queen et al. |
| 5,698,417 | A | 12/1997 | Robinson et al. |
| 5,705,154 | A | 1/1998 | Dalie et al. |
| 5,714,147 | A | 2/1998 | Capon et al. |
| 5,733,743 | A | 3/1998 | Johnson et al. |
| 5,750,078 | A | 5/1998 | Shitara et al. |
| 5,750,375 | A | 5/1998 | Sledziewski et al. |
| 5,750,666 | A | 5/1998 | Caruthers et al. |
| 5,770,403 | A | 6/1998 | Dalie et al. |
| 5,843,725 | A | 12/1998 | Sledziewski et al. |
| 5,861,310 | A | 1/1999 | Freeman et al. |
| 5,874,240 | A | 2/1999 | Ni et al. |
| 5,928,893 | A | 7/1999 | Kang et al. |
| 5,942,607 | A | 8/1999 | Freeman et al. |
| 6,018,026 | A | 1/2000 | Sledziewski et al. |
| 6,210,669 | B1 | 4/2001 | Aruffo et al. |
| 6,291,212 | B1 | 9/2001 | Sledziewski et al. |
| 6,291,646 | B1 | 9/2001 | Sledziewski et al. |
| 6,297,008 | B1 | 10/2001 | Okamoto et al. |
| 6,300,099 | B1 | 10/2001 | Sledziewski et al. |
| 6,303,121 | B1 | 10/2001 | Kwon |
| 6,323,323 | B1 | 11/2001 | Sledziewski et al. |
| 6,355,779 | B1 | 3/2002 | Goodwin et al. |
| 6,423,885 | B1 | 7/2002 | Waterhouse et al. |
| 6,458,934 | B1 | 10/2002 | Hong et al. |
| 6,630,575 | B2 | 10/2003 | Coyle et al. |
| 6,635,750 | B1 | 10/2003 | Coyle et al. |
| 6,740,493 | B1 | 5/2004 | Long et al. |
| 6,743,619 | B1 | 6/2004 | Tang et al. |
| 6,803,192 | B1 | 10/2004 | Chen |
| 6,891,030 | B2 | 5/2005 | Chen |
| 6,919,193 | B2 | 7/2005 | Tang et al. |
| 6,943,150 | B1 | 9/2005 | Altieri |
| 6,965,018 | B2 | 11/2005 | Mikesell et al. |
| 7,029,674 | B2 | 4/2006 | Carreno et al. |
| 7,030,219 | B2 | 4/2006 | Pardoll et al. |
| 7,122,351 | B2 | 10/2006 | Moore et al. |
| 7,279,567 | B2 | 10/2007 | Mikesell et al. |
| 7,358,354 | B2 | 4/2008 | Mikesell et al. |
| 7,368,531 | B2 | 5/2008 | Rosen et al. |
| 7,381,794 | B2 | 6/2008 | Moore et al. |
| 7,414,122 | B2 | 8/2008 | Fox et al. |
| 7,432,059 | B2 | 10/2008 | Freeman et al. |
| 7,432,062 | B2 | 10/2008 | Coyle et al. |
| 7,432,351 | B1 | 10/2008 | Chen |
| 7,449,300 | B2 | 11/2008 | Chen et al. |
| 7,560,540 | B2 | 7/2009 | Pardoll et al. |
| 7,563,869 | B2 | 7/2009 | Honjo et al. |
| 7,582,439 | B2 | 9/2009 | Cory et al. |
| 7,595,048 | B2 | 9/2009 | Honjo et al. |
| 7,651,686 | B2 | 1/2010 | Chen et al. |
| 7,709,214 | B2 | 5/2010 | Freeman et al. |
| 7,723,479 | B2 | 5/2010 | Mikesell et al. |
| 7,794,710 | B2 | 9/2010 | Chen et al. |
| 7,892,540 | B2 | 2/2011 | Chen et al. |
| 8,008,449 | B2 | 8/2011 | Korman et al. |
| 8,039,589 | B1 | 10/2011 | Chen |
| 8,053,414 | B2 | 11/2011 | Pardoll et al. |
| 8,053,558 | B2 | 11/2011 | Pardoll et al. |
| 8,163,550 | B2 | 4/2012 | Chen et al. |
| 8,268,635 | B2 | 9/2012 | Ferrante et al. |
| 8,273,864 | B2 | 9/2012 | Chen |
| 8,383,405 | B2 | 2/2013 | Orme |
| 8,460,927 | B2 | 6/2013 | Chen |
| 8,518,409 | B2 | 8/2013 | Orme |
| 8,772,026 | B2 | 7/2014 | Chen et al. |
| 8,901,120 | B2 | 12/2014 | Bearss et al. |
| 8,981,063 | B2 | 3/2015 | Chen |
| 9,302,005 | B2 | 4/2016 | Dong et al. |
| 9,534,058 | B2 | 1/2017 | Stull et al. |
| 9,598,491 | B2 | 3/2017 | Ahmed et al. |
| 9,730,988 | B2 | 8/2017 | Ince et al. |
| 11,246,890 | B2 | 2/2022 | Lin et al. |
| 11,344,578 | B2 * | 5/2022 | Rezvani ................. A61K 40/31 |
| 11,419,898 | B2 | 8/2022 | Lu et al. |
| 2002/0076409 | A1 | 6/2002 | March et al. |
| 2002/0091246 | A1 | 7/2002 | Pardoll et al. |
| 2002/0095024 | A1 | 7/2002 | Mikesell et al. |
| 2002/0106730 | A1 | 8/2002 | Coyle et al. |
| 2002/0107363 | A1 | 8/2002 | Fox et al. |
| 2002/0110836 | A1 | 8/2002 | Freeman et al. |
| 2002/0119121 | A1 | 8/2002 | Vitiello et al. |
| 2002/0160395 | A1 | 10/2002 | Altieri et al. |
| 2002/0160973 | A1 | 10/2002 | Pero et al. |
| 2002/0164600 | A1 | 11/2002 | Freeman et al. |
| 2002/0168719 | A1 | 11/2002 | Kwon |
| 2002/0177551 | A1 | 11/2002 | Terman |
| 2003/0039653 | A1 | 2/2003 | Chen et al. |
| 2003/0142359 | A1 | 7/2003 | Bean et al. |
| 2003/0171551 | A1 | 9/2003 | Rosenblatt et al. |
| 2003/0208058 | A1 | 11/2003 | Fiscella et al. |
| 2003/0223989 | A1 | 12/2003 | Pluenneke |
| 2003/0232323 | A1 | 12/2003 | Freeman et al. |
| 2004/0010134 | A1 | 1/2004 | Rosen et al. |
| 2004/0109847 | A1 | 6/2004 | Chen et al. |
| 2004/0180047 | A1 | 9/2004 | Chen |
| 2004/0247563 | A1 | 12/2004 | Lynch et al. |
| 2005/0013811 | A1 | 1/2005 | Chen et al. |
| 2005/0228170 | A1 | 10/2005 | Fox et al. |
| 2005/0260716 | A1 | 11/2005 | Moore et al. |
| 2006/0034826 | A1 | 2/2006 | Carreno et al. |
| 2006/0068386 | A1 | 3/2006 | Slesarev et al. |
| 2006/0084794 | A1 | 4/2006 | Rosen et al. |
| 2006/0110383 | A1 | 5/2006 | Honjo et al. |
| 2006/0159685 | A1 | 7/2006 | Mikesell et al. |
| 2006/0223088 | A1 | 10/2006 | Rosen et al. |
| 2006/0276422 | A1 | 12/2006 | Usman et al. |
| 2007/0037206 | A1 | 2/2007 | Rosen et al. |
| 2007/0041963 | A1 | 2/2007 | Rosen et al. |
| 2007/0065427 | A1 | 3/2007 | Freeman et al. |
| 2007/0092504 | A1 | 4/2007 | Carreno et al. |
| 2007/0099833 | A1 | 5/2007 | Rosen et al. |
| 2007/0122378 | A1 | 5/2007 | Freeman et al. |
| 2007/0224663 | A1 | 9/2007 | Rosen et al. |
| 2007/0231344 | A1 | 10/2007 | Leadbetter et al. |
| 2008/0025979 | A1 | 1/2008 | Honjo et al. |
| 2008/0118511 | A1 | 5/2008 | Freeman et al. |
| 2008/0226662 | A1 | 9/2008 | Pardoll et al. |
| 2008/0241175 | A1 | 10/2008 | Pardoll et al. |
| 2009/0042292 | A1 | 2/2009 | Chen |
| 2009/0068193 | A1 | 3/2009 | Chen et al. |
| 2009/0075338 | A1 | 3/2009 | Moore et al. |
| 2009/0176317 | A1 | 7/2009 | Kwon et al. |
| 2009/0215084 | A1 | 8/2009 | Kwon et al. |
| 2009/0269783 | A1 | 10/2009 | Coyle et al. |
| 2009/0304711 | A1 | 12/2009 | Pardoll et al. |
| 2010/0015642 | A1 | 1/2010 | Kwon et al. |
| 2010/0080816 | A1 | 4/2010 | Hadeiba et al. |
| 2010/0092470 | A1 | 4/2010 | Bhatt et al. |
| 2010/0285039 | A1 | 11/2010 | Chen |
| 2011/0010409 | A1 | 1/2011 | DeLaquil et al. |
| 2011/0020325 | A1 | 1/2011 | Kwon et al. |
| 2012/0065374 | A1 | 3/2012 | Pardoll et al. |
| 2012/0065385 | A1 | 3/2012 | Pardoll et al. |
| 2012/0225043 | A1 | 9/2012 | Chen et al. |
| 2013/0058936 | A1 | 3/2013 | Bruenker et al. |
| 2013/0123566 | A1 | 5/2013 | Lupold et al. |
| 2013/0251736 | A1 | 9/2013 | Kwon et al. |
| 2013/0273656 | A1 | 10/2013 | Hendrickson |

(56) References Cited

U.S. PATENT DOCUMENTS

| | | | |
|---|---|---|---|
| 2014/0031260 A1 | 1/2014 | O'Donnell et al. | |
| 2014/0242080 A1 | 8/2014 | Roche | |
| 2014/0271674 A1 | 9/2014 | Dong | |
| 2014/0322275 A1 | 10/2014 | Brogdon et al. | |
| 2014/0329248 A1 | 11/2014 | Kwon et al. | |
| 2014/0335541 A1 | 11/2014 | Kwon et al. | |
| 2015/0111232 A1 | 4/2015 | Kwon et al. | |
| 2015/0203580 A1 | 7/2015 | Papadopoulos et al. | |
| 2015/0273033 A1 | 10/2015 | Bosch et al. | |
| 2015/0337048 A1 | 11/2015 | Stull et al. | |
| 2016/0045581 A1 | 2/2016 | Ince et al. | |
| 2016/0051651 A1 | 2/2016 | Brogdon et al. | |
| 2016/0068601 A1 | 3/2016 | Brogdon et al. | |
| 2016/0153996 A1 | 6/2016 | Kwon et al. | |
| 2016/0154000 A1 | 6/2016 | Kwon | |
| 2016/0176967 A1 | 6/2016 | Dong et al. | |
| 2016/0237407 A1* | 8/2016 | Wagner | A61K 40/11 |
| 2016/0251437 A1 | 9/2016 | Dong et al. | |
| 2017/0044500 A1 | 2/2017 | Cooper et al. | |
| 2017/0089918 A1 | 3/2017 | Dong | |
| 2017/0121416 A1 | 5/2017 | Stull et al. | |
| 2017/0173030 A1 | 6/2017 | Dong | |
| 2017/0274095 A1 | 9/2017 | Meyer et al. | |
| 2017/0275375 A1 | 9/2017 | Rossi et al. | |
| 2017/0327590 A1 | 11/2017 | Lowy et al. | |
| 2017/0363634 A1 | 12/2017 | Kwon et al. | |
| 2018/0105573 A1 | 4/2018 | Pule et al. | |
| 2018/0139940 A1 | 5/2018 | Macdonald et al. | |
| 2018/0154183 A1 | 6/2018 | Sahadevan | |
| 2019/0038671 A1 | 2/2019 | Fan et al. | |
| 2019/0107537 A1 | 4/2019 | Chaudhary | |
| 2019/0112380 A1 | 4/2019 | Chaudhary | |
| 2019/0292539 A1 | 9/2019 | Fulga et al. | |
| 2019/0298774 A1* | 10/2019 | Lin | C07K 14/7051 |
| 2019/0315869 A1 | 10/2019 | Dong | |
| 2019/0361033 A1 | 11/2019 | Dong | |
| 2020/0054673 A1 | 2/2020 | Ports et al. | |
| 2020/0061077 A1 | 2/2020 | Dong | |
| 2020/0147117 A1 | 5/2020 | Ben Yakar et al. | |
| 2020/0190196 A1 | 6/2020 | Dong | |
| 2020/0270355 A1 | 8/2020 | Faustman | |
| 2020/0271656 A1 | 8/2020 | Cumba-Garcia et al. | |
| 2020/0338112 A1 | 10/2020 | Lou et al. | |
| 2021/0003556 A1 | 1/2021 | Dong | |
| 2021/0145830 A1 | 5/2021 | Kenderian et al. | |
| 2021/0145881 A1 | 5/2021 | Kenderian et al. | |
| 2021/0238253 A1 | 8/2021 | Li et al. | |
| 2021/0355190 A1 | 11/2021 | Kenderian et al. | |
| 2021/0401886 A1 | 12/2021 | Kenderian et al. | |
| 2022/0041686 A1 | 2/2022 | Mackall et al. | |
| 2023/0045174 A1 | 2/2023 | Rezvani et al. | |

FOREIGN PATENT DOCUMENTS

| | | |
|---|---|---|
| CN | 105949323 | 9/2016 |
| CN | 106459918 | 2/2017 |
| CN | 107406517 | 11/2017 |
| CN | 107849112 | 3/2018 |
| CN | 109608549 | 4/2019 |
| CN | 109734813 | 5/2019 |
| EP | 1074617 | 2/2001 |
| EP | 1537878 | 6/2005 |
| EP | 2997141 | 3/2016 |
| EP | 3130350 | 2/2017 |
| EP | 2968415 | 7/2019 |
| EP | 3964265 | 3/2022 |
| WO | WO 1990/007861 | 7/1990 |
| WO | WO 1991/010741 | 7/1991 |
| WO | WO 1991/011465 | 8/1991 |
| WO | WO 1991/017271 | 11/1991 |
| WO | WO 1992/000092 | 1/1992 |
| WO | WO 1992/001047 | 1/1992 |
| WO | WO 1992/020791 | 11/1992 |
| WO | WO 1993/001222 | 1/1993 |
| WO | WO 1995/005464 | 2/1995 |
| WO | WO 1995/007707 | 3/1995 |
| WO | WO 1996/029348 | 9/1996 |
| WO | WO 1997/017613 | 5/1997 |
| WO | WO 1997/017614 | 5/1997 |
| WO | WO 1997/024447 | 7/1997 |
| WO | WO 1998/016249 | 4/1998 |
| WO | WO 1998/023635 | 6/1998 |
| WO | WO 1998/033914 | 8/1998 |
| WO | WO 1998/036096 | 8/1998 |
| WO | WO 1999/036093 | 7/1999 |
| WO | WO 1999/064597 | 12/1999 |
| WO | WO 2000/026342 | 5/2000 |
| WO | WO 2000/029445 | 5/2000 |
| WO | WO 2000/029582 | 5/2000 |
| WO | WO 2000/041508 | 7/2000 |
| WO | WO 2000/055375 | 9/2000 |
| WO | WO 2000/061612 | 10/2000 |
| WO | WO 2001/034629 | 5/2001 |
| WO | WO 2001/062905 | 8/2001 |
| WO | WO 2001/070979 | 9/2001 |
| WO | WO 2001/083750 | 11/2001 |
| WO | WO 2001/094413 | 12/2001 |
| WO | WO 2002/000692 | 1/2002 |
| WO | WO 2002/000730 | 1/2002 |
| WO | WO 2002/002587 | 1/2002 |
| WO | WO 2002/002891 | 1/2002 |
| WO | WO 2002/008279 | 1/2002 |
| WO | WO 2002/078731 | 1/2002 |
| WO | WO 2002/024891 | 3/2002 |
| WO | WO 2002/046449 | 6/2002 |
| WO | WO 2002/057453 | 7/2002 |
| WO | WO 2002/079474 | 10/2002 |
| WO | WO 2002/081731 | 10/2002 |
| WO | WO 2002/086083 | 10/2002 |
| WO | WO 2003/006632 | 1/2003 |
| WO | WO 2003/008583 | 1/2003 |
| WO | WO 2003/049755 | 6/2003 |
| WO | WO 2004/085418 | 10/2004 |
| WO | WO 2006/042237 | 4/2006 |
| WO | WO 2006/050172 | 5/2006 |
| WO | WO 2006/133396 | 12/2006 |
| WO | WO 2008/037080 | 4/2008 |
| WO | WO 2008/083174 | 7/2008 |
| WO | WO 2009/023566 | 2/2009 |
| WO | WO 2009/029342 | 3/2009 |
| WO | WO 2009/114110 | 9/2009 |
| WO | WO 2010/027423 | 3/2010 |
| WO | WO 2010/027827 | 3/2010 |
| WO | WO 2010/027828 | 3/2010 |
| WO | WO 2010/098788 | 9/2010 |
| WO | WO 2011/066342 | 6/2011 |
| WO | WO 2011/066389 | 6/2011 |
| WO | WO 2011/072246 | 6/2011 |
| WO | WO 2013/003112 | 2/2013 |
| WO | WO 2013/019906 | 2/2013 |
| WO | WO 2013/090552 | 6/2013 |
| WO | WO 2013/132044 | 9/2013 |
| WO | WO 2014/110045 | 7/2014 |
| WO | WO 2014/144666 | 9/2014 |
| WO | WO 2014/163684 | 10/2014 |
| WO | WO 2014/184143 | 11/2014 |
| WO | WO 2015/049280 | 4/2015 |
| WO | WO 2015/050663 | 4/2015 |
| WO | WO 2015/061668 | 4/2015 |
| WO | WO 2015/066262 | 5/2015 |
| WO | WO 2015/142314 | 9/2015 |
| WO | WO 2015/157252 | 10/2015 |
| WO | WO 2015/179654 | 11/2015 |
| WO | WO 2016/014148 | 1/2016 |
| WO | WO 2016/014576 | 1/2016 |
| WO | WO 2016/018920 | 2/2016 |
| WO | WO 2016/120219 | 8/2016 |
| WO | WO 2016/164731 | 10/2016 |
| WO | WO 2016/201394 | 12/2016 |
| WO | WO 2017/023803 | 2/2017 |
| WO | WO 2017/066561 | 4/2017 |
| WO | WO 2017/075389 | 5/2017 |
| WO | WO 2017/091546 | 6/2017 |
| WO | WO 2017/100587 | 6/2017 |

(56) References Cited

FOREIGN PATENT DOCUMENTS

| | | |
|---|---|---|
| WO | WO 2017/143094 | 8/2017 |
| WO | WO 2017/172981 | 10/2017 |
| WO | WO 2017/173360 | 10/2017 |
| WO | WO 2017/177179 | 10/2017 |
| WO | WO 2017/220704 | 12/2017 |
| WO | WO 2017/222593 | 12/2017 |
| WO | WO 2018/005712 | 1/2018 |
| WO | WO 2018/013918 | 1/2018 |
| WO | WO 2018/045069 | 3/2018 |
| WO | WO 2018/073391 | 4/2018 |
| WO | WO 2018/195339 | 10/2018 |
| WO | WO 2019/036724 | 2/2019 |
| WO | WO 2019/108756 | 6/2019 |
| WO | WO 2019/133793 | 7/2019 |
| WO | WO 2019/178334 | 9/2019 |
| WO | WO 2019/195142 | 10/2019 |
| WO | WO 2019/217423 | 11/2019 |
| WO | WO 2019/232370 | 12/2019 |
| WO | WO 2020/018620 | 2/2020 |
| WO | WO 2021/092577 | 5/2021 |
| WO | WO 2022/236049 | 11/2022 |
| WO | WO 2022/236142 | 11/2022 |
| WO | WO 2022/266396 | 12/2022 |
| WO | WO 2024/097852 | 5/2024 |

OTHER PUBLICATIONS

Chen et al. (Recent advances in CAR-MSCs: the new engine of cellular immunotherapy evolution. J Hematol Oncol 18, 92 (2025). https://doi.org/10.1186/s13045-025-01746-7 (Year: 2025).*

Academic Press Dictionary of Science and Technology (definition for the term "polyclonal"; Oxford: Elsevier Science & Technology (1996); retrieved Oct. 22, 2008, from http://www.credoreference.com/entry/3144515/.

Acsadi et al., "Direct gene transfer and expression into rat heart in vivo," New Biol., 3(1):71-81, Jan. 1991.

Adachi et al., "Enhanced and accelerated lymphoproliferation in Fas-null mice.," Proc Natl Acad Sci USA., 93(5):2131-2136, Mar. 5, 1996.

Adachi et al., "Aberrant transcription caused by the insertion of an early transposable element in an intron of the Fas antigen gene of lpr mice," Proc Natl Acad Sci USA., 90(5):1756-1760, Mar. 1, 1993.

Adada et al., "906: Favorable Modulation of Chimeric Antigen Receptor T Cells Safety and Efficacy by the Non-Covalent BTK Inhibitor Vecabrutinib," Abstract, Presented at Proceedings of the American Society of Hematology Annual Meeting & Exposition, Dec. 11-14, 2021, Atlanta, GA, USA, 3 pages.

Adusumilli et al., "Regional delivery of mesothelin-targeted CAR T cell therapy generates potent and long-lasting CD4-dependent tumor immunity," Sci. Transl. Medicine, Nov. 5, 2014, 6(261):261ra151, 15 pages.

Afonina et al., "Cytotoxic and non-cytotoxic roles of the CTL/NK protease granzyme B," Immunol Rev., 235(1):105-116, May 2010.

Agace et al., "T-lymphocyte-epithelial-cell interactions: integrin αE(CD103)ß7, LEEP-CAM and chemokines," Curr. Opin. Cell Biology, Oct. 1, 2000, 12(5):563-568.

Agata et al., "Expression of the PD-1 antigen on the surface of stimulated mouse T and B lymphocytes," Int Immunol., 8(5):765-772, May 1996.

Ahmadzadeh et al., "Tumor antigen-specific CD8 T cells infiltrating the tumor express high levels of PD-1 and are functionally impaired," Blood, 114(8):1537-1544, May 7, 2009.

Ahonen et al., "Combined TLR and CD40 triggering induces potent CD8+ T cell expansion with variable dependence on type I IFN," J Exp Med., 199(6):775-784, Mar. 8, 2004.

Alderson et al., "Molecular and biological characterization of human 4-1BB and its ligand," Eur J Immunol., 24(9):2219-2227, Sep. 1994.

Aldovini et al., "Humoral and cell-mediated immune responses to live recombinant BCG-HIV vaccines," Nature, 351(6326):479-482, Jun. 6, 1991.

Alizadeh et al., "Chemotherapeutic targeting of cancer-induced immunosuppressive cells," Cancer Res., 74(10):2663-2668, May 15, 2014.

Allie et al., "Programmed death 1 regulates development of central memory CD8 T cells after acute viral infection," J Immunol., 186(11):6280-6286, Apr. 27, 2011.

Altin et al., "The role of CD45 and CD45-associated molecules in T cell activation," Immunol. Cell Biology, 75(5):430-445, Oct. 1997.

Altschul et al., "Gapped BLAST and PSI-BLAST: a new generation of protein database search programs," Nucleic Acids Research, Sep. 1, 1997, 25(17):3389-3402.

Ambrosini et al., "A novel anti-apoptosis gene, survivin, expressed in cancer and lymphoma," Nat Med., 3(8): 917-921, Aug. 1997.

An et al., "Anti-Multiple Myeloma Activity of Nanobody-Based Anti-CD38 Chimeric Antigen Receptor T Cells," Mol. Pharmaceutics, Sep. 5, 2018, 15(10):4577-4588.

Anders et al., "HTSeq—a Python framework to work with high-throughput sequencing data," Bioinformatics, 31(2):166-169, Jan. 15, 2015.

Anderson, "Human gene therapy," Science, 256(5058):808-813, May 8, 1992.

Andorsky et al., "Programmed death ligand 1 is expressed by non-hodgkin lymphomas and inhibits the activity of tumor-associated T cells," Clin Cancer Res., 17(13):4232-4244, May 3, 2011.

Anikeeva et al., "Distinct role of lymphocyte function-associated antigen-1 in mediating effective cytolytic activity by cytotoxic T lymphocytes," Proc Natl Acad Sci USA., 102(18):6437-6442, Apr. 25, 2005.

Ansari et al., "The programmed death-1 (PD-1) pathway regulates autoimmune diabetes in nonobese diabetic (NOD) mice," J Exp Med., 198(1):63-69, Jul. 7, 2003.

Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," Microbes Infect., 8(6):1450-1454, Mar. 29, 2006.

Ao et al., "Anti-αFR CAR-engineered NK-92 Cells Display Potent Cytotoxicity Against aFR-positive Ovarian Cancer," J. Immunotherapy, Oct. 2019, 42(8):284- 296.

Attwood et al., "Genomics. The Babel of bioinformatics," Science, 290(5491):471-473, Oct. 20, 2000.

Azuma et al., "B7-H1 is a ubiquitous antiapoptotic receptor on cancer cells," Blood., 111(7):3635-3643, Jan. 25, 2008.

Baitsch et al., "Exhaustion of tumor-specific CD8+ T cells in metastases from melanoma patients," J Clin Invest., 121(6):2350-2360, May 9, 2011.

Bajorath et al., "Molecular modeling of CD28 and three-dimensional analysis of residue conservation in the CD28/CD152 family," J Mol Graph Model., 15(2):135-139, 108-111, Apr. 1997.

Baldrick, "Pharmaceutical excipient development: the need for preclinical guidance," Regul Toxicol Pharmacol., 32(2):210-218, Oct. 2000.

Banáth et al., "Residual gammaH2AX foci as an indication of lethal DNA lesions," BMC Cancer., 10:4, Jan. 5, 2010.

Barber et al., "Restoring function in exhausted CD8 T cells during chronic viral infection," Nature, 439(7077):682-687, Dec. 28, 2005.

Barlic et al., "IL-15 and IL-2 oppositely regulate expression of the chemokine receptor CX3CR1," Blood, 102(10):3494-3503, Nov. 15, 2003.

BD PharmingenTM Technical Data Sheet, "Purified Rat Anti-Mouse Ly-6G (Gr-1) Monoclonal Antibody for Immunohistochemistry (IHC)" 1 page, 2003.

Belov et al., "Extensive surface protein profiles of extracellular vesicles from cancer cells may provide diagnostic signatures from blood samples," J. Extracell. Vesicles, Apr. 15, 2016, 5:25355, 12 pages.

Benita et al., "Characterization of drug-loaded poly(d,l-lactide) microspheres," J Pharm Sci., 73(12):1721-1724, Dec. 1984.

(56) References Cited

OTHER PUBLICATIONS

Benlalam et al., "Comprehensive analysis of the frequency of recognition of melanoma-associated antigen (MAA) by CD8 melanoma infiltrating lymphocytes (TIL) implications for immunotherapy," Eur J Immunol., 31(7):2007-2015, Jul. 31, 2001.
Bennardo et al., "Alternative-NHEJ is a mechanistically distinct pathway of mammalian chromosome break repair," PLoS Genet., 4(6):e1000110, Jun. 27, 2008.
Berman et al., "The Protein Data Bank," Nucleic Acids Res., 28(1):235-242, Jan. 1, 2000.
Berrien-Elliott et al., "Durable adoptive immunotherapy for leukemia produced by manipulation of multiple regulatory pathways of CD8+ T-cell tolerance," Cancer Res., 73(2):605-616, Jan. 15, 2013.
Berthon et al., "In acute myeloid leukemia, B7-H1 (PD-L1) protection of blasts from cytotoxic T cells is induced by TLR ligands and interferon-gamma and can be reversed using MEK inhibitors," Cancer Immunol Immunother., 59(12):1839-1849, Sep. 4, 2010.
Betts et al., "Sensitive and viable identification of antigen-specific CD8+ T cells by a flow cytometric assay for degranulation," J Immunol Methods, 281(1-2):65-78, Oct. 1, 2003.
Bezu et al., "Combinatorial strategies for the induction of immunogenic cell death," Front Immunol., 6:187, Apr. 24, 2015, 11 pages.
Bibikova et al., "Enhancing gene targeting with designed zinc finger nucleases," Science, May 2, 2003, 300(5620):764.
Bielamowics et al., "Trivalent CAR T cells overcome interpatient antigenic variability in glioblastoma," Neuro-Oncology, Sep. 16, 2017, 20(4):506-518.
Bird et al., "Single-chain antigen-binding proteins," Science, 242(4877):423-426, Oct. 21, 1988.
Bitinaite et al., "FokI dimerization is required for DNA cleavage," Proc. Natl. Acad. Sci. USA, Sep. 1, 1998, 95(18):10570-10575.
Black et al., "Activation of the PD-1/PD-L1 immune checkpoint confers tumor cell chemoresistance associated with increased metastasis," Oncotarget, 7(9):10557-10567, Mar. 2016.
Blank et al., "Blockade of PD-L1 (B7-H1) augments human tumor-specific T cell responses in vitro," Int J Cancer, 119(2):317-327, Jul. 15, 2006.
Blank et al., "Interaction of PD-L1 on tumor cells with PD-1 on tumor-specific T cells as a mechanism of immune evasion: implications for tumor immunotherapy," Cancer Immunol Immunother., 54(4):307-314, Dec. 15, 2004.
Blank et al., "PD-L1/B7H-1 inhibits the effector phase of tumor rejection by T cell receptor (TCR) transgenic CD8+ T cells," Cancer Res., 64(3):1140-1145, Feb. 1, 2004.
Blat et al., "Suppression of Murine Colitis and its Associated Cancer by Carcinoembryonic Antigen-Specific Regulatory T Cells," Mol. Therapy, May 2014, 22(5):1018-1028.
Blazar et al., "Infusion of anti-B7.1 (CD80) and anti-B7.2 (CD86) monoclonal antibodies inhibits murine graft-versus-host disease lethality in part via direct effects on CD4+ and CD8+ T cells," J Immunol., 157(8):3250-3259, Oct. 15, 1996.
Block, "Medicated Applications," Remington's Pharmaceutical Sciences, 18th edition, Mack Publishing Company, Easton, PA, Chpt 87, pp. 1596-1614, 1990.
Bodine, "mTOR signaling and the molecular adaptation to resistance exercise," Med Sci Sports Exerc., 38(11):1950-1957, Nov. 2006.
Boggio et al., "Interleukin 12-mediated prevention of spontaneous mammary adenocarcinomas in two lines of Her-2/neu transgenic mice," J Exp Med., 188(3):589-596, Aug. 3, 1998.
Boise et al., "CD28 costimulation can promote T cell survival by enhancing the expression of Bcl-XL," Immunity, 3(1):87-98, Jul. 1995.
Boletta et al., "High efficient non-viral gene delivery to the rat kidney by novel polycationic vectors," J Am Soc Nephrol., 7(9):1728, abstr A2409, Sep. 1, 1996.
Bolger et al., "Trimmomatic: a flexible trimmer for Illumina sequence data," Bioinformatics, 30(15):2114-2120, Aug. 1, 2014.
Bona et al., "Immune response: Idiotype anti-idiotype network," CRC Crit Rev Immunol., 33-81, Mar. 1981.
Bonfoco et al., "Inducible nonlymphoid expression of Fas ligand is responsible for superantigen-induced peripheral deletion of T cells," Immunity, 9(5):711-720, Nov. 1998.
Bonifaz et al., "Efficient targeting of protein antigen to the dendritic cell receptor DEC-205 in the steady state leads to antigen presentation on major histocompatibility complex class I products and peripheral CD8+ T cell tolerance," J Exp Med., 196(12):1627-1638, Dec. 16, 2002.
Bonifaz et al., "In vivo targeting of antigens to maturing dendritic cells via the DEC-205 receptor improves T cell vaccination," J Exp Med., 199(6):815-824, Mar. 15, 2004.
Bonni et al., "Cell survival promoted by the Ras-MAPK signaling pathway by transcription-dependent and -independent mechanisms," Science, 286(5443):1358-1362, Nov. 12, 1999.
Boon et al., "Human T cell responses against melanoma," Annu Rev Immunol., 24:175-208, 2006.
Borson et al., "Brain-infiltrating cytolytic T lymphocytes specific for Theiler's virus recognize H2Db molecules complexed with a viral VP2 peptide lacking a consensus anchor residue," J Virol., 71(7):5244-5250, Jul. 1997.
Bottcher et al., "Functional classification of memory CD8(+) T cells by CX3CR1 expression," Nat Commun., 6:8306, Sep. 25, 2015.
Bouillet and O'Reilly, "CD95, BIM and T cell homeostasis," Nat Rev Immunol., 9(7):514-519, Jul. 2009.
Bowie et al., "Deciphering the message in protein sequences: tolerance to amino acid substitutions," Science, 247(4948):1306-1310, Mar. 16, 1990.
Boyiadzis et al., "The emerging roles of tumor-derived exosomes in hematological malignancies," Leukemia, Mar. 21, 2017, 31(6):1259-1268.
Boysen et al., "Dynamics of microvesicle generation in B-cell chronic lymphocytic leukemia: implication in disease progression," Leukemia, 31(2):350-360, Aug. 2, 2016.
Brahmer et al., "Safety and activity of anti-PD-L1 antibody in patients with advanced cancer," N Engl J Med., 366(26):2455-2465, Jun. 2, 2012.
Brand et al., "Collagen-induced arthritis," Nat. Protoc., 2(5):1269-1275, May 17, 2007.
Braquet et al., "Effect of endothelin-1 on blood pressure and bronchopulmonary system of the guinea pig," J Cardiovasc Pharmacol., 13(Suppl 5):S143-146, discussion S150, 1989.
Brinkmann et al., "FTY720: altered lymphocyte traffic results in allograft protection," Transplantation., 72(5):764-769, Sep. 15, 2001.
Britton et al., "Leprosy," Lancet, 363(9416):1209-1219, Apr. 10, 2004.
Brooks, "Translational genomics: the challenge of developing cancer biomarkers," Genome Res., 22(2):183-187, Feb. 2012.
Brown et al., "A mass spectrometry-based assay for improved quantitative measurements of efflux pump inhibition," PLoS One, 10(5):e0124814, May 11, 2015, 12 pages.
Brown et al., "Blockade of programmed death-1 ligands on dendritic cells enhances T cell activation and cytokine production.," J Immunol., 170(3):1257-1266, Feb. 1, 2003.
Brown et al., "CAR T cell therapy: inroads to response and resistance," Nat. Rev. Immunology, 19(2):73-74, Jan. 10, 2019.
Brozovic et al., "Activation of mitogen-activated protein kinases by cisplatin and their role in cisplatin-resistance," Cancer Lett., 251(1):1-16, Nov. 27, 2006.
Bu et al., "Learning from PD-1 Resistance: New Combination Strategies," Trends Mol Med., 22(6):448-451, Jun. 2016.
Bubenik, "Genetically engineered dendritic cell-based cancer vaccines (Review)," Int J Oncol., 18(3):475-478, Mar. 2001.
Burmer et al., "Frequency and spectrum of c-Ki-ras mutations in human sporadic colon carcinoma, carcinomas arising in ulcerative colitis, and pancreatic adenocarcinoma," Environ Health Perspect., 93:27-31, Jun. 1991.
Businesswire.com [online], "Incyte Reports Third Quarter 2011 Financial Results and Provides Update on Key Clinical Programs," Oct. 27, 2011, retrieved on Mar. 24, 2021, retrieved from URL<https://www.businesswire.com/news/home/20111027005220/en/Incyte-

(56) References Cited

OTHER PUBLICATIONS

Reports-Third-Quarter-2011-Financial-Results-and-Provides-Update-on-Key-Clinical-Programs>, 4 pages.
Buskens et al., "Adenocarcinomas of the gastro-esophageal junction: A comparative study of the gastric cardia and the esophagus with respect to cyclooxygenase-2 expression," Digestive Disease Week Abstracts and Itinerary Planner, abstract No. 850, 2003.
Butte et al., "Interaction of human PD-L1 and B7-1," Mol Immunol., 45(13):3567-3572, Jun. 27, 2008.
Butte et al., "PD-L1 interacts specifically with B7-1 to inhibit T cell proliferation," Immunity., 27:111-122, 2007.
Cairns et al., "Immortalization of multipotent growth-factor dependent hemopoietic progenitors from mice transgenic for GATA-1 driven SV40 tsA58 gene," EMBO J., 13(19):4577-4586, Oct. 3, 1994.
Caivano et al., "Extracellular Vesicles In Hematological Malignancies: From Biology to Therapy," Int. J. Mol. Sciences, Jun. 2, 2017, 18(6):1183, 23 pages.
Cannons et al., "4-1BB ligand induces cell division, sustains survival, and enhances effector function of CD4 and CD8 T cells with similar efficacy," J Immunol., 167(3):1313-1324, Aug. 1, 2001.
Cao et al., "B7-H1 overexpression regulates epithelial-mesenchymal transition and accelerates carcinogenesis in skin," Cancer Res., 71(4):1235-1243, Dec. 15, 2010.
Carreno et al., "The B7 family of ligands and its receptors: new pathways for costimulation and inhibition of immune responses," Annu Rev Immunol., 20:29-53, Oct. 4, 2001.
Carter et al., "PD-1:PD-L inhibitory pathway affects both CD4(+) and CD8(+) T cells and is overcome by IL-2," Eur J Immunol., 32(3):634-643, Mar. 2002.
Carter et al., "Humanization of an anti-p185HER2 antibody for human cancer therapy," Proc Natl Acad Sci USA., 89(10):4285-4289, May 15, 1992.
Caruso et al., "Tuning Sensitivity of CAR to EGFR Density Limits Recognition of Normal Tissue While Maintaining Potent Antitumor Activity," Cancer Research, Sep. 2015, 75(17):3505-3518.
Catalano et al., "Inhibiting extracellular vesicles formation and release: a review of EV inhibitors," J. Extracell. Vesicles, 9(1):1703244, Dec. 19, 2019, 22 pages.
Chakrabarti et al., "Vaccinia virus expression vector: coexpression of beta-galactosidase provides visual screening of recombinant virus plaques," Mol Cell Biol., 5(12):3403-3409, Dec. 1985.
Chambers et al., "Co-stimulation in T cell responses," Curr Opin Immunol., 9(3):396-404, Jun. 1997.
Champiat et al., "Hyperprogressive Disease Is a New Pattern of Progression in Cancer Patients Treated by Anti-PD-1/PD-L1," Clin Cancer Res., 23(8):1920-1928, Apr. 15, 2017.
Chan et al., "Arthritis and Tenosynovitis Associated With the Anti-PD1 Antibody Pembrolizumab in Metastatic Melanoma," J. Immunother., 38(1):37-39, Jan. 2015.
Chan et al., "Autophosphorylation of the DNA-dependent protein kinase catalytic subunit is required for rejoining of DNA double-strand breaks," Genes Dev., 16(18):2333-2338, Sep. 15, 2002.
Chapoval et al., "B7-H3: A costimulatory molecule for T cell activation and IFN-y production," Nat Immunol., 2(3):269-274, Mar. 2001.
Charman, "Lipids, lipophilic drugs, and oral drug delivery-some emerging concepts," J. Pharm. Sci., 89(8):967-978, Aug. 2000.
Chaurand et al., "Peptide and Protein Identification by Matrix-Assisted Laser Desorption Ionization (MALDI) and MALDI-Post-Source Decay Time-of-Flight Mass Spectrometry," J Am Soc Mass Spectrom., 10(2):91-103, Feb. 1999.
Chen et al., "Anti-PD-1/PD-L1 therapy of human cancer: past, present, and future," J. Clin. Investigation, 125(9):3384-3391, Sep. 2015.
Chen et al., "CD44-deficient mice exhibit enhanced hepatitis after concanavalin A injection: evidence for involvement of CD44 in activation-induced cell death," J Immunol., 166(10):5889-5897, May 1, 2001.
Chen et al., "Costimulation of antitumor immunity by the B7 counterreceptor of the T lymphocyte molecules CD28 and CTLA-4," Cell, 71(7):1093-1102, Dec. 24, 1992.
Chen et al., "Development of a sandwich ELISA for evaluating soluble PD-L1 (CD274) in human sera of different ages as well as supernatants of PD-L1+ cell lines," Cytokine, 56(2):231-238, Nov. 2011.
Chen et al., "Molecular Pathways: Next-Generation Immunotherapy—Inhibiting Programmed Death-Ligand 1 and Programmed Death-1," Clin. Cancer Research, 18(24):6580-6587, Oct. 19, 2012.
Chen et al., "PD-L1 Expression Promotes Epithelial to Mesenchymal Transition in Human Esophageal Cancer," Cell Physiol. Biochemistry, 42(6):2267-2280, Aug. 17, 2017.
Chen et al., "Tumor immunogenicity determines the effect of co-stimulation by B7 on T-cell mediated tumor immunity," J Exp Med., 179(2):523-532, Feb. 1, 1994.
Chen et al., "Upregulation of PD-L1 by EGFR Activation Mediates the Immune Escape in EGFR-Driven NSCLC: Implication for Optional Immune Targeted Therapy for NSCLC Patients with EGFR Mutation," J. Thorac. Oncology, 10(6):910-923, Jun. 2015.
Chen, "Co-inhibitory molecules of the B7-CD28 family in the control of T-cell immunity," Nat Rev Immunol., 4(5):336-347, May 2004.
Cheville et al., "Comparisons of outcome and prognostic features among histologic subtypes of renal cell carcinoma," Am J Surg Pathol., 27(5):612-624, May 2003.
Chi et al., "Significantly increased anti-tumor activity of carcinoembryonic antigen-specific chimeric antigen receptor T cells in combination with recombinant human IL-12," Cancer Medicine, Jun. 25, 2019, 8(10):4753-4765.
Cho et al., "Targeted genome engineering in human cells with the Cas9 RNA-guided endonuclease," Nat. Biotechnology, 31(3):230-232, Jan. 29, 2013.
Choi et al., "Genomic Organization and expression Analysis of B7-H4, an Immune Inhibitory Molecule of the B7 Family," J Immunol., 171(9):4650-4654, Nov. 1, 2003.
Chowdhury et al., "Programmed death-ligand 1 overexpression is a prognostic marker for aggressive papillary thyroid cancer and its variants," Oncotarget, 7(22):32318-32328, May 31, 2016.
Chu et al., "CS1-specific chimeric antigen receptor (CAR)-engineered natural killer cells enhance in vitro and in vivo antitumor activity against human multiple myeloma," Leukemia, Apr. 2014, 28(4):917-927.
Chung et al., "Seeding Open Innovation Drug Discovery and Translational Collaborations to Leverage Government Funding: A Case Study of Strategic Partnership between Sanford-Burnham and Mayo Clinic," Collaborative Innovation in Drug Discovery: Strategies for Public and Private Partnerships, 27:451-486, Apr. 2014.
ClinicalTrials.gov [online], "First-in-human Study of Oral TP-0903 (a Novel Inhibitor of AXL Kinase) in Patients With Advanced Solid Tumors," NCT02729298, last updated Jan. 25, 2021, retrieved on Apr. 23, 2021, retrieved from URL<https://www.clinicaltrials.gov/ct2/show/NCT02729298>, 24 pages.
ClinicalTrials.gov [online], "Phase 1/2 Study of TP-0903 (an Inhibitor of AXL Kinase) in Patients With Previously Treated CLL," NCT03572634, last updated Feb. 2, 2021, retrieved on Apr. 23, 2021, retrieved from URL<https://clinicaltrials.gov/ct2/show/NCT03572634>, 34 pages.
ClinicalTrials.gov [online], "Safety, PK, PD, and Antitumor Activity of Vecabrutinib (SNS-062) in B Lymphoid Cancers," NCT03037645, last updated Oct. 19, 2020, retrieved on Jan. 5, 2022, retrieved from URL<https://clinicaltrials.gov/ct2/show/NCT03037645>, 21 pages.
Cocuzza et al., "[Importance and evaluation of red cell indices obtained with semi-automatic cell counters during the screening of heterozygote beta-thalassemia]," Minerva Med, 74(18):1017-1020, Apr. 28, 1983 (with Machine English Abstract).
Cogoni et al., "Gene silencing in Neurospora crassa requires a protein homologous to RNA-dependent RNA polymerase," Nature, 399(6732):166-169, May 13, 1999.
Cogoni et al., "Transgene silencing of the al-1 gene in vegetative cells of Neurospora is mediated by a cytoplasmic effector and does not depend on DNA-DNA interactions or DNA methylation ," EMBO J., 15(12):3153-3163, Jun. 17, 1996.

(56) References Cited

OTHER PUBLICATIONS

Cohen et al., "B cell maturation antigen-specific CAR T cells are clinically active in multiple myeloma," J. Clin. Investigation, Mar. 21, 2019, 129(6):2210-2221.
Cohen et al., "Lpr and gld: Single Gene Models of Systemic Autoimmunity and Lymphoproliferative Disease," Annu Rev Immunol., 9:243-269, 1991.
Colado et al., "Effect of the BTK inhibitor ibrutinib on macrophage- and gammadelta T cell-mediated response against *Mycobacterium tuberculosism*" Blood Cancer Journal, Nov. 5, 2018, 8(11):100, 6 pages.
Cole et al., "The EBV-hybridoma technique and its application to human lung cancer," Monoclonal Antibodies and Cancer Therapy, 27:77-96, Jan./Feb. 1985.
Collins et al., "The B7 family of immune-regulatory ligands," Genome Biol., 6(6):223, May 31, 2005, 7 pages.
Collis et al., "The life and death of DNA-PK," Oncogene., 24(6):949-961, Feb. 3, 2005.
Conacci-Sorrell et al., "Autoregulation of E-cadherin expression by cadherin-cadherin interactions: the roles of beta-catenin signaling, Slug, and MAPK," J Cell Biol., 163(4):847-857, Nov. 17, 2003.
Cone et al., "High-efficiency gene transfer into mammalian cells: generation of helper-free recombinant retrovirus with broad mammalian host range," Proc Natl Acad Sci USA., 81(20):6349-6353, Oct. 1984.
Cong et al., "Multiplex genome engineering using CRISPR/Cas systems," Science, 339(6121):819-823, Jan. 3, 2013.
Connolly, "Analytical molecular surface calculation," J Appl Crystallogr., 16(5):548-558, Oct. 1, 1983.
Cooley et al., "Trans-presentation of IL-15 modulates STAT5 activation and Bcl-6 expression in THI cells," Sci Rep, 5:15722, Oct. 26, 2015, 9 pages.
Corcoran et al., "Docetaxel-Resistance in Prostate Cancer: Evaluating Associated Phenotypic Changes and Potential for Resistance Transfer via Exosomes," PLoS One, Dec. 10, 2012, 7(12):e50999, 12 pages.
Corpet, "Multiple sequence alignment with hierarchical clustering," Nucleic Acids Res., 16(22):10881-10890, Nov. 25, 1988.
Cote et al., "Generation of human monoclonal antibodies reactive with cellular antigens," Proc Natl Acad Sci USA., 80(7):2026-2030, Apr. 1983.
Coumans et al., "Methodological Guidelines to Study Extracellular Vesicles," Circ. Research, 120(10):1632-1648, May 12, 2017.
Coyle et al., "The expanding B7 superfamily: increasing complexity in costimulatory signals regulating T cell function," Nat Immunol., 2(3):203-209, Mar. 2001.
Crispe et al., "The liver as a site of T-cell apoptosis: graveyard, or killing field?" Immunol Rev., 174:47-62, Apr. 2000.
Crispe, "Hepatic T cells and liver tolerance," Nat Rev Immunol., 3(1):51-62, Jan. 2003.
Cristiano et al., "Molecular conjugates: a targeted gene delivery vector for molecular medicine," J Mol Med (Berl)., 73(10):479-486, Oct. 1995.
Cruz-Guilloty et al., "Runx3 and T-box proteins cooperate to establish the transcriptional program of effector CTLs," J. Exp. Med., 206(1):51-59, Jan. 16, 2009.
Crystal, "Gene therapy strategies for pulmonary disease" Am J Med., 92(suppl 6A):44S-52S, Jun. 22, 1992.
Curiel et al., "Blockade of B7-H1 improves myeloid dendritic cell-mediated antitumor immunity," Nat Med., 9(5):562-567, Apr. 21, 2003.
Dahlhamer et al., "Prevalence of Inflammatory Bowel Disease Among Adults Aged 18 Years—United States, 2015," MMWR Morb. Mortal. Wkly Report, Oct. 28, 2016, 65(42):1166-1169.
Daly et al., "Clinical Trials Integrating Immunotherapy and Radiation for Non-Small-Cell Lung Cancer," J. Thorac. Oncology, 10(12):1685-1693, Dec. 1, 2015.
Daniele et al., "A role for Rab7 in the movement of secretory granules in cytotoxic T lymphocytes," Traffic, 12(7):902-911, Jul. 2011.
Dao et al., "Involvement of CD1 in peripheral deletion of T lymphocytes is independent of NK T cells," J Immunol., 166(5):3090-3097, Mar. 1, 2001.
Database EM-MUS [Online]EMBL; Accession No. AF142780.1 (version 1), Jun. 1, 1999, 2 pages.
Datta et al., "Akt phosphorylation of BAD couples survival signals to the cell-intrinsic death machinery," Cell., 91(2):231-241, Oct. 17, 1997.
Daud et al., "Tumor immune profiling predicts response to anti-PD-1 therapy in human melanoma," J. Clin. Invest., 126(9):3447-3452, Sep. 1, 2016.
Davidson et al., "Phenotypic, functional, and molecular genetic comparisons of the abnormal lymphoid cells of C3H-lpr/lpr and C3H-gld/gld mice," J Immunol., 136(11):4075-4084, Jun. 1, 1986.
Davidson et al., "Small Molecules, Inhibitors of DNA-PK, Targeting DNA Repair, and Beyond," Front Pharmacol., 4(5):1-7, Jan. 31, 2013.
Davis et al., "Proline 326 in the C terminus of murine CX3CR1 prevents G-protein and phosphatidylinositol 3-kinase-dependent stimulation of Akt and extracellular signal-regulated kinase in Chinese hamster ovary cells," J. Pharmacol. Exp. Ther., 316(1):356-363, Jan. 2006.
De StGroth et al., "Production of monoclonal antibodies: strategy and tactics," J Immunol Methods., 35(1-2):1-21, 1980.
Debs et al., "Lung-specific delivery of cytokines induces sustained pulmonary and systemic immunomodulation in rats," J Immunol., 140(10):3482-3488, May 15, 1988.
Del Peso et al., "Interleukin-3-induced phosphorylation of BAD through the protein kinase Akt," Science, 278(5338):687-689, Oct. 24, 1997.
Dezutter-Dambuyan et al., "A novel regulation of PD-1 ligands on mesenchymal stromal cells through MMP-mediated proteolytic cleavage," OncoImmunology, 5(3):e1091146, Mar. 2016, 24 pages.
Dheda et al., "Lung remodeling in tuberculosis," J Infect Dis., 192(7):1201-1209, Aug. 29, 2005.
Dicarlo et al., "Genome engineering in Saccharomyces cerevisiae using CRISPR-Cas systems," Nucleic Acids Research, 41(7):4226-4343, Mar. 4, 2013.
Diehl et al., "In vivo triggering through 4-1BB enables Th-independent priming of CTL in the presence of an intact CD28 costimulatory pathway," J Immunol., 168(8):3755-3762, Apr. 15, 2002.
Dimopoulos et al., "Elotuzumab plus Pomalidomide and Dexamethasone for Multiple Myeloma," N. Engl. J. Medicine, Nov. 8, 2018, 379(19):1811-1822.
Ding et al., "Release of reactive nitrogen intermediates and reactive oxygen intermediates from mouse peritoneal macrophages. Comparison of activating cytokines and evidence for independent production," J Immunol., 141(7):2407-2412, Oct. 1, 1988.
Dini, "Recognizing death: liver phagocytosis of apoptotic cells," Eur J Histochem., 44(3):217-227, 2000.
Dobin et al., "STAR: ultrafast universal RNA-seq aligner," Bioinformatics, 29(1):15-21, Jan. 2013.
Doering et al., "Network analysis reveals centrally connected genes and pathways involved in CD8+ T cell exhaustion versus memory," Immunity, 37(6):1130-1144, Nov. 15, 2012.
Dong et al., "A novel method for identifying downstream signals in tumor-reactive T cells following PD-1 engagement and monitoring endogenous tumor immunity and immunotherapy," Journal of Clinical Oncology, 32(15):Abstract3049-3049, 2014.
Dong et al., "B7-H1 determines accumulation and deletion of intrahepatic CD8(+) T lymphocytes," Immunity., 20(3):327-336, Mar. 2004.
Dong et al., "B7-H1 pathway and its role in the evasion of tumor immunity" J Mol Med (Berl)., 81(5):281-287, Apr. 30, 2003.
Dong et al., "B7-H1, a third member of the B7 family, co-stimulates T-cell proliferation and interleukin-10 secretion," Nat Med., 5(12):1365-1369, Dec. 1999.
Dong et al., "Immune regulation by novel costimulatory molecules," Immunol Res., 28(1):39-48, 2003.
Dong et al., "Immunoregulatory role of B7-H1 in chronicity of inflammatory responses," Cell Mol Immunol., 3(3):179-187, Jun. 2006.

(56) References Cited

OTHER PUBLICATIONS

Dong et al., "Tumor-associated B7-H1 promotes T-cell apoptosis: A potential mechanism of immune evasion," Nat. Med., 8(8):793-800, Jun. 2002.
Dragoi et al., "DNA-PKcs, but not TLR9, is required for activation of Akt by CpG-DNA," EMBO J., 24(4):779-789, Jan. 27, 2005.
Dronca et al., "BCL-2-interacting mediator of cell death (Bim) is a novel biomarker for response to anti-PD-1 therapy in patients with advanced melanoma," Immunotherapy., 8(12)1351-1353, Dec. 1, 2016.
Dronca et al., "Bim and soluble PD-L1 (sPD-L1) as predictive biomarkers of response to anti-PD-1 therapy in patients with melanoma and lung carcinoma," J Clin Oncol., 35(15suppl):11534, May 30, 2017.
Dronca et al., "Soluble PD-L1 (sPD-L1) is associated with decreased survival in metastatic melanoma ," Abstract, Presented at Proceedings of Society for Melanoma Research 2015 Congress, San Francisco, CA, Nov. 18-21, 2015, 2 pages.
Dronca et al., "T cell Bim levels reflect responses to anti-PD-1 cancer therapy," JCI Insight., 1(6):e86014, May 5, 2016, 14 pages.
Dudler et al., "Gene transfer of programmed death Ligand-1.lg prolongs cardiac allograft survival," Transplantation, 82(12):1733-1737, Dec. 27, 2006.
Dunussi-Joannopoulos et al., "Gene therapy with B7.1 and GM-CSF vaccines in a murine AML model," J Pediatr Hematol Oncol., 19(6):536-540, Nov./Dec. 1997.
Durai et al., "Zinc finger nucleases: custom-designed molecular scissors for genome engineering of plant and mammalian cells," Nucleic Acids Research, Oct. 26, 2005, 33(18):5978-5990.
Duraiswamy et al., "Phenotype, function, and gene expression profiles of programmed death-1(hi) CD8 T cells in healthy human adults," J Immunol., 186(7):4200-4212, Apr. 1, 2011.
Duraiswamy et al., "Replenish the source within Rescuing tumor-infiltrating lymphocytes by double checkpoint blockade," Oncol., 2(10):e25912, Oct. 2013, 3 pages.
Ehl et al., "Different susceptibility of cytotoxic T cells to CD95 (Fas/Apo-1) ligand-mediated cell death after activation in vitro versus in vivo," J Immunol., 156(7):2357-2360, Apr. 1, 1996.
Elliott et al., "Mitoxantrone in combination with an inhibitor of DNA-dependent protein kinase: a potential therapy for high risk B-cell chronic lymphocytic leukaemia," Br J Haematol., 152(1):61-71, Nov. 18, 2010.
EMBL-EBI Accession No. AF 142780.2 "Mus musculus butyrophilin-like protein (Btdc) mRNA, complete cds," created Jun. 1, 1999, 2 pages.
EMBL-EBI Accession No. Q9WUL5, "Programmed cell death 1 ligand 2," Nov. 1, 1999, 5 pages.
Engh et al., "Accurate bond and angle parameters for X-ray protein structure refinement," Acta Cryst., A47(4):392-400, Jul. 1, 1991.
Ennis et al., "Effect of Novel Limited Spectrum MMP Inhibitor XL784 in Abdominal Aortic Aneurysms, " J. Cardiovasc. Pharmacol. Ther., 17(4):417-426, Dec. 2012.
Escudier et al., "Treatment Beyond Progression in Patients with Advanced Renal Cell Carcinoma Treated with Nivolumab in CheckMate 025," Eur Urol., 72(3):368-376, Apr. 12, 2017.
Falkner et al., "pUV I: a new vaccinia virus insertion and expression vector," Nucleic Acids Res., 15(17):7192, Sep. 11, 1987.
Fan et al., "HNS, a nuclear-cytoplasmic shuttling sequence in HuR," Proc. Natl. Acad. Sci. USA, 95(26):15293-15298, Dec. 1998.
Farley et al., "p38 mitogen-activated protein kinase mediates the Fas-induced mitochondrial death pathway in CD8+ T cells," Mol Cell Biol., 26(6):2118-2129, Mar. 2006.
Favre et al., "DOK4 and DOK5: new dok-related genes expressed in human T cells," Genes Immunity, Jan. 16, 2003, 4(1):40-45.
Fechteler et al., "Prediction of protein three-dimensional structures in insertion and deletion regions: a procedure for searching data bases of representative protein fragments using geometric scoring criteria," J Mol Biol., 253(1):114-131, Oct. 13, 1995.
Feng et al., "Identification of a PKB/Akt hydrophobic motif Ser-473 kinase as DNA-dependent protein kinase," J Biol Chem., 279(39):41189-41196, Jul. 15, 2004.
Ferrari et al., "Flow cytometric analysis of circulating dendritic cell subsets and intracellular cytokine production in advanced breast cancer patients," Oncol Rep., 14(1):113-120, Jul. 2005.
Figlin et al., "Treatment of metastatic renal cell carcinoma with nephrectomy, interleukin-2 and cytokine-primed or CD8(+) selected tumor infiltrating lymphocytes from primary tumor," J Urol., 158(3 Pt 1):740-745, Sep. 1997.
Finck et al., "Treatment of Murine Lupus with CTLA4lg," Science, 265(5176):1225-1227, Aug. 26, 1994.
Fire et al., "Potent and specific genetic interference by double-stranded RNA in Caenorhabditis elegans," Nature, 391(6669):806-811, Feb. 19, 1998.
Flaherty et al., "Phase III trial of carboplatin and paclitaxel with or without sorafenib in metastatic melanoma," J Clin Oncol., 31(3):373-379, Jan. 20, 2013.
Fleming et al., Selective expression of Ly-6G on myeloid lineage cells in mouse bone marrow. RB6-8C5 mAb to granulocyte-differentiation antigen (Gr-1) detects members of the Ly-6 family, J Immunol., 151(5):2399-2408, Sep. 1, 1993.
Foell et al., "CD137 costimulatory T cell receptor engagement reverses acute disease in lupus-prone NZB x NZW F1 mice," J Clin Invest., 111(10):1505-1518, May 2003.
Foell et al., "CD137-Mediated T Cell Co-Stimulation Terminates Existing Autoimmune Disease in SLE-Prone NZB/NZW F1 Mice," Ann N Y Acad Sci., 987:230-235, Apr. 2003.
Forsberg et al., "HER2 CAR-T Cells Eradicate Uveal Melanoma and T-cell Therapy-Resistant Human Melanoma in IL2 Transgenic NOD/SCID IL2 Receptor Knockout Mice," Cancer Research, Mar. 2019, 79(5):899-904.
Forsman et al., "Size Matters: Identification of Larger Size CD19 Positive Extracellular Vesicles in Chronic Lymphocytic Leukemia That Inhibit Chimeric Antigen Receptor T Cell Functions," Blood, Nov. 29, 2018, 132(S1):1865.
Fortugno et al., "Survivin exists in immunochemically distinct subcellular pools and is involved in spindle microtubule function," J Cell Sci., 115(Pt 3):575-585, Feb. 1, 2002.
Fraietta et al., "Author Correction: Determinants of response and resistance to CD19 chimeric antigen receptor (CAR) T cell therapy of chronic lymphocytic leukemia," Nat. Medicine, 27(3):561, Feb. 5, 2021.
Fraietta et al., "Determinants of response and resistance to CD19 chimeric antigen receptor (CAR) T cell therapy of chronic lymphocytic leukemia," Nat. Medicine, 24(5):563-571, Apr. 30, 2018.
Fraietta et al., "Disruption of TET2 promotes the therapeutic efficacy of CD19-targeted T cells," Nature, 558(7709):307-312, May 30, 2018.
Franciszkiewicz et al., "Role of chemokines and chemokine receptors in shaping the effector phase of the anti tumor immune response," Cancer Res., 72(24):6325-6332, Dec. 15, 2012.
Frank et al., "An outcome prediction model for patients with clear cell renal cell carcinoma treated with radical nephrectomy based on tumor stage, size, grade and necrosis: the SSIGN score," J Urol., 168(6):2395-2400, Dec. 2002.
Freeman et al., "B7, a new member of the Ig superfamily with unique expression on activated and neoplastic B cells," J Immunol., 143(8):2714-2722, Oct. 15, 1989.
Freeman et al., "Cloning of B7-2: a CTLA-4 counter-receptor that co stimulates human T cell proliferation," Science, 262(5135):909-911, Nov. 5, 1993.
Freeman et al., "Engagement of the PD-1 Immunolnhibitory receptor by a novel B7 family member leads to negative regulation of lymphocyte activation," J Exp Med., 192(7):1027-1034, Oct. 2, 2000.
Freeman et al., "Structure, expression, and T cell proliferation costimulatory activity of the murine homologue of the human B lymphocyte activation antigen B7," J Exp Med., 174(3):625-631, Sep. 1, 1991.
Friedlander et al., "miRDeep2 accurately identifies known and hundreds of novel microRNA genes in seven animal clades," Nucleic Acids Research, 40(1):37-52, Jan. 1, 2012.

(56) References Cited

OTHER PUBLICATIONS

Friedman et al., "Clinical Benefit of INCB7839, a Potent and Selective Inhibitor of ADAM10 and ADAM17, in Combination with Trastuzumab in Metastatic HER2 Positive Breast Cancer Patients," Cancer Res., 69(24 Suppl):Abstract5056, Dec. 2009.
Friedmann et al., "Interaction of the epidermal growth factor receptor and the DNA-dependent protein kinase pathway following gefitinib treatment," Mol Cancer Ther., 5(2):209-218, Feb. 2006.
Frigola et al., "Identification of a soluble form of B7-H 1 that retains immunosuppressive activity and is associated with aggressive renal cell carcinoma," Clin Cancer Res., 17(7):1915-1923, Apr. 2011.
Frigola et al., "Soluble B7-H1: Differences in production between dendritic cells and T cells," Immunol Lett., 142(1-2):78-82, Feb. 29, 2012.
Fry et al., "CD22-targeted Car T cells induce remission in B-ALL that is naive or resistant to CD19-targeted CAR immunotherapy," Nat. Medicine, Nov. 20, 2017, 24(1):20-28.
Fuerst et al., "Transfer of the inducible lac repressor/operator system from *Escherichia coli* to a vaccinia expression vector," Proc Natl Acad Sci USA., 86(8):2549-2553, Apr. 1989.
Fyfe et al., "Results of treatment of 255 patients with metastatic renal cell carcinoma who received high-dose recombinant interleukin-2 therapy," J Clin Oncol., 13(3):688-696, Mar. 1995.
Gai et al., "Extracellular vesicles in onco-nephrology," Exp. Mol. Medicine, 51:1-8, Mar. 15, 2019.
Gao et al., "CYSLTR1 promotes adenoid hypertrophy by activating ERK1/2," Exp. Ther. Medicine, Aug. 2018, 16(2):966-970.
Garon et al., "Pembrolizumab for the Treatment of Non-Small-Cell Lung Cancer," N Engl J Med., 372(21):2018-2028, May 21, 2015.
Gauthier et al., "Efficacy and Toxicity of CD19-Specific Chimeric Antigen Receptor T Cells Alone or in Combination with Ibrutinib for Relapsed and/or Refractory CLL," Biol. Blood Marrow Transplantation, 25(3S):S9-S10, Mar. 2019.
Geller et al., "Combination therapy with IL-15 superagonist (ALT-803) and PD-1 blockade enhances human NK cell immunotherapy against ovarian cancer," Gynecologic Oncology, 145(S1):19, Jun. 1, 2017.
GenBank Accession No. AAC51660 "apoptosis inhibitor survivin [*Homo sapiens*]," Sep. 2, 2004, 2 pages.
GenBank Accession No. AAH32229.1, "Axl receptor tyrosine kinase [*Homo sapiens*]," dated Jul. 15, 2006, 3 pages.
GenBank Accession No. AAP37283, "immune costimulatory protein B7-H4 [*Homo sapiens*]," Jun. 1, 2003, 1 page.
GenBank Accession No. AK001872.1,"*Homo sapiens* cDNA FLJ11010 fis, clone PLACE1003145," Feb. 22, 2000, 2 pages.
GenBank Accession No. AL162253, "Human DNA sequence from clone RP11-574F11 on chromosome 9 contains the gene for B7-H1 protein (PD-L1), the gene for programmed death ligand 2 (PDL2) (PDCD1L2) and a novel gene, complete sequence" Feb. 24, 2008, 35 pages.
GenBank Accession No. AY280972, "*Homo sapiens* immune costimulatory protein B7-H4 mRNA, complete cds," Jun. 1, 2003, 1 page.
GenBank Accession No. EAW57023.1, "AXL receptor tyrosine kinase, isoform CRA_b [*Homo sapiens*]," dated Mar. 23, 2015, 2 pages.
GenBank Accession No. M76125.1, "Human tyrosine kinase receptor (axl) mRNA, complete cds," dated Jan. 14, 1995, 2 pages.
GenBank Accession No. NM_001699.5, "*Homo sapiens* AXL receptor tyrosine kinase (AXL), transcript variant 2, mRNA," dated Oct. 6, 2016, 5 pages.
GenBank Accession No. NM_005191.3 (Gi No. 113722122), "*Homo sapiens* CD80 molecule (CD80), mRNA," Jun. 15, 2013, 5 pages.
GenBank Accession No. NP_000052.1, "tyrosine-protein kinase BTK isoform 1 [*Homo sapiens*]," dated Nov. 1, 2020, 4 pages.
GenBank Accession No. NP_005182.1 (Gi No. 4885123), "T-lymphocyte activation antigen CD80 precursor [*Homo sapiens*]," Jun. 15, 2013, 3 pages.
GenBank Accession No. U75285 "*Homo sapiens* apoptosis inhibitor survivin gene, complete cds," Sep. 2, 2004, 5 pages.
GenBank® Accession No. AAF25807 (GI No. 6708119), "B7-H1 [*Homo sapiens*]," Jan. 18, 2000, 2 pages.
GenBank® Accession No. AAH74740.1, GI No. 49902307, "Programmed cell death 1 [*Homo sapiens*]," Jul. 15, 2006, 2 pages.
GenBank® Accession No. AAX29153.1, GI No. 60652917, "integrin alpha L, partial [synthetic construct]," Mar. 29, 2005, 2 pages.
GenBank® Accession No. AF177937 (GI No. 6708118), "*Homo sapiens* B7-H1 mRNA, complete cds," Jan. 18, 2000, 1 page.
GenBank® Accession No. BC008777.2, GI No. 33870544, "*Homo sapiens* integrin, alpha L (antigen CD11A (p180), lymphocyte function-associated antigen 1; alpha polypeptide), mRNA (cDNA clone MGC:1714 IMAGE:3142951), complete cds," Jul. 28, 2005, 4 pages.
GenBank® Accession No. BC074740.2, GI No. 50960296, "*Homo sapiens* programmed cell death 1, mRNA (cDNA clone MGC:103817 IMAGE:30915198), complete cds," Jul. 15, 2006, 3 pages.
GenPept Accession No. Q9NZQ7.1, RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen-CD274; Flags: Precursor, Nov. 30, 2016, 5 pages.
Gérard et al., "Dok-4 is a novel negative regulator of T cell activation," J. Immunology, Jun. 2009, 182(12):7681-7689.
Gerdes et al. "Cell cycle analysis of a cell proliferation-associated human nuclear antigen defined by the monoclonal antibody Ki-67," J Immunol., 133(4):1710-1715, Oct. 1984.
Gerlach et al., "The Chemokine Receptor CX3CR1 Defines Three Antigen-Experienced CD8 T Cell Subsets with Distinct Roles in Immune Surveillance and Homeostasis," Immunity, 45(6):1270-1284, Dec. 20, 2016.
Gerstmayer et al., "Costimulation of T cell proliferation by a chimeric B7-2 antibody fusion protein specifically targeted to cells expressing the erbB2 proto-oncogene," J Immunol., 158(10):4584-4590, May 15, 1997.
Gerstmayer et al., "Costimulation of T-cell proliferation by a chimeric B7 antibody fusion protein," Cancer Immunol Immunother., 45(3-4):156-158, Nov./Dec. 1997.
Gevaert et al., "Protein identification based on matrix assisted laser desorption/ionization-post source decay-mass spectrometry," Electrophoresis, 22(9):1645-1651, May 2001.
Ghebeh et al., "Doxorubicin downregulates cell surface B7-H1 expression and upregulates its nuclear expression in breast cancer cells: role of B7-H1 as an anti-apoptotic molecule," Breast Cancer Res., 12(4):R48, Jul. 13, 2010.
Ghebeh et al., "The B7-H1 (PD-L1) T lymphocyte-inhibitory molecule is expressed in breast cancer patients with infiltrating ductal carcinoma: correlation with important high risk prognostic factors," Neoplasia, 8(3):190-198, Mar. 2006.
Ghiringhelli et al., "Metronomic cyclophosphamide regimen selectively depletes CD4+CD25+ regulatory T cells and restores T and NK effector functions in end stage cancer patients," Cancer Immunol Immunother., 56(5):641-648, May 2007.
Gibbons et al., "B7-H1 limits the entry of effector CD8(+) T cells to the memory pool by upregulating Bim," Oncoimmunology, 1(7):1061-1073, Oct. 1, 2012.
Gibbons Johnson et al., "Functional Expression of Programmed Death-Ligand 1 (B7-H1) by Immune Cells and Tumor Cells," Front Immunol, 8:961, Aug. 10, 2017, 9 pages.
Gilbert et al., "RNA Immunoprecipitation for Determining RNA-Protein Associations In Vivo," Curr. Protoc. Mol. Biology, Chapter 27, Unit 27.4, Aug. 2006, 11 pages.
Gill et al., "Preclinical targeting of human acute myeloid leukemia and myeloablation using chimeric antigen receptor-modified T cells," Blood, Apr. 10, 2014, 123(15):2343-2354.
Gillings et al., "Apoptosis and autophagy: BIM as a mediator of tumour cell death in response to oncogene-targeted therapeutics," FEBS J., 276(21):6050-6062, Sep. 29, 2009.
Gimmi et al., "B-cell surface antigen B7 provides a costimulatory signal that induces T cells to proliferate and secrete interleukin 2," Proc Natl Acad Sci USA., 88(9):3671-3675, May 1, 1991.
Gomes et al., "Analytical Considerations in Nanoscale Flow Cytometry of Extracellular Vesicles to Achieve Data Linearity," Thromb. Haemost., 118(9):1612-1624, Sep. 2018.

(56) References Cited

OTHER PUBLICATIONS

Gomes-Silva et al., "Tonic 4-1BB Costimulation in Chimeric Antigen Receptors Impedes T Cell Survival and Is Vector-Dependent," Cell Reports, 21(1):17-26, Oct. 3, 2017.
Goodwin et al., "Molecular cloning and expression of the type 1 and type 2 murine receptors for tumor necrosis factor," Mol Cell Biol., 11(6):3020-3026, Jun. 1991.
Goodwin et al., "Molecular cloning of a ligand for the inducible T cell gene 4-1BB: a member of an emerging family of cytokines with homology to tumor necrosis factor," Eur J Immunol., 23(10):2631-2641, Oct. 1993.
Gottesman et al., "Multidrug resistance in cancer: role of ATP-dependent transporters," Nat Rev Cancer, 2(1):48-58, Jan. 2002.
Grayson et al., "Cutting edge: increased expression of Bcl-2 in antigen-specific memory CD8+ T cells," J Immunol., 164(8):3950-3954, Apr. 15, 2000.
Green et al., "Activation-induced cell death in T cells," Immunol Rev., 193:70-81, Jun. 2003.
Green et al., "Antigen-specific human monoclonal antibodies from mice engineered with human Ig heavy and light chain YACs," Nat Genet., 7(1):13-21, May 1994.
Greenwald et al., "The B7 family revisited," Annu Rev Immunol., 23:515-548, 2005.
Griffiths-Jones et al., "miRBase: microRNA sequences, targets and gene nomenclature," Nucleic Acids Research, 34(suppl_1):D140-D144, Jan. 1, 2006.
Griffiths-Jones et al., "miRBase: tools for microRNA genomics," Nucleic Acids Research, 36(suppl 1):D154-D158, Jan. 1, 2008.
Griffiths-Jones, "The microRNA Registry," Nucleic Acids Research, 32(suppl 1):D109-D111, Jan. 1, 2004.
Grivennikov et al. "Immunity, inflammation, and cancer," Cell., 140(6):883-899, Mar. 19, 2010.
Gros et al., "PD-1 identifies the patient-specific CD8(+) tumor-reactive repertoire infiltrating human tumors," J Clin Invest., 124(5):2246-2259, May 2014.
Gros et al., "Prospective identification of neoantigen-specific lymphocytes in the peripheral blood of melanoma patients," Nat Med., 22(4):433-438, Apr. 2016.
Grupp et al., "Chimeric antigen receptor-modified T cells for acute lymphoid leukemia," N. Engl. J. Medicine, 368(16):1509-1518, Apr. 18, 2013.
Gu et al., "R gene expression induced by a type-III effector triggers disease resistance in rice," Nature, 435(7045):1122-1125, Jun. 23, 2005.
Guatelli et al., "Isothermal, in vitro amplification of nucleic acids by a multi enzyme reaction modeled after retroviral replication," Proc Natl Acad Sci USA., 87(5):1874-1878, Mar. 1990.
Guinn et al., "4-1BBL cooperates with B7-1 and B7-2 in converting a B cell lymphoma cell line into a long-lasting antitumor vaccine," J Immunol., 162(8):5003-5010, Apr. 15, 1999.
Gunn et al., "Correct end use during end joining of multiple chromosomal double strand breaks is influenced by repair protein RAD50, DNA-dependent protein kinase DNA-PKcs, and transcription context," J Biol Chem., 286(49):42470-42482, Oct. 24, 2011.
Guo et al., "A novel fusion protein of IP1 O-scFv retains antibody specificity and chemokine function," Biochem Biophys Res Commun., 320(2):506-513, Jul. 23, 2004.
Guo et al., "Axl Inhibition Induces the Antitumor Immune Response Which Can Be Further Potentiated by PD-1 Blockade in The Mouse Cancer Models," Oncotarget, Sep. 21, 2017, 8(52):89761-8977.
Guo et al., "Directed evolution of an enhanced and highly efficient FokI cleavage domain for zinc finger nucleases," J Mol. Biology, Jul. 2, 2010, 400(1):96-107.
Haas et al., "Phase I Study of Lentiviral-Transduced Chimeric Antigen Receptor-Modified T Cells Recognizing Mesothelin in Advanced Solid Cancers," Mol. Therapy, Nov. 6, 2019, 27(11):1919-1929.
Haendeler et al., "Nitric Oxide and Apoptosis," Vitam Horm., 57:49-77, 1999.
Hamanishi et al., "PD-1/PD-L1 blockade in cancer treatment: perspectives and issues," Int. J. Clin. Oncology, 21(3):462-473, Jun. 2016.
Hamid et al., "Safety and Tumor Responses with Lambrolizumab (Anti-PD-1) in Melanoma," N Engl J Med., 369(2):134-144, Jul. 11, 2013.
Hansen et al., "Monoclonal antibodies identifying a novel T-cell antigen and Ia antigens of human lymphocytes," Immunogenetics, 10(1-4):247-260, Feb. 1, 1980.
Hardenberg et al., "A Yin and Yang in Epithelial Immunology: The Roles of the αE(CD103)B7 Integrin in T Cells," J. Invest. Dermatology, Jan. 2018, 138(1):23-31.
Harlow and Lane., "Antibodies: A Laboratory Manual," Cold Spring Harbor Laboratory Press, Cold Spring Harbor, NY, pp. 553, 555-582, 584-589, 591-612, 1988.
Harrington et al., "Differentiating between memory and effector CD8 T cells by altered expression of cell surface O-glycans," J Exp Med., 191(7):1241-1246, Apr. 3, 2000.
Hatzoglou et al., "Hepatic gene transfer in animals using retroviruses containing the promoter from the gene for phosphoenolpyruvate carboxykinase" J Biol Chem., 265(28):17285-17293, Oct. 5, 1990.
Haugland et al., "Unit 16.5 antibody conjugates for cell biology," Current Protocols in Cell Biology, 6:16.5:16.5-16.5.22, May 1, 2001.
Hawiger et al., "Dendritic cells induce peripheral T cell unresponsiveness under steady state conditions in vivo," J Exp Med., 194(6):769-779, Sep. 17, 2001.
Hayakawa et al., "Inhibition of BAD phosphorylation either at serine 112 via extracellular signal-regulated protein kinase cascade or at serine 136 via Akt cascade sensitizes human ovarian cancer cells to cisplatin," Cancer Res., 60(21):5988-5994, Nov. 1, 2000.
He et al., "Development of PD-1/PD-L1 Pathway in Tumor Immune Microenvironment and Treatment for Non-Small Cell Lung Cancer," Sci. Reports, 5:13110, Aug. 17, 2015, 9 pages.
He et al., "Identification of a novel splice variant of human PD-L1 mRNA encoding an isoform-lacking Igv-like domain," Acta. Pharmacol. Sin., 26(4):462-468, Apr. 2005.
Heinz et al., "Simple Combinations of Lineage-Determining Transcription Factors Prime cis-Regulatory Elements Required for Macrophage and B Cell Identities," Mol. Cell, 38(4):576-589, May 28, 2010.
Hellstrom et al., "T cell immunity to tumor antigens," Crit Rev Immunol., 18(1-2):1-6, 1998.
Henry et al., "Cloning, structural analysis, and mapping of the B30 and B7 multigenic families to the major histocompatibility complex (MHC) and other chromosomal regions," Immunogenetics, 46(5):383-395, 1997.
Henry et al., "Structure and evolution of the extended B7 family," Immunol Today, 20(6):285-288, Jun. 1999.
Hentikoff, "Amino acid substitution matrices from protein blocks," Proc Natl Acad Sci USA., 89(22):10915-10919, Nov. 15, 1992.
Her et al., "Increased expression of soluble inducible costimulator ligand (ICOSL) in patients with systemic lupus erythematosus," Lupus, 18(6):501-507, May 2009.
Herold et al., "Impact of conditional deletion of the pro-apoptotic BCL-2 family member BIM in mice," Cell Death Dis., 5(10):e1446, Oct. 9, 2014, 7 pages.
Hestdal et al., "Characterization and regulation of RB6-8C5 antigen expression on murine bone marrow cells," J Immunol., 147(1):22-28, Jul. 1, 1991.
Hidalgo et al., "The transcriptome of human cytotoxic T cells: similarities and disparities among allostimulated CD4( +) CTL, CD8( +) CTL and NK cells," Am J Transplant., 8(3):627-636, Mar. 2008.
Hildeman et al., "Activated T cell death in vivo mediated by proapoptotic bcl-2 family member bim," Immunity, 16(6):759-767, Jun. 2002.
Hirano et al., "Blockade of B7-H1 and PD-1 by monoclonal antibodies potentiates cancer therapeutic immunity," Cancer Res., 65(3):1089-1096, Feb. 1, 2005.

(56) References Cited

OTHER PUBLICATIONS

Hiroishi et al., "Interferon-alpha gene therapy in combination with CDSO transduction reduces tumorigenicity and growth of established tumor in poorly immunogenic tumor models," Gene Ther., 6(12):1988-1994, Dec. 1999.
Hochman et al., "An active antibody fragment (Fv) composed of the variable portions of heavy and light chains," Biochemistry, 12(6):1130-1135, Mar. 13, 1973.
Hock et al., "Retrovirus-mediated transfer and expression of drug resistance genes in human haematopoietic progenitor cells," Nature, 320:275-277, 1986.
Hodi et al., "Evaluation of Immune-Related Response Criteria and RECIST v1.1 in Patients With Advanced Melanoma Treated With Pembrolizumab," J Clin Oncol., 34(13):1510-1517, May 1, 2016.
Hoeijmakers, "Genome maintenance mechanisms for preventing cancer," Nature, 411(6835):366-374, May 17, 2011.
Hoffman, "T Cells in the Pathogenesis of Systemic Lupus Erythematosus," Front Biosci., 6:D1369-D1378, Oct. 1, 2001.
Hoffmann et al., "Only the CD45RA+ subpopulation of CD4+ CD25high T cells gives rise to homogeneous regulatory T-cell lines upon in vitro expansion," Blood, Dec. 15, 2006, 108(13):4260-4267.
Hoiseth et al., "Aromatic-dependent Salmonella typhimurium are non-virulent and effective as live vaccines," Nature, 291(5812):238-239, May 21, 1981.
Hollinger et al., "Diabodies": small bivalent and bispecific antibody fragments, Proc Natl Acad Sci USA., 90(14):6444-6448, Jul. 15, 1993.
Holt et al., "Domain antibodies: proteins for therapy," Trends Biotechnol., 21(11):484-490, Nov. 2003.
Hoos et al., "CCR 20th Anniversary Commentary: Immune-Related Response Criteria—Capturing Clinical Activity in Immuno-Oncology," Clin Cancer Res., 21(22):4989-4991, Nov. 2015.
Hori et al., "B7-H1-induced apoptosis as a mechanism of immune privilege of corneal allografts," J Immunol., 177(9):5928-5935, Nov. 1, 2006.
Hou et al., "Correlation between infiltration of FOXP3+ regulatory T cells and expression of B7-H1 in the tumor tissues of gastric cancer," Exp. Mot. Pathol., 96(3):284-291, Jun. 2014.
Houseley et al., "The many pathways of RNA degradation," Cell, 136(4):763-776, Feb. 20, 2009.
Hua et al., "B7-H1 expression is associated with expansion of regulatory T cells in colorectal carcinoma," World J. Gastroenterol., 18(9):971-978, Mar. 2012.
Huai et al., "Inducible gene expression with the Tet-on system in CD4+ T cells and thymocytes of mice," Genesis, 45(7):427-431, Jul. 2007.
Huang et al., "CDK2-Dependent Phosphorylation of FOXO1 as an Apoptotic Response to DNA Damage," Science, 314(5797):294-297, Oct. 13, 2006.
Huang et al., "Fragile Histidine Triad (FHIT) Suppresses Proliferation and Promotes Apoptosis in Cholangiocarcinoma Cells by Blocking PI3K-Akt Pathway," Scientific World Journal, Mar. 16, 2014, 2014:179698, 8 pages.
Huang et al., "T-cell invigoration to tumour burden ratio associated with anti-PD-1 response," Nature, 545(7652):60-65, Apr. 10, 2017.
Huang et al., "The liver eliminates T cells undergoing antigen-triggered apoptosis in vivo," Immunity, 1(9):741-749, Dec. 31, 1994.
Huang, "Structural chemistry and therapeutic intervention of protein-protein interactions in immune response, human immunodeficiency virus entry, and apoptosis," Pharmacol Ther., 86(3):201-215, Jun. 2000.
Hubbard et al., "Anti-neutrophil-elastase defenses of the lower respiratory tract in alpha 1-antitrypsin deficiency directly augmented with an aerosol of alpha I-antitrypsin," Ann Intern Med., 111(3):206-212, Aug. 1, 1989.
Hui et al., "T cell costimulatory receptor CD28 is a primary target for PD-1-mediated inhibition," Science, 355(6332):1428-1433, Mar. 9, 2017.
Hunter, "Diabetes in pregnancy," Effective Care in Pregnancy and Childbirth, Chalmers et al. (eds.), Oxford University Press, 1:578-593, 1989.
Huse et al., "Generation of a large combinatorial library of the immunoglobulin repertoire in phage lambda," Science, 246(4935):1275-1281, Dec. 8, 1989.
Huston et al., "Protein engineering of antibody binding sites: recovery of specific activity in an anti-digoxin single-chain Fv analogue produced in *Escherichia coli*," Proc Natl Acad Sci USA., 85(16):5879-5883, Aug. 1988.
Hutloff et al., "ICOS is an inducible T-cell co-stimulator structurally and functionally related to CD28," Nature, 397(6716):263-266, Jan. 21, 1999.
Hwang et al., "Efficient genome editing in zebrafish using a CRISPR-Cas system," Nat. Biotechnology, 31(3):227-229, Jan. 29, 2013.
Hyrup et al., "Peptide nucleic acids (PNA): synthesis, properties and potential applications," Bioorg Med Chem., 4(1):5-23, Jan. 31, 1996.
Ice et al., "AB0143: Immunomodulation followed by quantitative transcriptional profiling to characterize the functional role of the sjÖgren's-associated ncrna ac092580.4," Ann Rheum Dis., 76(S2):1096, Jun. 15, 2017.
Ichikawa and Chen, "Role of B7-H1 and B7-H4 molecules in down-regulating effector phase of T-cell immunity: novel cancer escaping mechanisms," Front Biosci., 10:2856-2860, Sep. 1, 2005.
Ikemizu et al., "Structure and dimerization of a soluble form of B7-1," Immunity, 12(1):51-60, Jan. 2000.
Ikonomidis, "Delivery of a viral antigen to the class I processing and presentation pathway by Listeria monocytogenes," J Exp Med., 180(6):2209-2218, Dec. 1, 1994.
Imai et al., "Identification and molecular characterization of fractalkine receptor CX3CR1, which mediates both leukocyte migration and adhesion," Cell, 91(4):521-530, Nov. 14, 1997.
Infante et al., "A multicenter phase Ib study of the safety, pharmacokinetics, biological activity and clinical efficacy of INCB7839, a potent and selective inhibitor of ADAM10 and ADAM17," Breast Cancer Res. Treat., 106(1):S269, 6064, Dec. 2007.
Inman et al. "PD-L1 (B7-H1) expression by urothelial carcinoma of the bladder and BCG-induced granulomata: associations with localized stage progression," Cancer, 109(8):1499-1505, Apr. 15, 2007.
Inman et al., "Questionable relevance of gamma delta T lymphocytes in renal cell carcinoma," J Immunol., 180(5):3578-3584, Mar. 1, 2008.
Ishida et al., "Differential expression of PD-L1 and PD-L2, ligands for an inhibitory receptor PD-1, in the cells of lymphohematopoietic tissues," Immunol Lett., 84(1):57-62, Oct. 21, 2002.
Ishida et al., "Induced expression of PD-1, a novel member of the immunoglobulin gene superfamily, upon programmed cell death," EMBO J., 11(11):3887-3895, Nov. 1992.
Iwai et al., "Involvement of PD-L1 on tumor cells in the escape from host immune system and tumor immunotherapy by PD-L1 blockade," Proc Natl Acad Sci USA., 99(19):12293-12297, Sep. 6, 2002.
Iwai et al., "PD-1 inhibits antiviral immunity at the effector phase in the liver," J Exp Med., 198(1):39-50, Jul. 7, 2003.
Jacinto et al., "SIN1/MIP1 maintains rictor-mTOR complex integrity and regulates Akt phosphorylation and substrate specificity," Cell, 127(1):125-137, Sep. 7, 2006.
Jacobs et al., "Regulatory T cells in melanoma: the final hurdle towards effective immunotherapy?," Lancet Oncol., 13(1):e32-42, Jan. 2012.
Jacobsohn et al., "Acute graft versus host disease," Orphanet. J. Rare Diseases, Sep. 4, 2007, 2:35, 9 pages.
Jacobson et al., "Unique site of IgG2a and rheumatoid factor production in MRL/lpr mice," Immunol Rev., 156:103-110, Apr. 1997.
Jacquelot et al., "Predictors of responses to immune checkpoint blockade in advanced melanoma," Nat. Commun., 8(1):592, Sep. 19, 2017.
Jamaly et al., "Impact of preanalytical conditions on plasma concentration and size distribution of extracellular vesicles using Nanoparticle Tracking Analysis," Sci. Reports, 8:17216, Nov. 21, 2018, 11 pages.

(56) References Cited

OTHER PUBLICATIONS

Janeway et al. "Immunobiology: the Immune System in Health and Disease," Elsevier Science., 4:36, 1999.
Jayaraman, "Flow cytometric determination of mitochondrial membrane potential changes during apoptosis of T lymphocytic and pancreatic beta cell lines: comparison of tetramethylrhodamineethylester (TMRE), chloromethyl-X-rosamine (H2-CMX-Ros) and MitoTracker Red 580 (MTR580)," J Immunol Methods., 306(1-2):68-79, Sep. 29, 2005.
Jeannin et al., "Soluble CD86 is a costimulatory molecule for human T lymphocytes," Immunity, 13(3):303-312, Sep. 2000.
Jemal et al., "Cancer Statistics, 2005," CA Cancer J Clin, 55(1):10-30, January/Feb. 2005.
Jerne, "Towards a network theory of the immune system," Ann Immunol (Paris)., 125C(1-2):373-389, Jan. 1974.
Jiang et al., "Genome-wide association study for biomarker identification of Rapamycin and Everolimus using a lymphoblastoid cell line system," Front Genet., 4:166, Aug. 30, 2013.
Jiang et al., "RNA-guided editing of bacterial genomes using CRISPR-Cas systems," Nat. Biotechnology, 31(3):233-239, Jan. 29, 2013.
Jiang et al., "Selective Targeting of Glioblastoma with EGFRvIII/EGFR Bitargeted Chimeric Antigen Receptor T Cell," Cancer Immunol. Research, Nov. 2018, 6(11):1314-1326.
Jinek et al., "A programmable dual-RNA-guided DNA endonuclease in adaptive bacterial immunity," Science, 337(6096):816-821, Jun. 28, 2012.
Johnsen et al., "What is the blood concentration of extracellular vesicles? Implications for the use of extracellular vesicles as blood-borne biomarkers of cancer," Biochim. Biophys. Acta. Rev. Cancer, 1871(1):109-116, Jan. 2019.
Johnson et al., "Combinatorial therapy with an IL-15 superagonist (ALT-803) and anti-PD-L1 mAb augment T cell mediated anti-tumor immunity in mice," J. Immunother. Cancer, 2(Suppl. 3):P234, Nov. 6, 2014.
Johnson et al., "Fulminant Myocarditis with Combination Immune Checkpoint Blockade," N. Engl. J. Med., 375(18):1749-1755, Nov. 2016.
Johnston et al., "Biolistic transformation of animal tissue," In Vitro Cell Dev Biol Anim., 27P:11-14, 1991.
Jones et al., "Replacing the complementarity-determining regions in a human antibody with those from a mouse," Nature, 321(6069):522-525, May 29-Jun. 4, 1986.
June et al., "CAR T cell immunotherapy for human cancer," Science, 359(6382):1361-1365, Mar. 23, 2018.
June et al., "Chimeric Antigen Receptor Therapy," N. Engl. J. Medicine, 379(1):64-73, Jul. 5, 2018.
Juvet et al., "Phosphodiesterase 3b Inhibition Expands Stable Regulatory T Cells for Cell Therapy in Transplantation," J. Heart Lung Transplantation, Apr. 2015, 34(4):S147.
Kabat et al., "Sequences of Proteins of Immunological Interest, Fifth Edition," U.S. Department of Health and Human Services, NIH Publication No. 91-3242, Table of Contents, 20 pages, 1991.
Kaech et al., "Transcriptional control of effector and memory CD8+ T cell differentiation," Nat Rev Immunol., 12(11):749-761, Nov. 2012.
Kalafatovic et al., "Cell-Penetrating Peptides: Design Strategies beyond Primary Structure and Amphipathicity," Molecules, 22(11):1929, Nov. 8, 2017, 38 pages.
Kaleko et al., "Persistent gene expression after retroviral gene transfer into liver cells in vivo," Hum Gene Ther., 2(1):27-32, 1991.
Kaliyaperumal et al., "Antigen-specific therapy of murine lupus nephritis using nucleosomal peptides: tolerance spreading impairs pathogenic function of autoimmune T and B cells," J Immunol., 162(10):5775-5783, May 15, 1999.
Kalled et al., "Anti-CD40 ligand antibody treatment of SNF1 mice with established nephritis: preservation of kidney function," J Immunol., 160(5):2158-2165, Mar. 1, 1998.
Kalos et al., "T cells with chimeric antigen receptors have potent antitumor effects and can establish memory in patients with advanced leukemia," Sci. Transl. Medicine, 3(95):95ra73, Aug. 10, 2011, 11 pages.
Kamphorst et al., "Proliferation of PD-1+ CD8 T cells in peripheral blood after PD-1-targeted therapy in lung cancer patients," Proc Natl Acad Sci USA., 114(19):4993-4998, May 9, 2017.
Kamphorst et al., "Rescue of exhausted CD8 T cells by PD-1-targeted therapies is CD28-dependent," Science, 355(6332):1423-1427, Mar. 31, 2017.
Kanai et al., "Blockade of B7-H1 suppresses the development of chronic intestinal inflammation," J Immunol., 171(8):4156-4163, Oct. 15, 2003.
Kaneko et al., "Augmentation of Va14 NKT cell-mediated cytotoxicity by interleukin 4 in an autocrine mechanism resulting in the development of concanavalin A-induced hepatitis," J Exp Med., 191(1):105-114, Jan. 3, 2000.
Kang et al., "Current clinical trials testing the combination of immunotherapy with radiotherapy," J. Immunother. Cancer, 4:51, Sep. 20, 2016, 20 pages.
Kantarjian et al., "Inotuzumab Ozogamicin versus Standard Therapy for Acute Lymphoblastic Leukemia," N. Engl. J. Medicine, Aug. 25, 2016, 375(8):740-753.
Karakhanova et al., "ERK/p38 MAP-kinases and PI3K are involved in the differential regulation of B7-H1 expression in DC subsets," Eur J Immunol., 40(1):254-266, Jan. 2010.
Kataoka et al., "Flow cytometric analysis of phosphorylated histone H2AX following exposure to ionizing radiation in human microvascular endothelial cells," J Radiat Res., 47(3-4):245-257, Sep. 2006.
Katou et al., "Differing phenotypes between intraepithelial and stromal lymphocytes in early-stage tongue cancer," Cancer Res., 67(23):11195-11201, Dec. 1, 2007.
Katz et al., "Phase I Hepatic Immunotherapy for Metastases Study of Intra-Arterial Chimeric Antigen Receptor-Modified T-cell Therapy for CEA+ Liver Metastases," Clin. Cancer Research, Jul. 2015, 21(14):3149-3159.
Kaufman et al., "A phase I trial of intra lesional RV-B7.1 vaccine in the treatment of malignant melanoma," Hum Gene Ther., 11(7):1065-1082, May 1, 2000.
Kawabe et al., "Programmed cell death and extrathymic reduction of Vβ8+ CD4+ T cells in mice tolerant to *Staphylococcus aureus* enterotoxin B," Nature, 349(6306):245-248, Jan. 17, 1991.
Kawalekar et al., "Distinct Signaling of Coreceptors Regulates Specific Metabolism Pathways and Impacts Memory Development in CAR T Cells," Immunity, 44(2):380-390, Feb. 16, 2016.
Kay et al., "A bacterial effector acts as a plant transcription factor and induces a cell size regulator," Science, 318(5850):648-651, Oct. 26, 2007.
Kee et al., "Antitumor immune activity by chemokine CX3CL1 in an orthotopic implantation of lung cancer model in vivo," Mol Clin Oncol., 1(1):35-40, Jan. 2013.
Keir et al., "PD-1 and its ligands in tolerance and immunity," Annu Rev Immunol., 26:677-704, 2008.
Kelley et al., "Cytokines in the Pathogenesis of Systemic Lupus Erythematosus," Semin Nephrol., 19(1):57-66, Jan. 1999.
Kellner et al., "The Fc-engineered CD19 antibody MOR208 (XmAb5574) induces natural killer cell-mediated lysis of acute lymphoblastic leukemia cells from pediatric and adult patients," Leukemia, Jan. 1, 2013, 27(7): 1595-1598.
Kemp et al., "Lck Mediates Th2 Differentiation through Effects on T-bet and GATA-3," J. Immunology, Apr. 15, 2010, 184(8):4178-4184.
Kenderian et al., "CD33-specific chimeric antigen receptor T cells exhibit potent preclinical activity against human acute myeloid leukemia," Leukemia, Feb. 27, 2015, 29(8):1637-1647.
Kenderian et al., "Chimeric antigen receptor T-cell therapy to target hematologic malignancies," Cancer Research, 74(22):6383-6389, Nov. 4, 2014.
Kenderian et al., "Identification of PD1 and TIM3 As Checkpoints That Limit Chimeric Antigen Receptor T Cell Efficacy in Leukemia," Blood, Dec. 3, 2015, 126(23):852.
Kenderian et al., "Leukemia Stem Cells Are Characterized by CLEC12A Expression and Chemotherapy Refractoriness That Can

(56) References Cited

OTHER PUBLICATIONS be Overcome by Targeting with Chimeric Antigen Receptor T Cells," Blood, Dec. 2, 2016, 128(22):766.
Kenderian et al., "Ruxolitinib Prevents Cytokine Release Syndrome after CART Cell Therapy without Impairing the Anti-Tumor Effect in a Xenograft Model," Blood, Dec. 2, 2016, 128(22):652.
Kennerdell et al., "Use of dsRNA-mediated genetic interference to demonstrate that frizzled and frizzled 2 act in the wingless pathway," Cell, 95(7):1017-1026, Dec. 23, 1998.
Kharbanda et al., "Translocation of SAPK/JNK to mitochondria and interaction with Bcl-x(L) in response to DNA damage," J Biol Chem., 275(1):322-327, Jan. 7, 2000.
Kiessling et al., "High-throughput mutation profiling of CTCL samples reveals KRAS and NRAS mutations sensitizing tumors toward inhibition of the RAS/RAF/MEK signaling cascade," Blood, 117(8):2433-2440, Jan. 5, 2011.
Kim et al., "Fas ligand-positive membranous vesicles isolated from sera of patients with oral cancer induce apoptosis of activated T lymphocytes," Clin. Cancer Research, 11(3):1010-1020, Feb. 1, 2005.
Kim et al., "Features of responding T cells in cancer and chronic infection," Curr Opin Immunol., 22(2):223-230, Mar. 6, 2010.
Kim et al., "Hybrid restriction enzymes: zinc finger fusions to Fok I cleavage domain," Proc. Natl. Acad Sci. USA, 93(3):1156-1160, Feb. 6, 1996.
Kim et al., "Therapeutic potential of 4-1BB (CD137) as a regulator for effector CD8(+) T cells," J Hematother Stem Cell Res., 10(4):441-449, Aug. 2001.
Kim et al., "TNFR2-deficient memory CD8 T cells provide superior protection against tumor cell growth," J. Immunology, Nov. 15, 2009, 183(10):6051-6057.
Kim et al., "TopHat2: accurate alignment of transcriptomes in the presence of insertions, deletions and gene fusions," Genome Biology, 14:R36, Apr. 25, 2013, 13 pages.
Klimka et al., "Human anti-CD30 recombinant antibodies by guided phage antibody selection using cell panning," Brit. J. Can., 83(2):252-260, Jul. 2000.
Köhler et al., "Continuous cultures of fused cells secreting antibody of predefined specificity," Nature, 256(5517):495-497, Aug. 7, 1975.
Kohn et al. "Gene therapy for genetic diseases," Cancer Invest., 7(2):179-192, 1989.
Konem et al., "IL-12 secreting tumor-targeted chimeric antigen receptor T cells eradicate ovarian tumors in vivo," Oncoimmunology, Jan. 23, 2015, 4(3):e994446, 11 pages.
Koneru et al., "IL-12 secreting tumor-targeted chimeric antigen receptor T cells eradicate ovarian tumors in vivo," Oncoimmunology, Jan. 23, 2015, 4(3):e994446, 11 pages.
Kong et al., "Suppression of Human Glioma Xenografts with Second-Generation IL 13R-Specific Chimeric Antigen Receptor-Modified T Cells," Clin. Cancer Research, Nov. 2012, 18(21):5949-5960.
Konieczny et al., "The combination of IgM subunits and proteolytic IgG fragment by controlled formation of interchain disulphides," Haematologia (Budap)., 14(1):95-99, 1981.
Korkola et al., "Gene expression-based classification of nonseminomatous male germ cell tumors," Oncogene, 24(32):5101-5107, Jul. 28, 2005.
Kosari et al., "Clear cell renal cell carcinoma: gene expression analyses identify a potential signature for tumor aggressiveness," Clin Cancer Res., 11(14):5128-5139, Jul. 15, 2005.
Kozbor et al. "The production of monoclonal antibodies from human lymphocytes," Immunology Today, 4(3):72-79, Mar. 1, 1983.
Kozomara et al., "miRBase: annotating high confidence microRNAs using deep sequencing data," Nucleic Acids Research, 42(D1):D68-D73, Jan. 1, 2014.
Kozomara et al., "miRBase: from microRNA sequences to function," Nucleic Acids Research, 47(D1):D155-D162, Jan. 8, 2019.
Kozomara et al., "miRBase: integrating microRNA annotation and deepsequencing data," Nucleic Acids Research, 39(suppl_1):D152-D157, Jan. 1, 2011.
Kramer et al., "Causal analysis approaches in Ingenuity Pathway Analysis," Bioinformatics, 30(4):523-530, Feb. 15, 2014.
Kreitman et al., "Moxetumomab pasudotox in relapsed/refractory hairy cell leukemia," Leukemia, Jul. 20, 2018, 32(8):1768-1777.
Krempski et al., "Tumor-infiltrating programmed death receptor-1+ dendritic cells mediate immune suppression in ovarian cancer," J Immunol., 186(12):6905-6913, May 6, 2011.
Krieg et al., "High-dimensional single-cell analysis predicts response to anti-PD-1 immunotherapy," Nat Med., 24:144-153, Jan. 8, 2018.
Kruege et al., "The role of CD95 in the regulation of peripheral T-cell apoptosis," Immunol Rev., 193:58-69, Jun. 2003.
Krummel et al., "CTLA-4 engagement inhibits IL-2 accumulation and cell cycle progression upon activation of resting T cells," J Exp Med., 183(6):2533-2540, Jun. 1, 1996.
Kuiper et al., "B7.1 and Cytokines: Synergy in cancer gene therapy," Adv Exp Med Biol., 465:381-390, 2000.
Kulakovskiy et al., "HOCOMOCO: a comprehensive collection of human transcription factor binding sites models," Nucl. Acids Research, 41(Database issue):D195-D202, Jan. 2013.
Kurtulus et al., "Bcl-2 allows effector and memory CD8+ T cells to tolerate higher expression of Bim," J Immunol., 186(10):5729-5737, May 15, 2011.
Kusmartsev et al., "Gr-1+ myeloid cells derived from tumor-bearing mice inhibit primary T cell activation induced through CD3/CD28 costimulation," J Immunol., 165(2):779-785, Jul. 15, 2000.
Kwon et al., "4-1BB: Still in the Midst of Darkness," Mol Cells., 10(2):119-126, Apr. 30, 2000.
Labaer, "So, you want to look for biomarkers (introduction to the special biomarkers issue)," J Proteome Res., 4(4):1053-1059, Jul./Aug. 2005.
Langer et al., "Carboplatin and pemetrexed with or without pembrolizumab for advanced, non-squamous non-small-cell lung cancer: a randomised, phase 2 cohort of the open-label KEYNOTE-021 study," Lancet Oncol., 17(11):1497-1508, Nov. 2016.
Larkin et al., "Combined Nivolumab and Ipilimumab or Monotherapy in Untreated Melanoma," N Engl J Med., 373(1):23-34, Jul. 2, 2015.
Larrubia et al., "Bim-mediated apoptosis and PD-1/PD-L1 pathway impair reactivity of PD1(+)/CD127(-) HCV-specific CD8(+) cells targeting the virus in chronic hepatitis C virus infection," Cell Immunol., 269(2):104-114, Mar. 17, 2011.
Latchman et al., "PD-L2 is a second ligand for PD-1 and inhibits T cell activation," Nat Immunol., 2(3):261-268, Mar. 2001.
Lau et al., "Exacerbation of myasthenia gravis in a patient with melanoma treated with pembrolizumab," Muscle Nerve, 54(1):157-161, Jun. 2016.
Laurenzana et al., "Extracellular Vesicles: A New Prospective in Crosstalk between Microenvironment and Stem Cells in Hematological Malignancies," Stem Cells International, May 27, 2018, 2018:9863194, 11 pages.
Lawson et al., "Treatment of murine lupus with cDNA encoding IFN-gammaR/Fc," J Clin Invest., 106(2):207-215, Jul. 2000.
Lazarevic and Glimcher, "T-bet in disease," Nat Immunol., 12(7):597-606, Jun. 20, 2011.
Lee et al., "Survivin expression and its clinical significance in pancreatic cancer," BMC Cancer, 5:127, Oct. 4, 2005.
Lee et al., "Increased vaccine-specific T cell frequency after peptide-based vaccination correlates with increased susceptibility to in vitro stimulation but does not lead to tumor regression," J Immunol., 163(11):6292-6300, Dec. 1, 1999.
Lee et al., "Preclinical Optimization of a CD20-specific Chimeric Antigen Receptor Vector and Culture Conditions," J. Immunotherapy, Jan. 2018, 41(1):19-31.
Leggett et al., "Sequencing quality assessment tools to enable data-driven informatics for high throughput genomics," Front. Genetics, 4:288, Dec. 2013, 5 pages.
Leibovich et al., "Prediction of progression after radical nephrectomy for patients with clear cell renal cell carcinoma: a stratification tool for prospective clinical trials," Cancer, 97(7):1663-1671, Apr. 1, 2003.

(56) References Cited

OTHER PUBLICATIONS

Lenardo et al., "Mature T lymphocyte apoptosis—immune regulation in a dynamic and unpredictable antigenic environment," Annu Rev Immunol., 17:221-253, 1999.
Lenschow et al., "CD28/B7 system of T cell costimulation," Annu Rev Immunol., 14:233-258, 1996.
Leuci et al., "CD44v6 as innovative sarcoma target for CAR-redirected CIK cells," Oncoimmnunology, Feb. 15, 2018, 7(5):e1423167, 10 pages.
Levitt, "Accurate modeling of protein conformation by automatic segment matching," J Mol Biol., 226(2):507-533, Jul. 20, 1992.
Lewinski et al., "Retroviral DNA integration: viral and cellular determinants of target-site selection," PLoS Pathog., 2(6):e60, Jun. 23, 2006.
Lewis et al., "Conserved seed pairing, often flanked by adenosines, indicates that thousands of human genes are microRNA targets," Cell, 120(1):15-20, Jan. 14, 2005.
Lewis et al., "Surrogate tumor antigen vaccination induces tumor-specific immunity and the rejection of spontaneous metastases," Cancer Res., 65(7):2938-2946, Apr. 1, 2005.
Lewis, "PCR's Competitors Are Alive and Well and Moving Rapidly Towards Commercialization," Genetic Engineering News, vol. 12, 3 pages, 1992.
Ley et al., "Regulatory phosphorylation of Bim: sorting out the ERK from the JNK," Cell Death Differ., 12(8):1008-1014, Aug. 2005.
Li et al., "Anti-programmed death-1 synergizes with granulocyte macrophage colony- stimulating factor—secreting tumor cell immunotherapy providing therapeutic benefit to mice with established tumors," Clin Cancer Res., 15(5):1623-1634, Feb. 10, 2009.
Li et al., "Gemcitabine and arabinosylcytosin pharmacogenomics: genome-wide association and drug response biomarkers," PLoS One., 4(11):e7765, Nov. 9, 2009.
Li et al., "The emerging roles and therapeutic potential of exosomes in epithelial ovarian cancer," Mol. Cancer, 16:92, May 15, 2017, 10 pages.
Liang et al., "Autoantibody responses and pathology regulated by B7-1 and B7-2 costimulation in MRL/lpr lupus," J Immunol., 165(6):3436-3443, Sep. 15, 2000.
Liao et al., "featureCounts: an efficient general purpose program for assigning sequence reads to genomic features," Bioinformatics, 30(7):923-930, Apr. 2014.
Lim et al., "The Principles of Engineering Immune Cells to Treat Cancer," Cell, 168, 168(4):724-740, Feb. 9, 2017.
Lin et al., "The PD-1/PD-L1 complex resembles the antigen-binding Fv domains of antibodies and T cell receptors," Proc Natl Acad Sci USA., 105(8):3011-3016, Feb. 26, 2008.
Linsley et al., "Binding of the B cell activation antigen B7 to CD28 costimulates T cell proliferation and interleukin 2 mRNA accumulation" J Exp Med., 173(3):721-730, Mar. 1, 1991.
Linsley et al., "Extending the B7 (CD80) gene family," Protein Sci., 3(8):1341-1343, Aug. 1994.
Linsley et al., "T-cell antigen CD28 mediates adhesion with B cells by interacting with activation antigen 87188-1," Proc Natl Acad Sci USA., 87(13):5031-5035, Jul. 1990.
Liu et al., "B7DC/PDL2 promotes tumor immunity by a PD-1-independent mechanism," J Exp Med., 197(12):1721-1730, Jun. 16, 2003.
Liu et al., "B7-H3 silencing increases paclitaxel sensitivity by abrogating Jak2/Stat3 phosphorylation," Mol Cancer Ther., 10(6):960-971, Apr. 25, 2011.
Liu et al., "CRISPR-Cas9-mediated multiplex gene editing in CAR-T cells," Cell Research, Jan. 2017, 27(1):154-157.
Liu et al., CTL- vs Treg lymphocyte-attracting chemokines, CCL4 and CCL20, are strong reciprocal predictive markers for survival of patients with oesophageal squamous cell carcinoma. Br J Cancer, 113(5):747-755, Sep. 1, 2015.
Liu et al., "Endogenous tumor-reactive CD8+ T cells are differentiated effector cells expressing high levels of CD11a and PD-1 but are unable to control tumor growth," Oncoimmunology., 2(6):e23972, Jun. 6, 2013.
Liu et al., "Fas-mediated apoptosis causes elimination of virus-specific cytotoxic T cells in the virus-infected liver," J Immunol., 166(5):3035-3041, Mar. 1, 2001.
Liu et al., "Interferon gamma plays a critical role in induced cell death of effector T cell: a possible third mechanism of self-tolerance," J Exp Med., 172(6):1735-1739, Dec. 1, 1990.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway," Blood, 110(1):296-304, Mar. 15, 2007.
Liu et al., "RAxML and FastTree: Comparing Two Methods for Large-Scale Maximum Likelihood Phylogeny Estimation," PLoS One, Nov. 21, 2011, 6(11):e27731, 11 pages.
Liu et al., "Targeting Alpha-Fetoprotein (AFP)-MHC Complex with CAR T-Cell Therapy for Liver Cancer," Clin. Cancer Research, Jan. 2017, 23(2):478-488.
Liu, "Differential Expression of Cell Surface Molecules in Prostate Cancer Cells," Cancer Research, July 1, 200, 60:3429-3434.
Locke et al., "Long-term safety and activity of axicabtagene ciloleucel in refractory large B-cell lymphoma (ZUMA-1): a single-arm, multicentre, phase 1-2 trial," Lancet Oncology, 20(1):31-42, Jan. 2019.
Lonberg et al., "Antigen-specific human antibodies from mice comprising four distinct genetic modifications," Nature, 368(6474):856-859, Apr. 28, 1994.
Long et al., "4-1BB costimulation ameliorates T cell exhaustion induced by tonic signaling of chimeric antigen receptors," Nat. Medicine, 21(6):581-590, May 4, 2015.
Losman et al., "Baboon anti-idiotype antibodies mimic a carcinoembryonic antigen epitope," Int J Cancer., 46(2):310-314, Aug. 15, 1990.
Love et al., "Moderated estimation of fold change and dispersion for RNA-seq data with DESeq2," Genome Biology, 15:550, Dec. 5, 2014, 21 pages.
Lu et al., "EGF-IL-18 fusion protein as a potential anti-tumor reagent by induction of immune response and apoptosis in cancer cells," Cancer Lett., 260(1-2):187-197, 2008.
Luciano et al., "Phosphorylation of Bim-EL by Erk1/2 on serine 69 promotes its degradation via the proteasome pathway and regulates its proapoptotic function," Oncogene., 22(43):6785-6793, Oct. 2, 2003.
Ludwinski et al., "Critical roles of Bim in T cell activation and T cell-mediated autoimmune inflammation in mice," J Clin Invest., 119(6):1706-1713, Jun. 2009.
Luettig et al., "Naive and memory T lymphocytes migrate in comparable Nos. through normal rat liver: activated T cells accumulate in the periportal field," J Immunol., 163(8):4300-4307, Oct. 15, 1999.
Luke et al., "Targeted agents and immunotherapies: optimizing outcomes in melanoma," Nat Rev Clin Oncol., 14(8):463-482, Aug. 2017.
Lunsford et al., "Targeting LFA-1 and cd154 suppresses the in vivo activation and development of cytolytic (cd4-Independent) CD8+ T cells," J Immunol., 175(12):7855-7866, Dec. 15, 2005.
Luo et al., "Bim inhibits autophagy by recruiting Beclin 1 to microtubules," Mol Cell, 47(3):359-370, Aug. 10, 2012.
Lynn et al., "c-Jun overexpression in CAR T cells induces exhaustion resistance," Nature, 576(7786):293-300, Dec. 4, 2019.
Ma et al., "The DNA-dependent protein kinase catalytic subunit phosphorylation sites in human Artemis," J Biol Chem., 280(40):33839-33846, Aug. 10, 2005.
Ma et al., "The Role of PD-1 Ligand in Immune Evasion by Breast Cancer," Dana-Farber Cancer Institute Annual Summary Report May 1, 2002-Apr. 30, 2005, pp. 5-6, 9, 11, report date: May 2005.
Maacha et al., "Extracellular vesicles-mediated intercellular communication: roles in the tumor microenvironment and anti-cancer drug resistance," Mol. Cancer, 18(1):55, Mar. 30, 2019, 16 pages.
Macdonald et al., "Alloantigen-specific regulatory T cells generated with a chimeric antigen receptor," J. Clin. Investigation, Mar. 21, 2016, 126(4):1413-1424.
Machanick et al., "MEME-ChIP: motif analysis of large DNA datasets," Bioinformatics, 27(12):1696-1697, Jun. 15, 2011.

(56) References Cited

OTHER PUBLICATIONS

Mah et al., "gammaH2AX: a sensitive molecular marker of DNA damage and repair," Leukemia, 24(4):679-686, Feb. 4, 2010.
Mahotka et al., "Distinct in vivo expression patterns of survivin splice variants in renal cell carcinomas," Int J Cancer, 100(1):30-36, Jul. 1, 2002.
Majzner et al., "Clinical lessons learned from the first leg of the CAR T cell journey," Nat. Medicine, 25(9):1341-1355, Sep. 9, 2019.
Makarova et al., "Evolution and classification of the CRISPR-Cas systems," Nat. Rev. Microbiology, 9(6):467-477, May 9, 2011.
Mali et al., "RNA-guided human genome engineering via Cas9," Science, 339(6121):823-826, Feb. 15, 2013.
Mandell et al., "Zinc Finger Tools: custom DNA-binding domains for transcription factors and nucleases," Nucleic Acids Research, Jul. 1, 2006, 34(suppl_2):W516-W523.
Mann et al., "Construction of a retrovirus packaging mutant and its use to produce helper-free defective retrovirus" Cell, 33(1):153-159, May 1983.
Martin et al. "Combination gene therapy with CD86 and the MHC Class II transactivator in the control of lung tumor growth," J Immunol., 162(11):6663-6670, Jun. 1, 1999.
Martin et al., "National Institutes of Health Consensus Development Project on Criteria for Clinical Trials in Chronic Graft-versus-Host Disease: VI. The 2014 Clinical Trial Design Working Group Report," Biol. Blood Marrow Transplantation, Aug. 2015, 21(8):1343-1359.
Martin, "Cutadapt removes adapter sequences from high-throughput sequencing reads," EMBnet. Journal, 17(1):10-12, Aug. 2, 2011.
Matejcek et al., "Pharmaco-EEG and Psychometric study of the effect of single doses of temazepam and nitrazepam," Neuropsychobiology, 9(1):52-65, 1983.
Mathiowitz et al., "Morphology of poly anhydride microsphere delivery systems," Scanning Microsc., 4(2):329-340, Jun. 1990.
Mathiowitz et al., "Polyanhydride microspheres as drug carriers. I. Hot-melt microencapsulation," J. Controlled Release, 5(1):13-22, Jun. 1, 1987.
Mathiowitz et al., "Polyanhydride microspheres. IV. Morphology and characterization of systems made by spray drying," J. Annl. Polymer Sci. 45(1): 125-134, May 5, 1992.
Mathiowitz, Novel microcapsules for delivery systems, Reactive Polymers, 6(2):275-283, Oct. 31, 1987.
Mathiowitz, "Polyanhydride microspheres as drug carriers, II. Microencapsulation by solvent removal," J. Appl. Polymer Sci., 35(3): 755-774, Feb. 20, 1988.
Matsumoto et al., "CIS, a cytokine inducible SH2 protein, is a target of the JAK-STAT5 pathway and modulates STAT5 activation," Blood, 89(9):3148-3154, May 1, 1997.
Maude et al., "Tisagenlecleucel in Children and Young Adults with B-Cell Lymphoblastic Leukemia," N. Engl. J. Medicine, 378(5):439-448, Feb. 1, 2018.
Mayo Clinic, "Mayo Clinic Discovers Potential Marker for Aggressive Kidney Cancer," Science Daily, Retrieved from the Internet: <URL: https://www.sciencedaily.com/releases/2004/11/041130200858.htm>, Dec. 9, 2004, 2 pages.
Mayo.edu [online] "Center for Clinical and Translational Science (CCaTS): Study Design," Available on or before Oct. 12, 2012, via Internet Archive: Wayback Machine URL<https://web.archive.org/web/20121012161818/http://www.mayo.edu/ctsa/education/professional-development/online-courses/study-design>, retrieved on Mar. 23, 2021, retrieved from URL<https://web.archive.org/web/20170816080726/http://www.mayo.edu/ctsa/education/professional-development/online-courses/study-design>, 2 pages.
McCubrey et al., "Roles of the Raf/MEK/ERK pathway in cell growth, malignant transformation and drug resistance," Biochim Biophys Acta., 1773(8):1263-1284, Oct. 7, 2006.
McDermott et al., "PD-1 as a potential target in cancer therapy," Cancer Med., 2(5):662-673. Jul. 21, 2013.
McLachlin et al., "Retroviral-mediated gene transfer," Prog Nucleic Acid Res Mol Biol., 38:91-135, 1990.
Mehal et al., "Antigen presentation by liver cells controls intrahepatic T cell trapping, whereas bone marrow-derived cells preferentially promote intrahepatic T cell apoptosis," J Immunol., 167(2):667-673, Jul. 15, 2001.
Mehal et al., "TCR ligation on CD8+ T cells creates double-negative cells in vivo," J Immunol., 161(4):1686-1693, Aug. 15, 1998.
Mejstrikova et al., "CD19-negative relapse of pediatric B-cell precursor acute lymphoblastic leukemia following blinatumomab treatment," Blood Cancer Journal, Dec. 20, 2017, 7(12):659, 5 pages.
Melero et al., "Amplification of tumor immunity by gene transfer of the co-stimulatory 4-1BB ligand: synergy with the CD28 co-stimulatory pathway," Eur J Immunol., 28(3):1116-1121, Mar. 1998.
Melero et al., "Monoclonal antibodies against the 4-1BB T-cell activation molecule eradicate established tumors," Nat Med., 3(6):682-685, Jun. 1997.
Melero et al., "NK1.1 cells express 4-1BB (CDw137) costimulatory molecule and are required for tumor immunity elicited by anti-4-1BB monoclonal antibodies," Cell Immunol., 190(2):167-172, Dec. 15, 1998.
Melief et al., "Strategies for immunotherapy of cancer," Advances in Immunology, 75:235-282, Jan. 1, 2000.
Mellado et al., "A potential immune escape mechanism by melanoma cells through the activation of chemokine-induced T cell death," Curr Biol., 11(9):691-696, May 1, 2001.
Mendez-Fernandez et al., "Clearance of Theiler's virus infection depends on the ability to generate a CD8+ T cell response against a single immunodominant viral peptide," Eur J Immunol., 33(9):2501-2510, Sep. 2003.
Merrill, "Emergence of targeted immune therapies for systemic lupus," Expert Opin Emerg Drugs, 10(1):53-65, Feb. 2005.
Merritt et al., "Activation of p38 mitogen-activated protein kinase in vivo selectively induces apoptosis of CD8(+) but not CD4(+) T cells," Mol Cell Biol., 20(3):936-946, Feb. 2000.
Metzler et al., "Solution structure of human CTLA-4 and delineation of a CD80/CD86 binding site conserved in CD28," Nat Struct Biol., 4(7):527-531, Jul. 1997.
Meyts et al., "Deficiency of Adenosine Deaminase 2 (DADA2): Updates on the Phenotype, Genetics, Pathogenesis, and Treatment," J. Clin. Immunology, Jun. 27, 2018, 38(5):569-578.
Mezzadra et al., "Identification of CMTM6 and CMTM4 as PD-L1 Protein Regulators," Nature, 549(7670):106-110, Sep. 7, 2017.
Miller et al., "Gene transfer by retrovirus vectors occurs only in cells that are actively replicating at the time of infection," Mol Cell Biol., 10(8):4239-4242, Aug. 1990.
Miller et al., "Generation of helper-free amphotropic retroviruses that transduce a dominant-acting, methotrexate-resistant dihydrofolate reductase gene," Mol Cell Biol., 5(3):431-437, Mar. 1985.
Miller et al., "Molecular Pathways: Receptor Ectodomain Shedding in Treatment, Resistance, and Monitoring of Cancer," Clin. Cancer Research, 23(3):623-629, Feb. 1, 2017.
Miller et al., "Redesign of retrovirus packaging cell lines to avoid recombination leading to helper virus production," Mol Cell Biol., 6(8):2895-2902, Aug. 1986.
Miller, "Human gene therapy comes of age," Nature, 357(6378):455-460, Jun. 11, 1992.
Milone et al., "Chimeric receptors containing CD137 signal transduction domains mediate enhanced survival of T cells and increased antileukemic efficacy in vivo," Mol. Therapy, Aug. 2009, 17(8):1453-1464.
Minderman et al., "DiOC2(3) is not a substrate for multidrug resistance protein (MRP)-mediated drug efflux," Cytometry, 25(1):14-20, Sep. 1, 1996.
Misquitta et al., "Targeted disruption of gene function in Drosophila by RNA interference (RNA-i): A role for nautilus in embryonic somatic muscle formation," Proc Natl Acad Sci USA., 96(4):1451-1456, Feb. 16, 1999.
Mizuhara et al., "T cell activation-associated hepatic injury: mediation by tumor necrosis factors and protection by interleukin 6," J Exp Med., 179(5):1529-1537, May 1, 1994.

(56) References Cited

OTHER PUBLICATIONS

Mohammadi et al., "Exosomes and cancer: From oncogenic roles to therapeutic applications," IUBMB Life, 72(4):724-728, Oct. 16, 2019.
Mohan et al., "Interaction between CD40 and its ligand gp39 in the development of murine lupus nephritis," J Immunol., 154(3):1470-1480, Feb. 1, 1995.
Montesano et al., "Genetic alterations in esophageal cancer and their relevance to etiology and pathogenesis: a review," Int J Cancer., 69(3):225-235, Jun. 21, 1996.
Morrison et al., "Chimeric human antibody molecules: mouse antigen-binding domains with human constant region domains," Proc Natl Acad Sci USA., 81(21):6851-6855, Nov. 1984.
Morse et al., "Abnormalities induced by the mutant gene Ipr: expansion of a unique lymphocyte subset," J Immunol., 129(6):2612-2615, Dec. 1982.
Moskowitz et al., "PD-1 Blockade with the Monoclonal Antibody Pembrolizumab (MK-3475) in Patients with Classical Hodgkin Lymphoma after Brentuximab Vedotin Failure: Preliminary Results from a Phase 1b Study (KEYNOTE-013)," Blood, 124(21):290, Dec. 6, 2014.
Moss, "Poxvirus expression vectors," Curr Top Microbiol Immunol., 158:25-38, 1992.
Moss, "Poxvirus vectors: cytoplasmic expression of transferred genes," Curr Opin Genet Dev., 3(1):86-90, Feb. 1993.
Moss, "Use of vaccinia virus as an infectious molecular cloning and expression vector," Gene Amplif Anal., 3:201-213, 1983.
Moss, "Vaccinia virus vectors," Biotechnology, 20:345-362, 1992.
Moss, "Vaccinia virus: a tool for research and vaccine development," Science, 252(5013):1662-1667, Jun. 21, 1991.
Motzer et al., "Nivolumab versus Everolimus in Advanced Renal-Cell Carcinoma," N Engl J Med., 373(19):1803-1813, Nov. 5, 2015.
Motzer et al., "Renal Cell Carcinoma," N Engl J Med., 335(12):865-75, Sep. 19, 1996.
Mukherjee et al., "DNA-PK phosphorylates histone H2AX during apoptotic DNA fragmentation in mammalian cells," DNA Repair (Amst)., 5(5):575-590, Mar. 29, 2006.
Muller et al., "Tumor-derived exosomes regulate expression of immune function-related genes in human T cell subsets," Sci. Reports, 6:20254, Feb. 4, 2016, 13 pages.
Mumprecht et al., "Programmed death 1 signaling on chronic myeloid leukemia-specific T cells results in T-cell exhaustion and disease progression," Blood, 114(8):1528-1536, May 6, 2009.
Murooka et al., "CCL5-CCR5-mediated apoptosis in T cells: Requirement for glycosaminoglycan binding and CCL5 aggregation," J Biol Chem., 281(35):25184-25194, Sep. 1, 2006.
Muyldermans, "Single domain camel antibodies: current status," J Biotechnol., 74(4):277-302, Jun. 2001.
Myers et al., "AXL Inhibitors in Cancer: A Medicinal Chemistry Perspective," J. Med. Chemistry, Nov. 10, 2015, 59(8):3593-3608.
Nabel et al., "Recombinant gene expression in vivo within endothelial cells of the arterial wall," Science, 244(4910):1342-1344, Jun. 16, 1989.
National Cancer Institute, "Fact Sheet: Tumor Markers," cancer.gov [online] Dec. 7, 2011 [retrieved on Apr. 3, 2014]. Retrieved from the Internet: <URL: http://www.cancer.gov/cancertopics/factsheet/detection/tumor-markers/print>, 8 pages.
National Comprehensive Cancer Network, "NCCN Clinical Practice Guidelines in Oncology (NCCN Guidelines): Melanoma—Version 3.2016," Jul. 7, 2016, 154 pages.
Nava-Parada et al., "Peptide vaccine given with a Toll-like receptor agonist is effective for the treatment and prevention of spontaneous breast tumors," Cancer Res., 67(3):1326-1334, Feb. 1, 2007.
Nechiporuk et al., "The mouse SCA2 gene: cDNA sequence, alternative splicing and protein expression," Hum Mol Genet., 7(8):1301-1309, Aug. 1998.
Needleman et al., "A general method applicable to the Search for similarities in the amino acid sequence of two proteins," J Mol Biol., 48(3):443-453, Mar. 1970.
Neelapu et al., "Axicabtagene Ciloleucel CAR T-Cell Therapy in Refractory Large B-Cell Lymphoma," N. Engl. J. Medicine, 377(26):2531-2544, Dec. 28, 2017.
Neer, "Vasopressin-responsive, Soluble Adenylate Cyclase from the Rat Renal Medulla," J. Biol. Chemistry, 248(10):3742-3744, May 25, 1973.
Nellan et al., "Durable regression of Medulloblastoma after regional and intravenous delivery of anti-HER2 chimeric antigen receptor T cells," J. Immunotherapy, Cancer, 6(1):30, 14 pages.
Nelson et al., "Tumor progression despite efficient tumor antigen cross-presentation and effective "arming" of tumor antigen-specific CTL," J Immunol., 166(9):5557-5566, May 1, 2001.
Nevala et al., "Evidence of systemic Th2-driven chronic inflammation in patients with metastatic melanoma," Clin Cancer Res., 15(6):1931-1939, Mar. 15, 2009.
Neves et al., "Surgical treatment of renal cancer with vena cava extension," Br J Urol., 59(5):390-395, May 1987.
Newmark et al., "Preparation and properties of adducts of streptokinase and streptokinase-plasmin complex with poly ethylene glycol and pluronic polyol F38," J Appl Biochem., 4:185-189, 1982.
Newton et al., "Clinical benefit of INCB7839, a potent and selective ADAM inhibitor, in combination with trastuzumab in patients with metastatic HER2+ breast cancer.," J. Clin. Oncol., 28(15 Suppl):3025, May 2010.
Neyns et al., "Dose-dense temozolomide regimens: antitumor activity, toxicity, and immunomodulatory effects," Cancer, 116(12):2868-2877, Jun. 15, 2010.
Ngiow et al., "A Threshold Level of Intratumor CD8+ T-cell PD1 Expression Dictates Therapeutic Response to Anti-PD1," Cancer Res., 75(18):3800-3811, Sep. 15, 2015.
Nicolau et al., "In vivo expression of rat insulin after intravenous administration of the liposome-entrapped gene for rat insulin I," Proc Natl Acad Sci USA., 80(4):1068-1072, Feb. 1983.
Nielsen et al., "Melanoma vaccines: the paradox of T cell activation without clinical response," Cancer Chemother Pharmacol., 46 Suppl:S62-S66, 2000.
Nielsen et al., "Peptide nucleic acid (PNA). a DNA mimic with a peptide backbone," Bioconjug Chem., 5(1):3-7, Jan./Feb. 1994.
Nielsen et al., "Sequence-selective recognition of DNA by strand displacement with a thymine-substituted polyamide," Science, 254(5037):1497-1500, Dec. 6, 1991.
Nishimura et al., "Autoimmune dilated cardiomyopathy in PD-1 receptor-deficient mice," Science, 291(5502):319-322, Jan. 12, 2001.
Nishimura et al., "Development of lupus-like autoimmune diseases by disruption of the PD-1 gene encoding an ITIM motif-carrying immunoreceptor," Immunity, 11(2):141-151, Aug. 1999.
Nishimura et al., "Dual functions of fractalkine/CX3C ligand 1 in trafficking of perforin+/granzyme B+ cytotoxic effector lymphocytes that are defined by CX3CR1 expression," J Immunol., 168(12):6173-6180, Jun. 15, 2002.
Nishimura et al., "Immunological studies on PD-1-deficient mice: implication of PD-1 as a negative regulator for B cell responses," Int Immunol., 10(10):1563-1572, Oct. 1998.
Nishino et al., "Monitoring immune-checkpoint blockade: response evaluation and biomarker development," Nat. Reviews, 14(11):655-668, Nov. 2017.
Nisonhoff et al., "Separation of univalent fragments from the bivalent rabbit antibody molecule by reduction of disulfide bonds," Arch Biochem Biophys., 89:230-244, Aug. 1960.
Ohaegbulam et al., "Human cancer immunotherapy with antibodies to the PD-1 and PD-L1 pathway," Trends. Mol. Medicine, 21(1):24-33, Jan. 2015.
Ohigashi et al., "Clinical significance of programmed death-1 ligand-1 and programmed death-1 ligand-2 expression in human esophageal cancer," Clin Cancer Res., 11(8):2947-2953, Apr. 15, 2005.
Ohnishi et al., "Prolonged survival of mice with human gastric cancer treated with an anti-c-ErbB-2 monoclonal antibody," Br. J. Cancer, May 1, 1995, 71(5):969-973.
Okazaki et al., "PD-1 and PD-1 ligands: from discovery to clinical application," Int Immunol., 19(7):813-824, Jul. 2, 2007.
Okazaki et al., "PD-1 immunoreceptor inhibits B cell receptor-mediated signaling by recruiting src homology 2-domain-

(56) References Cited

OTHER PUBLICATIONS containing tyrosine phosphatase 2 to phosphotyrosine," Proc Natl Acad Sci USA., 98(24):13866-13871, Nov. 20, 2001.
Oksvold et al., "Expression of B-Cell Surface Antigens in Subpopulations of Exosomes Released From B-Cell Lymphoma Cells," Clin. Therapeutics, Jun. 18, 2014, 36(6):847-862.el.
Opferman al., "Linear differentiation of cytotoxic effectors into memory T lymphocytes," Science, 283(5408):1745-1748, Mar. 12, 1999.
O'Reilly et al., "MEK/ERK-mediated phosphorylation of Bim is required to ensure survival of T and B lymphocytes during mitogenic stimulation," J Immunol., 183(1):261-269, Jul. 1, 2009.
Orlandi et al., "Cloning immunoglobulin variable domains for expression by the polymerase chain reaction," Proc Natl Acad Sci USA., 86(10):3833-3837, May 1989.
Orme et al., "Disparate outcomes of patients with Multiple Myeloma based on geographic distance from NCI-Designated National Cancer Centers: A Seer based analysis," Blood, 130(S1):4689, Dec. 7, 2017.
Orme et al., "Heightened cleavage of Axl receptor tyrosine kinase by ADAM metalloproteases may contribute to disease pathogenesis in SLE," Clin, Immunol., 169:58-68, Aug. 2016.
Orme et al., "Leukocyte betacatenin expression is disturbed in systemic lupus erythematosus," PLoS One, 11(8):e0161682, 14 pages.
Orme et al., "Macrophage subpopulations in systemic lupus erythematosus.," Discov. Med., 13(69):151-158, Feb. 2012.
Orme et al., "Macrophages and neutrophils in SLE-An online molecular catalog," Autoimmun. Rev., 11(5):365-372, Mar. 2012.
Ormhøj et al., "Chimeric Antigen Receptor T Cells Targeting CD79b Show Efficacy in Lymphoma with or without Cotargeting CD19," Clin. Cancer Research, Dec. 2019, 25(23):7046-7057.
Ostrov et al., "Structure of murine CTLA-4 and its role in modulating T cell responsiveness," Science, 290(5492):816-819, Oct. 27, 2000.
Otano et al., "Human CD8 T cells are susceptible to TNF-mediated activation-induced cell death," Theranostics, Mar. 15, 2020, 10(10):4481-4489.
Ott et al., "Pembrolizumab in Patients With Extensive-Stage Small-Cell Lung Cancer: Results From the Phase Ib KEYNOTE-028 Study," J. Clin. Oncol., 35(34):3823-3829, Aug. 16, 2017.
Ozkaynak et al., "Programmed death-1 targeting can promote allograft survival," J Immunol., 169(11):6546-6553, Dec. 1, 2002.
Palmer et al., "Cish actively silences TCR signaling in CD8+ T cells to maintain tumor tolerance," J Exp Med., 212(12):2095-2113, Nov. 2, 2015.
Panta et al., "ATM and the catalytic subunit of DNA-dependent protein kinase activate NF-kappaB through a common MEK/extracellular signal-regulated kinase/p90(rsk) signaling pathway in response to distinct forms of DNA damage," Mol Cell Biol., 24(5):1823-1835, Mar. 2004.
Pantuck et al., "The changing natural history of renal cell carcinoma," J Urol., 166(5):1611-1623, Nov. 2001.
Pardoll, "Spinning molecular immunology into successful immunotherapy," Nat Rev Immunol., 2(4):227-238, Apr. 2002.
Pardoll., "The Blockade of Immune Checkpoints in Cancer Immunotherapy," Nat Review., 12:252-264, Apr. 2012.
Parihar et al., "NK Cells Expressing a Chimeric Activating Receptor Eliminate MDSCs and Rescue Impaired CAR-T Cell Activity against Solid Tumors," Cancer Immunol. Research, Mar. 2019, 7(3):363-375.
Parikh, "Chronic lymphocytic leukemia treatment algorithm 2018," Blood Cancer J., Oct. 3, 2018, 8:93, 10 pages.
Park et al., "B7-H1/CD80 interaction is required for the induction and maintenance of peripheral T-cell tolerance," Blood., 116(8):1291-1298, May 14, 2010.
Park et al., "CD70 as a target for chimeric antigen receptor T cells in head and neck squamous cell carcinoma," Oral Oncology, Mar. 2018, 78:145-150.
Park et al., "Increased Response Rates to Salvage Chemotherapy Administered after PD-1/PD-L1 Inhibitors in Patients with Non-Small Cell Lung Cancer," J Thorac Oncol., 13(1):106-111, Jan. 2018.
Park et al., "PD-1 Restrains Radiotherapy-Induced Abscopal Effect," Cancer Immunol Res., 3(6):610-619, Jun. 2015.
Parker et al., "Potential utility of uroplakin III, thrombomodulin, high molecular weight cytokeratin, and cytokeratin 20 in noninvasive, invasive, and metastatic urothelial (transitional cell) carcinomas," Am J Surg Pathol., 27(1):1-10, Jan. 2003.
Parmentier et al., "Human TH2 cells respond to cysteinyl leukotrienes through selective expression of cysteinyl leukotriene receptor 1," J. Allergy Clin. Immunology, Apr. 2012, 129(4):1136-1142.
Parry et al., "CTLA-4 and PD-1 receptors inhibit T-cell activation by distinct mechanisms," Mol Cell Biol., 25(21):9543-9553, Nov. 2005.
Parsa et al., "Loss of tumor suppressor PTEN function increases B7-H1 expression and immunoresistance in glioma," Nat Med., 13(1):84-88, Dec. 10, 2006.
Paterson et al., "The PD-L1:B7-1 pathway restrains diabetogenic effector T cells in vivo," J Immunol., 187(3):1097-1105, Aug. 1, 2011.
Patrone et al., "Nuclear Run-On Assay Using Biotin Labeling, Magnetic Bead Capture and Analysis by Fluorescence-Based RT-PCR," BioTechniques, 29(5):1012-1017, Nov. 2000.
Patsoukis et al., "Selective effects of PD-1 on Akt and Ras pathways regulate molecular components of the cell cycle and inhibit T cell proliferation," Sci Signal., 5(230):ra46, Jun. 26, 2012.
Pavelko et al., "The epitope integration site for vaccine antigens determines virus control while maintaining efficacy in an engineered cancer vaccine," Mol Ther., 21(5):1087-1095, Apr. 9, 2013.
PCT International Preliminary Report on Patentability in International Appln. No. PCT/US2019/026544, dated May 19, 2022, 11 pages.
PCT International Search Report and Written Opinion in International Appln. No. PCT/US2020/059720, dated Mar. 12, 2021, 14 pages.
Peach et al., "Both extracellular immunoglobulin-like domains of CD80 contain residues critical for binding T cell surface receptors CTLA-4 and CD28," J Biol Chem., 270(36):21181-21187, Sep. 8, 1995.
Pece and Gutkind, "Signaling from E-cadherins to the MAPK pathway by the recruitment and activation of epidermal growth factor receptors upon cell-cell contact formation," J Biol Chem., 275(52):41227-41233, Dec. 29, 2000.
Pedraza-Alva et al., "Activation of p38 MAP kinase by DNA double-strand breaks in V(D)J recombination induces a G2/M cell cycle checkpoint," EMBO J., 25(4):763-773, Feb. 2, 2006.
Peghini et al, [Immunophaenotyping in the diagnosis of lymphoma]. Praxis (Bern 1994)., 93(41):1687-1692, Oct. 6, 2004, Article in German, English abstract included.
Pei et al., "FKBP51 affects cancer cell response to chemotherapy by negatively regulating Akt," Cancer Cell., 16(3):259-266, Sep. 8, 2009.
Pemmaraju et al., "Tagraxofusp in Blastic Plasmacytoid Dendritic-Cell Neoplasm," N. Engl. J. Medicine, Apr. 25, 2019, 380(17):1628-1637.
Peng et al., "PD-1 blockade enhances T-cell migration to tumors by elevating IFN-gamma inducible chemokines," Cancer Res, 72(20):5209-5218, Oct. 15, 2012.
Penix et al., "Two essential regulatory elements in the human interferon gamma promoter confer activation specific expression in T cells," J Exp Med., 178(5):1483-1496, Nov. 1, 1993.
Perriman et al., "Effective ribozyme delivery in plant cells," Proc Natl Acad Sci USA., 92(13):6175-6179, Jun. 20, 1995.
Petroff et al., "B7 family molecules: novel immunomodulators at the maternal-fetal interface," Placenta, 23 Suppl A:S95-101, Apr. 2002.
Piccini, "Vaccinia: virus, vector, vaccine," Adv Virus Res., 34:43-64, 1988.
Pitt et al., "Resistance Mechanisms to Immune-Checkpoint Blockade in Cancer: Tumor-Intrinsic and -Extrinsic Factors," Immunity, 44(6):1255-1269, Jun. 21, 2016.

(56) References Cited

OTHER PUBLICATIONS

Plückthun et al., "Expression of functional antibody Fv and Fab fragments in *Escherichia coli*," Methods Enzymol., 178:497-515, 1989.
Plückthun, "Antibodies from *Escherichia coli*." The Pharmacology of Monoclonal Antibodies. Handbook of Experimental Pharmacology, Springer Berlin Heidelberg, pp. 269-315, 1994.
Poirier, "Protective immunity evoked by oral administration of attenuated aroA *Salmonella typhimurium* expressing cloned streptococcal M protein," J Exp Med., 168(1):25-32, Jul. 1, 1988.
Pollok et al., "4-1BB T-cell antigen binds to mature B cells and macrophages, and costimulates anti-mu-primed splenic B cells," Eur J Immunol., 24(2):367-374, Feb. 1994.
Pollok et al., "Inducible T Cell Antigen 4-1BB," J Immunol., 150(3):771-781, Feb. 1, 1993.
Ponder et al., "Tertiary templates for proteins. Use of packing criteria in the enumeration of allowed sequences for different structural classes," J Mol Biol., 193(4):775-791, Feb. 20, 1987.
Porter et al., "Chimeric antigen receptor T cells persist and induce sustained remissions in relapsed refractory chronic lymphocytic leukemia," Sci. Transl. Medicine, 7(303):303ra139, Sep. 2, 2015, 13 pages.
Porter et al., "Chimeric antigen receptor-modified T cells in chronic lymphoid leukemia," N. Engl. J. Medicine, 365(8):725-733, Aug. 25, 2011.
Porter, "The hydrolysis of rabbit γ-globulin and antibodies with crystalline papain," Biochem J., 73:119-126, Sep. 1959.
Porteus et al., "Gene targeting using zinc finger nucleases," Nat. Biotechnology, Aug. 2005, 23(8):967-973.
Posey Jr. et al., "Distinguishing Truncated and Normal MUC1 Glycoform Targeting from Tn-MUC1-Specific CAR T Cells: Specificity Is the Key to Safety," Immunity, Nov. 15, 2016, 45(5):947-948.
Postow et al., "Immune Checkpoint Blockade in Cancer Therapy," J. Clin. Oncology, 33(17):1974-1982, Jun. 10, 2015.
Powell et al., "Compendium of excipients for parenteral formulations," PDA J Pharm Sci Technol., 52(5):238-311, Sep./Oct. 1998.
Powles et al., "MPDL3280A (anti-PD-L1) treatment leads to clinical activity in metastatic bladder cancer," Nature, 515(7528):558-562, Nov. 27, 2014.
Prabhu et al., "Gamma interferon regulates contraction of the influenza virus-specific CD8 T cell response and limits the size of the memory population," J Virol., 87(23):12510-12522, Dec. 2013.
Prasad et al., "B7S1, a novel B7 family member that negatively regulates T cell activation," Immunity, 18(6):863-873, Jun. 2003.
Presta, "Antibody engineering," Curr Opin Biotechnol., 2(4):593-596, 1992.
Presta, "Antibody engineering," Curr Opin Biotechnol., 3(4):394-398, Aug. 1992.
Prévost-Blondel et al., "Tumor-infiltrating lymphocytes exhibiting high ex vivo cytolytic activity fail to prevent murine melanoma tumor growth in vivo," J Immunol., 161(5):2187-2194, Sep. 1, 1998.
Priceman et al., "Regional Delivery of Chimeric Antigen Receptor-Engineered T Cells Effectively Targets HER2+ Breast Cancer Metastasis to the Brain," Clin. Cancer Research, Jan. 2018, 24(1):95-105.
Prlic et al., "Exploring regulatory mechanisms of CD8+ T cell contraction," Proc Natl Acad Sci USA., 105(43):16689-16694, Oct. 28, 2008.
PRNewswire.com [online], "Global $4.92 Billion Programmed Death-1 (PD-1) & Programmed Death Ligand-1 (PD-L1) Inhibitors Pipeline Analysis 2017-2025—Research and Markets," Mar. 13, 2017, retrieved on Mar. 25, 2021, retrieved from URL<https://www.prnewswire.com/news-releases/global-492-billion-programmed-death-1-pd-1--programmed-death-ligand-1-pd-l1-inhibitors-pipeline-analysis-2017-2025---research-and-markets-300422553.html>, 3 pages.
Probst-Cousin et al., "Annexin-1 is no useful surrogate marker of multiple sclerosis—an immunocytochemical study of the cerebrospinal fluid," Clin. Neuropathol., 30(1):18-24, Jan. 2011.
Pu et al., "Mechanisms and functions of lysosome positioning," J Cell Sci., 129(23):4329-4339, Dec. 2016.
Pulko et al., "B7-h1 expressed by activated CD8 T cells is essential for their survival," J Immunol., 187(11):5606-5614, Oct. 24, 2011.
Pulko et al., "TLR3-stimulated dendritic cells up-regulate B7-H1 expression and influence the magnitude of CD8 T cell responses to tumor vaccination," J Immunol., 183(6):3634-3641, Aug. 26, 2009.
Qi et al., "Evidence that Ser87 of BimEL is phosphorylated by Akt and regulates BimEL apoptotic function," J Biol Chem., 281(2):813-823, Nov. 10, 2005.
Radhakrishnan et al., "Dendritic cells activated by cross-linking B7-DC (PD-L2) block inflammatory airway disease," J Allergy Clin Immunol., 116(3):668-674, Sep. 2005.
Rai et al., "Tracking the total CD8 T cell response to infection reveals substantial discordance in magnitude and kinetics between inbred and outbred hosts," J Immunol., 183(12):7672-7681, Dec. 15, 2009.
Raje et al., "Anti-BCMA CAR T-Cell Therapy bb2121 in Relapsed or Refractory Multiple Myeloma," N. Engl. J. Medicine, May 2, 2019, 380(18):1726-1737.
Rajewsky et al., "Genetics, expression, and function of idiotypes," Annu Rev Immunol., 1:569-607, 1983.
Rathmell et al., "The central effectors of cell death in the immune system," Annu. Rev. Immunol., 17:781-828, 1999.
Razi-Wolf, "Expression and function of the murine B7 antigen, the major costimulatory molecule expressed by peritoneal exudate cells," Proc Natl Acad Sci USA., 89(9):4210-4214, May 1, 1992.
Refaeli et al., "Interferon gamma is required for activation-induced death of T lymphocytes," J Exp Med., 196(7):999-1005, Oct. 7, 2002.
Ren et al., "Analysis of the Effects of the Bruton's tyrosine kinase (Btk) Inhibitor Ibrutinib on Monocyte Fcgamma Receptor (FcgammaR) Function," J. Biol. Chemistry, Feb. 5, 2016, 291(6):3043-3052.
Renauld et al., "Expression cloning of the murine and human interleukin 9 receptor cDNAs," Proc Natl Acad Sci USA., 89(12):5690-5694, Jun. 15, 1992.
Ribas et al., "Association of Pembrolizumab With Tumor Response and Survival Among Patients With Advanced Melanoma," JAMA, 315(15):1600-1609, Apr. 19, 2016.
Ribas et al., "Pembrolizumab versus investigator-choice chemotherapy for ipilimumab-refractory melanoma (KEYNOTE-002): a randomised, controlled, phase 2 trial," Lancet Oncol., 16(8):908-918, Aug. 2015.
Riechmann et al., "Reshaping human antibodies for therapy," Nature, 332(6162):323-327, Mar. 24, 1988.
Rincon et al., "Signal transduction by MAP kinases in T lymphocytes," Oncogene, Apr. 30, 2001, 20(19):2490-2497.
Rincon et al., "JNK and p38 MAP kinases in CD4+ and CD8+ T cells," Immunol Rev., 192:131-142, Apr. 2003.
Rios-Doria et al., "A Monoclonal Antibody to ADAM17 Inhibits Tumor Grovrth by Inhibiting EGFR and Non-EGFR-Mediated Pathways," Mol. Cancer Ther., 14(7):1637-1649, Jul. 2015.
Rios-Doria et al., "Doxil synergizes with cancer immunotherapies to enhance antitumor responses in syngeneic mouse models," Neoplasia, 17(8):661-670, Aug. 2015.
Ritz et al., "Bioassay analysis using R," J Stat Softw., 12(5):1-22, Jan. 19, 2005.
Rivoltini et al., "Immunity to cancer: attack and escape in T lymphocyte-tumor cell interaction," Immunol Rev., 188:97-113, Oct. 2002.
Rizvi et al., "Nivolumab in Combination With Platinum-Based Doublet Chemotherapy for First-Line Treatment of Advanced Non-Small-Cell Lung Cancer," J Clin Oncol., 34(25):2969-2979, Sep. 1, 2016.
Robbins et al., "Regulation of immune responses by extracellular vesicles," Nat. Rev. Immunology, 14(3):195-208, Feb. 25, 2014.
Robert et al., "Anti-programmed-death-receptor-1 treatment with pembrolizumab in ipilimumab-refractory advanced melanoma: a randomised dose-comparison cohort of a phase 1 trial," Lancet, 384(9948):1109-1117, Sep. 20, 2014.

(56) References Cited

OTHER PUBLICATIONS

Robert et al., "Nivolumab in previously untreated melanoma without BRAF mutation," N Engl J Med., 372(4):320-330, Jan. 22, 2015.
Robert et al., "Pembrolizumab versus Ipilimumab in Advanced Melanoma," N Engl J Med., 372(26):2521-2532, Jun. 25, 2015.
Robison-Cox, "Multiple estimation of concentrations in immunoassay using logistic models," J Immunol Methods, 186(1):79-88, Oct. 12, 1995.
Romano et al., "Quelling: transient inactivation of gene expression in Neurospora crassa by transformation with homologous sequences," Mol Microbiol., 6(22):3343-3353, Nov. 1992.
Romer et al., "Plant pathogen recognition mediated by promoter activation of the pepper Bs3 resistance gene," Science, 318(5850):645-648, Oct. 26, 2007.
Romero et al., "Ex vivo staining of metastatic lymph nodes by class I major histocompatibility complex tetramers reveals high numbers of antigen-experienced tumor-specific cytolytic T lymphocytes," J Exp Med., 188(9):1641-1650, Nov. 2, 1998.
Romero et al., "Four functionally distinct populations of human effector-memory CD8+ T lymphocytes," J Immunol., 178(7):4112-4119, Apr. 1, 2007.
Roos et al., "DNA damage and the balance between survival and death in cancer biology," Nat. Rev. Cancer, 16(1):20-33, Jan. 2016.
Rosenberg, "Progress in human tumor immunology and immunotherapy," Nature, 411(6835):380-384, May 17, 2001.
Rosenfeld et al., "Adenovirus-mediated transfer of a recombinant alpha 1-antitrypsin gene to the lung epithelium in vivo," Science, 252(5004):431-434, Apr. 19, 1991.
Rousseaux et al., "Optimal conditions for the preparation of proteolytic fragments from monoclonal IgG of different rat IgG subclasses," Methods Enzymol., 121:663-669, 1986.
Rowe et al., "PDL-1 blockade impedes T cell expansion and protective immunity primed by attenuated Listeria monocytogenes," J Immunol., 180(11):7553-7557, Jun. 1, 2008.
Ruella et al., "Catch me if you can: Leukemia Escape after CD19-Directed T Cell Immunotherapies," Comput. Struct. Biotechnol. Journal, Sep. 28, 2016, 14:357-362.
Ruella et al., "Combination of Anti-CD123 and Anti-CD19 Chimeric Antigen Receptor T Cells for the Treatment and Prevention of Antigen-Loss Relapses Occurring after CD19-Targeted Immunotherapies," Blood, 126(23):2523, Dec. 3, 2015, 8 pages.
Ruella et al., "Overcoming the Immunosuppressive Tumor Microenvironment of Hodgkin Lymphoma Using Chimeric Antigen Receptor T Cells," Cancer Discovery, 7(10):1154-1167, Oct. 2017.
Ruppert et al., "The major isoforms of Bim contribute to distinct biological activities that govern the processes of autophagy and apoptosis in interleukin-7 dependent lymphocytes," Biochim Biophys Acta., 1823(10):1877-1893, Oct. 2012.
Sadoff, "Oral salmonella typhimurium vaccine expressing circumsporozoite protein protects against malaria," Science, 240(4850):336-338, Apr. 15, 1988.
Saito et al., "Metformin suppresses the growth of leukemia cells partly through downregulation of AXL receptor tyrosine kinase," Leukemia Research, May 15, 2020, 94:106383, 6 pages.
Sakemura et al., "Axl-RTK Inhibition Modulates T Cell Functions and Synergizes with Chimeric Antigen Receptor T Cell Therapy in B Cell Malignancies," Biol. Blood Marrow Transplantation, Mar. 2019, 25(3S):S165.
Sakemura et al., "Targeting Cancer Associated Fibroblasts in the Bone Marrow Prevents Resistance to Chimeric Antigen Receptor T Cell Therapy in Multiple Myeloma," Blood, 134(Supplement_1):865, Nov. 13, 2019, 7 pages.
Salama et al., "Critical role of the programmed death-1 (PD-1) pathway in regulation of experimental autoimmune encephalomyelitis," J Exp Med., 198(1):71-78, Jul. 7, 2003.
Salib et al., "Utilization of sodium alginate in drug microencapsulation," Pharm Ind., 40(11a):1230-1234, 1978.
Salih et al., "4-1 BB ligand—just another costimulating molecule?," Int J Clin Pharmacol Ther., 40(8):348-353, Aug. 2002.
Salih et al., "The role of leukemia-derived B7-H1 (PD-L1) in tumor-T-call interactions in humans," Exp Hematol., 34(7):888-894, Jul. 2006.
Sallusto et al., "Two subsets of memory T lymphocytes with distinct homing potentials and effector functions," Nature, 401(6754):708-712, Oct. 14, 1999.
Salomon et al., "Complexities of CD28/B7: CTLA-4 costimulatory pathways in autoimmunity and transplantation," Annu Rev Immunol., 19:225-252, 2001.
Sampson et al., "Greater chemotherapy-induced lymphopenia enhances tumor-specific immune responses that eliminate EGFRvIII-expressing tumor cells in patients with glioblastoma," Neuro Oncol., 13(3):324-333, Dec. 10, 2010.
Samulski, "Targeted integration of adenoassociated virus (AAV) into human chromosome 19," EMBO J., 10(12):3941-3950, Dec. 1991.
Sandhu, "Protein engineering of antibodies," Crit Rev Biotechnol., 12(5-6):437-462, 1992.
Sandström et al., "A novel CD44v6 targeting antibody fragment with improved tumor-to-blood ratio," Int. J. Oncology, Feb. 1, 2012, 40(5):1525-1532.
Sanjana et al., "Improved vectors and genome-wide libraries for CRISPR screening," Nat. Methods, 11(8):783-784, Aug. 2014.
Sanni et al., "Evolution of aminoacyl-tRNA synthetase quaternary structure and activity: *Saccharomyces cerevisiae* mitochondrial phenylalanyl-tRNA synthetase," Proc Natl Acad Sci USA., 88(19):8387-8391, Oct. 1, 1991.
Sarbassov et al., "Phosphorylation and regulation of Akt/PKB by the rictor-mTOR complex," Science, 307(5712):1098-1101, Feb. 18, 2005.
Satelli et al., "Potential role of nuclear PD-L1 expression in cell-surface vimentin positive circulating tumor cells as a prognostic marker in cancer patients," Sci Rep., 6:28910, Jul. 1, 2016, 7 pages.
Sawhney et al., "Bioerodible hydrogels based on photopolymerized poly(ethylene glycol)-co-poly(.alpha.-hydroxy acid) diacrylate macromers," Macromolecules, 26(4):581-587, Jul. 1993.
Schafer, "Induction of a cellular immune response to a foreign antigen by a recombinant Listeria monocytogenes vaccine," J Immunol., 149(1):53-59, Jul. 1, 1992.
Schinkel et al., "Mammalian drug efflux transporters of the ATP binding cassette (ABC) family: an overview," Adv Drug Deliv Rev., 55(1):3-29, Jan. 21, 2003.
Schmid et al., "Expression of AMPA receptor subunit flip/flop splice variants in the rat auditory brainstem and inferior colliculus," J Comp Neurol., 430(2):160-171, Feb. 5, 2001.
Schmidt et al., "Extreme CD8 T cell requirements for anti-malarial liver-stage immunity following immunization with radiation attenuated sporozoites," PLoS Pathog., 6(7):e1000998, Jul. 15, 2010.
Schmits et al., "LFA-1-deficient mice show normal CTL responses to virus but fail to reject immunogenic tumor," J Exp Med., 183(4):1415-1426, Apr. 1, 1996.
Schornack et al., "Gene-for-gene-mediated recognition of nuclear-targeted AvrBs3-like bacterial effector proteins," J. Plant Physiology, 163(3):256-272, Feb. 2006.
Schoumacher et al., "Key Roles of AXL and MER Receptor Tyrosine Kinases in Resistance to Multiple Anticancer Therapies," Curr. Oncol. Rep. Curr. Science, Mar. 2017, 19(3):19, 14 pages.
Schurich et al., "The third signal cytokine IL-12 rescues the anti-viral function of exhausted HBV-specific CD8 T cells," PLoS Pathog., 9(3):e1003208, Mar. 14, 2013.
Schuster et al., "Chimeric Antigen Receptor T Cells in Refractory B-Cell Lymphomas," N. Engl. J. Medicine, 377(26):2545-2554, Dec. 28, 2017.
Schwartz et al., "Costimulation of T lymphocytes: the role of CD28, CTLA-4, and B7/BBI in interluekin-2 production and immunotherapy," Cell, 71(7):1065-1068, Dec. 24, 1992.
Schwartz et al., "Structural basis for co-stimulation by the human CTLA-4/B7-2 complex," Nature, 410(6828):604-608, Mar. 29, 2001.
Schwartz et al., "Structural mechanisms of costimulation," Nat Immunol., 3(5):427-434, May 2002.
Sedletska et al., "Cisplatin is a DNA-damaging antitumour compound triggering multifactorial biochemical responses in cancer

(56) References Cited

OTHER PUBLICATIONS cells: importance of apoptotic pathways," Curr Med Chem Anticancer Agents., 5(3):251-265, May 2005.
Seiwert et al., "Antitumor activity and safety of pembrolizumab in patients (pts) with advanced squamous cell carcinoma of the head and neck (SCCHIN): Preliminary results from KEYNOTE-012 expansion cohort," J. Clin. Oncol., 33(18 Suppl):LBA6008, Jun. 20, 2015.
Seki et al., "Tumor-specific CTL kill murine renal cancer cells using both perforin and Fas ligand-mediated lysis in vitro, but cause tumor regression in vivo in the absence of perforin, " J Immunol., 168(7):3484-3492, Apr. 1, 2002.
Selenko-Gebauer et al., "B7-H1 (programmed death-1 ligand) on dendritic cells is involved in the induction and maintenance of T cell anergy," J Immunol., 170(7):3637-3644, Apr. 1, 2003.
Seo et al., "Blockade of endogenous B7-H1 suppresses antibacterial protection after primary Listeria monocytogenes infection," Immunology, 123(1):90-99, Oct. 25, 2007.
Seymour et al., "iRECIST: guidelines for response criteria for use in trials testing immunotherapeutics," Lancet Oncol., 18(3):e143-e152, Mar. 2017.
Shaknovich et al., "The promyelocytic leukemia zinc finger protein affects myeloid cell growth, differentiation, and apoptosis," Mol Cell Biol., 18(9):5533-5545, Sep. 1998.
Shalem et al., "Genome-scale CRISPR-Cas9 knockout screening in human cells," Science, 343(6166):84-87, Jan. 3, 2014.
Shao et al., "Deficiency of the DNA repair enzyme ATM in rheumatoid arthritis," J Exp Med., 206(6):1435-1449, May 18, 2009.
Shao et al., "DNA-dependent protein kinase catalytic subunit mediates T-cell loss in rheumatoid arthritis," EMBO Mol Med., 2(10):415-427, Oct. 2010.
Shao et al., "ERK2 phosphorylation of serine 77 regulates Bmf pro-apoptotic activity," Cell Death Dis., 3(1):e253, Jan. 19, 2012, 10 pages.
Sharma et al., "Immune checkpoint targeting in cancer therapy: toward combination strategies with curative potential," Cell, 161(2):205-214, Apr. 9, 2015.
Sharma et al., "The future of immune checkpoint therapy," Science, 348(6230):56-61, Apr. 3, 2015.
Sharon et al., "Preparation of Fv fragment from the mouse myeloma XRPC-25 immunoglobulin possessing anti-dinitrophenyl activity," Biochemistry, 15(7):1591-1594, Apr. 6, 1976.
Sheather, "Density Estimation," Statistical Sci., 19(4):588-597, 2004.
Shenoy et al., "Exosomes Associated with Human Ovarian Tumors Harbor a Reversible Checkpoint of T-cell Responses," Cancer Immunol. Research, 6(2):236-247, Feb. 2018.
Shenoy et al., "IL-15 regulates Bcl-2 family members Bim and Mcl-1 through JAK/STAT and PI3K/AKT pathways in T cells," Eur J Immunology, 44(8):2500-2507, Aug. 2014.
Shin et al., "Cooperative B7-1/2 (CD80/CD86) and B7-DC costimulation of CD4+ T cells independent of the PD-1 receptor," J Exp Med., 198(1):31-38, Jul. 7, 2003.
Sica et al., "B7-H4, a molecule of the B7 family, negatively regulates T cell immunity," Immunity, 18(6):849-861, Jun. 2003.
Sica et al., "Biochemical and immunological characteristics of 4-1BB (CD137) receptor and ligand and potential applications in cancer therapy," Arch Immunol Ther Exp (Warsz)., 47(5):275-279, 1999.
Siddiqi et al., "Rapid Undetectable MRD (uMRD) Responses in Patients with Relapsed/Refractory (R/R) Chronic Lymphocytic Leukemia/Small Lymphocytic Lymphoma (CLL/SLL) Treated with Lisocabtagene Maraleucel (liso-cel), a CD19-Directed CAR T Cell Product: Updated Results from Transcend CLL 004, a Phase 1/2 Study Including Patients with High-Risk Disease Previously Treated with Ibrutinib," Blood, 134(Suppl 1):503, Nov. 13, 2019, 7 pages.
Siddiqui et al., "Enhanced recruitment of genetically modified CX3CR1-positive human T cells into Fractalkine/CX3CL1 expressing tumors: importance of the chemokine gradient," J. Immunotherapy, 4:21, Apr. 19, 2016, 12 pages.
Siddiqui et al., "Tumor-infiltrating Foxp3-CD4+CD25+ T cells predict poor survival in renal cell carcinoma," Clin Cancer Res., 13(7):2075-2081, Apr. 1, 2007.
Simon et al., "B7-h4 is a novel membrane-bound protein and a candidate serum and tissue biomarker for ovarian cancer," Cancer Res., 66(3):1570-1575, Feb. 1, 2006.
Singer et al., "Optimal humanization of 1B4, an Anti-CD18 murine monoclonal antibody, is achieved by correct choice of human v-region framework sequences," J Immunol., 150(7):2844-2857, Apr. 1, 1993.
Skerra et al., "Assembly of a functional immunoglobulin Fv fragment in *Escherichia coli*," Science, 240(4855):1038-1041, May 20, 1988.
Skolnick et al., "From genes to protein structure and function: novel applications of computational approaches in the genomic era," Trends Biotechnol., 18(1):34-39, Jan. 2000.
Smallwood et al., "Extracellular vesicles released by CD40/IL-4-stimulated CLL cells confer altered functional properties to CD4+ T cells," Blood, 128(4):542-552, Jul. 28, 2016.
Smith et al., "BCMA-Targeted CAR T-cell Therapy plus Radiotherapy for the Treatment of Refractory Myeloma Reveals Potential Synergy," Cancer Immunol. Research, Jul. 2019, 7(7):1047-1053.
Smith et al., Differential outcome of IL-2/anti-IL-2 complex therapy on effector and memory CD8+ T cells following vaccination with an adenoviral vector encoding EBV epitopes, J Immunol., 186(10):5784-5790, Apr. 11, 2011.
Smith et al., "GPRC5D is a target for the immunotherapy of multiple myeloma with rationally designed CAR T cells," Sci. Transl. Medicine, Mar. 27, 2019, 11(485)eaau7746, 15 pages.
Smith et al., "Pulmonary deposition and clearance of aerosolized alpha-1-proteinase inhibitor administered to dogs and to sheep," J Clin Invest., 84(4):1145-1154, Oct. 1989.
Sneller et al., "A novel lymphoproliferative/autoimmune syndrome resembling murine lpr/gld disease," J Clin Invest., 90(2):334-341, Aug. 1992.
Socie et al., "Acute graft-versus-host disease: from the bench to the bedside," Blood, Nov. 12, 2009, 114(20):4327-4336.
Solier et al., "Death receptor-induced activation of the Chk2- and histone H2AX-associated DNA damage response pathways," Mol Cell Biol., 29(1):68-82, Oct. 27, 2008.
Song et al., "Effective adoptive immunotherapy of triple-negative breast cancer by folate receptor-alpha redirected CAR T cells is influenced by surface antigen expression level," J. Hematol. Oncology, Jul. 20, 2016, 9(1):56, 12 pages.
Sorge et al., "Amphotropic retrovirus vector system for human cell gene transfer," Mol Cell Biol., 4(9):1730-1737, Sep. 1984.
Soriano, "Targeted and nontargeted liposomes for in vivo transfer to rat liver cells of a plasmid containing the preproinsulin I gene," Proc Natl Acad Sci USA., 80(23):7128-7131, Dec. 1983.
Sotillo et al., "Convergence of Acquired Mutations and Alternative Splicing of CD19 Enables Resistance to CART-19 Immunotherapy," Cancer Discovery, 5(12):1282-1295, Dec. 2015.
Soubeyrand et al., "Artemis phosphorylated by DNA-dependent protein kinase associates preferentially with discrete regions of chromatin," J Mol Biol., 358(5):1200-1211, Mar. 20, 2006.
Stammers et al., "BTL-II: A polymorphic locus with homology to the butyrolphilin gene family, located at the border of the major histocompatibility complex class II and class III regions in human and mouse," Immunogenetics, 51(4-5):373-382, Apr. 2000.
Stamper et al., "Crystal structure of the B7-1/CTLA-4 complex that inhibits human immune responses," Nature, 410(6828):608-611, Mar. 29, 2001.
Sterner et al., "GM-CSF inhibition reduces cytokine release syndrome and neuroinflammation but enhances CAR-T cell function in xenografts," Blood, 133(7):697-709, Feb. 14, 2019.
Sterner et al., "Myeloid cell and cytokine interactions with chimeric antigen receptor-T-cell therapy: implication for future therapies," Curr. Opin. Hematology, 27(1):41-48, Jan. 2020.

(56) References Cited

OTHER PUBLICATIONS

Sterner et al., "Using CRISPR/Cas9 to Knock Out GMCSF in CAR-T Cells," J. Vis. Experiments, 149:e59629, Jul. 2019, 6 pages.
Stoklasek et al., "Combined IL-15/IL-15Ralpha immunotherapy maximizes IL-15 activity in vivo," J Immunol., 177(9):6072-6080, Nov. 1, 2006.
Strasser, "The role of BH3-only proteins in the immune system," Nat Rev Immunol., 5:189-200, Feb. 18, 2005.
Strome et al., "B7-H1 blockade augments adoptive T-cell immunotherapy for squamous cell carcinoma," Cancer Res., 63(19):6501-6505, Oct. 1, 2003.
Strome et al., "Enhanced therapeutic potential of adoptive immunotherapy by in vitro CD28/4-1BB costimulation of tumor-reactive T cells against a poorly immunogenic, major histocompatibility complex class I-negative A9P melanoma," J Immunother., 23(4):430-437, Jul./Aug. 2000.
Stroncek et al., "Myeloid cells in peripheral blood mononuclear cell concentrates inhibit the expansion of chimeric antigen receptor T cells," Cytotherapy, 18(7):893-901, Jul. 2016.
Subudhi et al., "Local expression of B7-H1 promotes organ-specific autoimmunity and transplant rejection," J Clin Invest., 113(5):694-700, Mar. 2004.
Suda et al., "Why do defects in the Fas-Fas ligand system cause autoimmunity?" J Allergy Clin Immunol., 100(6 Pt 2):S97-S101, Dec. 1997.
Sugio et al., "Two type III effector genes of *Xanthomonas oryzae* pv. oryzae control the induction of the host genes OsTFIIAγ1 and OsTFX1 during bacterial blight of rice," Proc. Natl. Acad. Sci. USA, 104(25):10720-10725, Jun. 19, 2007.
Summerton et al., "Morpholino antisense oligomers: design, preparation, and properties," Antisense Nucleic Acid Drug Dev., 7(3):187-195, Jun. 1997.
Sun et al., "CAP-miRSeq: a comprehensive analysis pipeline for microRNA sequencing data," BMC Genomics, 15:423, Jun. 3, 2014, 10 pages.
Sun et al., "Safety and efficacy of targeting CD138 with a chimeric antigen receptor for the treatment of multiple myeloma," Oncotarget, Mar. 22, 2019, 10(24):2369-2383.
Sun et al., "Administration of agonistic anti-4-1BB monoclonal antibody leads to the amelioration of experimental autoimmune encephalomyelitis," J Immunol., 168(3):1457-1465, Feb. 1, 2002.
Sun et al., "Costimulatory molecule-targeted antibody therapy of a spontaneous autoimmune disease," Nat Med., 8(12):1405-1413, Nov. 11, 2002.
Sun et al., "Signaling of 4-1BB Leads to Amelioration of Experimental Autoimmune Encephalomyelitis," FASEB J., vol. 5, p. A1210 Abstract 950.9, 2001.
Sutter et al., "Nonreplicating vaccinia vector efficiently expresses recombinant genes," Proc Natl Acad Sci USA., 89(22):10847-10851, Nov. 15, 1992.
Suzuki et al., "T cell-specific loss of Pten leads to defects in central and peripheral tolerance," Immunity, 14(5):523-534, May 2001.
Suzuki et al., "The dual functions of fas ligand in the regulation of peripheral CD8+ and CD4+ T cells," Proc Natl Acad Sci USA., 97(4):1707-1712, Feb. 15, 2000.
Swallow et al., "B7h, a novel costimulatory homolog of B7.1 and B7.2, is induced by TNFalpha," Immunity, 11(4):423-432, Oct. 1999.
Szajnik et al., "Tumor-derived microvesicles induce, expand and up-regulate biological activities of human regulatory T cells (Treg)," PLoS One, 5(7):e11469, Jul. 22, 2010, 13 pages.
Takahashi et al., "Serum levels of soluble programmed cell death ligand 1 as a prognostic factor on the first-line treatment of metastatic or recurrent gastric cancer," J. Cancer Res. Clin. Oncol., 142(8):1727-1738, Aug. 2016.
Takahashi et al., "Cutting edge: 4-1BB is a bona fide CD8 T cell survival signal," J Immunol., 162(9):5037-5040, May 1, 1999.
Takeda et al., "Critical contribution of liver natural killer T cells to a murine model of hepatitis," Proc Natl Acad Sci USA., 97(10):5498-5503, May 9, 2000.
Tamura et al., "B7-H1 costimulation preferentially enhances CD28-indepenent T-helper cell function," Blood, 97(6):1809-1816, Mar. 15, 2001.
Tamura et al., "Marrow stromal cells induce B7-H1 expression on myeloma cells, generating aggressive characteristics in multiple myeloma," Leukemia, 27(2):464-472, 2013.
Tang et al., "In Vitro-expanded Antigen-specific Regulatory T Cells Suppress Autoimmune Diabetes," J. Exp. Medicine, Jun. 7, 2004, 199(11):1455-1465.
Taylor et al., "Glycogen Synthase Kinase 3 Inactivation Drives T-bet-Mediated Downregulation of Co-receptor PD-1 to Enhance CD8(+) Cytolytic T Cell Responses," Immunity, 44(2):274-286, Feb. 16, 2016.
Taylor et al., "Tumour-derived exosomes and their role in cancer-associated Tcell signalling defects," Br. J. Cancer, 92(2):305-311, Jan. 18, 2005.
Taylor et al., "Human immunoglobulin transgenes undergo rearrangement, somatic mutation and class switching in mice that lack endogenous IgM," Int Immunol., 6(4):579-591, Apr. 1994.
Tazi-Ahnini et al., "Cloning, localization, and structure of new members of the butyrophilin gene family in the juxtatelomenc region of the major histocompatibility complex," Immunogenetics, 47(1):55-63, 1997.
Teh et al., "TNF receptor 2-deficient CD8 T cells are resistant to Fas/Fas ligand-induced cell death," J. Immunology, Nov. 1, 2000, 165(9):4814-4821.
Temin, "Safety considerations in somatic gene therapy of human disease with retrovirus vectors," Hum Gene Ther., 1(2):111-123, Summer 1990.
Templeton et al., "Improved DNA: liposome complexes for increased systemic delivery and gene expression," Nat Biotechnol., 15(7):647-652, Jul. 1997.
Tham et al., "Melanoma-initiating cells exploit M2 macrophage TGFbeta and arginase pathway for survival and proliferation," Oncotarget, 5(23):12027-12042, Dec. 15, 2014.
Theofilopoulos et al., "Tumour necrosis factor and other cytokines in murine lupus," Ann Rheum Dis., 58(suppl 1):149-55, Nov. 1, 1999.
Theofilopoulos et al., "Etiopathogenesis of Murine SLE," Immunol Rev., 55:179-216, 1981.
Thery et al., "Minimal information for studies of extracellular vesicles 2018 (MISEV2018): a position statement of the International Society for Extracellular Vesicles and update of the MISEV2014 guidelines," J. Extracell. Vesicles, 7(1):1535750, Nov. 23, 2018, 47 pages.
Thistlethwaite et al., "The clinical efficacy of first-generation carcinoembryonic antigen (CEACAM5)-specific CAR T cells is limited by poor persistence and transient pre-conditioning-dependent respiratory toxicity," Cancer Immunol. Immunotherapy, Jun. 28, 2017, 66(11):1425-1436.
Thompson et al., "cis-acting sequences required for inducible interleukin-2 enhancer function bind a novel Ets-related protein, Elf-1," Mol Cell Biol., 12(3):1043-1053, Mar. 1992.
Thompson et al., "Costimulatory B7-H1 in renal cell carcinoma patients: Indicator of tumor aggressiveness and potential therapeutic target," Proc Natl Acad Sci USA., 101(49):17174-17179, Nov. 29, 2004.
Thompson et al., "Costimulatory molecule B7-H1 in primary and metastatic clear cell renal cell carcinoma," Cancer, 104(10):2084-2091, Nov. 15, 2005.
Thompson et al., "PD-1 is expressed by tumor-infiltrating immune cells and is associated with poor outcome for patients with renal cell carcinoma," Clin Cancer Res., 13(6):1757-1761, Mar. 15, 2007.
Thompson et al., "Tumor B7-H1 is associated with poor prognosis in renal cell carcinoma patients with long-term follow-up," Cancer Res., 66(7):3381-3385, Apr. 1, 2006.
Thompson et al., "Tumor masses support naive T cell infiltration, activation, and differentiation into effectors," J Exp Med., 207(8):1791-1804, Jul. 26, 2010.
Tian et al., "The relationship between the down-regulation of DNA-PKcs or Ku70 and the chemosensitization in human cervical carcinoma cell line HeLa," Oncol Rep., 18(4):927-932, Oct. 2007.

(56) References Cited

OTHER PUBLICATIONS

Tickner et al., "Functions and therapeutic roles of exosomes in cancer," Front. Oncology, 4:127, May 27, 2014, 8 pages.
Tiedt et al., "RNA-Seq Identifies Circulating miR-125a-5p, miR-125b-5p, and miR-143-3p as Potential Biomarkers for Acute Ischemic Stroke," Circ. Research, 121(8):970-980, Sep. 29, 2017.
Tiegs et al., "A T cell-dependent experimental liver injury in mice inducible by concanavalin A," J Clin Invest., 90(1):196-203, Jul. 1992.
Titomirov, "In vivo electroporation and stable transformation of skin cells of newborn mice by plasmid DNA," Biochim Biophys Acta., 1088(1):131-134, Jan. 17, 1991.
Tocknnan et al., "Considerations in bringing a cancer biomarker to clinical application," Cancer Res., 52(9 Suppl.):2711s-2718s, May 1992.
Todd et al., "Transcription of the interleukin 4 gene is regulated by multiple promoter elements," J Exp Med., 177(6):1663-1674, Jun. 1, 1993.
Topalian et al., "Safety, Activity, and Immune Correlates of Anti-PD-1 Antibody in Cancer," N Engl J Med, 366(26):2443-2454, Jun. 28, 2012.
Townsend et al., "Tumor rejection after direct costimulation of CD8+ T cells by B7-transfected melanoma cells," Science, 259(5093):368-370, Jan. 15, 1993.
Trabattoni et al. "B7-H1 is up-regulated in HIV infection and is a novel surrogate marker of disease progression" Blood, 101(7):2514-2520, Dec. 5, 2002.
Tringler et al., "B7-h4 is highly expressed in ductal and lobular breast cancer," Clin Cancer Res., 11(5):1842-1848, Mar. 1, 2005.
Truneh et al., "Early steps of lymphocyte activation bypassed by synergy between calcium ionophores and phorbol ester," Nature., 313(6000):318-320, Jan. 24, 1985.
Tsai et al., "Long noncoding RNA as modular scaffold of histone modification complexes," Science, 329(5992):689-693, Aug. 6, 2010.
Tseng et al., "B7-DC, a new dendritic cell molecule with potent costimulatory properties for T cells," J Exp Med., 193(7):839-846, Apr. 2, 2001.
Tsuchiya et al., "Differential expression of N-cadherin and E-cadherin in normal human tissues," Arch. Histol. Cytology, Jun. 2006, 69(2):135-145.
Tumeh et al., "PD-1 blockade induces responses by inhibiting adaptive immune resistance," Nature, 515(7528):568-571, Nov. 27, 2014.
Turman et al., "Characterization of a novel gene (NKG7) on human chromosome 19 that is expressed in natural killer cells and T cells," Hum Immunol., 36(1):34-40, Jan. 1993.
Turtle et al., "A distinct subset of self-renewing human memory CD8+ T cells survives cytotoxic chemotherapy," Immunity, 31(5):834-844, Nov. 20, 2009.
Turtle et al., "CD19 CAR-T cells of defined CD4+:CD8+ composition in adult B cell ALL patients," J. Clin. Investigation, 126(6):2123-2138, Jun. 1, 2016.
Turtle et al., "Durable Molecular Remissions in Chronic Lymphocytic Leukemia Treated With CD19-Specific Chimeric Antigen Receptor-Modified T Cells After Failure of Ibrutinib," J. Clin. Oncology, 35(26):3010-3020, Sep. 10, 2017.
Ueda et al., "Sequence-specific DNA damage induced by reduced mitomycin C and 7-N-(p-hydroxyphenyl)mitomycin C.," Nucleic Acids Res., 12(17):6673-6683, Sep. 11, 1984.
Ueha et al., "Robust Antitumor Effects of Combined Anti-CD4-Depleting Antibody and Anti-PD-1/PD-L1 Immune Checkpoint Antibody Treatment in Mice," Cancer Immunol Res., 3(6):631-640, Jun. 2015.
Umansky et al., "Myeloid-derived suppressor cells in malignant melanoma," J Dtsch Dermatol Ges., 12(11):1021-1027, Nov. 2014.
Verhoeyen et al., "Reshaping human antibodies: grafting an antilysozyme activity," Science, 239(4847):1534-1536, Mar. 25, 1988.
Vesely et al., "Natural innate and adaptive immunity to cancer," Annu Rev Immunol., 29:235-271, 2011.
Veuger et al., "Radiosensitization and DNA repair inhibition by the combined use of novel inhibitors of DNA-dependent protein kinase and poly(ADP-ribose) polymerase-1," Cancer Res., 63(18):6008-6015, Sep. 15, 2003.
Vinay et al., "Role of 4-1BB in immune responses," Semin Immunol., 10(6):481-489, Dec. 1998.
Wahl et al., "Improved radioimaging and tumor localization with monoclonal F(ab')2" J Nucl Med., 24(4):316-25, Apr. 1983.
Wallin et al., "Atezolizumab in combination with bevacizumab enhances antigen-specific T-cell migration in metastatic renal cell carcinoma," Nat Commun., 7:12624, Aug. 30, 2016, 8 pages.
Walter et al., "The peripheral benzodiazepine receptor ligand PK11195 overcomes different resistance mechanisms to sensitize AML cells to gemtuzumab ozogamicin," Blood, 103(11):4276-4284, Jun. 1, 2004.
Walunas et al., "CTLA-4 ligation blocks CD28-dependent T cell activation," J Exp Med., 183(6):2541-2550, Jun. 1, 1996.
Wang et al., "Costimulation of T cells by B7-H2, a B7-like molecule that binds ICOS," Blood, 96(8):2808-2813, Oct. 15, 2000.
Wang et al., "Doxorubicin induces apoptosis in normal and tumor cells via distinctly different mechanisms. intermediacy of H(2)O(2)- and p53-dependent pathways," J Biol Chem., 279(24):25535-25543, Mar. 30, 2004.
Wang et al., "Lenalidomide Enhances the Function of CS1 Chimeric Antigen Receptor-Redirected T Cells Against Multiple Myeloma," Clin. Cancer Research, Jan. 1, 2018, 24(1):106-119.
Wang et al., "Ligand binding sites of inducible costimulator and high avidity mutants with improved function," J Exp Med., 195(8):1033-1041, Apr. 15, 2002.
Wang et al., "Molecular modeling and functional mapping of B7-H1 and B7-DC uncouple costimulatory function from PD-1 interaction," J Exp Med., 197(9):1083-1091, Apr. 28, 2003.
Wang et al., "Multiple Functions of the RNA-Binding Protein HuR in Cancer Progression, Treatment Responses and Prognosis," Int J Mol Sci., 14(5):10015-10041, May 10, 2013.
Wang et al., "RVboost: RNA-seq variants prioritization using a boosting method," Bioinformatics, 30(23):3414-3416, Dec. 1, 2014.
Wang et al., "Serum levels of soluble programmed death ligand 1 predict treatment response and progression free survival in multiple myeloma," Oncotarget, 6(38):41228-36, Dec. 2015.
Wang et al., "Targeting Fibroblast Activation Protein in Tumor Stroma with Chimeric Antigen Receptor T Cells Can Inhibit Tumor Growth and Augment Host Immunity without Severe Toxicity," Cancer Immunol. Research, Feb. 2014, 2(2):154-166.
Wang, "Lyophilization and development of solid protein pharmaceuticals," Int J Pharm., 203(1-2):1-60, Aug. 10, 2000.
Wang, "pH-sensitive immunoliposomes mediate target-cell-specific delivery and controlled expression of a foreign gene in mouse," Proc Natl Acad Sci USA., 84(22):7851-7855, Nov. 1987.
Ward et al., "Binding activities of a repertoire of single immunoglobulin variable domains secreted from *Escherichia coli*," Nature, 341(6242):544-546, Oct. 12, 1989.
Webster et al., "Targeting molecular and cellular inhibitory mechanisms for improvement of antitumor memory responses reactivated by tumor cell vaccine," J Immunol., 179(5):2860-2869, Sep. 1, 2007.
Weide et al., "Myeloid-derived suppressor cells predict survival of patients with advanced melanoma: comparison with regulatory T cells and NY-ESO-1-or melan-A-specific T cells," Clin Cancer Res., 20(6):1601-1609, Mar. 15, 2014.
Weiss, "Hot Prospect for New Gene Amplifier: Ligase chain reaction, a combination DNA amplifier and genetic screen could do for DNA diagnostics what PCR has done for basic molecular biology," Science, 254(5036):1292-1293, Nov. 29, 1991.
Wherry et al., "Lineage relationship and protective immunity of memory CD8 T cell subsets," Nat Immunol., 4(3):225-234, Feb. 3, 2003.
Whilding et al., "CAR T-cell immunotherapy: The path from the by-road to the freeway?," Mol. Oncology, Oct. 23, 2015, 9(10):1994-2018.
White et al., "Fractalkine has anti-apoptotic and proliferative effects on human vascular smooth muscle cells via epidermal growth factor receptor signalling," Cardiovasc Res., 85(4):825-835, Mar. 1, 2010.

(56) References Cited

OTHER PUBLICATIONS

Wick et al., "The hepatic immune system," Crit Rev Immunol., 22(1):47-103, 2002.
Wieckowski et al., "Tumor-derived microvesicles promote regulatory T cell expansion and induce apoptosis in tumor-reactive activated CD8+ T lymphocytes," J. Immunology, 183(6):3720-3730, Sep. 15, 2009.
Wilcox et al., "Provision of antigen and CD137 signaling breaks immunological ignorance, promoting regression of poorly immunogenic tumors," J Clin Invest., 109(5):651-659, Mar. 2002.
Williams et al., "Introduction of foreign genes into tissues of living mice by DNA-coated microprojectiles," Proc Natl Acad Sci USA., 88(7):2726-2730, Apr. 1, 1991.
Williams et al., "T cell immune reconstitution following lymphodepletion," Semin Immunol., 19(5):318-330, Oct. 2007.
Williams et al., "The immunoglobulin superfamily—domains for cell surface recognition," Annu Rev Immunol., 6:381-405, 1988.
Williams et al., "Nitric oxide synthase plays a signaling role in TCR-triggered apoptotic death," J Immunol., 161(12):6526-6531, Dec. 15, 1998.
Willmore et al., "A novel DNA-dependent protein kinase inhibitor, NU7026, potentiates the cytotoxicity of topoisomerase II poisons used in the treatment of leukemia," Blood, 103(12):4659-4665, Mar. 9, 2004.
Winter et al., "Man-made antibodies," Nature, 349(6307): 293-299, Jan. 24, 1991.
Winter et al., "Making antibodies by phage display technology," Annu Rev Immunol., 12:433-455, 1994.
Wintterle et al., "Expression of the B7-related molecule B7-H1 by glioma cells: a potential mechanism of immune paralysis," Cancer Res., 63(21):7462-7467, Nov. 1, 2003.
Wofsy et al., "The proliferating cells in autoimmune MRL/lpr mice lack L3T4, an antigen on "helper" T cells that is involved in the response to class II major histocompatibility antigens," J Immunol., 132(6):2686-2689, Jun. 1984.
Wofsy, "Treatment of murine lupus with anti-CD4 monoclonal antibodies," Immunol Ser., 59:221-236, 1993.
Wojciechowski et al., "Bim/Bcl-2 balance is critical for maintaining naive and memory T cell homeostasis," J Exp Med., 204(7):1665-1675, Jul. 9, 2007.
Wolff, "Direct gene transfer into mouse muscle in vivo," Science, 247(4949 Pt 1):1465-1468, Mar. 23, 1990.
Wolke et al., "Assigning the phenotype of a natural regulatory T-cell to the human T-cell line, KARPAS-299," Int J Mol Med., 17(2):275-278, Feb. 2006.
Wong et al., "Human GM-CSF: molecular cloning of the complementary DNA and purification of the natural and recombinant proteins," Science, 228(4701):810-815, May 17, 1985.
Wu et al., "Emerging roles and therapeutic value of exosomes in cancer metastasis," Mol. Cancer, 18(1):53, Mar. 30, 2019, 11 pages.
Wu et al., "Targeting B7-H1 (PD-L1) Sensitizes Cancer Cells to Chemotherapy," Heliyon, 4(12):e01039, Dec. 18, 2018, 24 pages.
Wu et al., "The double-edged sword of activation-induced cytidine deaminase," J Immunol., 174(2):934-941, Jan. 15, 2005.
Wu, "Receptor-mediated gene delivery and expression in vivo," J Biol Chem., 263(29):14621-14624, Oct. 15, 1988.
Wu, "Targeting genes: delivery and persistent expression of a foreign gene driven by mammalian regulatory elements in vivo," J Biol Chem., 264(29):16985-16987, Ocober. 15, 1989.
Xu et al., "A potential new pathway for PD-L1 costimulation of the CD8-T cell response to Listeria monocytogenes infection," PLoS One, 8(2):e56539, Feb. 11, 2013, 8 pages.
Xu et al., "Autophagy is essential for effector CD8(+) T cell survival and memory formation," Nat Immunol., 15(12):1152-1161, Dec. 2014.
Xu et al., "Exploratory trial of a biepitopic CAR T-targeting B cell maturation antigen in relapsed/refractory multiple myeloma," Proc. Natl. Acad. Sci. USA, May 7, 2019, 116(19):9543-9551.
Xu et al., "The inducible expression of the tumor suppressor gene PTEN promotes apoptosis and decreases cell size by inhibiting the PI3K/Akt pathway in Jurkat T cells," Cell Growth Differ., 13(7):285-296, Jul. 2002.
Yalniz et al., "Safety and Efficacy of Infliximab Therapy in the Setting of Steroid-Refractory Acute Graft-versus-Host Disease," Biol. Blood Marrow Transplantation, Sep. 2017, 23(9):1478-1484.
Yamamoto et al., "B7-H1 expression is regulated by MEK/ERK signaling pathway in anaplastic large cell lymphoma and Hodgkin lymphoma," Cancer Sci., 100(11):2093-2100, Aug. 1, 2009.
Yamauchi et al., "23.02: Defining CD8+ T-cell Subsets that are Rescued by Pd-1/PD-L1 Blockade in the Tumor Microenvironment," Abstract, presented at Proceedings of the 13th Annual Academic Surgical Congress, Jacksonville, FL, Jan. 30-Feb. 1, 2018, 4 pages.
Yamazaki et al., "Effective expansion of alloantigen-specific Foxp3+ CD25+ CD4+ regulatory T cells by dendritic cells during the mixed leukocyte reaction," Proc. Natl. Acad. Sci. USA, Feb. 21, 2006, 103(8):2758-2763.
Yamazaki et al., "Expression of programmed death 1 ligands by murine T cells and APC," J Immunol., 169(10):5538-5545, Nov. 15, 2002.
Yan et al., "CX3CR1 identifies PD-1 therapy-responsive CD8+ T cells that withstand chemotherapy during cancer chemoimmunotherapy," JCI Insight, 3(8):e97828, Apr. 19, 2018, 13 pages.
Yan et al., "Effect of paclitaxel and carboplatin on tumor-reactive T cells and the efficacy of PD-1 blockade," J. Clin. Oncology, 35(7S):65, Mar. 1, 2017.
Yan et al., "The Mayo Clinic experience in patients with metastatic melanoma who have failed previous pembrolizumab treatment," J Clin Oncol., 34(15 Suppl):e21014, May 20, 2016.
Yang et al., "In vitro priming of tumor-reactive cytolytic T lymphocytes by combining IL-10 with B7-CD28 costimulation," J Immunol., 155(8):3897-3903, Oct. 15, 1995.
Yang et al., "In vivo and in vitro gene transfer to mammalian somatic cells by particle bombardment," Proc Natl Acad Sci USA., 87(24):9568-9572, Dec. 1990.
Yang et al., "Os8N3 is a host disease-susceptibility gene for bacterial blight of rice," Proc. Natl. Acad. Sci. USA, 103(27):10503-10508, Jul. 5, 2006.
Yang et al., "T cells expressing NKG2D chimeric antigen receptors efficiently eliminate glioblastoma and cancer stem cells," J. Immunother. Cancer, Jul. 9, 2019, 7(1):171, 13 pages.
Yang, "Gene transfer into mammalian somatic cells in vivo," Crit Rev Biotechnol., 12(4):335-356, 1992.
Yao et al., "Interferon regulatory factor 4 sustains CD8(+) T cell expansion and effector differentiation," Immunity, 39(5):833-845, Nov. 14, 2013.
Yin et al., "Checkpoint Blockade Reverses Anergy in IL-13Ralpha2 Humanized scFv-Based CAR T Cells to Treat Murine and Canine Gliomas," Mol. Ther. Oncolytics, 11:20-38, Aug. 28, 2018.
Yin et al., "CpG-induced antitumor immunity requires IL-12 in expansion of effector cells and down-regulation of PD-1," Oncotarget, 7(43):70223-70231, Oct. 25, 2016.
Yokosuka et al., "Programmed cell death 1 forms negative costimulatory microclusters that directly inhibit T cell receptor signaling by recruiting phosphatase SHP2," J Exp Med., 209(6):1201-1217, Jun. 4, 2012.
Yoon et al., "FVIII-specific human chimeric antigen receptor T-regulatory cells suppress T- and B-cell responses to FVIII," Blood, Jan. 12, 2017, 129(2):238-245.
Yoshida et al., "All-trans retinoic acid enhances cytotoxic effect of T cells with an anti-CD38 chimeric antigen receptor in acute myeloid leukemia," Clin. Transl. Immunology, Dec. 9, 2016, 5(12):e116, 7 pages.
Yoshinaga et al., "T-cell co-stimulation through B7RP-1 and ICOS," Nature, 402(6763):827-832, Dec. 16, 1999.
Yotsumoto et al., "Endosomal translocation of CpG-oligodeoxynucleotides inhibits DNA-PKcs-dependent IL-10 production in macrophages," J Immunol., 180(2):809-816, Jan. 15, 2008.

(56) References Cited

OTHER PUBLICATIONS

Youngnak et al., "Differential binding properties of B7-H1 and B7-DC to programmed death-1," Biochem Biophys Res Commun., 307(3):672-677, Aug. 1, 2003.
Yu et al., "Bim is required for T-cell allogeneic responses and graft-versus-host disease in vivo," Am J Blood Res., 2(1):77-85, Jan. 15, 2012.
Yuan et al., "Focus on histone variant H2AX: to be or not to b," FEBS Lett., 584(17):3717-3724, May 21, 2010.
Zang et al., "B7x: a widely expressed b7 family member that inhibits T cell activation," Proc Natl Acad Sci USA., 100(18):10388-10392, Aug. 14, 2003.
Zang et al., "The B7 family and cancer therapy: costimulation and coinhibition," Clin Cancer Res., 13(18 Pt 1):5271-5279, Sep. 15, 2007.
Zavialov et al., "Human adenosine deaminase 2 induces differentiation of monocytes into macrophages and stimulates proliferation of T helper cells and macrophages," J. Leukoc. Biology, Aug. 2010, 88(2):279-290.
Zeiser et al., "Acute Graft-versus-Host Disease—Biologic Process, Prevention, and Therapy," N. Engl. J. Medicine, Nov. 30, 2017, 377(22):2167-2179.
Zelenin et al., "Genetic transformation of mouse cultured cells with the help of high-velocity mechanical DNA injection," FEBS Lett., 244(1):65-67, Feb. 13, 1989.
Zelenin et al., "High-velocity mechanical DNA transfer of the chloramphenicolacetyl transferase gene into rodent liver, kidney and mammary gland cells in organ explants and in vivo," FEBS Lett., 280(1):94-96, Mar. 11, 1991.
Zhang et al., "A high M1/M2 ratio of tumor-associated macrophages is associated with extended survival in ovarian cancer patients," J Ovarian Res., 7:19, Feb. 8, 2014.
Zhang et al., "An Anti-CD103 Immunotoxin Promotes Long-Term Survival of Pancreatic Islet Allografts," Am. J. Transplantation, Aug. 20, 2009, 9(9):2012-2023.
Zhang et al., "Exosomes and cancer: a newly described pathway of immune suppression," Clin. Cancer Research, 17(5):959-964, Mar. 1, 2011.
Zhang et al., "PD-1/PD-L1 interactions inhibit antitumor immune responses in a murine acute myeloid leukemia model," Blood, 114(8):1545-1552, May 5, 2009.
Zhang et al., "Theiler's virus-infected L-selectin-deficient mice have decreased infiltration of CD8(+) T lymphocytes in central nervous system but clear the virus," J Neuroimmunol., 116(2):178-187, Jun. 1, 2001.
Zhang et al., "Treatment of CD20-directed Chimeric Antigen Receptor-modified T cells in patients with relapsed or refractory B-cell non-Hodgkin lymphoma: an early phase IIa trial report," Signal Transduct. Target. Therapy, Mar. 11, 2016, 1:16002.
Zhao et al., "A phase 1, open-label study of LCAR-B38M, a chimeric antigen receptor T cell therapy directed against B cell maturation antigen, in patients with relapsed or refractory multiple myeloma," J. Hematol. Oncology, Dec. 20, 2018, 11(1):141, 8 pages.
Zhao et al., "In vivo activated CD103+CD4+ regulatory T cells ameliorate ongoing chronic graft-versus-host disease," Blood, Sep. 1, 2008, 112(5):2129-2138.
Zhou et al., "Inducible-costimulator-mediated suppression of human immunodeficiency virus type 1 replication in CD4+ T lymphocytes," Virology, 325(2):252-263, Aug. 1, 2004.
Zitvogel et al., "Immunological aspects of cancer chemotherapy," Nat Rev Immunol., 8(1):59-73, Jan. 2008.
Zou et al., "Inhibitory B7-family molecules in the tumour microenvironment," Nat Rev Immunol., 8(6):467-477, Jun. 2008.
Zula et al., "The role of cell type-specific responses in IFN-β therapy of multiple sclerosis," Proc Natl Acad Sci USA., 108(49):19689-19694, Nov. 21, 2011.
Zumla et al. "Granulomatous infections: etiology and classification," Clin Infect Dis., 23(1):146-158, Jul. 1996.
Zwiebel et al., "Drug delivery by genetically engineered cell implants," Ann NY Acad Sci., 618:394-404, 1991.
Office Action in European Appln. No. 19780974.2, dated Jul. 11, 2023, 14 pages.
Grupp et al., "T cells engineered with a chimeric antigen receptor (CAR) targeting CD19 (CTL019) produce significant in vivo proliferation, complete responses and long-term persistence without GVHD in children and adults with relapsed, refractory ALL" Blood, Nov. 15, 2013, 122(21):67, 3 pages.
ClinicalTrials.gov [online], "A Clinical Research of CAR T Cells Targeting EpCAM Positive Cancer (CARTEPC)," NCT03013712, Jan. 2017, last updated Jan. 2017, retrieved from URL<https://www.clinicaltrials.gov/study/NCT03013712>, 9 pages.
PCT International Search Report and Written Opinion in International Appln. No. PCT/US2023/078478, mailed on Feb. 7, 2024, 11 pages.
Zhang et al., "Chimeric Antigen Receptor (CAR) Treg: A Promising Approach to Inducing Immunological Tolerance," Front. Immunol., Oct. 2018, 9:2359, 8 pages.
Agarwal et al., "In vivo generated human CAR T cells eradicate tumor cells," Oncoimmunology, Oct. 10, 2019, 8(12):E1671761, 7 pages.
Bender et al., "Receptor-Targeted Nipah Virus Glycoproteins Improve Cell-Type Selective Gene Delivery and Reveal a Preference for Membrane-Proximal Cell Attachment," PLOS Pathogens, Jun. 9, 2016, 12(6):E1005641, 28 pages.
Buchholz et al., "Surface-Engineered Viral Vectors for Selective and Cell Type-Specific Gene Delivery," Trends in Biotechnology, Dec. 2015, 33(12):777-790.
Frank et al., "Surface-Engineered Lentiviral Vectors for Selective Gene Transfer into Subtypes of Lymphocytes," Mol. Ther. Methods Clin. Development, Mar. 2019, 12:19-31.
Pfeiffer et al., "In vivo generation of human CD19-CAR T cells results in B-cell depletion and signs of cytokine release syndrome," EMBO Mol. Medicine, Sep. 17, 2018, 10(11):E9158, 11 pages.
Zhou et al., "Exclusive Transduction of Human CD4+ T Cells upon Systemic Delivery of CD4-Targeted Lentiviral Vectors," J. Immunology, Jul. 31, 2015, 195(5):2493-2501.
Baek et al., "In vitro migration capacity of human adipose tissue-derived mesenchymal stem cells reflects their expression of receptors for chemokines and growth factors," Exp. Mol. Medicine, Oct. 2011, 43(10):596-603.
Barbarino et al., "Functional role of Bruton's tyrosine kinase inhibitor therapy in the tumor microenvironment of B-cell malignancies," Oncol Res Treat, Oct. 2019, 42(suppl 4):220-221, 5 pages (Abstract Only).
Beyersdorf et al., "CD28 co-stimulation in T-cell homeostasis: a recent perspective," Immunotargets Therapy, May 2015, 4:111-122.
Boardman et al., "Expression of a Chimeric Antigen Receptor Specific for Donor HLA Class I Enhances the Potency of Human Regulatory T Cells in Preventing Human Skin Transplant Rejection," Am. J. Transplantation, Feb. 2017, 17(4):931-943.
Boroughs et al., "Chimeric antigen receptor costimulation domains modulate human regulatory T cell function," JCI Insight, Mar. 2019, 5(8):e126194, 19 pages.
Charvet et al., "Vav1 promotes T cell cycle progression by linking TCR/CD28 costimulation to FOXO1 and p27kipl expression," J. Immunology, Oct. 2006, 177(8):5024-5031.
Cheng et al., "The influence of fibroblast growth factor 2 on the senescence of human adipose-derived mesenchymal stem cells during long-term culture," Stem Cells Transl. Medicine, Dec. 2019, 9(4):518-530.
Cox et al., "GM-CSF disruption in CART cells modulates T cell activation and enhances CART cell anti-tumor activity," Leukemia, 36:1635-1645, Apr. 19, 2022.
Cox et al., "Leukemic extracellular vesicles induce chimeric antigen receptor T cell dysfunction in chronic lymphocytic leukemia," Mol. Therapy, Jan. 2021, 29(4):1529-1540.
Dmitrieva et al., "Bone marrow- and subcutaneous adipose tissue-derived mesenchymal stem cells: differences and similarities," Cell Cycle, Jan. 2012, 11(2):377-383.

(56) References Cited

OTHER PUBLICATIONS

Dominici et al., "Minimal criteria for defining multipotent mesenchymal stromal cells. The International Society for Cellular Therapy position statement," Cytotherapy, Feb. 2006, 8(4):315-317.
Dorronsoro et al., "Human mesenchymal stromal cells modulate T-cell responses through TNF-α-mediated activation of NF-κB," Eur. J. Immunology, Dec. 2013, 44(2):480-488.
Dorronsoro et al., "Intracellular role of IL-6 in mesenchymal stromal cell immunosuppression and proliferation," Sci. Reports, Dec. 2020, 10(1):21853, 12 pages.
English et al., "IFN-γ and TNF-α differentially regulate immunomodulation by murine mesenchymal stem cells," Immunol. Letters, Apr. 2007, 110(2):91-100.
Estrada-Capetillo et al., "CD28 is expressed by macrophages with anti-inflammatory potential and limits their T-cell activating capacity," Eur. J. Immunology, Nov. 2020, 51(4):824-834.
Extended European Search Report in European Appln. No. 19780974.2, dated Nov. 30, 2021, 14 pages.
Extended European Search Report in European Appln. No. 19784411.1, dated Dec. 20, 2021, 12 pages.
Extended European Search Report in European Appln. No. 19879051.1, dated Dec. 14, 2022, 8 pages.
Extended European Search Report in European Appln. No. 19880748.9, dated Jun. 29, 2022, 10 pages.
Fan et al., "Mesenchymal stem cells alleviate experimental autoimmune cholangitis through immunosuppression and cytoprotective function mediated by galectin-9," Stem Cell Res. Therapy, Sep. 2018, 9(1):237, 12 pages.
Fraietta et al., "Ibrutinib enhances chimeric antigen receptor T-cell engraftment and efficacy in leukemia," Blood, Mar. 2016, 127(9):1117-1127.
Gao et al., "Mesenchymal stem cells and immunomodulation: current status and future prospects," Cell Death Disease, Jan. 2016, 7:e2062, 11 pages.
GenBank Accession No. AB032738.1, "*Homo sapiens* gene for chemokine receptor CXCR3, partial cds," dated Jul. 26, 2016, 2 pages.
GenBank Accession No. AC003959.1, "*Homo sapiens* chromosome 5, P1 clone 1029A7 (LBNL H15), complete sequence," dated Jul. 24, 2016, 23 pages.
GenBank Accession No. AC011377.6, "*Homo sapiens* chromosome 5 clone CTB-120L21, complete sequence," dated Aug. 15, 2001, 13 pages.
GenBank Accession No. AF363458.1, "*Homo sapiens* programmed cell death 1 (PDCD1) gene, exons 1 through 5 and complete cds," dated Mar. 18, 2003, 4 pages.
GenBank Accession No. AL136985.11, "Human DNA sequence from clone RP11-63G10 on chromosome 1p32.1-32.3, complete sequence," dated Jan. 24, 2013, 33 pages.
GenBank Accession No. CH471059.2, "*Homo sapiens* 211000035844098 genomic scaffold, whole genome shotgun sequence," dated Mar. 23, 2015, 7 pages.
GenBank Accession No. CH471062.2, "*Homo sapiens* 211000035832302 genomic scaffold, whole genome shotgun sequence," dated Mar. 23, 2015, 6 pages.
GenBank Accession No. CQ834184.1, "Sequence 55 from Patent WO2004058805," dated Jul. 29, 2004, 2 pages.
GenBank Accession No. DQ789232.1, "*Homo sapiens* interferon regulatory factor-1 (IRF1) gene, promoter region and complete cds," dated Jul. 11, 2007, 3 pages.
GenBank Accession No. EF064716.1, "*Homo sapiens* programmed cell death 1 (PDCD1) gene, complete cds," dated Nov. 13, 2006, 7 pages.
GenBank Accession No. NM_000572.2, "*Homo sapiens* interleukin 10 (IL10), mRNA," dated Oct. 6, 2016, 3 pages.
GenBank Accession No. NM_000594.3, "*Homo sapiens* tumor necrosis factor (TNF), mRNA," dated Oct. 6, 2016, 4 pages.
GenBank Accession No. NM_000758.3, "*Homo sapiens* colony stimulating factor 2 (CSF2), mRNA," dated Jan. 16, 2016, 3 pages.
GenBank Accession No. NM_000759.3, "*Homo sapiens* colony stimulating factor 3 (CSF3), transcript variant 1, mRNA," dated Oct. 6, 2016, 4 pages.
GenBank Accession No. NM_001008540.2, "*Homo sapiens* C-X-C motif chemokine receptor 4 (CXCR4), transcript variant 1, mRNA," dated Apr. 8, 2017, 4 pages.
GenBank Accession No. NM_001142797.1, "*Homo sapiens* C-X-C motif chemokine receptor 3 (CXCR3), transcript variant 2, mRNA," dated Oct. 6, 2016, 4 pages.
GenBank Accession No. NM_001165412.1, "*Homo sapiens* nuclear factor kappa B subunit 1 (NFKB1), transcript variant 2, mRNA," dated May 18, 2016, 7 pages.
GenBank Accession No. NM_001319226.1, "*Homo sapiens* nuclear factor kappa B subunit 1 (NFKB1), transcript variant 3, mRNA," dated May 18, 2016, 7 pages.
GenBank Accession No. NM_001330163.1, "*Homo sapiens* galectin 9 (LGALS9), transcript variant 4, mRNA," dated Sep. 11, 2016, 3 pages.
GenBank Accession No. NM_001348056.1, "*Homo sapiens* C-X-C motif chemokine receptor 4 (CXCR4), transcript variant 3, mRNA," dated Apr. 8, 2017, 4 pages.
GenBank Accession No. NM_001348059.1, "*Homo sapiens* C-X-C motif chemokine receptor 4 (CXCR4), transcript variant 4, mRNA," dated Apr. 8, 2017, 4 pages.
GenBank Accession No. NM_001354924.1, "*Homo sapiens* interferon regulatory factor 1 (IRF1), transcript variant 2, mRNA," dated Aug. 29, 2017, 4 pages.
GenBank Accession No. NM_001354925.1, "*Homo sapiens* interferon regulatory factor 1 (IRF1), transcript variant 3, mRNA," dated Aug. 29, 2017, 4 pages.
GenBank Accession No. NM_001361665.1, "*Homo sapiens* fibroblast growth factor 2 (FGF2), mRNA," dated Mar. 28, 2018, 5 pages.
GenBank Accession No. NM_001382624.1, "*Homo sapiens* interleukin 10 (IL10), transcript variant 2, mRNA," dated May 18, 2020, 3 pages.
GenBank Accession No. NM_001382625.1, "*Homo sapiens* nuclear factor kappa B subunit 1 (NFKB1), transcript variant 4, mRNA," dated May 18, 2020, 8 pages.
GenBank Accession No. NM_001411087.1, "*Homo sapiens* RELB proto-oncogene, NF-kB subunit (RELB), transcript variant 2, mRNA," dated Aug. 22, 2022, 5 pages.
GenBank Accession No. NM_001504.1, "*Homo sapiens* C-X-C motif chemokine receptor 3 (CXCR3), transcript variant 1, mRNA," dated Oct. 6, 2016, 5 pages.
GenBank Accession No. NM_002006.4, "*Homo sapiens* fibroblast growth factor 2 (FGF2), mRNA," dated Oct. 6, 2016, 6 pages.
GenBank Accession No. NM_002198.2, "*Homo sapiens* interferon regulatory factor 1 (IRF1), mRNA," dated Aug. 12, 2016, 4 pages.
GenBank Accession No. NM_002228.3, "*Homo sapiens* Jun proto-oncogene, AP-1 transcription factor subunit (JUN), mRNA," dated Jan. 4, 2017, 6 pages.
GenBank Accession No. NM_002308.3, "*Homo sapiens* galectin 9 (LGALS9), transcript variant 2, mRNA," dated Sep. 10, 2016, 4 pages.
GenBank Accession No. NM_002986.2, "*Homo sapiens* C-C motif chemokine ligand 11 (CCL11), mRNA," dated Mar. 3, 2016, 4 pages.
GenBank Accession No. NM_005018.2, "*Homo sapiens* programmed cell death 1 (PDCD1), mRNA," dated Sep. 15, 2016, 4 pages.
GenBank Accession No. NM_006509.3, "*Homo sapiens* RELB proto-oncogene, NF-kB subunit (RELB), mRNA," dated May 1, 2016, 4 pages.
GenBank Accession No. NM_009587.2, "*Homo sapiens* galectin 9 (LGALS9), transcript variant 1, mRNA," dated Sep. 10, 2016, 4 pages.
GenBank Accession No. NM_032782.4, "*Homo sapiens* hepatitis A virus cellular receptor 2 (HAVCR2), mRNA," dated Sep. 1, 2016, 4 pages.
GenBank Accession No. NM_172219.2, "*Homo sapiens* colony stimulating factor 3 (CSF3), transcript variant 2, mRNA," dated Oct. 6, 2016, 4 pages.

(56) References Cited

OTHER PUBLICATIONS

Golovina et al., "CD28 costimulation is essential for human T regulatory expansion and function," J. Immunology, Aug. 2008, 181(4):2855-2868.
Guess et al., "Safety Profile of Good Manufacturing Practice Manufactured Interferon gamma-Primed Mesenchymal Stem/Stromal Cells for Clinical Trials," Stem Cells Transl. Medicine, Sep. 2017, 6(10):1868-1879.
Guo et al., "Interleukin-1β induces CXCR3-mediated chemotaxis to promote umbilical cord mesenchymal stem cell transendothelial migration," Stem Cell Res. Therapy, Oct. 2018, 9(1):281, 15 pages.
Guo et al., "NF-KappaB Pathway Is Involved in Bone Marrow Stromal Cell-Produced Pain Relief," Front. Integr. Neuroscience, Oct. 2018, 12:49, 10 pages.
Gyorgy et al., "Membrane vesicles, current state-of-the-art: emerging role of extracellular vesicles," Cell. Mol. Life Sciences, May 2011, 68(16):2667-2688.
Hacein-Bey et al., "A serious adverse event after successful gene therapy for X-linked severe combined immunodeficiency," N. Engl. J. Medicine, Jan. 2003, 348(3):255-266.
Haring et al., "Interfering With Inflammation: Heterogeneous Effects of Interferons in Graft-Versus-Host Disease of the Gastrointestinal Tract and Inflammatory Bowel Disease," Front. Immunology, Jun. 2021, 12:705342, 16 pages.
Harrell et al., "Mesenchymal Stem Cell-Derived Exosomes and Other Extracellular Vesicles as New Remedies in the Therapy of Inflammatory Diseases," Cells, Dec. 2019, 8(12):1605, 22 pages.
Hefazi et al., "Regulatory T Cell Therapy of Graft-versus-Host Disease: Advances and Challenges," Int. J. Mol. Sciences, Sep. 2021, 22(18):9676, 27 pages.
Howe et al., "Insertional mutagenesis combined with acquired somatic mutations causes leukemogenesis following gene therapy of SCID-X1 patients," J. Clin. Investigation, Sep. 2008, 118(9):3143-3150.
Jutz et al., "Assessment of costimulation and coinhibition in a triple parameter T cell reporter line: Simultaneous measurement of NF-kappaB, NFAT and AP-1," J. Immunol. Methods, Jan. 2016, 430:10-20.
Kalimuthu et al., "In Vivo Tracking of Chemokine Receptor CXCR4-Engineered Mesenchymal Stem Cell Migration by Optical Molecular Imaging," Stem Cells International, Jun. 2017, 2017:8085637, 10 pages.
Kaltschmidt et al., "The Transcription Factor NF-kappaB in Stem Cells and Development," Cells, Aug. 2021, 10(8):2042, 17 pages.
Kanai et al., "Interferon-gamma enhances the therapeutic effect of mesenchymal stem cells on experimental renal fibrosis," Sci. Reports, Jan. 2021, 11(1):850, 14 pages.
Kim et al., "Enhanced Immunosuppressive Properties of Human Mesenchymal Stem Cells Primed by Interferon-gamma," EBioMedicine, Jan. 2018, 28:261-273.
Kim et al., "Galectin-9 is Involved in Immunosuppression Mediated by Human Bone Marrow-derived Clonal Mesenchymal Stem Cells," Immune Network, Oct. 2015, 15(5):241-251.
Kim et al., "MicroRNAs miR-125a and miR-125b constitutively activate the NF-κB pathway by targeting the tumor necrosis factor alpha-induced protein 3 (TNFAIP3, A20)," Proc. Natl. Acad. Sci. USA, May 2012, 109(20):7865-7870.
Krämer et al., "Causal analysis approaches in Ingenuity Pathway Analysis," Bioinformatics, Dec. 2013, 30(4):523-530.
Lai et al., "Fibroblast growth factor 2 (Fgf2) inhibits differentiation of mesenchymal stem cells by inducing Twist2 and Spry4, blocking extracellular regulated kinase activation, and altering Fgf receptor expression levels," Stem Cells, Jul. 2011, 29(7):1102-1111.
Lamb et al., "Gut-Selective Integrin-Targeted Therapies for Inflammatory Bowel Disease," J. Crohns Colitis, Aug. 2018, 12(S2):S653-S668.
Lin et al., "Efficient lentiviral transduction of human mesenchymal stem cells that preserves proliferation and differentiation capabilities," Stem Cells Transl. Medicine, Nov. 2012, 1(12):886-897.
Lin et al., "Preconditioning of murine mesenchymal stem cells synergistically enhanced immunomodulation and osteogenesis," Stem Cell Res. Therapy, Dec. 2017, 8:277, 9 pages.
Lio et al., "CD28 facilitates the generation of Foxp3(-) cytokine responsive regulatory T cell precursors," J. Immunology, Apr. 2010, 184(11):6007-6013.
Liotta et al., "Toll-like receptors 3 and 4 are expressed by human bone marrow-derived mesenchymal stem cells and can inhibit their T-cell modulatory activity by impairing Notch signaling," Stem Cells, Oct. 2007, 26(1):279-289.
Liu et al., "Immunosuppressive Property of MSCs Mediated by Cell Surface Receptors," Front. Immunology, Jul. 2020, 11:1076, 15 pages.
Luz-Crawford et al., "Mesenchymal stem cells generate a CD4+ CD25+Foxp3+ regulatory T cell population during the differentiation process of Th1 and Th17 cells," Stem Cell Res. Therapy, Jun. 2013, 4(3):65, 12 pages.
Makita et al, "Clinical development of anti-CD19 chimeric antigen receptor T-cell therapy for B-cell non-Hodgkin lymphoma," Cancer Science, Jun. 2017, 108(6):1109-1118.
Melief et al., "Multipotent stromal cells induce human regulatory T cells through a novel pathway involving skewing of monocytes toward anti-inflammatory macrophages," Stem Cells, Sep. 2013, 31(9):1980-1991.
Molinero et al., "High TCR stimuli prevent induced regulatory T cell differentiation in a NF-kappaB-dependent manner," J. Immunology, Mar. 2011, 186(8):4609-4617.
Murata et al., "Off-the-shelf bone marrow-derived mesenchymal stem cell treatment for acute graft-versus-host disease: real-world evidence," Bone Marrow Transplantation, May 2021, 56(10):2355-2366.
Naji et al., "Biological functions of mesenchymal stem cells and clinical implications," Cell. Mol. Life Sciences, May 2019, 76(17):3323-3348.
Niu et al., "TLR-4/microRNA-125a/NF-KB signaling modulates the immune response to *Mycobacterium tuberculosis* infection," Cell Cycle, Sep. 2018, 17(15):1931-1945.
Noronha et al., "Priming approaches to improve the efficacy of mesenchymal stromal cell-based therapies," Stem Cell Res. Therapy, May 2019, 10:131, 21 pages.
Noyan et al., "Prevention of Allograft Rejection by Use of Regulatory T Cells With an MHC-Specific Chimeric Antigen Receptor," Am. J. Transplantation, Feb. 2017, 17(4):917-930.
Orabona et al., "CD28 induces immunostimulatory signals in dendritic cells via CD80 and CD86," Nat. Immunology, Oct. 2004, 5(11):1134-1142.
Ouyang et al., "Novel Foxol-dependent transcriptional programs control T(reg) cell function," Nature, Nov. 2012, 491(7425):554-559, 8 pages.
Patsoukis et al., "Revisiting the PD-1 pathway," Sci. Advances, Sep. 2020, 6(38):eabd2712, 14 pages.
PCT International Preliminary Report on Patentability in International Appln. No. PCT/US2019/026108, mailed on Oct. 15, 2020, 7 pages.
PCT International Preliminary Report on Patentability in International Appln. No. PCT/US2019/026544, mailed on Oct. 22, 2020, 7 pages.
PCT International Preliminary Report on Patentability in International Appln. No. PCT/US2019/059113, mailed on May 14, 2021, 9 pages.
PCT International Preliminary Report on Patentability in International Appln. No. PCT/US2019/059260, mailed on May 14, 2021, 9 pages.
PCT International Search Report and Written Opinion in International Appln. No. PCT/US2019/026108, mailed on Jun. 11, 2019, 13 pages.
PCT International Search Report and Written Opinion in International Appln. No. PCT/US2019/026544, mailed on Jun. 27, 2019, 10 pages.
PCT International Search Report and Written Opinion in International Appln. No. PCT/US2019/059113, mailed on Jan. 31, 2020, 18 pages.

(56) References Cited

OTHER PUBLICATIONS

PCT International Search Report and Written Opinion in International Appln. No. PCT/US2019/059260, mailed on Jan. 31, 2020, 15 pages.
PCT International Search Report and Written Opinion in International Appln. No. PCT/US2022/028139, mailed on Aug. 30, 2022, 13 pages.
Phinney et al., "MSCs: science and trials," Nat. Medicine, Jul. 2013, 19(7):812.
Ping et al., "Activation of NF-KB driven inflammatory programs in mesenchymal elements attenuates hematopoiesis in low-risk myelodysplastic syndromes," Leukemia, Oct. 2018, 33(2):536-541.
Pittenger et al., "Multilineage potential of adult human mesenchymal stem cells," Science, Apr. 1999, 284(5411):143-147.
Ponten et al., "The Human Protein Atlas—a tool for pathology," J Pathol, Sep. 2008, 216(4):387-393.
Potenza et al., "Molecular mechanisms governing microRNA-125a expression in human hepatocellular carcinoma cells," Sci. Reports, Sep. 2017, 7:10712, 9 pages.
Prasanna et al., "Pro-Inflammatory Cytokines, IFNc and TNFa, Influence Immune Properties of Human Bone Marrow and Wharton Jelly Mesenchymal Stem Cells Differentially," PLoS One, Feb. 2010, 5(2):e9016, 16 pages.
Puissant et al., "Immunomodulatory effect of human adipose tissue-derived adult stem cells: comparison with bone marrow mesenchymal stem cells," Br. J. Haematology, Apr. 2005, 129(1):118-129.
Riches et al., "T cells from CLL patients exhibit features of T-cell exhaustion but retain capacity for cytokine production," Blood, Feb. 2013, 121(9):1612-1621.
Sakemura et al., "Development of a Clinically Relevant Reporter for Chimeric Antigen Receptor T-cell Expansion, Trafficking, and Toxicity," Cancer Immunol. Research, Jul. 2021, 9(9):1035-1046.
Sakemura et al., "Resistance to CART cell therapy: lessons learned from the treatment of hematological malignancies," Leuk. Lymphoma, Mar. 2021, 62(9):2052-2063.
Sarkar et al., "Engineered cell homing," Blood, Oct. 2011, 118(25):e184-e191.
Schmitz et al., "Controlling NF-κB activation in T cells by costimulatory receptors," Cell Death Differentiation, Jan. 2006, 13:834-842.
Scholler et al., "Decade-long safety and function of retroviral-modified chimeric antigen receptor T cells," Sci. Transl. Medicine, May 2012, 4(132):1-7, 43 pages.
Shi et al., "Immunoregulatory mechanisms of mesenchymal stem and stromal cells in inflammatory diseases," Nat. Rev. Nephrology, Aug. 2018, 14(8):493-507.
Sirpilla et al., "Chimeric Antigen Receptor Engineering of Mesenchymal Stromal Cells (CAR-MSC) Enhance Immunosuppression and Outcomes in Graft Versus Host Disease (GvHD) Preclinical Models," Blood, Nov. 2022, 140(S1):1579-1580, 7 pages.
Smith et al., "miR-29ab1 deficiency identifies a negative feedback loop controlling Th1 bias that is dysregulated in multiple sclerosis," J. Immunology, Aug. 2012, 189(4):1567-1576.
Steiner et al., "MicroRNA-29 regulates T-box transcription factors and interferon-y production in helper T cells," Immunity, Aug. 2011, 35(2):169-181.
Strauss et al., "Targeted deletion of PD-1 in myeloid cells induces antitumor immunity," Sci. Immunology, Jan. 2020, 5(43):1-14.
Teshima et al., "Acute Graft-versus-Host Disease: Novel Biological Insights," Biol. Blood Marrow Transplantation, Oct. 2015, 22(1):11-16.
Thaker et al., "TCR and CD28 activate the transcription factor NF-kappaB in T-cells via distinct adaptor signaling complexes," Immunol. Letters, Oct. 2014, 163(1):113-119.
Thiele et al., "miR-9 enhances IL-2 production in activated human CD4(+) T cells by repressing Blimp-1," Eur. J. Immunology, Aug. 2012, 42(8):2100-2108.
Uccelli et al., "Mesenchymal stem cells in health and disease," Nat. Rev. Immunology, Sep. 2008, 8(9):726-736.
Wang et al., "NF-kB—YY1—miR-29 Regulatory Circuitry in Skeletal Myogenesis and Rhabdomyosarcoma," Cancer Cell, Nov. 2008, 14(5):369-381.
Wu et al., "MicroRNA Roles in the Nuclear Factor Kappa B Signaling Pathway in Cancer," Front. Immunology, Mar. 2018, 9:546, 9 pages.
Yañez et al., "Improved efficacy of mesenchymal stromal cells stably expressing CXCR4 and IL-10 in a xenogeneic graft versus host disease mouse model," Front Immunol., Feb. 2023, 14:1-15.
Zeng et al., "miR-9 enhances the transactivation of nuclear factor of activated T cells by targeting KPNB1 and DYRK1B," Am. J. Physiol. Cell Physiology, May 2015, 308(9):C720-C728.
Zhao et al., "Galectin-9 Mediates the Therapeutic Effect of Mesenchymal Stem Cells on Experimental Endotoxemia," Front. Cell Dev. Biology, Feb. 2022, 10:700702, 17 pages.
Zheng et al., "MiR-125b regulates proliferation and apoptosis of nasopharyngeal carcinoma by targeting A20/NF-κB signaling pathway," Cell Death Disease, Jun. 2017, 8(6):e2855, 13 pages.
Ding et al., "[Human adipose-derived mesenchymal stem cells and inflammatory bowel disease]," Anhui Medical and Pharmaceutical Journal, Apr. 2010, 14(4):378-380 (with English Abstract).
Doğan et al., "E-cadherin expression in intestinal epithelium," J. Clin. Pathol., 1995, 48(2):143-146.
Sakemura et al., "Targeting Cancer-Associated Fibroblasts in the Bone Marrow Prevents Resistance to CART-Cell Therapy in Multiple Myeloma," Blood, Jun. 2022, 139(26):3708-3721.
Xiaoxia et al., "[Function of diamine oxidase and E-cadherin in Intestinal Injury of Nronatal Rats]," J. Med. Res., Nov. 2012, 41(11):169-172 (with English Abstract).
Zhang et al., "Expressions of E-cadherin, p120ctn, β-catenin and NF-κB in ulcerative colitis," Journal of Huazhong University of Science and Technology [Medical Sciences], Jun. 2015, 35:368-373.
Weitzel et al., "microRNA 184 regulates expression of NFAT1 in umbilical cord blood CD4+T cells," Blood, Jun. 25, 2009, 113(26):6648-6657.
Golinelli et al., "Targeting GD2-positive glioblastoma by chimeric antigen receptor empowered mesenchymal progenitors," Cancer Gene Ther., Aug. 2020, 27(7-8):558-570.
Panes et al., "Long-term Efficacy and Safety of Stem Cell Therapy (Cx601) for Complex Perianal Fistulas in Patients With Crohn's Disease," Gastroenterology, Apr. 2018, 154(5):1334-1342.e4.
Park et al., "Adipose-derived stem cells ameliorate colitis by suppression of inflammasome formation and regulation of M1-macrophage population through prostaglandin E2," Biochem. Biophys. Res. Commun., Apr. 2018, 498(4):988-995.
Partial Supplementary European Search Report in European Appln. No. 20883700.5, dated Sep. 4, 2024, 17 pages.
Zhang et al., "Mesenchymal Stem Cells to Treat Crohn's Disease with Fistula," Hum. Gene Ther., Jul. 2017, 28(7):534-540.
Extended European Search Report in European Appln. No. 20883700.5, mailed on Nov. 26, 2024, 14 pages.

* cited by examiner

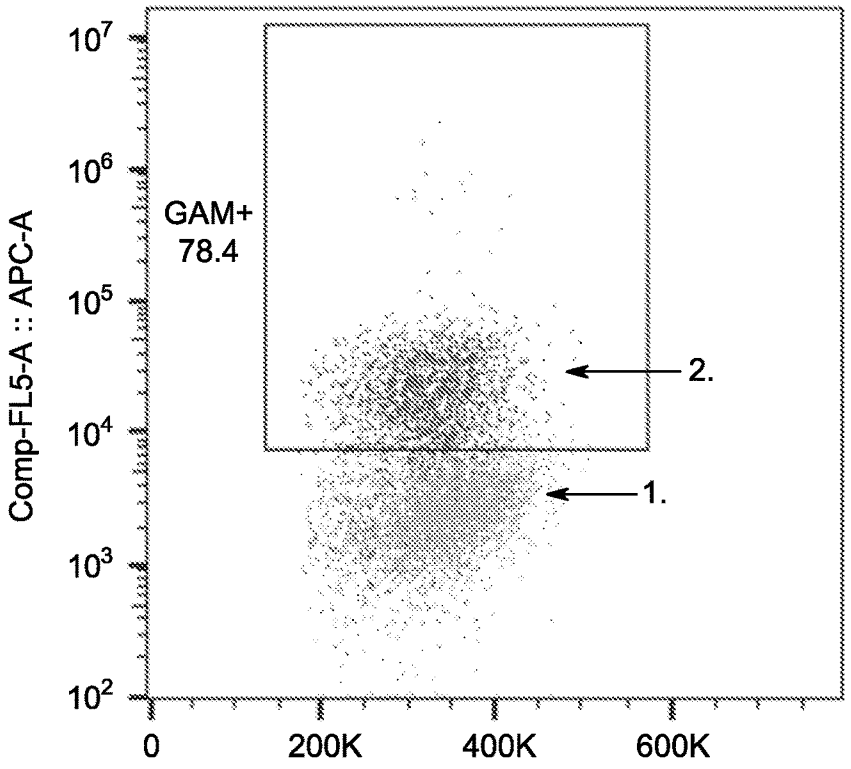
| | | Sample Name | Subset Name | Count |
|---|---|---|---|---|
| 1. | | UTD_GAM.fcs | Live | 3761 |
| 2. | | K80-CART_GAM.fcs | Live | 2514 |
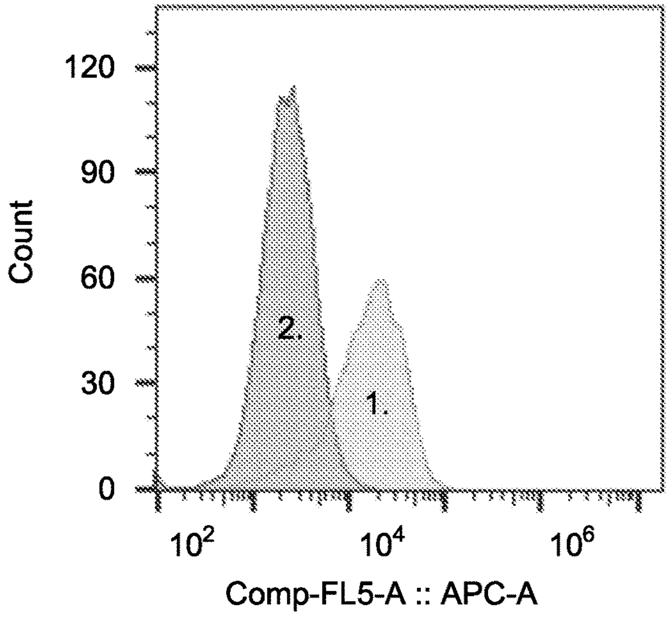
FIG. 11

SEQ ID NO:1 atggccttaccagtgaccgccttgctcctgccgctggccttgctgctccacgcc
gccaggccgCAGATCCTGTTGGTGCAGTCTGGACCTGAGCTGAAGAAGCCTGGA
GAGACAGTCAAGATCTCCTGCAAGGCTTCTAATTATACCTTCACAGACTATGGA
ATGCACTGGGTGAAGCAGGCTCCAGGAAAGGGTTTAAAGTGGATGGGCTGGATA
AACCCCAAGACTGGTGTGGCATCATATGCAGATGACTTCAAGGGAAGATTTGCC
TTCTCTTTGGAAACCTCTGCCAGCACTGCCTATTTGCAGATCAACAACCTCGAA
AATGAGGACACGTCTATATATTTCTGTGCTAGATTTTTTGACTACTGGGGCCAA
GGCACCACTCTCACAGTCTCCTCAggaggtggcggatcaggcggaggaggcagc
ggcggaggtggatcaggaggcggagggtcaGATATTGTGCTGACACAGTCTCCA
CTCTCCCTGCTTGTCAGTCTTGGAGATCAAGCCTCCATCTCTTGCAGATCTAGT
CAGAGCCTTGTACACAGTAATGGAAACACCTATTTACATTGGTATCTGCAGAAG
CCAGGCCAGTCTCCAAACCTCCTGATCTTCAAAGTTTCCAACCGATTTTCTGGG
GTCCCAGACAGGTTCAGTGGCAGTGGATCAGGGACAGATTTCACACTCAGGATC
AGCAGAGTGGAGGCTGAGGATCTGGGAGTTTATTTCTGCTCTCAAACTACACAT
GTGTGGACGTTCGGTGGAGGCACCAAGCTGGAAATCAAACTCGAGCCCAAATCT
TGTGACAAAACTCACACATGCCCACCGTGCCCGGATCCCAAATTTTGGGTGCTG
GTGGTGGTTGGTGGAGTCCTGGCTTGCTATAGCTTGCTAGTAACAGTGGCCTTT
ATTATTTTCTGGGTGAGGAGTAAGAGGAGCAGGCTCCTGCACAGTGACTACATG
AACATGACTCCCCGCCGCCCCGGGCCCACCCGCAAGCATTACCAGCCCTATGCC
CCACCACGCGACTTCGCAGCCTATCGCTCCAGAGTGAAGTTCAGCAGGAGCGCA
GACGCCCCCGCGTACAAGCAGGGCCAGAACCAGCTCTATAACGAGCTCAATCTA
GGACGAAGAGAGGAGTACGATGTTTTGGACAAGAGACGTGGCCGGGACCCTGAG
ATGGGGGGAAAGCCGAGAAGGAAGAACCCTCAGGAAGGCCTGTACAATGAACTG
CAGAAAGATAAGATGGCGGAGGCCTACAGTGAGATTGGGATGAAAGGCGAGCGC
CGGAGGGGCAAGGGGCACGATGGCCTTTACCAGGGTCTCAGTACAGCCACCAAG
GACACCTACGACGCCCTTCACATGCAGGCCCTGCCCCCTCGCTAA

FIG. 12A

SEQ ID NO:2

MALPVTALLLPLALLLHAARPQILLVQSGPELKKPGETVKISCKASNYTFTDYG
MHWVKQAPGKGLKWMGWINPKTGVASYADDFKGRFAFSLETSASTAYLQINNLE
NEDTSIYFCARFFDYWGQGTTLTVSSGGGGSGGGGSGGGGSGGGGSDIVLTQSP
LSLLVSLGDQASISCRSSQSLVHSNGNTYLHWYLQKPGQSPNLLIFKVSNRFSG
VPDRFSGSGSGTDFTLRISRVEAEDLGVYFCSQTTHVWTFGGGTKLEIKLEPKS
CDKTHTCPPCPDPKFWVLVVVGGVLACYSLLVTVAFIIFWVRSKRSRLLHSDYM
NMTPRRPGPTRKHYQPYAPPRDFAAYRSRVKFSRSADAPAYKQGQNQLYNELNL
GRREEYDVLDKRRGRDPEMGGKPRRKNPQEGLYNELQKDKMAEAYSEIGMKGER
RRGKGHDGLYQGLSTATKDTYDALHMQALPPR

FIG. 12B

SEQ ID NO:3 atggcAttaccagtTaccgcAttATTActgccgctggcAttgctgTtAcaTgcA
gcACgTccgGATATTGAACTGACCCAGAGTCCCAGTAGCCTGGCCGTGAGTGCC
GGCGAGAAAGTGACCATGAGCTGCAAAAGCAGCCAGAGCCTGCTGAACAGCGGC
AACCAGAAAAACTACCTGGCCTGGTACCAGCAGAAACCCGGCCTGCCTCCTAAG
CTGCTGATCTACGGCGCCAGCACCAGAGAAAGCGGCGTGCCCGATAGATTCACC
GGCTCTGGCTCTGGCACCGACTTCACCCTGACCATCAGCAGCGTGCAGGCCGAA
GACCTGGCCGTGTACTACTGCCAGAACGACCACAGCTACCCCCTGACCTTCGGC
GCCGGCACCAAGCTGGAGATCAAGGGTGGAGGTGGTTCGGGAGGTGGAGGTAGC
GGAGGTGGTGGAAGCGAGGTGAAGCTGCACGAGAGCGGCGCAGGTCTGGTGAAG
CCCGGCGCCAGCGTGGAGATCAGCTGCAAGGCCACCGGCTACACCTTCAGCAGC
TTCTGGATCGAGTGGGTGAAGCAGAGACCCGGCCACGGCCTGGAGTGGATCGGC
GAGATCCTGCCCGGCAGAGGCAGAACCAACTACAACGAGAAGTTCAAGGGCAAG
GCCACCTTCACCGCCGAGACCAGCAGCAACACCGCCTACATGCAGCTGAGCAGC
CTGACCAGCGAGGACAGCGCCGTGTACTACTGCGCCACCGGCAACACCATGGTG
AACATGCCCTACTGGGGCCAGGGCACCACCGTGACCGTGAGCAGCCTCGAGCCC
AAATCTTGTGACAAAACTCACACATGCCCACCGTGCCCGGATCCCAAATTTTGG
GTGCTGGTGGTGGTTGGTGGAGTCCTGGCTTGCTATAGCTTGCTAGTAACAGTG
GCCTTTATTATTTTCTGGGTGAGGAGTAAGAGGAGCAGGCTCCTGCACAGTGAC
TACATGAACATGACTCCCCGCCGCCCCGGTCCCACCCGCAAGCATTACCAGCCC
TATGCCCCACCACGCGACTTCGCAGCCTATCGCTCCAGAGTGAAGTTCAGCAGG
AGCGCAGACGCCCCCGCGTACAAGCAGGGCCAGAACCAGCTCTATAACGAGCTC
AATCTAGGACGAAGAGAGGAGTACGATGTTTTGGACAAGAGACGTGGCCGGGAC
CCTGAGATGGGAGGAAAGCCGAGAAGGAAGAACCCTCAGGAAGGCCTGTACAAT
GAACTGCAGAAAGATAAGATGGCGGAGGCCTACAGTGAGATTGGGATGAAAGGC
GAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGCTAA

FIG. 13A

SEQ ID NO:4

MALPVTALLLPLALLLHAARPDIELTQSPSSLAVSAGEKVTMSCKSSQSLLNSG
NQKNYLAWYQQKPGLPPKLLIYGASTRESGVPDRFTGSGSGTDFTLTISSVQAE
DLAVYYCQNDHSYPLTFGAGTKLEIKGGGGSGGGGSGGGGSEVKLHESGAGLVK
PGASVEISCKATGYTFSSFWIEWVKQRPGHGLEWIGEILPGRGRTNYNEKFKGK
ATFTAETSSNTAYMQLSSLTSEDSAVYYCATGNTMVNMPYWGQGTTVTVSSLEP
KSCDKTHTCPPCPDPKFWVLVVVGGVLACYSLLVTVAFIIFWVRSKRSRLLHSD
YMNMTPRRPGPTRKHYQPYAPPRDFAAYRSRVKFSRSADAPAYKQGQNQLYNEL
NLGRREEYDVLDKRRGRDPEMGGKPRRKNPQEGLYNELQKDKMAEAYSEIGMKG
ERRRGKGHDGLYQGLSTATKDTYDALHMQALPPR

FIG. 13B

SEQ ID NO:5

ATGCTCAGGCTGCTCTTGGCTCTCAACTTATTCCCTTCAATTCAAGTAACAGGA
GAATTTCTGATGACCCAGACCCCGCTGAGCCTGAGCGTGAGCGCGGGCGAAAAA
GTGACCATGAGCTGCAAAAGCAGCCAGAGCCTGCTGAACAGCGGCAACCAGAAA
AACTATCTGGCGTGGTATCAGCAGAAACCGGGCCTGCCGCCGAAACTGCTGATT
TATGGCGCGAGCACCCGCGAAAGCGGCGTGCCGGATCGCTTTACCGGCAGCGGC
AGCGGCACCGATTTTACCCTGACCATTAGCAGCGTGCAGGCGGAAGATCTGGCG
GTGTATTATTGCCAGAACGATCATAGCTATCCGCTGACCTTTGGCGCGGGCACC
AAACTGGAACTGAAACGCGCGGATGCGGCGCCGACCGGTGGAGGTGGTTCGGGA
GGTGGAGGTAGCGGAGGTGGTGGAAGCCAGGTGAAACTGCAGCAGAGCGGCGCG
GAACTGATGAAACCGGGCGCGAGCGTGGAAATTAGCTGCAAAGCGACCGGCTAT
ACCTTTAGCAGCTTTTGGATTGAATGGGTGAAACAGCGCCCGGGCCATGGCCTG
GAATGGATTGGCGAAATTCTGCCGGGCCGCGGCCGCACCAACTATAACGAAAAA
TTTAAAGGCAAAGCGACCTTTACCGCGGAAACCAGCAGCAACACCGCGTATATG
CAGCTGAGCAGCCTGACCAGCGAAGATAGCGCGGTGTATTATTGCGCGACCGGC
AACACCATGGTGAACATGCCGTATTGGGGTCAGGGTACAACATTAACAGTTTCT
TCTGCACGTCAGACAACACCGCCGAGCGTGTATGGCGCGGTGGAAGCGGTGCCG
CGCGATTGCGGCTGCAAACCGTGCATTTGCACCCCGGAAGTGAGCAGCGGCCTC
GAGCCCAAATCTTGTGACAAAACTCACACATGCCCACCGTGCCCGGATCCCAAA
TTTTGGGTGCTGGTGGTGGTTGGTGGAGTCCTGGCTTGCTATAGCTTGCTAGTA
ACAGTGGCCTTTATTATTTTCTGGGTGAGGAGTAAGAGGAGCAGGCTCCTGCAC
AGTGACTACATGAACATGACTCCTAGACGCCCTGGTCCCACCCGCAAGCATTAC
CAGCCCTATGCCCCACCACGCGACTTCGCAGCCTATCGCTCCAGAGTGAAGTTC
AGCAGGAGCGCAGACGCCCCCGCGTACAAGCAGGGCCAGAACCAGCTCTATAAC
GAGCTCAATCTAGGACGAAGAGAGGAGTACGATGTTTTGGACAAGAGACGTGGC
CGGGACCCTGAGATGGGGGGAAAGCCGAGAAGGAAGAACCCTCAGGAAGGCCTG
TACAATGAACTGCAGAAAGATAAGATGGCGGAGGCCTACAGTGAGATTGGGATG
AAAGGCGAGCGCCGGAGGGGCAAGGGGCACGATGGCCTTTACCAGGGTCTCAGT
ACAGCCACCAAGGACACCTACGACGCCCTTCACATGCAGGCCCTGCCCCCTCGC
TAA

FIG. 13C

SEQ ID NO:6

MLRLLLALNLFPSIQVTGEFLMTQTPLSLSVSAGEKVTMSCKSSQSLLNSGNQK
NYLAWYQQKPGLPPKLLIYGASTRESGVPDRFTGSGSGTDFTLTISSVQAEDLA
VYYCQNDHSYPLTFGAGTKLELKRADAAPTGGGGSGGGGSGGGGSQVKLQQSGA
ELMKPGASVEISCKATGYTFSSFWIEWVKQRPGHGLEWIGEILPGRGRTNYNEK
FKGKATFTAETSSNTAYMQLSSLTSEDSAVYYCATGNTMVNMPYWGQGTTLTVS
SARQTTPPSVYGAVEAVPRDCGCKPCICTPEVSSGLEPKSCDKTHTCPPCPDPK
FWVLVVVGGVLACYSLLVTVAFIIFWVRSKRSRLLHSDYMNMTPRRPGPTRKHY
QPYAPPRDFAAYRSRVKFSRSADAPAYKQGQNQLYNELNLGRREEYDVLDKRRG
RDPEMGGKPRRKNPQEGLYNELQKDKMAEAYSEIGMKGERRRGKGHDGLYQGLS
TATKDTYDALHMQALPPR

FIG. 13D

SEQ ID NO:7 atggcAttaccagtTaccgcAttATTActgccgctggcAttgctgTtAcaTgcA
gcACgTccgGAGGTGAAGCTGCACGAGAGCGGCGCAGGTCTGGTGAAGCCCGGC
GCCAGCGTGGAGATCAGCTGCAAGGCCACCGGCTACACCTTCAGCAGCTTCTGG
ATCGAGTGGGTGAAGCAGAGACCCGGCCACGGCCTGGAGTGGATCGGCGAGATC
CTGCCCGGCAGAGGCAGAACCAACTACAACGAGAAGTTCAAGGGCAAGGCCACC
TTCACCGCCGAGACCAGCAGCAACACCGCCTACATGCAGCTGAGCAGCCTGACC
AGCGAGGACAGCGCCGTGTACTACTGCGCCACCGGCAACACCATGGTGAACATG
CCCTACTGGGGCCAGGGCACCACCGTGACCGTGAGCAGCGGTGGAGGTGGTTCG
GGAGGTGGAGGTAGCGGAGGTGGTGGAAGCGATATTGAACTGACCCAGAGTCCC
AGTAGCCTGGCCGTGAGTGCCGGCGAGAAAGTGACCATGAGCTGCAAAAGCAGC
CAGAGCCTGCTGAACAGCGGCAACCAGAAAAACTACCTGGCCTGGTACCAGCAG
AAACCCGGCCTGCCTCCTAAGCTGCTGATCTACGGCGCCAGCACCAGAGAAAGC
GGCGTGCCCGATAGATTCACCGGCTCTGGCTCTGGCACCGACTTCACCCTGACC
ATCAGCAGCGTGCAGGCCGAAGACCTGGCtGTcTACTACTGCCAGAACGACCAC
AGCTACCCCCTGACCTTCGGCGCCGGCACCAAGCTGGAGATCAAGCTCGAGCCC
AAATCTTGTGACAAAACTCACACATGCCCACCGTGCCCGGATCCCAAATTTTGG
GTGCTGGTGGTGGTTGGTGGAGTCCTGGCTTGCTATAGCTTGCTAGTAACAGTG
GCCTTTATTATTTTCTGGGTGAGGAGTAAGAGGAGCAGGCTCCTGCACAGTGAC
TACATGAACATGACTCCCCGCCGCCCCGGTCCCACCCGCAAGCATTACCAGCCC
TATGCCCCACCACGCGACTTCGCAGCCTATCGCTCCAGAGTGAAGTTCAGCAGG
AGCGCAGACGCCCCCGCGTACAAGCAGGGCCAGAACCAGCTCTATAACGAGCTC
AATCTAGGACGAAGAGAGGAGTACGATGTTTTGGACAAGAGACGTGGCCGGGAC
CCTGAGATGGGAGGAAAGCCGAGAAGGAAGAACCCTCAGGAAGGCCTGTACAAT
GAACTGCAGAAAGATAAGATGGCGGAGGCCTACAGTGAGATTGGGATGAAAGGC
GAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGCTAA

FIG. 13E

SEQ ID NO:8

MALPVTALLLPLALLLHAARPEVKLHESGAGLVKPGASVEISCKATGYTFSSFW
IEWVKQRPGHGLEWIGEILPGRGRTNYNEKFKGKATFTAETSSNTAYMQLSSLT
SEDSAVYYCATGNTMVNMPYWGQGTTVTVSSGGGGSGGGGSGGGGSDIELTQSP
SSLAVSAGEKVTMSCKSSQSLLNSGNQKNYLAWYQQKPGLPPKLLIYGASTRES
GVPDRFTGSGSGTDFTLTISSVQAEDLAVYYCQNDHSYPLTFGAGTKLEIKLEP
KSCDKTHTCPPCPDPKFWVLVVVGGVLACYSLLVTVAFIIFWVRSKRSRLLHSD
YMNMTPRRPGPTRKHYQPYAPPRDFAAYRSRVKFSRSADAPAYKQGQNQLYNEL
NLGRREEYDVLDKRRGRDPEMGGKPRRKNPQEGLYNELQKDKMAEAYSEIGMKG
ERRRGKGHDGLYQGLSTATKDTYDALHMQALPPR

FIG. 13F

SEQ ID NO:9

TCTAGAATGGCCTTACCAGTGACCGCCTTGCTCCTGCCGCTGGCCTTGCTGCTC
CACGCCGCCAGGCCGGATATCCAGATGACCCAGTCCCCGAGCTCCCTGTCCGCC
TCTGTGGGCGATAGGGTCACTATCACCTGCCGTGCCAGTCAGGATGTGAATACT
GCTGTAGCCTGGTATCAACAGAAACCCGGAAAGGCCCCGAAACTGCTGATTTAC
TCGGCATCCTTCCTCTACTCTGGAGTCCCTTCTCGCTTCTCTGGTTCCCGCTCT
GGGACGGATTTCACTCTGACCATCAGCTCCCTGCAGCCGGAAGACTTCGCAACT
TATTACTGTCAGCAACACTATACTACTCCTCCGACGTTCGGACAGGGTACCAAG
GTGGAGATCAAACGTACCGTGGCGGCGCCAGGAGGTGGCGGATCAGGCGGAGGA
GGCAGCGGCGGAGGTGGATCAGGAGGCGGAGGGTCAGAGGTTCAGCTGGTGGAG
TCTGGCGGTGGCCTGGTGCAGCCCGGGGGCTCTCTCCGTTTGTCCTGTGCAGCT
TCTGGCTTCAACATTAAAGACACCTATATCCACTGGGTGCGTCAGGCTCCGGGT
AAGGGCCTGGAGTGGGTTGCAAGGATTTATCCTACGAATGGTTATACTCGTTAT
GCCGATAGCGTCAAGGGCCGTTTCACTATAAGCGCAGACACTTCGAAAAACACA
GCCTACCTCCAGATGAACAGCCTGCGTGCTGAGGACACTGCCGTCTATTATTGT
AGCAGATGGGGTGGGGACGGCTTCTATGCTATGGACTACTGGGGTCAAGGTACA
CTAGTCACCGTCAGCAGCGCTAGCACCAAGGGCACCACGACGCCAGCGCCGCGA
CCACCAACACCGGCGCCCACCATCGCGTCGCAGCCCCTGTCCCTGCGCCCAGAG
GCGTGCCGGCCAGCGGCGGGGGGCGCAGTGCACACGAGGGGGCTGGACTTCGCC
TGTGATATCTACATCTGGGCGCCCTTGGCCGGGACTTGTGGGGTCCTTCTCCTG
TCACTGGTTATCACCCTTTACTGCAAACGGGGCAGAAAGAAACTCCTGTATATA
TTCAAACAACCATTTATGAGACCAGTACAAACTACTCAAGAGGAAGATGGCTGT
AGCTGCCGATTTCCAGAAGAAGAAGAAGGAGGATGTGAACTGAGAGTGAAGTTC
AGCAGGAGCGCAGACGCCCCCGCGTACAAGCAGGGCCAGAACCAGCTCTATAAC
GAGCTCAATCTAGGACGAAGAGAGGAGTACGATGTTTTGGACAAGAGACGTGGC
CGGGACCCTGAGATGGGGGGAAAGCCGAGAAGGAAGAACCCTCAGGAAGGCCTG
TACAATGAACTGCAGAAAGATAAGATGGCGGAGGCCTACAGTGAGATTGGGATG
AAAGGCGAGCGCCGGAGGGGCAAGGGGCACGATGGCCTTTACCAGGGTCTCAGT
ACAGCCACCAAGGACACCTACGACGCCCTTCACATGCAGGCCCTGCCCCCTCGC
GTCGAC

FIG. 14A

SEQ ID NO:10

SRMALPVTALLLPLALLLHAARPDIQMTQSPSSLSASVGDRVTITCRASQDVNT
AVAWYQQKPGKAPKLLIYSASFLYSGVPSRFSGSRSGTDFTLTISSLQPEDFAT
YYCQQHYTTPPTFGQGTKVEIKRTVAAPGGGGSGGGGSGGGGSGGGGSEVQLVE
SGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGT
LVTVSSASTKGTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGC
SCRFPEEEEGGCELRVKFSRSADAPAYKQGQNQLYNELNLGRREEYDVLDKRRG
RDPEMGGKPRRKNPQEGLYNELQKDKMAEAYSEIGMKGERRRGKGHDGLYQGLS
TATKDTYDALHMQALPPRVD

FIG. 14B

Figure 15
A
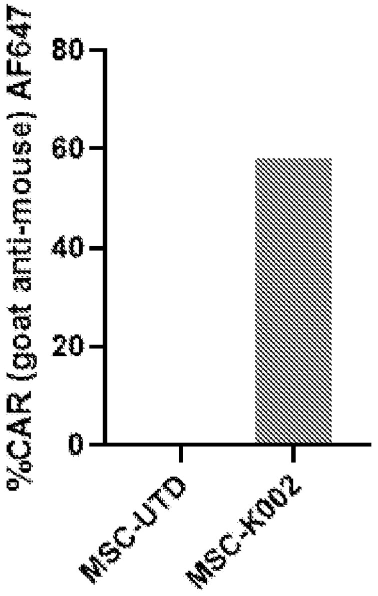
B
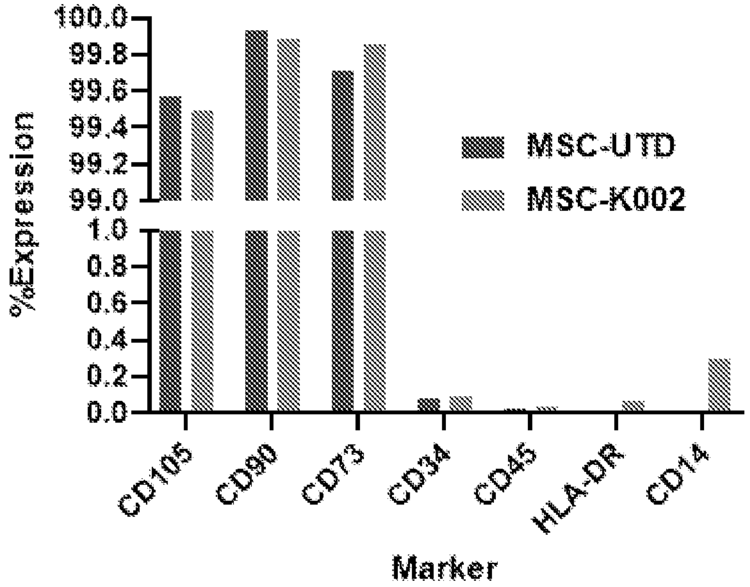

Figure 19
A
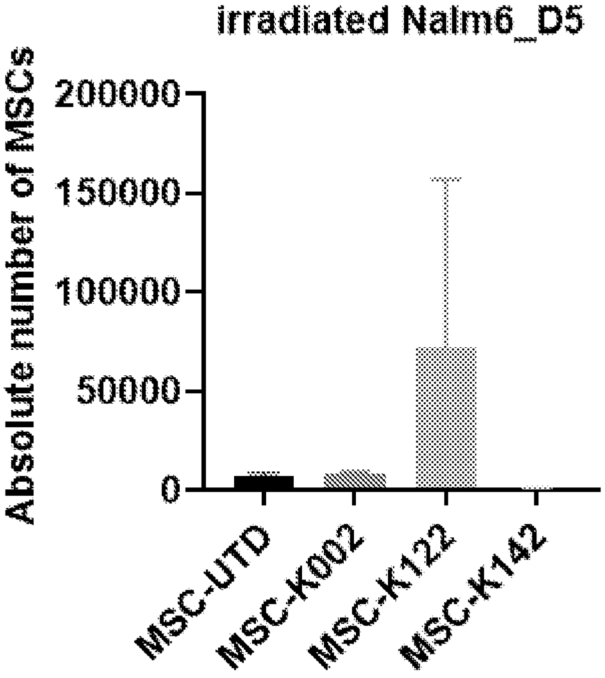
B
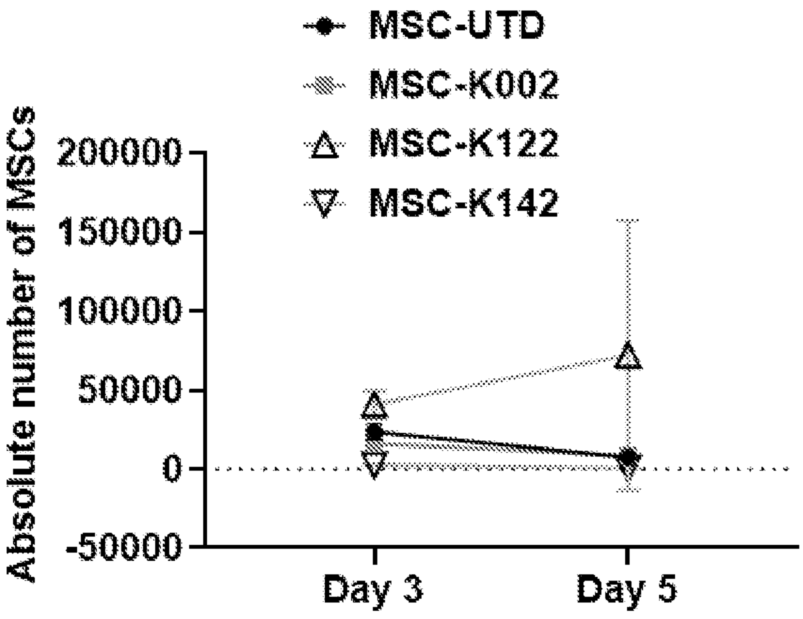

Figure 23
A
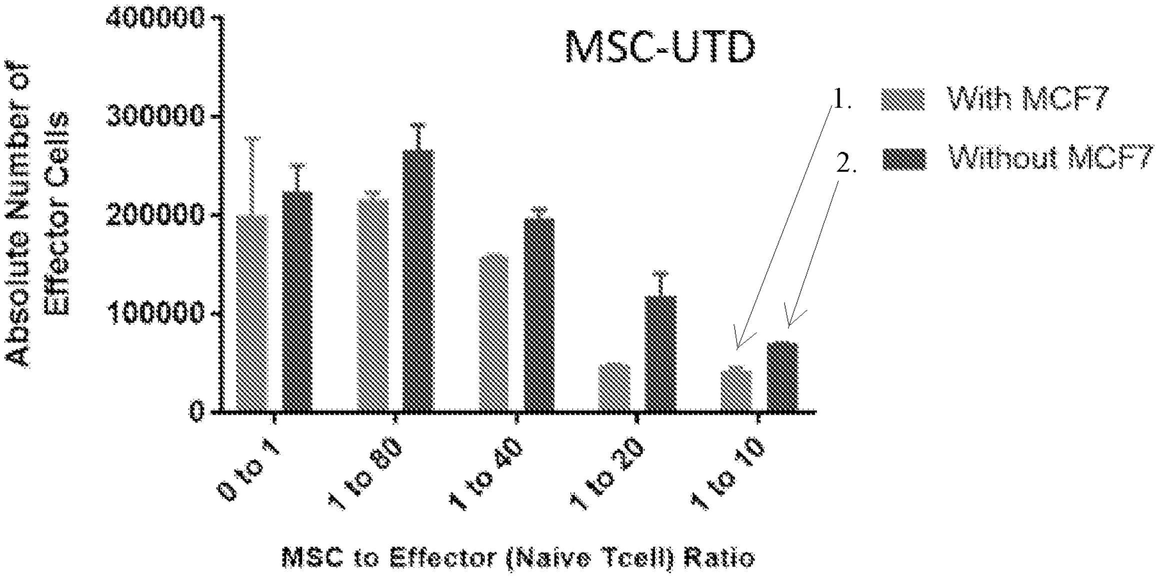
B
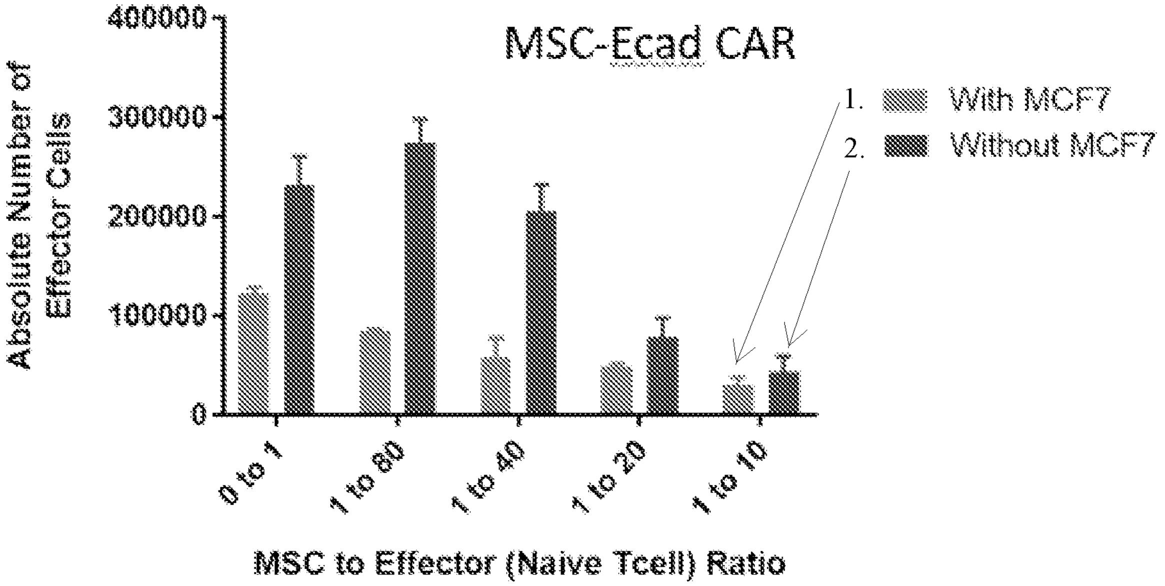

Figure 24
A
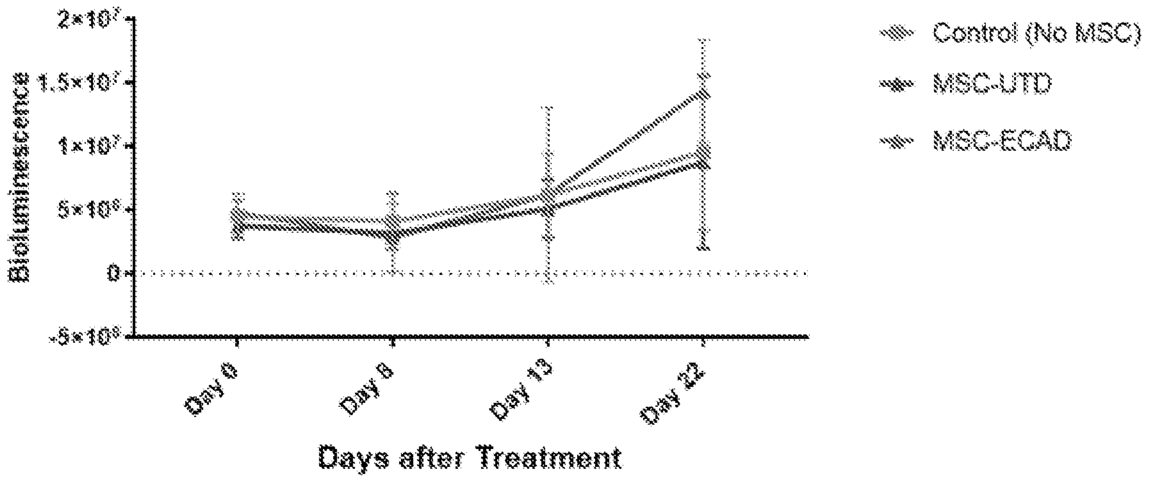
B
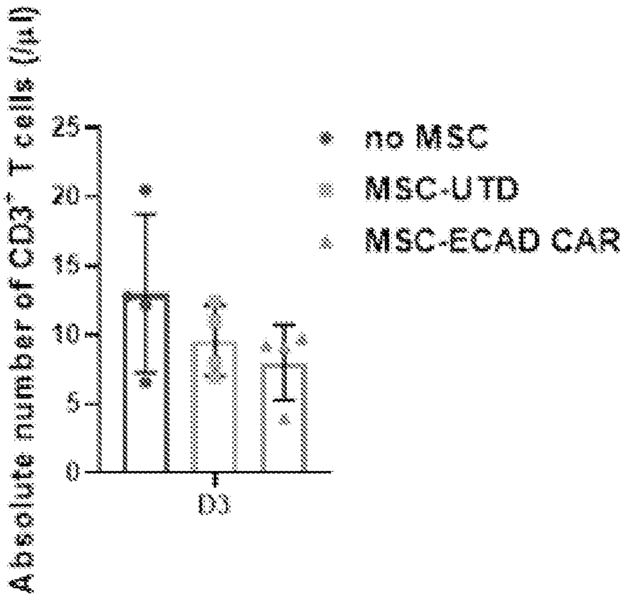

SEQUENCE LISTING

```
<160> NUMBER OF SEQ ID NOS: 45

<210> SEQ ID NO 1
<211> LENGTH: 1395
<212> TYPE: DNA
<213> ORGANISM: Artificial
<220> FEATURE:
<223> OTHER INFORMATION: nucleic acid sequence encoding a CAR-ECAD

<400> SEQUENCE: 1

atggccttac cagtgaccgc cttgctcctg ccgctggcct tgctgctcca cgccgccagg      60
ccgcagatcc tgttggtgca gtctggacct gagctgaaga agcctggaga gacagtcaag     120
atctcctgca aggcttctaa ttataccttc acagactatg gaatgcactg ggtgaagcag     180
gctccaggaa agggtttaaa gtggatgggc tggataaacc ccaagactgg tgtggcatca     240
tatgcagatg acttcaaggg aagatttgcc ttctctttgg aaacctctgc cagcactgcc     300
tatttgcaga tcaacaacct cgaaaatgag gacacgtcta tatatttctg tgctagattt     360
tttgactact ggggccaagg caccactctc acagtctcct caggaggtgg cggatcaggc     420
ggaggaggca gcggcggagg tggatcagga ggcggagggt cagatattgt gctgacacag     480
tctccactct ccctgcttgt cagtcttgga gatcaagcct ccatctcttg cagatctagt     540
cagagccttg tacacagtaa tggaaacacc tatttacatt ggtatctgca gaagccaggc     600
cagtctccaa acctcctgat cttcaaagtt tccaaccgat tttctggggt cccagacagg     660
ttcagtggca gtggatcagg gacagatttc acactcagga tcagcagagt ggaggctgag     720
gatctgggag tttatttctg ctctcaaact acacatgtgt ggacgttcgg tggaggcacc     780
aagctggaaa tcaaactcga gcccaaatct tgtgacaaaa ctcacacatg cccaccgtgc     840
ccggatccca aattttgggt gctggtggtg gttggtggag tcctggcttg ctatagcttg     900
ctagtaacag tggcctttat tattttctgg gtgaggagta agaggagcag gctcctgcac     960
agtgactaca tgaacatgac tccccgccgc cccgggccca cccgcaagca ttaccagccc    1020
tatgccccac cacgcgactt cgcagcctat cgctccagag tgaagttcag caggagcgca    1080
gacgcccccg cgtacaagca gggccagaac cagctctata acgagctcaa tctaggacga    1140
agagaggagt acgatgtttt ggacaagaga cgtggccggg accctgagat ggggggaaag    1200
ccgagaagga agaaccctca ggaaggcctg tacaatgaac tgcagaaaga taagatggcg    1260
gaggcctaca gtgagattgg gatgaaaggc gagcgccgga ggggcaaggg gcacgatggc    1320
ctttaccagg gtctcagtac agccaccaag gacacctacg acgcccttca catgcaggcc    1380
ctgccccctc gctaa                                                     1395

<210> SEQ ID NO 2
<211> LENGTH: 464
```

<212> TYPE: PRT
<213> ORGANISM: Artificial
<220> FEATURE:
<223> OTHER INFORMATION: amino acid sequence of a CAR-ECAD

<400> SEQUENCE: 2

Met Ala Leu Pro Val Thr Ala Leu Leu Leu Pro Leu Ala Leu Leu Leu
1 5 10 15

His Ala Ala Arg Pro Gln Ile Leu Leu Val Gln Ser Gly Pro Glu Leu
20 25 30

Lys Lys Pro Gly Glu Thr Val Lys Ile Ser Cys Lys Ala Ser Asn Tyr
35 40 45

Thr Phe Thr Asp Tyr Gly Met His Trp Val Lys Gln Ala Pro Gly Lys
50 55 60

Gly Leu Lys Trp Met Gly Trp Ile Asn Pro Lys Thr Gly Val Ala Ser
65 70 75 80

Tyr Ala Asp Asp Phe Lys Gly Arg Phe Ala Phe Ser Leu Glu Thr Ser
85 90 95

Ala Ser Thr Ala Tyr Leu Gln Ile Asn Asn Leu Glu Asn Glu Asp Thr
100 105 110

Ser Ile Tyr Phe Cys Ala Arg Phe Phe Asp Tyr Trp Gly Gln Gly Thr
115 120 125

Thr Leu Thr Val Ser Ser Gly Gly Gly Gly Ser Gly Gly Gly Gly Ser
130 135 140

Gly Gly Gly Gly Ser Gly Gly Gly Gly Ser Asp Ile Val Leu Thr Gln
145 150 155 160

Ser Pro Leu Ser Leu Leu Val Ser Leu Gly Asp Gln Ala Ser Ile Ser
165 170 175

Cys Arg Ser Ser Gln Ser Leu Val His Ser Asn Gly Asn Thr Tyr Leu
180 185 190

His Trp Tyr Leu Gln Lys Pro Gly Gln Ser Pro Asn Leu Leu Ile Phe
195 200 205

Lys Val Ser Asn Arg Phe Ser Gly Val Pro Asp Arg Phe Ser Gly Ser
210 215 220

Gly Ser Gly Thr Asp Phe Thr Leu Arg Ile Ser Arg Val Glu Ala Glu
225 230 235 240

Asp Leu Gly Val Tyr Phe Cys Ser Gln Thr Thr His Val Trp Thr Phe
245 250 255

Gly Gly Gly Thr Lys Leu Glu Ile Lys Leu Glu Pro Lys Ser Cys Asp
260 265 270

Lys Thr His Thr Cys Pro Pro Cys Pro Asp Pro Lys Phe Trp Val Leu
275 280 285

Val Val Val Gly Gly Val Leu Ala Cys Tyr Ser Leu Leu Val Thr Val
290 295 300

Ala Phe Ile Ile Phe Trp Val Arg Ser Lys Arg Ser Arg Leu Leu His
305 310 315 320

Ser Asp Tyr Met Asn Met Thr Pro Arg Arg Pro Gly Pro Thr Arg Lys
325 330 335

His Tyr Gln Pro Tyr Ala Pro Pro Arg Asp Phe Ala Ala Tyr Arg Ser
340 345 350

Arg Val Lys Phe Ser Arg Ser Ala Asp Ala Pro Ala Tyr Lys Gln Gly
355 360 365

Gln Asn Gln Leu Tyr Asn Glu Leu Asn Leu Gly Arg Arg Glu Glu Tyr
370 375 380

```
Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460
```

<210> SEQ ID NO 3
<211> LENGTH: 1401
<212> TYPE: DNA
<213> ORGANISM: Artificial
<220> FEATURE:
<223> OTHER INFORMATION: nucleic acid sequence encoding a CAR-MOG

<400> SEQUENCE: 3

```
atggcattac cagttaccgc attattactg ccgctggcat tgctgttaca tgcagcacgt     60

ccggatattg aactgaccca gagtcccagt agcctggccg tgagtgccgg cgagaaagtg    120

accatgagct gcaaaagcag ccagagcctg ctgaacagcg gcaaccagaa aaactacctg    180

gcctggtacc agcagaaacc cggcctgcct cctaagctgc tgatctacgg cgccagcacc    240

agagaaagcg gcgtgcccga tagattcacc ggctctggct ctggcaccga cttcaccctg    300

accatcagca gcgtgcaggc cgaagacctg gccgtgtact actgccagaa cgaccacagc    360

taccccctga ccttcggcgc cggcaccaag ctggagatca agggtggagg tggttcggga    420

ggtggaggta gcggaggtgg tggaagcgag gtgaagctgc acgagagcgg cgcaggtctg    480

gtgaagcccg gcgccagcgt ggagatcagc tgcaaggcca ccggctacac cttcagcagc    540

ttctggatcg agtgggtgaa gcagagaccc ggccacggcc tggagtggat cggcgagatc    600

ctgcccggca gaggcagaac caactacaac gagaagttca agggcaaggc caccttcacc    660

gccgagacca gcagcaacac cgcctacatg cagctgagca gcctgaccag cgaggacagc    720

gccgtgtact actgcgccac cggcaacacc atggtgaaca tgccctactg gggccagggc    780

accaccgtga ccgtgagcag cctcgagccc aaatcttgtg acaaaactca cacatgccca    840

ccgtgcccgg atcccaaatt ttgggtgctg gtggtggttg gtggagtcct ggcttgctat    900

agcttgctag taacagtggc ctttattatt ttctgggtga ggagtaagag gagcaggctc    960

ctgcacagtg actacatgaa catgactccc cgccgccccg gtcccacccg caagcattac   1020

cagccctatg ccccaccacg cgacttcgca gcctatcgct ccagagtgaa gttcagcagg   1080

agcgcagacg cccccgcgta caagcagggc cagaaccagc tctataacga gctcaatcta   1140

ggacgaagag aggagtacga tgttttggac aagagacgtg gccgggaccc tgagatggga   1200

ggaaagccga gaaggaagaa ccctcaggaa ggcctgtaca atgaactgca gaaagataag   1260

atggcggagg cctacagtga gattgggatg aaaggcgagc gccggagggg caaggggcac   1320

gatggccttt accagggtct cagtacagcc accaaggaca cctacgacgc ccttcacatg   1380

caggccctgc cccctcgcta a                                             1401
```

<210> SEQ ID NO 4
<211> LENGTH: 466
<212> TYPE: PRT
<213> ORGANISM: Artificial
<220> FEATURE:

<223> OTHER INFORMATION: amino acid sequence of a CAR-MOG

<400> SEQUENCE: 4

Met Ala Leu Pro Val Thr Ala Leu Leu Leu Pro Leu Ala Leu Leu Leu
1               5                   10                  15

His Ala Ala Arg Pro Asp Ile Glu Leu Thr Gln Ser Pro Ser Ser Leu
            20                  25                  30

Ala Val Ser Ala Gly Glu Lys Val Thr Met Ser Cys Lys Ser Ser Gln
        35                  40                  45

Ser Leu Leu Asn Ser Gly Asn Gln Lys Asn Tyr Leu Ala Trp Tyr Gln
    50                  55                  60

Gln Lys Pro Gly Leu Pro Pro Lys Leu Leu Ile Tyr Gly Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Ala Glu Asp Leu Ala Val
            100                 105                 110

Tyr Tyr Cys Gln Asn Asp His Ser Tyr Pro Leu Thr Phe Gly Ala Gly
        115                 120                 125

Thr Lys Leu Glu Ile Lys Gly Gly Gly Gly Ser Gly Gly Gly Gly Ser
    130                 135                 140

Gly Gly Gly Gly Ser Glu Val Lys Leu His Glu Ser Gly Ala Gly Leu
145                 150                 155                 160

Val Lys Pro Gly Ala Ser Val Glu Ile Ser Cys Lys Ala Thr Gly Tyr
                165                 170                 175

Thr Phe Ser Ser Phe Trp Ile Glu Trp Val Lys Gln Arg Pro Gly His
            180                 185                 190

Gly Leu Glu Trp Ile Gly Glu Ile Leu Pro Gly Arg Gly Arg Thr Asn
        195                 200                 205

Tyr Asn Glu Lys Phe Lys Gly Lys Ala Thr Phe Thr Ala Glu Thr Ser
    210                 215                 220

Ser Asn Thr Ala Tyr Met Gln Leu Ser Ser Leu Thr Ser Glu Asp Ser
225                 230                 235                 240

Ala Val Tyr Tyr Cys Ala Thr Gly Asn Thr Met Val Asn Met Pro Tyr
                245                 250                 255

Trp Gly Gln Gly Thr Thr Val Thr Val Ser Ser Leu Glu Pro Lys Ser
            260                 265                 270

Cys Asp Lys Thr His Thr Cys Pro Pro Cys Pro Asp Pro Lys Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

```
Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465
```

<210> SEQ ID NO 5
<211> LENGTH: 1515
<212> TYPE: DNA
<213> ORGANISM: Artificial
<220> FEATURE:
<223> OTHER INFORMATION: nucleic acid sequence encoding a CAR-MOG

<400> SEQUENCE: 5

```
atgctcaggc tgctcttggc tctcaactta ttcccttcaa ttcaagtaac aggagaattt     60

ctgatgaccc agaccccgct gagcctgagc gtgagcgcgg gcgaaaaagt gaccatgagc    120

tgcaaaagca gccagagcct gctgaacagc ggcaaccaga aaaactatct ggcgtggtat    180

cagcagaaac cgggcctgcc gccgaaactg ctgatttatg gcgcgagcac ccgcgaaagc    240

ggcgtgccgg atcgctttac cggcagcggc agcggcaccg attttaccct gaccattagc    300

agcgtgcagg cggaagatct ggcggtgtat tattgccaga acgatcatag ctatccgctg    360

acctttggcg cgggcaccaa actggaactg aaacgcgcgg atgcggcgcc gaccggtgga    420

ggtggttcgg gaggtggagg tagcggaggt ggtggaagcc aggtgaaact gcagcagagc    480

ggcgcggaac tgatgaaacc gggcgcgagc gtggaaatta gctgcaaagc gaccggctat    540

acctttagca gcttttggat tgaatgggtg aaacagcgcc cgggccatgg cctggaatgg    600

attggcgaaa ttctgccggg ccgcggccgc accaactata acgaaaaatt taaaggcaaa    660

gcgaccttta ccgcggaaac cagcagcaac accgcgtata tgcagctgag cagcctgacc    720

agcgaagata gcgcggtgta ttattgcgcg accggcaaca ccatggtgaa catgccgtat    780

tggggtcagg gtacaacatt aacagtttct tctgcacgtc agacaacacc gccgagcgtg    840

tatggcgcgg tggaagcggt gccgcgcgat tgcggctgca aaccgtgcat ttgcaccccg    900

gaagtgagca gcggcctcga gcccaaatct tgtgacaaaa ctcacacatg cccaccgtgc    960

ccggatccca aattttgggt gctggtggtg gttggtggag tcctggcttg ctatagcttg   1020

ctagtaacag tggcctttat tattttctgg gtgaggagta agaggagcag gctcctgcac   1080

agtgactaca tgaacatgac tcctagacgc cctggtccca cccgcaagca ttaccagccc   1140

tatgccccac cacgcgactt cgcagcctat cgctccagag tgaagttcag caggagcgca   1200

gacgcccccg cgtacaagca gggccagaac cagctctata acgagctcaa tctaggacga   1260

agagaggagt acgatgtttt ggacaagaga cgtggccggg accctgagat ggggggaaag   1320

ccgagaagga agaaccctca ggaaggcctg tacaatgaac tgcagaaaga taagatggcg   1380

gaggcctaca gtgagattgg gatgaaaggc gagcgccgga ggggcaaggg gcacgatggc   1440

ctttaccagg gtctcagtac agccaccaag gacacctacg acgcccttca catgcaggcc   1500

ctgccccctc gctaa                                                    1515
```

<210> SEQ ID NO 6

<211> LENGTH: 504
<212> TYPE: PRT
<213> ORGANISM: Artificial
<220> FEATURE:
<223> OTHER INFORMATION: amino acid sequence of a CAR-MOG

<400> SEQUENCE: 6

```
Met Leu Arg Leu Leu Leu Ala Leu Asn Leu Phe Pro Ser Ile Gln Val
1               5                   10                  15

Thr Gly Glu Phe Leu Met Thr Gln Thr Pro Leu Ser Leu Ser Val Ser
            20                  25                  30

Ala Gly Glu Lys Val Thr Met Ser Cys Lys Ser Ser Gln Ser Leu Leu
        35                  40                  45

Asn Ser Gly Asn Gln Lys Asn Tyr Leu Ala Trp Tyr Gln Gln Lys Pro
    50                  55                  60

Gly Leu Pro Pro Lys Leu Leu Ile Tyr Gly Ala Ser Thr Arg Glu Ser
65                  70                  75                  80

Gly Val Pro Asp Arg Phe Thr Gly Ser Gly Ser Gly Thr Asp Phe Thr
                85                  90                  95

Leu Thr Ile Ser Ser Val Gln Ala Glu Asp Leu Ala Val Tyr Tyr Cys
            100                 105                 110

Gln Asn Asp His Ser Tyr Pro Leu Thr Phe Gly Ala Gly Thr Lys Leu
        115                 120                 125

Glu Leu Lys Arg Ala Asp Ala Ala Pro Thr Gly Gly Gly Gly Ser Gly
    130                 135                 140

Gly Gly Gly Ser Gly Gly Gly Gly Ser Gln Val Lys Leu Gln Gln Ser
145                 150                 155                 160

Gly Ala Glu Leu Met Lys Pro Gly Ala Ser Val Glu Ile Ser Cys Lys
                165                 170                 175

Ala Thr Gly Tyr Thr Phe Ser Ser Phe Trp Ile Glu Trp Val Lys Gln
            180                 185                 190

Arg Pro Gly His Gly Leu Glu Trp Ile Gly Glu Ile Leu Pro Gly Arg
        195                 200                 205

Gly Arg Thr Asn Tyr Asn Glu Lys Phe Lys Gly Lys Ala Thr Phe Thr
    210                 215                 220

Ala Glu Thr Ser Ser Asn Thr Ala Tyr Met Gln Leu Ser Ser Leu Thr
225                 230                 235                 240

Ser Glu Asp Ser Ala Val Tyr Tyr Cys Ala Thr Gly Asn Thr Met Val
                245                 250                 255

Asn Met Pro Tyr Trp Gly Gln Gly Thr Thr Leu Thr Val Ser Ser Ala
            260                 265                 270

Arg Gln Thr Thr Pro Pro Ser Val Tyr Gly Ala Val Glu Ala Val Pro
        275                 280                 285

Arg Asp Cys Gly Cys Lys Pro Cys Ile Cys Thr Pro Glu Val Ser Ser
    290                 295                 300

Gly Leu Glu Pro Lys Ser Cys Asp Lys Thr His Thr Cys Pro Pro Cys
305                 310                 315                 320

Pro Asp Pro Lys Phe Trp Val Leu Val Val Val Gly Gly Val Leu Ala
                325                 330                 335

Cys Tyr Ser Leu Leu Val Thr Val Ala Phe Ile Ile Phe Trp Val Arg
            340                 345                 350

Ser Lys Arg Ser Arg Leu Leu His Ser Asp Tyr Met Asn Met Thr Pro
        355                 360                 365

Arg Arg Pro Gly Pro Thr Arg Lys His Tyr Gln Pro Tyr Ala Pro Pro
    370                 375                 380
```

```
Arg Asp Phe Ala Ala Tyr Arg Ser Arg Val Lys Phe Ser Arg Ser Ala
385                 390                 395                 400

Asp Ala Pro Ala Tyr Lys Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500
```

<210> SEQ ID NO 7
<211> LENGTH: 1401
<212> TYPE: DNA
<213> ORGANISM: Artificial
<220> FEATURE:
<223> OTHER INFORMATION: nucleic acid sequence encoding a CAR-MOG

<400> SEQUENCE: 7

```
atggcattac cagttaccgc attattactg ccgctggcat tgctgttaca tgcagcacgt     60

ccggaggtga agctgcacga gagcggcgca ggtctggtga agcccggcgc cagcgtggag    120

atcagctgca aggccaccgg ctacaccttc agcagcttct ggatcgagtg ggtgaagcag    180

agacccggcc acggcctgga gtggatcggc gagatcctgc ccggcagagg cagaaccaac    240

tacaacgaga agttcaaggg caaggccacc ttcaccgccg agaccagcag caacaccgcc    300

tacatgcagc tgagcagcct gaccagcgag gacagcgccg tgtactactg cgccaccggc    360

aacaccatgg tgaacatgcc ctactggggc cagggcacca ccgtgaccgt gagcagcggt    420

ggaggtggtt cgggaggtgg aggtagcgga ggtggtggaa gcgatattga actgacccag    480

agtcccagta gcctggccgt gagtgccggc gagaaagtga ccatgagctg caaaagcagc    540

cagagcctgc tgaacagcgg caaccagaaa aactacctgg cctggtacca gcagaaaccc    600

ggcctgcctc ctaagctgct gatctacggc gccagcacca gagaaagcgg cgtgcccgat    660

agattcaccg gctctggctc tggcaccgac ttcaccctga ccatcagcag cgtgcaggcc    720

gaagacctgg ctgtctacta ctgccagaac gaccacagct accccctgac cttcggcgcc    780

ggcaccaagc tggagatcaa gctcgagccc aaatcttgtg acaaaactca cacatgccca    840

ccgtgcccgg atcccaaatt ttgggtgctg gtggtggttg gtggagtcct ggcttgctat    900

agcttgctag taacagtggc ctttattatt ttctgggtga ggagtaagag gagcaggctc    960

ctgcacagtg actacatgaa catgactccc cgccgccccg gtcccacccg caagcattac   1020

cagccctatg ccccaccacg cgacttcgca gcctatcgct ccagagtgaa gttcagcagg   1080

agcgcagacg cccccgcgta caagcagggc cagaaccagc tctataacga gctcaatcta   1140

ggacgaagag aggagtacga tgttttggac aagagacgtg gccgggaccc tgagatggga   1200

ggaaagccga gaaggaagaa ccctcaggaa ggcctgtaca atgaactgca gaaagataag   1260

atggcggagg cctacagtga gattgggatg aaaggcgagc gccggagggg caaggggcac   1320
```

gatggccttt accagggtct cagtacagcc accaaggaca cctacgacgc ccttcacatg 1380
caggccctgc cccctcgcta a 1401

<210> SEQ ID NO 8
<211> LENGTH: 466
<212> TYPE: PRT
<213> ORGANISM: Artificial
<220> FEATURE:
<223> OTHER INFORMATION: amino acid sequence of a CAR-MOG

<400> SEQUENCE: 8

```
Met Ala Leu Pro Val Thr Ala Leu Leu Leu Pro Leu Ala Leu Leu Leu
1               5                   10                  15

His Ala Ala Arg Pro Glu Val Lys Leu His Glu Ser Gly Ala Gly Leu
            20                  25                  30

Val Lys Pro Gly Ala Ser Val Glu Ile Ser Cys Lys Ala Thr Gly Tyr
        35                  40                  45

Thr Phe Ser Ser Phe Trp Ile Glu Trp Val Lys Gln Arg Pro Gly His
    50                  55                  60

Gly Leu Glu Trp Ile Gly Glu Ile Leu Pro Gly Arg Gly Arg Thr Asn
65                  70                  75                  80

Tyr Asn Glu Lys Phe Lys Gly Lys Ala Thr Phe Thr Ala Glu Thr Ser
                85                  90                  95

Ser Asn Thr Ala Tyr Met Gln Leu Ser Ser Leu Thr Ser Glu Asp Ser
            100                 105                 110

Ala Val Tyr Tyr Cys Ala Thr Gly Asn Thr Met Val Asn Met Pro Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Gly Ser Asp Ile Glu Leu Thr Gln
145                 150                 155                 160

Ser Pro Ser Ser Leu Ala Val Ser Ala Gly Glu Lys Val Thr Met Ser
                165                 170                 175

Cys Lys Ser Ser Gln Ser Leu Leu Asn Ser Gly Asn Gln Lys Asn Tyr
            180                 185                 190

Leu Ala Trp Tyr Gln Gln Lys Pro Gly Leu Pro Pro Lys Leu Leu Ile
        195                 200                 205

Tyr Gly Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp His Ser Tyr Pro Leu
                245                 250                 255

Thr Phe Gly Ala Gly Thr Lys Leu Glu Ile Lys Leu Glu Pro Lys Ser
            260                 265                 270

Cys Asp Lys Thr His Thr Cys Pro Pro Cys Pro Asp Pro Lys Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350
```

```
Arg Ser Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465


<210> SEQ ID NO 9
<211> LENGTH: 1518
<212> TYPE: DNA
<213> ORGANISM: Artificial
<220> FEATURE:
<223> OTHER INFORMATION: nucleic acid sequence encoding a CAR-HER2

<400> SEQUENCE: 9

tctagaatgg ccttaccagt gaccgccttg ctcctgccgc tggccttgct gctccacgcc     60

gccaggccgg atatccagat gacccagtcc ccgagctccc tgtccgcctc tgtgggcgat    120

agggtcacta tcacctgccg tgccagtcag gatgtgaata ctgctgtagc ctggtatcaa    180

cagaaacccg gaaaggcccc gaaactgctg atttactcgg catccttcct ctactctgga    240

gtcccttctc gcttctctgg ttcccgctct gggacggatt tcactctgac catcagctcc    300

ctgcagccgg aagacttcgc aacttattac tgtcagcaac actatactac tcctccgacg    360

ttcggacagg gtaccaaggt ggagatcaaa cgtaccgtgg cggcgccagg aggtggcgga    420

tcaggcggag gaggcagcgg cggaggtgga tcaggaggcg gagggtcaga ggttcagctg    480

gtggagtctg gcggtggcct ggtgcagccc gggggctctc tccgtttgtc ctgtgcagct    540

tctggcttca acattaaaga cacctatatc cactgggtgc gtcaggctcc gggtaagggc    600

ctggagtggg ttgcaaggat ttatcctacg aatggttata ctcgttatgc cgatagcgtc    660

aagggccgtt tcactataag cgcagacact tcgaaaaaca cagcctacct ccagatgaac    720

agcctgcgtg ctgaggacac tgccgtctat tattgtagca gatggggtgg ggacggcttc    780

tatgctatgg actactgggg tcaaggtaca ctagtcaccg tcagcagcgc tagcaccaag    840

ggcaccacga cgccagcgcc gcgaccacca acaccggcgc ccaccatcgc gtcgcagccc    900

ctgtccctgc gcccagaggc gtgccggcca gcggcggggg gcgcagtgca cacgaggggg    960

ctggacttcg cctgtgatat ctacatctgg gcgcccttgg ccgggacttg tggggtcctt   1020

ctcctgtcac tggttatcac cctttactgc aaacggggca gaaagaaact cctgtatata   1080

ttcaaacaac catttatgag accagtacaa actactcaag aggaagatgg ctgtagctgc   1140

cgatttccag aagaagaaga aggaggatgt gaactgagag tgaagttcag caggagcgca   1200

gacgcccccg cgtacaagca gggccagaac cagctctata acgagctcaa tctaggacga   1260

agagaggagt acgatgtttt ggacaagaga cgtggccggg accctgagat gggggggaaag   1320
```

```
ccgagaagga agaaccctca ggaaggcctg tacaatgaac tgcagaaaga taagatggcg   1380

gaggcctaca gtgagattgg gatgaaaggc gagcgccgga ggggcaaggg gcacgatggc   1440

ctttaccagg gtctcagtac agccaccaag gacacctacg acgcccttca catgcaggcc   1500

ctgccccctc gcgtcgac                                                   1518


<210> SEQ ID NO 10
<211> LENGTH: 506
<212> TYPE: PRT
<213> ORGANISM: Artificial
<220> FEATURE:
<223> OTHER INFORMATION: amino acid sequence of a CAR-HER2

<400> SEQUENCE: 10

Ser Arg Met Ala Leu Pro Val Thr Ala Leu Leu Leu Pro Leu Ala Leu
1               5                   10                  15

Leu Leu His Ala Ala Arg Pro Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Gly Gly Gly Gly Ser Gly Gly Gly
    130                 135                 140

Gly Ser Gly Gly Gly Gly Ser Gly Gly Gly Gly Ser Glu Val Gln Leu
145                 150                 155                 160

Val Glu Ser Gly Gly Gly Leu Val Gln Pro Gly Gly Ser Leu Arg Leu
                165                 170                 175

Ser Cys Ala Ala Ser Gly Phe Asn Ile Lys Asp Thr Tyr Ile His Trp
            180                 185                 190

Val Arg Gln Ala Pro Gly Lys Gly Leu Glu Trp Val Ala Arg Ile Tyr
        195                 200                 205

Pro Thr Asn Gly Tyr Thr Arg Tyr Ala Asp Ser Val Lys Gly Arg Phe
    210                 215                 220

Thr Ile Ser Ala Asp Thr Ser Lys Asn Thr Ala Tyr Leu Gln Met Asn
225                 230                 235                 240

Ser Leu Arg Ala Glu Asp Thr Ala Val Tyr Tyr Cys Ser Arg Trp Gly
                245                 250                 255

Gly Asp Gly Phe Tyr Ala Met Asp Tyr Trp Gly Gln Gly Thr Leu Val
            260                 265                 270

Thr Val Ser Ser Ala Ser Thr Lys Gly Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
```

```
                325                 330                 335

Cys Gly Val Leu Leu Leu Ser Leu Val Ile Thr Leu Tyr Cys Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Lys Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg Val Asp
            500                 505


<210> SEQ ID NO 11
<211> LENGTH: 113
<212> TYPE: PRT
<213> ORGANISM: Artificial
<220> FEATURE:
<223> OTHER INFORMATION: amino acid sequence of an anti-ECAD antibody
      heavy chain

<400> SEQUENCE: 11

Gln Ile Leu Leu Val Gln Ser Gly Pro Glu Leu Lys Lys Pro Gly Glu
1               5                   10                  15

Thr Val Lys Ile Ser Cys Lys Ala Ser Asn Tyr Thr Phe Thr Asp Tyr
            20                  25                  30

Gly Met His Trp Val Lys Gln Ala Pro Gly Lys Gly Leu Lys Trp Met
        35                  40                  45

Gly Trp Ile Asn Pro Lys Thr Gly Val Ala Ser Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Glu Asn Glu Asp Thr Ser Ile Tyr Phe Cys
                85                  90                  95

Ala Arg Phe Phe Asp Tyr Trp Gly Gln Gly Thr Thr Leu Thr Val Ser
            100                 105                 110

Ser


<210> SEQ ID NO 12
<211> LENGTH: 112
<212> TYPE: PRT
<213> ORGANISM: Artificial
<220> FEATURE:
<223> OTHER INFORMATION: amino acid sequence of an anti-ECAD antibody
      light chain

<400> SEQUENCE: 12
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asn Thr Tyr Leu Glu Trp Tyr Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ala Pro Trp Thr Phe Gly Gly Gly Thr Lys Val Glu Ile Lys
            100                 105                 110

<210> SEQ ID NO 13
<211> LENGTH: 111
<212> TYPE: PRT
<213> ORGANISM: Artificial
<220> FEATURE:
<223> OTHER INFORMATION: amino acid sequence of an anti-ECAD antibody light chain

<400> SEQUENCE: 13

Asp Ile Val Leu Thr Gln Ser Pro Leu Ser Leu Leu Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Asn Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Thr
                85                  90                  95

Thr His Val Trp Thr Phe Gly Gly Gly Thr Lys Leu Glu Ile Lys
            100                 105                 110

<210> SEQ ID NO 14
<211> LENGTH: 118
<212> TYPE: PRT
<213> ORGANISM: Artificial
<220> FEATURE:
<223> OTHER INFORMATION: amino acid sequence of an anti-MOG antibody heavy chain

<400> SEQUENCE: 14

Glu Val Lys Leu His Glu Ser Gly Ala Gly Leu Val Lys Pro Gly Ala
1               5                   10                  15

Ser Val Glu Ile Ser Cys Lys Ala Thr Gly Tyr Thr Phe Ser Ser Phe
            20                  25                  30

Trp Ile Glu Trp Val Lys Gln Arg Pro Gly His Gly Leu Glu Trp Ile
        35                  40                  45

Gly Glu Ile Leu Pro Gly Arg Gly Arg Thr Asn Tyr Asn Glu Lys Phe
    50                  55                  60

Lys Gly Lys Ala Thr Phe Thr Ala Glu Thr Ser Ser Asn Thr Ala Tyr
65                  70                  75                  80

```
Met Gln Leu Ser Ser Leu Thr Ser Glu Asp Ser Ala Val Tyr Tyr Cys
                85                  90                  95

Ala Thr Gly Asn Thr Met Val Asn Met Pro Tyr Trp Gly Gln Gly Thr
            100                 105                 110

Thr Val Thr Val Ser Ser
        115


<210> SEQ ID NO 15
<211> LENGTH: 113
<212> TYPE: PRT
<213> ORGANISM: Artificial
<220> FEATURE:
<223> OTHER INFORMATION: amino acid sequence of an anti-MOG antibody
      light chain

<400> SEQUENCE: 15

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Leu
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Ile
            100                 105                 110

Lys


<210> SEQ ID NO 16
<211> LENGTH: 170
<212> TYPE: PRT
<213> ORGANISM: Artificial
<220> FEATURE:
<223> OTHER INFORMATION: amino acid sequence of an anti-HER2 antibody
      heavy chain

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Thr Thr Thr
        115                 120                 125
```

```
Pro Ala Pro Arg Pro Pro Thr Pro Ala Pro Thr Ile Ala Ser Gln Pro
    130                 135                 140

Leu Ser Leu Arg Pro Glu Ala Cys Arg Pro Ala Ala Gly Gly Ala Val
145                 150                 155                 160

His Thr Arg Gly Leu Asp Phe Ala Cys Asp
                165                 170


<210> SEQ ID NO 17
<211> LENGTH: 113
<212> TYPE: PRT
<213> ORGANISM: Artificial
<220> FEATURE:
<223> OTHER INFORMATION: amino acid sequence of an anti-HER2 antibody
      light chain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro


<210> SEQ ID NO 18
<211> LENGTH: 361
<212> TYPE: DNA
<213> ORGANISM: Artificial
<220> FEATURE:
<223> OTHER INFORMATION: nucleic acid encoding an anti-ECAD antibody
      heavy chain

<400> SEQUENCE: 18

gaggtgcagc tggtggagtc tgggggaggc ttggtacagc ctggggggtc cctgagactc      60

tcctgtgcag cctctggatt caccttcagt agctatggca tgcactgggt ccgccaggct     120

ccagggaagg ggctggagtg ggttgcatac attactacta gaagtagtac catatactac     180

gcagactctg tgaagggccg attcaccatc tccagagaca atgccaagaa ctcactgtat     240

ctgcaaatga acagcctgag agccgaggac acggctgtgt attactgtac tagagaaccc     300

ctaactggat actatgctat ggactactgg ggtcaaggaa cctcagtcac cgtctcctca     360

g                                                                      361


<210> SEQ ID NO 19
<211> LENGTH: 339
<212> TYPE: DNA
<213> ORGANISM: Artificial
<220> FEATURE:
<223> OTHER INFORMATION: nucleic acid encoding an anti-ECAD antibody
      heavy chain

<400> SEQUENCE: 19
```

cagatcctgt tggtgcagtc tggacctgag ctgaagaagc ctggagagac agtcaagatc 60
tcctgcaagg cttctaatta taccttcaca gactatggaa tgcactgggt gaagcaggct 120
ccaggaaagg gtttaaagtg gatgggctgg ataaacccca agactggtgt ggcatcatat 180
gcagatgact tcaagggaag atttgccttc tctttggaaa cctctgccag cactgcctat 240
ttgcagatca acaacctcga aaatgaggac acgtctatat atttctgtgc tagatttttt 300
gactactggg gccaaggcac cactctcaca gtctcctca 339

<210> SEQ ID NO 20
<211> LENGTH: 336
<212> TYPE: DNA
<213> ORGANISM: Artificial
<220> FEATURE:
<223> OTHER INFORMATION: nucleic acid encoding an anti-ECAD antibody light chain

<400> SEQUENCE: 20
gatgttgtga tgactcagtc tccactctcc ctgcccgtca cccttggaca gccggcctcc 60
atctcctgca ggtctagtca aagcatcgta cacagtgatg gaaacaccta cttggaatgg 120
tatcagcaga ggccaggcca atctccaagg cgcctaattt ataaggtttc taaccggttc 180
tctggggtcc cagacagatt cagcggcagt gggtcaggca ctgatttcac actgaaaatc 240
agcagggtgg aggctgagga tgttggggtt attactgctt tcaaggttca catgctccgt 300
ggacgttcgg tggaggcacc aaggtggaaa tcaaac 336

<210> SEQ ID NO 21
<211> LENGTH: 333
<212> TYPE: DNA
<213> ORGANISM: Artificial
<220> FEATURE:
<223> OTHER INFORMATION: nucleic acid encoding an anti-ECAD antibody light chain

<400> SEQUENCE: 21
gatattgtgc tgacacagtc tccactctcc ctgcttgtca gtcttggaga tcaagcctcc 60
atctcttgca gatctagtca gagccttgta cacagtaatg gaaacaccta tttacattgg 120
tatctgcaga agccaggcca gtctccaaac ctcctgatct tcaaagtttc caaccgattt 180
tctggggtcc cagacaggtt cagtggcagt ggatcaggga cagatttcac actcaggatc 240
agcagagtgg aggctgagga tctgggagtt tatttctgct ctcaaactac acatgtgtgg 300
acgttcggtg gaggcaccaa gctggaaatc aaa 333

<210> SEQ ID NO 22
<211> LENGTH: 354
<212> TYPE: DNA
<213> ORGANISM: Artificial
<220> FEATURE:
<223> OTHER INFORMATION: nucleic acid encoding an anti-MOG antibody heavy chain

<400> SEQUENCE: 22
gaggtgaagc tgcacgagag cggcgcaggt ctggtgaagc ccggcgccag cgtggagatc 60
agctgcaagg ccaccggcta caccttcagc agcttctgga tcgagtgggt gaagcagaga 120
cccggccacg gcctggagtg gatcggcgag atcctgcccg gcagaggcag aaccaactac 180
aacgagaagt tcaagggcaa ggccaccttc accgccgaga ccagcagcaa caccgcctac 240
atgcagctga gcagcctgac cagcgaggac agcgccgtgt actactgcgc caccggcaac 300
accatggtga acatgcccta ctggggccag ggcaccaccg tgaccgtgag cagc 354

<210> SEQ ID NO 23
<211> LENGTH: 339
<212> TYPE: DNA
<213> ORGANISM: Artificial
<220> FEATURE:
<223> OTHER INFORMATION: nucleic acid encoding an anti-MOG antibody light chain

<400> SEQUENCE: 23
gatattgaac tgacccagag tcccagtagc ctggccgtga gtgccggcga gaaagtgacc 60
atgagctgca aaagcagcca gagcctgctg aacagcggca accagaaaaa ctacctggcc 120
tggtaccagc agaaacccgg cctgcctcct aagctgctga tctacggcgc cagcaccaga 180
gaaagcggcg tgcccgatag attcaccggc tctggctctg gcaccgactt caccctgacc 240
atcagcagcg tgcaggccga agacctggct gtctactact gccagaacga ccacagctac 300
cccctgacct tcggcgccgg caccaagctg gagatcaag 339

<210> SEQ ID NO 24
<211> LENGTH: 510
<212> TYPE: DNA
<213> ORGANISM: Artificial
<220> FEATURE:
<223> OTHER INFORMATION: nucleic acid encoding an anti-HER2 antibody heavy chain

<400> SEQUENCE: 24
gaggttcagc tggtggagtc tggcggtggc ctggtgcagc ccgggggctc tctccgtttg 60
tcctgtgcag cttctggctt caacattaaa gacacctata tccactgggt gcgtcaggct 120
ccgggtaagg gcctggagtg ggttgcaagg atttatccta cgaatggtta tactcgttat 180
gccgatagcg tcaagggccg tttcactata agcgcagaca cttcgaaaaa cacagcctac 240
ctccagatga acagcctgcg tgctgaggac actgccgtct attattgtag cagatggggt 300
ggggacggct tctatgctat ggactactgg ggtcaaggta cactagtcac cgtcagcagc 360
gctagcacca agggcaccac gacgccagcg ccgcgaccac caacaccggc gcccaccatc 420
gcgtcgcagc ccctgtccct gcgcccagag gcgtgccggc cagcggcggg gggcgcagtg 480
cacacgaggg ggctggactt cgcctgtgat 510

<210> SEQ ID NO 25
<211> LENGTH: 339
<212> TYPE: DNA
<213> ORGANISM: Artificial
<220> FEATURE:
<223> OTHER INFORMATION: nucleic acid encoding an anti-HER2 antibody light chain

<400> SEQUENCE: 25
gatatccaga tgacccagtc cccgagctcc ctgtccgcct ctgtgggcga tagggtcact 60
atcacctgcc gtgccagtca ggatgtgaat actgctgtag cctggtatca acagaaaccc 120
ggaaaggccc cgaaactgct gatttactcg gcatccttcc tctactctgg agtcccttct 180
cgcttctctg gttcccgctc tgggacggat ttcactctga ccatcagctc cctgcagccg 240
gaagacttcg caacttatta ctgtcagcaa cactatacta ctcctccgac gttcggacag 300
ggtaccaagg tggagatcaa acgtaccgtg gcggcgcca 339

<210> SEQ ID NO 26

<211> LENGTH: 21
<212> TYPE: PRT
<213> ORGANISM: Artificial
<220> FEATURE:
<223> OTHER INFORMATION: CD8 leader sequence

<400> SEQUENCE: 26

Met Ala Leu Pro Val Thr Ala Leu Leu Leu Pro Leu Ala Leu Leu Leu
1 5 10 15

His Ala Ala Arg Pro
20

<210> SEQ ID NO 27
<211> LENGTH: 15
<212> TYPE: PRT
<213> ORGANISM: Artificial
<220> FEATURE:
<223> OTHER INFORMATION: linker sequence

<400> SEQUENCE: 27

Gly Gly Gly Gly Ser Gly Gly Gly Gly Ser Gly Gly Gly Gly Ser
1 5 10 15

<210> SEQ ID NO 28
<211> LENGTH: 45
<212> TYPE: PRT
<213> ORGANISM: Artificial
<220> FEATURE:
<223> OTHER INFORMATION: CD8 hinge sequence

<400> SEQUENCE: 28

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 29
<211> LENGTH: 19
<212> TYPE: PRT
<213> ORGANISM: Artificial
<220> FEATURE:
<223> OTHER INFORMATION: CD28 hinge sequence

<400> SEQUENCE: 29

Leu Glu Pro Lys Ser Cys Asp Lys Thr His Thr Cys Pro Pro Cys Pro
1 5 10 15

Asp Pro Lys

<210> SEQ ID NO 30
<211> LENGTH: 24
<212> TYPE: PRT
<213> ORGANISM: Artificial
<220> FEATURE:
<223> OTHER INFORMATION: CD8 transmembrane domain sequence

<400> SEQUENCE: 30

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 31

<211> LENGTH: 27
<212> TYPE: PRT
<213> ORGANISM: Artificial
<220> FEATURE:
<223> OTHER INFORMATION: CD28 transmembrane domain sequence

<400> SEQUENCE: 31

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 32
<211> LENGTH: 41
<212> TYPE: PRT
<213> ORGANISM: Artificial
<220> FEATURE:
<223> OTHER INFORMATION: CD28 signaling domain sequence

<400> SEQUENCE: 32

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 33
<211> LENGTH: 112
<212> TYPE: PRT
<213> ORGANISM: Artificial
<220> FEATURE:
<223> OTHER INFORMATION: CD3zeta signaling domain sequence

<400> SEQUENCE: 33

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 34
<211> LENGTH: 42
<212> TYPE: PRT
<213> ORGANISM: Artificial
<220> FEATURE:
<223> OTHER INFORMATION: 41BB signaling domain sequence

<400> SEQUENCE: 34

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30
```

Pro Glu Glu Glu Glu Gly Gly Cys Glu Leu
35 40

<210> SEQ ID NO 35
<211> LENGTH: 151
<212> TYPE: PRT
<213> ORGANISM: Artificial
<220> FEATURE:
<223> OTHER INFORMATION: TLR3 signaling domain sequence

<400> SEQUENCE: 35

Phe Glu Tyr Ala Ala Tyr Ile Ile His Ala Tyr Lys Asp Lys Asp Trp
1 5 10 15

Val Trp Glu His Phe Ser Ser Met Glu Lys Glu Asp Gln Ser Leu Lys
20 25 30

Phe Cys Leu Glu Glu Arg Asp Phe Glu Ala Gly Val Phe Glu Leu Glu
35 40 45

Ala Ile Val Asn Ser Ile Lys Arg Ser Arg Lys Ile Ile Phe Val Ile
50 55 60

Thr His His Leu Leu Lys Asp Pro Leu Cys Lys Arg Phe Lys Val His
65 70 75 80

His Ala Val Gln Gln Ala Ile Glu Gln Asn Leu Asp Ser Ile Ile Leu
85 90 95

Val Phe Leu Glu Glu Ile Pro Asp Tyr Lys Leu Asn His Ala Leu Cys
100 105 110

Leu Arg Arg Gly Met Phe Lys Ser His Cys Ile Leu Asn Trp Pro Val
115 120 125

Gln Lys Glu Arg Ile Gly Ala Phe Arg His Lys Leu Gln Val Ala Leu
130 135 140

Gly Ser Lys Asn Ser Val His
145 150

<210> SEQ ID NO 36
<211> LENGTH: 168
<212> TYPE: PRT
<213> ORGANISM: Artificial
<220> FEATURE:
<223> OTHER INFORMATION: TLR4 signaling domain sequence

<400> SEQUENCE: 36

Asn Ile Tyr Asp Ala Phe Val Ile Tyr Ser Ser Gln Asp Glu Asp Trp
1 5 10 15

Val Arg Asn Glu Leu Val Lys Asn Leu Glu Glu Gly Val Pro Pro Phe
20 25 30

Gln Leu Cys Leu His Tyr Arg Asp Phe Ile Pro Gly Val Ala Ile Ala
35 40 45

Ala Asn Ile Ile His Glu Gly Phe His Lys Ser Arg Lys Val Ile Val
50 55 60

Val Val Ser Gln His Phe Ile Gln Ser Arg Trp Cys Ile Phe Glu Tyr
65 70 75 80

Glu Ile Ala Gln Thr Trp Gln Phe Leu Ser Ser Arg Ala Gly Ile Ile
85 90 95

Phe Ile Val Leu Gln Lys Val Glu Lys Thr Leu Leu Arg Gln Gln Val
100 105 110

Glu Leu Tyr Arg Leu Leu Ser Arg Asn Thr Tyr Leu Glu Trp Glu Asp
115 120 125

Ser Val Leu Gly Arg His Ile Phe Trp Arg Arg Leu Arg Lys Ala Leu 130 135 140

Leu Asp Gly Lys Ser Trp Asn Pro Glu Gly Thr Val Gly Thr Gly Cys
145 150 155 160

Asn Trp Gln Glu Ala Thr Ser Ile
165

<210> SEQ ID NO 37
<211> LENGTH: 63
<212> TYPE: DNA
<213> ORGANISM: Artificial
<220> FEATURE:
<223> OTHER INFORMATION: nucleic acid sequence encoding a CD8 leader sequence

<400> SEQUENCE: 37
atggccttac cagtgaccgc cttgctcctg ccgctggcct tgctgctcca cgccgccagg 60
ccg 63

<210> SEQ ID NO 38
<211> LENGTH: 45
<212> TYPE: DNA
<213> ORGANISM: Artificial
<220> FEATURE:
<223> OTHER INFORMATION: nucleic acid sequence encoding a linker

<400> SEQUENCE: 38
ggtggaggtg gttcgggagg tggaggtagc ggaggtggtg gatct 45

<210> SEQ ID NO 39
<211> LENGTH: 135
<212> TYPE: DNA
<213> ORGANISM: Artificial
<220> FEATURE:
<223> OTHER INFORMATION: nucleic acid sequence encoding a CD8 hinge

<400> SEQUENCE: 39
accactaccc ctgcaccgcg accaccaaca ccggcgccca ccattgcgtc gcagcctctg 60
tccctgcgcc cagaagcatg ccgtccagca gcaggtggtg cagttcatac tcgtggtctg 120
gatttcgcct gtgat 135

<210> SEQ ID NO 40
<211> LENGTH: 57
<212> TYPE: DNA
<213> ORGANISM: Artificial
<220> FEATURE:
<223> OTHER INFORMATION: nucleic acid sequence encoding a CD28 hinge

<400> SEQUENCE: 40
ctcgagccca aatcttgtga caaaactcac acatgcccac cgtgcccgga tcccaaa 57

<210> SEQ ID NO 41
<211> LENGTH: 72
<212> TYPE: DNA
<213> ORGANISM: Artificial
<220> FEATURE:
<223> OTHER INFORMATION: nucleic acid sequence encoding a CD8 transmembrane domain

<400> SEQUENCE: 41
atctacatct gggcgccctt ggccgggact tgtggggtcc ttctcctgtc actggttatc 60
accctttact gc 72

<210> SEQ ID NO 42
<211> LENGTH: 81
<212> TYPE: DNA
<213> ORGANISM: Artificial
<220> FEATURE:
<223> OTHER INFORMATION: nucleic acid sequence encoding a CD28 transmembrane domain

<400> SEQUENCE: 42
ttttgggtgc tggtggtggt tggtggagtc ctggcttgct atagcttgct agtaacagtg 60
gcctttatta ttttctgggt g 81

<210> SEQ ID NO 43
<211> LENGTH: 123
<212> TYPE: DNA
<213> ORGANISM: Artificial
<220> FEATURE:
<223> OTHER INFORMATION: nucleic acid sequence encoding a CD28 signaling domain

<400> SEQUENCE: 43
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 44
<211> LENGTH: 336
<212> TYPE: DNA
<213> ORGANISM: Artificial
<220> FEATURE:
<223> OTHER INFORMATION: nucleic acid sequence encoding a CD3zeta signaling domain

<400> SEQUENCE: 44
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 45
<211> LENGTH: 126
<212> TYPE: DNA
<213> ORGANISM: Artificial
<220> FEATURE:
<223> OTHER INFORMATION: nucleic acid sequence encoding a 41BB signaling domain

<400> SEQUENCE: 45
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

METHODS AND MATERIALS FOR USING ENGINEERED MESENCHYMAL STEM CELLS TO TREAT INFLAMMATORY CONDITIONS AND DEGENERATIVE DISEASES

CROSS-REFERENCE TO RELATED APPLICATIONS

This application is a National Stage application under 35 U.S.C. § 371 of International Application No. PCT/US2020/059720, having an International Filing Date Nov. 9, 2020, which claims the benefit of U.S. Provisional Application Ser. No. 62/932,610, filed Nov. 8, 2019. The disclosure of the prior application is considered part of (and is incorporated by reference in) the disclosure of this application.

SEQUENCE LISTING

This document contains a sequence listing that has been submitted electronically as an ASCII text file. The ASCII text file, created on Dec. 23, 2020, is 54 kilobytes in size. The material in the ASCII text file is hereby incorporated by reference in its entirety.

BACKGROUND

1. Technical Field

This document relates to methods and materials for using engineered mesenchymal stem cells (MSCs) to treat a mammal (e.g., a human) having, or at risk of developing, an inflammatory disease or condition and/or having, or at risk of developing, a degenerative disease. For example, this document provides engineered MSCs designed to express an antigen receptor (e.g., a chimeric antigen receptor (CAR)) having the ability to bind (e.g., bind specifically) to an antigen (e.g., a tissue-specific antigen). Such engineered MSCs can exert an immunosuppressive effect (e.g., can reduce or eliminate an immune response) in a targeted tissue and/or can regenerate tissue specific cells. In some cases, an MSC engineered to express an antigen receptor having the ability to bind to an antigen (e.g., a tissue specific cell that expresses the antigen targeted by the MSC) also can be engineered to express a polypeptide that can promote differentiation into a tissue specific cell. For example, a MSC can be designed to include nucleic acid encoding a polypeptide that can promote tissue specific cell differentiation and can differentiate into a tissue specific cell (e.g., a cardiac cell or a neuron). This document also provides methods for administering one or more MSCs expressing an antigen receptor having the ability to bind (e.g., specifically bind) a tissue-specific antigen to a mammal (e.g., a human) having, or at risk of developing, an inflammatory disease or condition to treat that inflammatory disease or condition within the mammal.

2. Background Information

Inflammation is a common factor in many diseases. In 2015, an estimated 1.3% of U.S. adults (about 3 million people) reported being diagnosed with IBD (either Crohn's disease or ulcerative colitis; Dahlhamer et al., *MMWR Morb Mortal Wkly Rep.* 2016, 65(42):1166-1169 (2015)).

SUMMARY

This document provides methods and materials involved in treating a mammal (e.g., a human) having, or at risk of developing, an inflammatory disease or condition and/or having, or at risk of developing, a degenerative disease. For example, one or more MSCs designed to express an antigen receptor (e.g., a CAR) capable of binding (e.g., specifically binding) to a tissue-specific antigen can be administered to a mammal to induce an immunosuppressive response (e.g., to reduce or eliminate an inflammatory immune response) within the mammal. In some cases, a CAR targeting an epithelial-specific antigen (e.g., epithelial cadherin (ECAD, also referred to as CDH1)) can be expressed by a MSC (e.g., a MSC-CAR) to target the MSC to epithelial tissues. In some cases, a CAR targeting a neural-specific antigen (e.g., myelin oligodendrocyte glycoprotein (MOG)) can be expressed by a MSC (e.g., a MSC-CAR) to target the MSC to neural tissues. In some cases, a CAR targeting a cardiac-specific antigen (e.g., human epidermal growth factor receptor 2 (HER2)) can be expressed by a MSC to target the MSC to cardiac tissues. For example, one or more MSCs designed to express a CAR capable of binding (e.g., specifically binding) to a tissue-specific antigen (e.g., an epithelial-specific antigen, a neural-specific antigen, or a cardiac-specific antigen) can be administered (e.g., by adoptive transfer) to a mammal (e.g., a human) having (or at risk of developing) an inflammatory disease or condition to treat that inflammatory disease or condition within the mammal. In some cases, one or more MSCs expressing a CAR capable of binding (e.g., specifically binding) to an epithelial-specific antigen (e.g., ECAD) can be administered (e.g., by adoptive transfer) to a mammal (e.g., a human) having, or at risk of developing, an inflammatory bowel disease (IBD; e.g., colitis) to treat that inflammatory bowel disease within the mammal. In some cases, one or more MSCs expressing a CAR capable of binding (e.g., specifically binding) to a neural-specific antigen (e.g., MOG) can be administered (e.g., by adoptive transfer) to a mammal (e.g., a human) having, or at risk of developing, multiple sclerosis to treat that multiple sclerosis within the mammal. In some cases, one or more MSCs expressing a CAR capable of binding (e.g., specifically binding) to a neural-specific antigen (e.g., MOG) can be administered (e.g., by adoptive transfer) to a mammal (e.g., a human) having, or at risk of developing, immune mediated encephalomyelitis to treat that immune mediated encephalomyelitis within the mammal. In some cases, one or more MSCs expressing a CAR capable of binding (e.g., specifically binding) to a cardiac-specific antigen (e.g., HER2) can be administered (e.g., by adoptive transfer) to a mammal (e.g., a human) having, or at risk of developing, myocarditis to treat that myocarditis within the mammal. For example, MSCs designed to express an antigen receptor (e.g., a CAR) capable of binding (e.g., specifically binding) to a tissue-specific antigen, also can be engineered to express a polypeptide that can promote differentiation into a tissue specific cell (e.g., can include nucleic acid encoding a polypeptide that can promote differentiation into a tissue specific cell). Such engineered MSCs can express a polypeptide that can promote differentiation of the MSC differentiation of the MSC and/or one or more resident progenitor cells into a tissue specific cell (e.g., a cardiac cell or a neuron) within the mammal. In some cases, one or more MSCs designed to express an antigen receptor (e.g., a CAR) capable of binding (e.g., specifically binding) to a tissue-specific antigen, and also designed to differentiate into a tissue specific cell can be administered (e.g., by adoptive transfer) to a mammal (e.g., a human) having, or at risk of developing, a degenerative disease to treat that degenerative disease within the mammal.

As demonstrated herein, MSCs (e.g., adipose-derived MSCs) can be engineered to express a CAR targeting a tissue-specific antigen (e.g., an antigen expressed on a target tissue). For example, MSCs can be designed to express a CAR that targets (e.g., binds to) ECAD (e.g., a CAR-ECAD) of epithelial tissues within a mammal and used to treat a disease or disorder characterized by inflammation of an epithelial tissue (e.g., colitis). In another example, MSCs can be designed to express a CAR that targets (e.g., binds to) MOG (e.g., a CAR-MOG) of neural tissue within a mammal and used to treat a disease or disorder characterized by inflammation of a neural tissue (e.g., multiple sclerosis and immune mediated encephalomyelitis). In some cases, MSCs can be designed to express a CAR that targets (e.g., binds to) an antigen expressed on a target tissue to exert an immunosuppressive effect (e.g., to reduce or eliminate an inflammatory immune response) within the targeted tissue. For example, MSCs expressing a CAR as described herein can be used to reduce or eliminate the proliferation of stimulated T cells in a targeted tissue (e.g., as compared to the levels present prior to administration of such MSCs).

Having the ability to treat inflammatory diseases and conditions as described herein can allow clinicians and patients to reduce inflammation within patients in an effective and efficient manner.

In general, one aspect of this document features methods for treating a mammal having colitis. The methods can include, or consist essentially of, administering to said mammal a composition including MSCs containing exogenous nucleic acid encoding a CAR targeting an epithelial-specific antigen, where the MSCs express the CAR. The mammal can be a human. The MSCs can be adipose derived-MSCs. The epithelial-specific antigen can be ECAD. The CAR can include a single chain variable fragment (scFv). The scFv can include a light chain and a heavy chain from an anti-CDH1 antibody. The anti-CDH1 antibody can be hSC10.17. The MSCs, prior to the administration, can be engineered to express the CAR ex vivo. A symptom of the colitis can be reduced at least 10 percent. The CAR can include a CD28 or TLR4 signaling domain.

In another aspect, one aspect of this document features methods for treating a mammal at risk of developing colitis. The methods can include, or consist essentially of, administering to the mammal a composition including MSCs containing exogenous nucleic acid encoding a CAR targeting an epithelial-specific antigen, where the MSCs express the CAR. The mammal can be a human. The MSCs can be adipose derived-MSCs. The epithelial-specific antigen can be ECAD. The CAR can include a scFv. The scFv can include a light chain and a heavy chain from an anti-CDH1 antibody. The anti-CDH1 antibody can be hSC10.17. The MSCs, prior to the administration, can be engineered to express the CAR ex vivo. The CAR can include a CD28 or TLR4 signaling domain.

In another aspect, one aspect of this document features methods for treating a mammal having multiple sclerosis. The methods can include, or consist essentially of, administering to the mammal a composition including MSCs containing exogenous nucleic acid encoding a CAR targeting a neural-specific antigen, where the MSCs express the CAR. The mammal can be a human. The MSCs can be adipose derived-MSCs. The neural-specific antigen can be MOG The CAR can include a scFv. The scFv can include a light chain and a heavy chain from an anti-MOG antibody. The anti-MOG antibody can be 8-18C5. The MSCs, prior to the administration, can be engineered to express the CAR ex vivo. A symptom of the multiple sclerosis can be reduced at least 10 percent. The MSCs also can contain exogenous nucleic acid encoding a polypeptide that can promote neural differentiation, where the MSCs express the polypeptide. The polypeptide that can promote neural cell differentiation can be a Oct3/4 polypeptide, a Klf4 polypeptide, a Sox2 polypeptide, a Glis1 polypeptide, a c□Myc polypeptide, a BMP4 polypeptide, a WNT polypeptide, a FGF2 polypeptide, a SHH polypeptide, a Sox11 polypeptide, a Sox2 polypeptide, a Sox3 polypeptide, a Zic1 polypeptide, a Zic2 polypeptide, a Irx1 polypeptide, a Irx2 polypeptide, a Irx3 polypeptide, a FoxD4 polypeptide, a MKx2.5 polypeptide, a cTnT polypeptide, or any combinations thereof. The CAR can include a CD28 or TLR4 signaling domain.

In another aspect, one aspect of this document features methods for treating a mammal at risk of developing multiple sclerosis. The methods can include, or consist essentially of, administering to the mammal a composition comprising MSCs containing exogenous nucleic acid encoding a CAR targeting a neural-specific antigen, where the MSCs express the CAR. The mammal can be a human. The MSCs can be adipose derived-MSCs. The neural-specific antigen can be MOG The CAR can include a scFv. The scFv can include a light chain and a heavy chain from an anti-MOG antibody. The anti-MOG antibody can be 8-18C5. The MSCs, prior to the administration, can be engineered to express the CAR ex vivo. The CAR can include a CD28 or TLR4 signaling domain.

In another aspect, one aspect of this document features methods for treating a mammal having immune mediated encephalomyelitis. The methods can include, or consist essentially of, administering to the mammal a composition including MSCs containing exogenous nucleic acid encoding a CAR targeting a neural-specific antigen, where the MSCs express the CAR. The mammal can be a human. The MSCs can be adipose derived-MSCs. The neural-specific antigen can be MOG The CAR can include a scFv. The scFv can include a light chain and a heavy chain from an anti-MOG antibody. The anti-MOG antibody can be 8-18C5. The MSCs, prior to the administration, can be engineered to express the CAR ex vivo. A symptom of the immune mediated encephalomyelitis can be reduced at least 10 percent. The MSCs also can contain exogenous nucleic acid encoding a polypeptide that can promote neural differentiation, where the MSCs express the polypeptide. The polypeptide that can promote neural differentiation can be a Oct3/4 polypeptide, a Klf4 polypeptide, a Sox2 polypeptide, a Glis1 polypeptide, a c□Myc polypeptide, a BMP4 polypeptide, a WNT polypeptide, a FGF2 polypeptide, a SHH polypeptide, a Sox11 polypeptide, a Sox2 polypeptide, a Sox3 polypeptide, a Zic1 polypeptide, a Zic2 polypeptide, a Irx1 polypeptide, a Irx2 polypeptide, a Irx3 polypeptide, a FoxD4 polypeptide, a MKx2.5 polypeptide, a cTnT polypeptide, or any combinations thereof. The CAR can include a CD28 or TLR4 signaling domain.

In another aspect, one aspect of this document features methods for treating a mammal at risk of developing immune mediated encephalomyelitis. The methods can include, or consist essentially of, administering to the mammal a composition comprising MSCs containing exogenous nucleic acid encoding a CAR targeting a neural-specific antigen, where the MSCs express the CAR. The mammal can be a human. The MSCs can be adipose derived-MSCs. The neural-specific antigen can be MOG The CAR can include a scFv. The scFv can include a light chain and a heavy chain from an anti-MOG antibody. The anti-MOG antibody can be 8-18C5. The MSCs, prior to the administration, can be engineered to express the CAR ex vivo. The CAR can include a CD28 or TLR4 signaling domain.

In another aspect, one aspect of this document features nucleic acid constructs encoding a CAR targeting a neural-specific antigen. The neural-specific antigen can be MOG The CAR can include a scFv. The CAR targeting the neural-specific antigen can be encoded by a nucleic acid sequence set forth in SEQ ID NO:3, SEQ ID NO:5, or SEQ ID NO:7. The nucleic acid construct also can encode a polypeptide that can promote neural differentiation. The polypeptide that can promote neural differentiation can be a Oct3/4 polypeptide, a Klf4 polypeptide, a Sox2 polypeptide, a Glis1 polypeptide, a c□Myc polypeptide, a BMP4 polypeptide, a WNT polypeptide, a FGF2 polypeptide, a SHH polypeptide, a Sox11 polypeptide, a Sox2 polypeptide, a Sox3 polypeptide, a Zic1 polypeptide, a Zic2 polypeptide, a Irx1 polypeptide, a Irx2 polypeptide, a Irx3 polypeptide, a FoxD4 polypeptide, a MKx2.5 polypeptide, a cTnT polypeptide, or any combinations thereof. The CAR can include a CD28 or TLR4 signaling domain.

In another aspect, one aspect of this document features methods for treating a mammal having myocarditis. The methods can include, or consist essentially of, administering to the mammal a composition including MSCs containing exogenous nucleic acid encoding a CAR targeting a cardiac-specific antigen, where the MSCs express the CAR. The mammal can be a human. The MSCs can be adipose derived-MSCs. The cardiac-specific antigen can be HER2. The CAR can include a scFv. The MSCs, prior to the administration, can be engineered to express the CAR ex vivo. A symptom of the myocarditis can be reduced at least 10 percent. The MSCs also can contain exogenous nucleic acid encoding a polypeptide that can promote cardiac cell differentiation, where the MSCs express the polypeptide. The polypeptide that can promote neural differentiation can be a GATA4 polypeptide, a MEF2C polypeptide, a TBX5 polypeptide, a ERRG polypeptide, a MESP1 polypeptide, and any combinations thereof. The CAR can include a CD28 or TLR4 signaling domain.

In another aspect, one aspect of this document features methods for treating a mammal at risk of developing myocarditis. The methods can include, or consist essentially of, administering to the mammal a composition including MSCs containing exogenous nucleic acid encoding a CAR targeting a cardiac-specific antigen, where the MSCs express the CAR. The mammal can be a human. The MSCs can be adipose derived-MSCs. The cardiac-specific antigen can be HER2. The CAR can include a scFv. The MSCs, prior to the administration, can be engineered to express the CAR ex vivo. The CAR can include a CD28 or TLR4 signaling domain.

In another aspect, one aspect of this document features nucleic acid constructs encoding a CAR targeting a cardiac-specific antigen. The cardiac-specific antigen can be HER2. The CAR can include a scFv. The CAR targeting said cardiac-specific antigen can be encoded by a nucleic acid sequence set forth in SEQ ID NO:9. The nucleic acid construct also can encode a polypeptide that can promote cardiac cell differentiation. The polypeptide that can promote neural differentiation can be a GATA4 polypeptide, a MEF2C polypeptide, a TBX5 polypeptide, a ERRG polypeptide, a MESP1 polypeptide, or any combinations thereof. The CAR can include a CD28 or TLR4 signaling domain.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 11. MSC expression of CAR-MOG.

FIGS. 12A-12B. A. Nucleic acid sequence (SEQ ID NO:1) encoding an exemplary CAR-ECAD. B. Amino acid sequence (SEQ ID NO:2) of an exemplary CAR-ECAD.

FIGS. 13A-13F. A. Nucleic acid sequence (SEQ ID NO:3) encoding an exemplary CAR-MOG. B. Amino acid sequence (SEQ ID NO:4) of an exemplary CAR-MOG. C. Nucleic acid sequence (SEQ ID NO:5) encoding an exemplary CAR-MOG. D. Amino acid sequence (SEQ ID NO:6) of an exemplary CAR-MOG. E. Nucleic acid sequence (SEQ ID NO:7) encoding an exemplary CAR-MOG. F. Amino acid sequence (SEQ ID NO:8) of an exemplary CAR-MOG.

FIGS. 14A-14B. A. Nucleic acid sequence (SEQ ID NO:9) encoding an exemplary CAR-HER2. B. Amino acid sequence (SEQ ID NO:10) of an exemplary CAR-HER2.

FIG. 15A is a graph plotting the percent of MSCs that are CAR positive following lentivirus transduction of MSC with K002 (CD19 directed CAR) compared to UTD (untransduced MSC). FIG. 15B is a graph plotting the percent of MSCs expressing the indicated marker two days after lentivirus transduction with CAR19 compared to untransduced MSC (UTD). The MSCs retain markers of stemness.

FIG. 19A is a graph plotting the absolute number of MSCs after 5 days of co-culture with irradiated $CD19^+$ NALM6 cells at 1:1 ratio of MSC:NALM6. NALM6 cells are included in this culture in order to stimulate MSC-CAR19 through the CAR. A co-culture of $CD19^+$ cells with MSC-CAR19-CD28 led to enhanced proliferation, compared to untransduced MSC (MSC-UTD), or MSC-K002, or MSC-K122, or MSC-K142. This indicates that antigen specific stimulation of MSC-CAR19 through the CAR results in signaling and altered proliferation of MSCs. FIG. 19B represents the MSC count on days 3 and 5 of the co-culture.

Transduction with CAR-E-cadherin-CD28 led to reduced MSC proliferation, compared to untransduced MSC (MSC-UTD), or MSC-transduced with GFP (MSC-ZSG).

Figure 21:
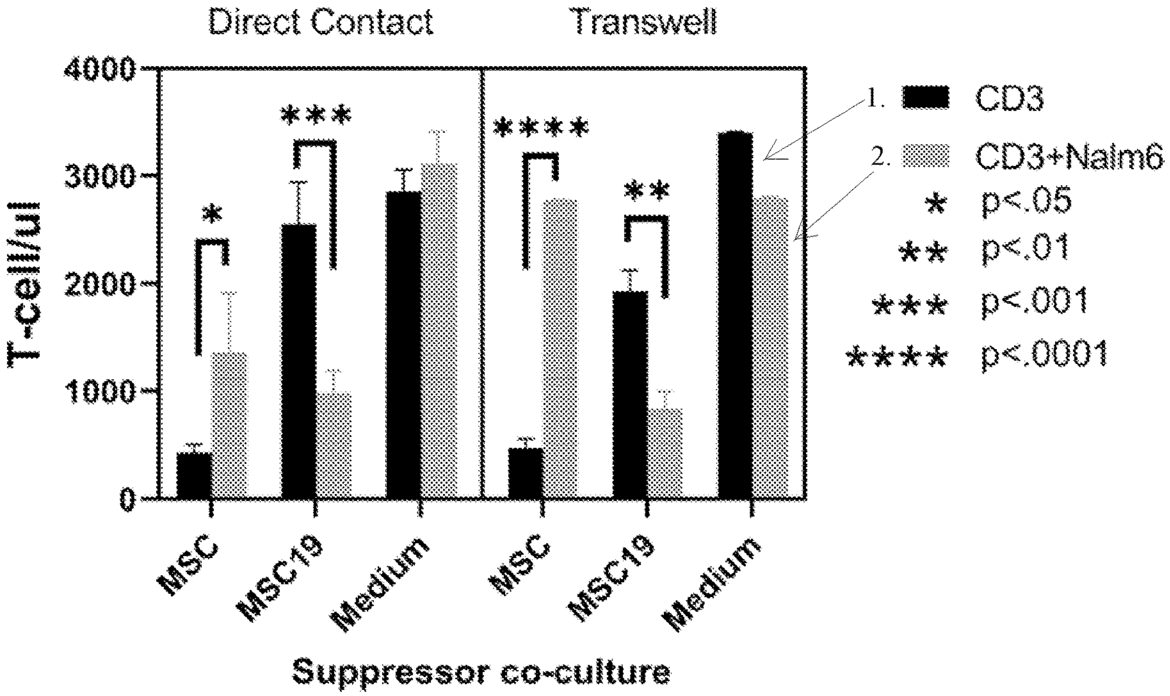

FIG. 21 is a bar graph plotting the number of T cells per μL, following their stimulation with CD3/CD28 beads in the presence of MSCs, and $CD19^+$ cells (to stimulate MSC-CARs), either in direct contact or in transwell experiments. A co-culture with MSC-CAR19 (containing CD28 stimulatory domain) with activated T cells, and $CD19^+$ cells led to inhibition of T cell proliferation both when cells were in direct contact or not in direct contact in a trans-well experiment. This indicates that MSC-CAR exert their suppressive functions both through direct, cell to cell contact and through secretion of soluble inhibitory factors/cytokines.

Figure 22:
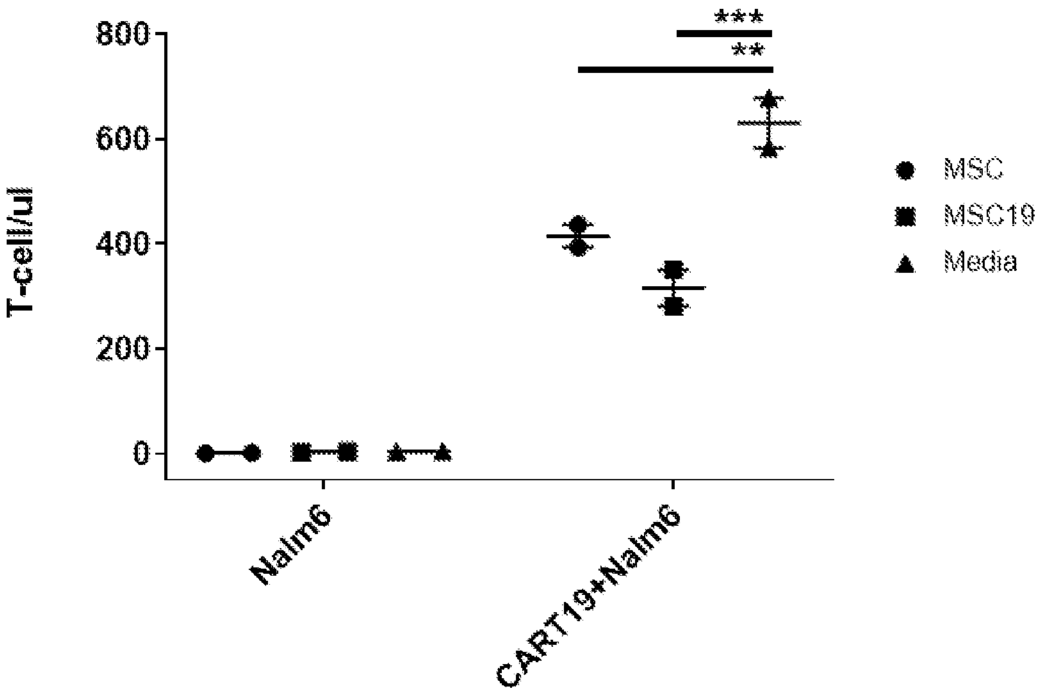

FIG. 22 is a graph plotting the number of T cells per μL after 5 days of stimulation with CD3/CD28 beads, following co-culture with untransduced MSCs, or MSC-CAR19 (CD28 containing CAR19, K122) at a higher E:S:T ratio. T cells are activated with CD3/CD28 beads and then co-cultured with different MSC conditions either in medium alone, or in the presence of irradiated $CD19^+$ cells as a strategy to stimulate MSC-CAR19 through the CAR. Proliferation of CD3 is inhibited in the presence of MSC-CAR19 (containing CD28 signaling domain), but not in the presence of un-transduced MSCs. T cells, MSCs, and NALM6 cells were cultured at ratio of 1:1:1 E (T cells (effectors):MSCs (suppressors):T (tumor). This demonstrates that MSC-CAR cells are able to suppress T cell proliferation when MSC-CAR cells contain a CD28 signaling domain, at different suppressor to T cell ratios, when the MSCs are activated through the CAR upon antigen specific stimulation.  represents P≤0.01; * represents P≤0.001.

FIGS. 23A-23B are graphs plotting the absolute number of live CD3 cells after 5 days of stimulation with CD3/CD28 beads, following co-culture with untransduced MSC (MSC-UTD, FIG. 24A), or MSC-CAR-E-cadherin (CD28 containing CAR-E-cadherin, FIG. 24B), in the presence or absence of the E-cadherin$^+$ cell line MCF-7, at different effector: suppressor (E:S) ratios. The co-culture of MSC-CAR-E-cadherin with T cells results in suppression of their antigen specific proliferation in the presence of the E-cadherin$^+$ cell line MCF-7, at a low effector:suppressor ratio.

FIG. 24A is a graph plotting bioluminescence from luciferase$^+$/E-cadherin$^+$ MCF-7 cells ($1\times10^6$) that were injected into NSG mice that were then treated with CAR-ECAD T cells in combination with either no MSCs, untransduced MSCs (MSC-UTD), or MSC-ECAD-CAR with CD28 signaling domain. Mice treated with MSC-ECAD exhibited more bioluminescence demonstrating that the MSC-ECAD inhibited the antitumor effects of the CAR-ECAD T cells. FIG. 24B is a bar graph plotting the absolute number of $CD3^+$ T cells in the NSG mice treated with CAR-ECAD T cells and either no MSCs, untransduced MSCs (MSC-UTD), or MSC-ECAD at day 3.

Figure 25:
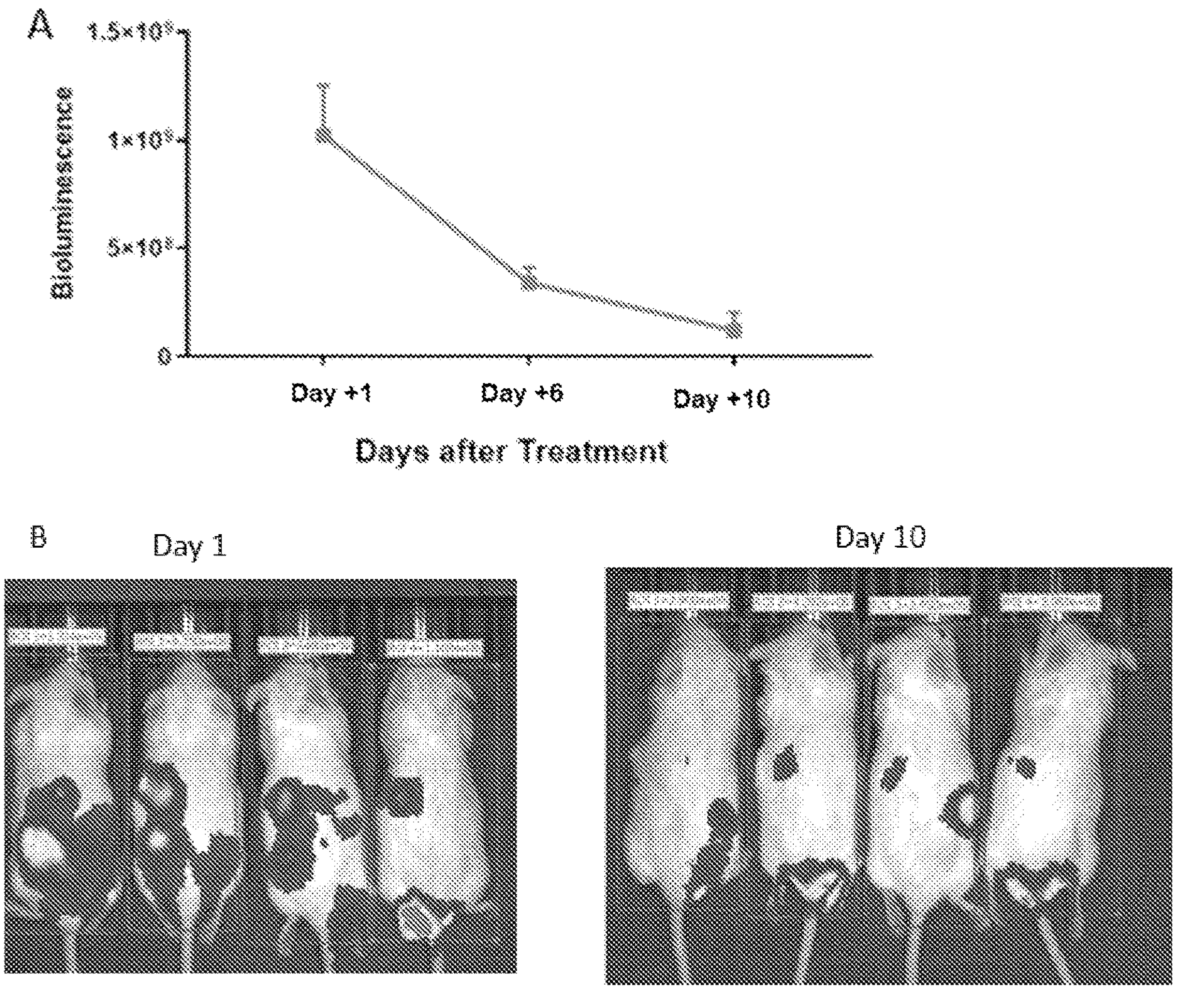

FIG. 25A is a graph plotting bioluminescence from luciferase$^+$ MSC-CAR-E-cadherin cells that were administered into immunocompromised NSG mice. FIG. 25B contains representative images of the bioluminescence from representative mice.

DETAILED DESCRIPTION

This document provides methods and materials involved in treating a mammal (e.g., a human) having, or at risk of developing, an inflammatory disease or condition and/or having, or at risk of developing, a degenerative disease. For example, one or more MSCs designed to express an antigen receptor (e.g., a CAR) capable of binding (e.g., specifically binding) to a tissue-specific antigen can be administered to a mammal to induce an immunosuppressive response (e.g., to reduce or eliminate an inflammatory immune response) within the mammal. In some cases, a CAR targeting an epithelial-specific antigen (e.g., ECAD) can be expressed by a MSC to target the MSC to epithelial tissues in a manner effective to treat a disease or disorder characterized by inflammation of an epithelial tissue (e.g., colitis). For example, MSCs engineered to express a CAR that can target (e.g., can target and bind to) an antigen (e.g., a cell surface antigen) expressed by epithelial cells (e.g., an epithelial-specific antigen or an epithelial antigen) can be administered to a mammal (e.g., a human) to treat or slow the progression of a disease or disorder characterized by inflammation and/or degeneration of epithelial tissue such as colitis, hepatitis, pneumonitis, asthma, pancreatitis, pulmonary fibrosis, colon strictures, colon fistulas, glomerulonephritis, renal infarction, or liver infarction.

In some cases, a CAR targeting a neural-specific antigen (e.g., MOG) can be expressed by a MSC to target the MSC to neural tissues in a manner effective to treat a disease or disorder characterized by inflammation of a neural tissue (e.g., multiple sclerosis and immune mediated encephalomyelitis). For example, MSCs engineered to express a CAR that can target (e.g., can target and bind to) an antigen (e.g., a cell surface antigen) expressed by neural cells (e.g., a neural-specific antigen or a neural antigen) can be administered to a mammal (e.g., a human) to treat or slow the progression of a disease or disorder characterized by inflammation and/or degeneration of a neural tissue such as multiple sclerosis, immune mediated encephalomyelitis, or amyotrophic lateral sclerosis.

In some cases, a CAR targeting a cardiac-specific antigen (e.g., HER2) can be expressed by a MSC to target the MSC to cardiac tissues in a manner effective to treat a disease or disorder characterized by inflammation of a cardiac tissue (e.g., myocarditis). For example, MSCs engineered to express a CAR that can target (e.g., can target and bind to) an antigen (e.g., a cell surface antigen) expressed by cardiac cells (e.g., a cardiac-specific antigen or a cardiac antigen) can be administered to a mammal (e.g., a human) to treat or slow the progression of a disease or disorder characterized by inflammation and/or degeneration of cardiac tissue such as myocarditis, myocardial infarction, heat failure, or endocarditis.

In some cases, one or more MSCs designed to express a CAR capable of binding (e.g., specifically binding) to a tissue-specific antigen (e.g., an epithelial-specific antigen) can be administered (e.g., by adoptive transfer) to a mammal (e.g., a human) having (or at risk of developing) an inflammatory disease or condition to treat that inflammatory disease or condition within the mammal. In some cases, one or more MSCs expressing a CAR capable of binding (e.g., specifically binding) to an epithelial-specific antigen (e.g., ECAD) can be administered (e.g., by adoptive transfer) to a mammal (e.g., a human) having, or at risk of developing, an inflammatory bowel disease (IBD; e.g., colitis) to treat that inflammatory bowel disease within the mammal. In some cases, one or more MSCs expressing a CAR capable of binding (e.g., specifically binding) to a neural-specific antigen (e.g., MOG) can be administered (e.g., by adoptive transfer) to a mammal (e.g., a human) having, or at risk of developing, multiple sclerosis to treat that multiple sclerosis within the mammal. In some cases, one or more MSCs expressing a CAR capable of binding (e.g., specifically binding) to a neural-specific antigen (e.g., MOG) can be administered (e.g., by adoptive transfer) to a mammal (e.g., a human) having, or at risk of developing, immune mediated encephalomyelitis to treat that immune mediated encephalomyelitis within the mammal. In some cases, one or more MSCs expressing a CAR capable of binding (e.g., specifically binding) to a cardiac-specific antigen (e.g., HER2) can be administered (e.g., by adoptive transfer) to a mammal (e.g., a human) having, or at risk of developing, myocarditis to treat that myocarditis within the mammal.

In some cases, one or more MSCs expressing a CAR capable of binding (e.g., specifically binding) to a cartilage antigen (e.g., CH65, human cartilage glycoprotein-39 (HC gp-39), CD44, thymocyte antigen-1 (Thy-1), CD90, CD24, lymphocyte function-associated antigen-3 (LFA-3) or to an osteocyte antigen (e.g., E11 or gp38) can be administered (e.g., by adoptive transfer) to a mammal (e.g., a human) to treat or slow the progression of a disease or disorder characterized by inflammation and/or degeneration of joints such as inflammatory arthritis, degenerative arthritis, autoimmune spondyloarthritis, psoriatic arthritis, osteogenesis imperfecta, or metachromatic leukodystrophy.

In some cases, MSCs designed to express an antigen receptor (e.g., a CAR) capable of binding (e.g., specifically binding) to a tissue-specific antigen, also can be engineered to express a polypeptide that can promote differentiation into a tissue specific cell (e.g., a cardiac cell or a neuron) within the mammal. In some cases, an MSC designed to express a polypeptide that can promote differentiation can promote differentiation of a cell (e.g., the MSC and/or one or more resident progenitor cells) into a tissue specific cell (e.g., a cardiac cell or a neuron) within the mammal. In some cases, an MSC designed to express a polypeptide that can promote differentiation can promote differentiation of a resident cell (e.g., a resident progenitor cell) into a tissue specific cell (e.g., a cardiac cell or a neuron) within the mammal. Such engineered MSCs that can express a polypeptide that can express a polypeptide that can promote differentiation into any appropriate tissue specific cell (e.g., a cardiac cell or a neuron) within the mammal. In some cases, a MSC including nucleic acid encoding a polypeptide that can promote cardiac cell differentiation can differentiate the MSC into a cardiac cell. In some cases, a MSC including nucleic acid encoding a polypeptide that can promote neural differentiation can differentiate the MSC into a neuron. For example, one or more MSCs designed to express an antigen receptor (e.g., a CAR) capable of binding (e.g., specifically binding) to a tissue-specific antigen, and also designed to differentiate into a tissue specific cell can be administered (e.g., by adoptive transfer) to a mammal (e.g., a human) having, or at risk of developing, a degenerative disease to treat that degenerative disease within the mammal. In some cases, one or more MSCs designed to differentiate into a cardiac cell (e.g., one or more MSCs including nucleic acid that can encode a polypeptide that can promote cardiac cell differentiation can be administered (e.g., by adoptive transfer) to a mammal (e.g., a human) having, or at risk of developing, a degenerative heart disease (e.g., congestive heart failure (CHF)) to treat that degenerative heart disease within the mammal (e.g., by regenerating cardiac cells within the mammal). In some cases, one or more MSCs designed to differentiate into a neuron (e.g., one or more MSCs including nucleic acid that can encode a polypeptide that can promote neural differentiation can be administered (e.g., by adoptive transfer) to a mammal (e.g., a human) having, or at risk of developing, a neurodegenerative disease (e.g., Parkinson's disease and Alzheimer's disease) to treat that neurodegenerative disease within the mammal (e.g., by regenerating neurons within the mammal).

In some cases, MSCs (e.g., MSCs engineered to express a CAR as described herein) can be designed to express one or more transcription factors to force their differentiation into a cardiomyocyte (e.g., BMP-4, FGF-4, FGF-basic, and/or TGF-beta). In such cases, the MSCs can be administered to a mammal (e.g., a human) to treat or slow the progression of a disease or disorder characterized by degeneration of the heart such as myocardial infarction or heart failure.

In some cases, MSCs (e.g., MSCs engineered to express a CAR as described herein) can be designed to express one or more transcription factors to force their differentiation into an osteocyte (e.g., BMP-2, BMP-4, BMP-6, FGF-basic, TGF-beta, PTH, and/or Wnt10b) or one or more transcription factors to force their differentiation into chrondrocytes (e.g., BMP-2, BMP-3, BMP-5, BMP-7, N-Cadherin, NCAN-1, and/or Perlecan). In such cases, the MSCs can be administered to a mammal (e.g., a human) to treat or slow the progression of a disease or disorder characterized by degeneration of the bones such as degenerative arthritis or osteogenesis imperfect.

A MSC described herein (e.g., a MSC expressing a CAR targeting a tissue-specific antigen such as an epithelial-specific antigen, a neural-specific antigen, or a cardiac-specific antigen and, optionally, expressing a polypeptide that can promote differentiation of the MSC and/or one or more resident progenitor cells into a tissue specific cell such as a cardiac cell or a neuron) can be any appropriate MSC. Examples of MSCs that can be used as described herein include, without limitation, adipose derived MSCs, osteoblasts (bone cells), chondrocytes (cartilage cells), myocytes (muscle cells), adipocytes (fat cells), neuronal precursor stem cells (neurons), dental pulp derived MSCs, cord blood derived MSCs, and umbilical cord derived MSCs. For example, a MSC expressing a CAR and, optionally, expressing a polypeptide that can promote differentiation into a tissue specific cell targeting a tissue-specific antigen can be an adipose derived MSC.

A CAR can include an antigen-binding domain and a signaling domain. An antigen-binding domain can be any appropriate antigen-binding domain. In some cases, an antigen-binding domain can include an antibody or a fragment thereof that targets an antigen (e.g., a tissue-specific antigen such as an epithelial-specific antigen, a neural-specific antigen, or a cardiac-specific antigen). Examples of antigen-binding domains include, without limitation, an antigen-binding fragment (Fab), a variable region of an antibody heavy (VH) chain, a variable region of a light (VL) chain, a single chain variable fragment (scFv), a polypeptide, a ligand, and a cytokine. In some cases, an antigen-binding domain can target (e.g., can target and bind to) a tissue-specific antigen (e.g., an epithelial-specific antigen, a neural-specific antigen, or a cardiac-specific antigen). For example, a MSC described herein can express (e.g., can be engineered to express) a CAR that can bind to a tissue-specific antigen (e.g., an antigen present on cells within a tissue with minimal, or no, expression on other cell types).

In some cases, a MSC can be engineered to express a CAR that can target (e.g., can target and bind to) an antigen (e.g., a cell surface antigen) expressed by epithelial cells (e.g., an epithelial-specific antigen or an epithelial antigen) in a mammal (e.g., a mammal having, or at risk of developing, a disease or disorder characterized by inflammation and/or degeneration of an epithelial tissue such as colitis). An epithelial-specific antigen can be any appropriate epithelial-specific antigen. An epithelial-specific antigen can be expressed on any appropriate type of epithelial cell (e.g., gastrointestinal tract cells such as colon cells and rectal cells, skin cells, lung cells, and liver cells). In some cases, an epithelial-specific antigen can be a cell adhesion molecule (CAM). Examples of epithelial-specific antigens include, without limitation, ECAD, CD103, hSC10.17, hSC10.178, CD234, EPCAM, EMA, MUC1, cytokeratin, CA125, ALCAM, HLA, Desmin, Eputheliam Antigen antibody, CD227, ESA, Galactin 3, GGT, HLA-DR, Lectin, LAMP-1, MMR, MOC-31, p16, p63, p-Cadherin, PSA, surfactant, Transthyretin, VAT-1, and Vimentin. For example, a MSC-CAR engineered to target epithelial tissues can bind to ECAD. In some cases, a MSC-CAR can be engineered to express a CAR-ECAD to target ECAD expressed by epithelial cells in a mammal having, or at risk of developing, an IBD (e.g., colitis).

In some cases, a MSC can be engineered to express a CAR that can target (e.g., can target and bind to) an antigen (e.g., a cell surface antigen) expressed by neural cells (e.g., a neural-specific antigen or a neural antigen) in a mammal (e.g., a mammal having, or at risk of developing, a disease or disorder characterized by inflammation and/or degeneration of a neural tissue such as multiple sclerosis and immune mediated encephalomyelitis). When an antigen is a neural-specific antigen, the neural-specific antigen can be any appropriate neural-specific antigen. A neural-specific antigen can be expressed on any appropriate type of neural cell (e.g., sensory neurons, motor neurons, interneurons, glial cells, and oligodendrocytes). A neural-specific antigen can be expressed on a neural cell in the central nervous system (CNS) and/or in the peripheral nervous system (PNS). In some cases, a neural-specific antigen can be a transmembrane protein. Examples of neural-specific antigens include, without limitation, MOG, MBP, PDGF receptor alpha, OSP, SOX10, Olig 1, Olig 2, Olig 3, and NG2. For example, a MSC-CAR engineered to target neural tissues can bind to MOG In some cases, a MSC-CAR can be engineered to express a CAR-MOG to target MOG expressed by neural cells in a mammal having, or at risk of developing, multiple sclerosis. In some cases, a MSC-CAR can be engineered to express a CAR-MOG to target MOG expressed by neural cells in a mammal having, or at risk of developing, immune mediated encephalomyelitis.

In some cases, a MSC can be engineered to express a CAR that can target (e.g., can target and bind to) an antigen (e.g., a cell surface antigen) expressed by cardiac cells (e.g., a cardiac-specific antigen or a cardiac antigen) in a mammal (e.g., a mammal having, or at risk of developing, a disease or disorder characterized by inflammation and/or degeneration of a cardiac tissue such as myocarditis). When an antigen is a cardiac-specific antigen, the cardiac-specific antigen can be any appropriate cardiac-specific antigen. A cardiac-specific antigen can be expressed on any appropriate type of cardiac cell (e.g., cardiomyocytes and endocardial cells). An example of a cardiac-specific antigen includes, without limitation, HER2. For example, a MSC-CAR engineered to target cardiac cells can bind to HER2. In some cases, a MSC-CAR can be engineered to express a CAR-HER2 to target HER2 expressed by cardiac cells in a mammal having, or at risk of developing, myocarditis.

A signaling domain can be any appropriate signaling domain. In some cases, a signaling domain of a CAR to be used within a MSC as described herein can be an intracellular signaling domain normally found within T cells or NK cells. Examples of signaling domains that can be used as described herein include, without limitation, CD3zeta signaling domains, CD28 signaling domains, Toll-like receptors (TLRs) (e.g., TLR3 and TLR4), 4-1BB, OX40, ICOS, CD2, and promotors (e.g., specific promotors such as cardiac specific promotors, neural specific promotors, T cell specific promotors, GI, pulmonary specific promotors, joint specific promotors, and cartilage specific promotors). In some cases, a signaling domain of a CAR expressed by a MSC as described herein can, upon activation of the CAR, induce the MSC to produce one or more cytokines (e.g., anti-inflammatory cytokines). Examples of cytokines that an engineered CAR of a MSC described herein can induce the MSC to produce include, without limitation, IFN-β, IL-10, IL-4, IL-2, MIP1B, IFNg, MIP1a, GM-CSF, IL-6, TNFa, and TNFb.

Any appropriate method can be used to express a CAR described herein (e.g., a CAR targeting a tissue-specific antigen such as an epithelial-specific antigen, a neural-specific antigen, or a cardiac-specific antigen) on the surface of a MSC described herein. For example, a nucleic acid encoding a CAR can be introduced into a MSC. In some cases, a nucleic acid encoding a CAR can be introduced into a MSC by transduction (e.g., viral transduction) or transfection. In some cases, a nucleic acid encoding a CAR described herein can be introduced ex vivo into one or more MSCs. For example, ex vivo engineering of MSCs to express a CAR described herein can include transducing isolated MSCs with a lentiviral vector encoding a CAR. In cases where MSCs are engineered ex vivo to express a CAR, the MSCs can be obtained from any appropriate source (e.g., a mammal such as the mammal to be treated or a donor mammal, or a cell line). In some cases, MSC-CARs can be prepared as described herein (see, e.g., FIG. 2 and Example 1). For example, a CAR-ECAD can be expressed on a MSC to direct the MSC to epithelial tissues by introducing one or more constructs containing a nucleic acid encoding the CAR (e.g., a CAR targeting ECAD) into the MSC. For example, a CAR-MOG can be expressed on a MSC to direct the MSC to neural tissues by introducing one or more constructs containing a nucleic acid encoding the CAR (e.g., a CAR targeting MOG) into the MSC. In some cases, MSC-CARs can be prepared as described elsewhere (see, e.g., Blat et al., *Mol. Ther.,* 22(5):1018-28 (2014); MacDonald et al., *J. Clin. Invest.,* 126(4):1413-24 (2016); and Yoon et al., *Blood,* 129(2):238-245 (2017)).

Also provided herein are CARs and constructs (e.g., nucleic acid constructs) encoding CARs described herein (e.g., CARs targeting a tissue-specific antigen such as an epithelial-specific antigen, a neural-specific antigen, or a cardiac-specific antigen). For example, a construct encoding a CAR targeting ECAD (e.g., a CAR-ECAD) can include a nucleic acid sequence encoding one or more molecules that bind ECAD described herein. In some cases, a CAR-ECAD can include an anti-ECAD antibody (e.g., hSC10.17 and hSC10.178) heavy chain and an anti-ECAD antibody (e.g., hSC10.17 and hSC10.178) light chain. For example, a construct encoding a CAR targeting MOG (e.g., a CAR-MOG) can include a nucleic acid sequence encoding one or more molecules that bind MOG described herein. In some cases, a CAR-MOG can include an anti-MOG antibody (e.g., 8-18C5) heavy chain and an anti-MOG antibody (e.g., 8-18C5) light chain. For example, a construct encoding a CAR targeting HER2 (e.g., a CAR-HER2) can include a nucleic acid sequence encoding one or more molecules that bind HER2 described herein. In some cases, a CAR-HER2 can include an anti-HER2 antibody (e.g., 4D5) heavy chain and an anti-ECAD antibody (e.g., 4D5) light chain. Exemplary nucleic acid sequences that can encode one or more molecules that bind a tissue-specific antigen described herein that can be included in a construct described herein include, without limitation, those that encode the following amino acid sequences:

anti-ECAD antibody heavy chain (SEQ ID NO: 11)
QILLVQSGPELKKPGETVKISCKASNYTFTDYGMHWVKQAPGKGLKWMGW

INPKTGVASYADDFKGRFAFSLETSASTAYLQINNLENEDTSIYFCARFF

DYWGQGTTLTVSS anti-ECAD antibody light chain (SEQ ID NO: 12)
DVVMTQSPLSLPVTLGQPASISCRSSQSIVHSDGNTYLEWYQQRPGQSPR

RLIYKVSNRFSGVPDRFSGSGSGTDFTLKISRVEAEDVGVYYCFQGSHAP

WTFGGGTKVEIK anti-ECAD antibody light chain (SEQ ID NO: 13)
DIVLTQSPLSLLVSLGDQASISCRSSQSLVHSNGNTYLHWYLQKPGQSPN

LLIFKVSNRFSGVPDRFSGSGSGTDFTLRISRVEAEDLGVYFCSQTTHVW

TFGGGTKLEIK anti-ECAD scFv clone 5 (SEQ ID NO: 55; light chain followed by linker in bold/underlined followed by heavy chain)
QAVVTQEPSLTVSPGGTVTLTCGSSTGAVTSGHYPHWFQQRPGQAPKSLI

YDIRSKYSSTPARFSGSLLGGKAALTVSGVQPEDEAEYYCLLYYGGAQVF

GGGTKLTVLGEGKSSGSGSESKASEVQLVESGAEVKKPGASVKVSCKASG

YMFTGYFLHWVRQAPGQGLEWMGWINPNSGDTNYPQKFQGRVTMTRDTSI

TTAYMELSRLTSNDTAMYYCARRAISLVRGIISNQFDPWGQGTLVTVSS anti-ECAD scFv clone 6 (SEQ ID NO: 56; light chain followed by linker in bold/underlined followed by heavy chain)
LPVLTQPPSASGTPGQRVTISCSGSSSNIGSNYVYWYQQLPGTAPKLLIY

RNNQRPSGVPDRFSGSKSGTSASLAISGLQSEDEADYYCASWDTSLRAWV

FGGGTKLTVLGEGKSSGSGSESKASEVQLVQSGGGLVQPGGSLRLSCAAS

GFTFSSYSMNWVRQAPGKGLEWVSYISSSSSTIYYVDSVKGRFTISRDNA

KNSLYLQMDSLRAEDTAVYYCARGGRVLVGALFDYWGQGTLVTVSS anti-ECAD scFv clone 7 (SEQ ID NO: 57; heavy chain followed by linker in bold/underlined followed by light chain)
EVQLVESGTDVKKPGASVTVSCKASGYTFTAYYIHWVRQAPGQGLEWMGW

INPYSGASNYAQKFLGRVTMTRDTSTNTVYMQLSSLRASDTAMYYCAKAA

CGSNGCYMREFDYWGQGTLVTVSSSEGKSSGSGSESKASDIVMTQSPLSL

PVTLGQPASISCRSSQSLVYSDGNTYLNWFQQRPGQSPRRLIYKVSNRDS

GVPDRFSGSGSGTDFTLKISRVEAEDVGIYYCMQGTYWPGAFGQGTKVDI

K anti-ECAD scFv clone 14 (SEQ ID NO: 58; light chain followed by linker in bold/underlined followed by heavy chain)
SSELTQDPAVSVALGQTVRITCQGDSLRSYYASWYQQKPGQAPVLVIYGK

NNRPSGIPDRFSGSSSGNTASLTITGAQAEDEADYYCNSRDSSGNPVFGG

GTKLTVLGEGKSSGSGSESKASEVQLVQSGGGLVKPGGSLRLSCAASGFT

FSDYYMSWIRQAPGKGLEWVSYISSSGSTIYYADSVKGRFTISRDNAKNS

LYLQMNSLRAEDTAVYYCARAQRQWGAFDYWGQGTLVTVSS anti-MOG antibody heavy chain (SEQ ID NO: 14)
EVKLHESGAGLVKPGASVEISCKATGYTFSSFWIEWVKQRPGHGLEWIGE

ILPGRGRTNYNEKFKGKATFTAETSSNTAYMQLSSLTSEDSAVYYCATGN

TMVNMPYWGQGTTVTVSS

-continued anti-MOG antibody light chain (SEQ ID NO: 15)
DIELTQSPSSLAVSAGEKVTMSCKSSQSLLNSGNQKNYLAWYQQKPGLPP

KLLIYGASTRESGVPDRFTGSGSGTDFTLTISSVQAEDLAVYYCQNDHSY

PLTFGAGTKLEIK anti-HER2 antibody heavy chain (SEQ ID NO: 16)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGTTTPAPRPPTPAPTIASQPLSLRPE

ACRPAAGGAVHTRGLDFACD anti-HER2 antibody light chain (SEQ ID NO: 17)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAP

In some cases, an amino acid segment that can bind a tissue-specific antigen described herein and can be encoded by a nucleic acid sequence that can be included in a construct described herein can have a sequence that deviates from a polypeptide sequence (e.g., a light chain polypeptide sequence or a heavy chain polypeptide sequence) set forth in any one of SEQ ID NOs:11-17, sometimes referred to as a variant sequence. For example, an amino acid segment that can bind a tissue-specific antigen described herein and can be encoded by a nucleic acid sequence that can be included in a construct described herein can have at least 80% sequence identity to any one of SEQ ID NOs:11-17. In some embodiments, an amino acid segment that can bind a tissue-specific antigen described herein and can be encoded by a nucleic acid sequence that can be included in a construct described herein can have at least 85% sequence identity, 90% sequence identity, 95% sequence identity, or at least 99% sequence identity to any one of SEQ ID NOs:11-17. Percent sequence identity is calculated by determining the number of matched positions in aligned polypeptide sequences, dividing the number of matched positions by the total number of aligned amino acids, respectively, and multiplying by 100. A matched position refers to a position in which identical amino acids occur at the same position in aligned sequences. The total number of aligned amino acids refers to the minimum number of amino acids in an amino acid segment that can bind a tissue-specific antigen described herein and can be encoded by a nucleic acid sequence that can be included in a construct described herein that are necessary to align the second sequence, and does not include alignment (e.g., forced alignment) with other sequences. For example, when an amino acid segment that can bind a tissue-specific antigen described herein and can be encoded by a nucleic acid sequence that can be included in a construct described herein is a heavy chain, the total number of aligned amino acids can exclude any light chain. The total number of aligned amino acids may correspond to the entire amino acid segment that can bind a tissue-specific antigen described herein and can be encoded by a nucleic acid sequence that can be included in a construct described herein or may correspond to fragments of the amino acid segment that can bind a tissue-specific antigen described herein and can be encoded by a nucleic acid sequence that can be included in a construct described herein. Sequences can be aligned using the algorithm described by Altschul et al. (*Nucleic Acids Res.*, 25:3389-3402 (1997)) as incorporated into BLAST (basic local alignment search tool) programs, available at ncbi.nlm.nih.gov on the World Wide Web. BLAST searches or alignments can be performed to determine percent sequence identity using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between an amino acid segment that can bind a tissue-specific antigen described herein and can be encoded by a nucleic acid sequence that can be included in a construct described herein and another sequence, the default parameters of the respective programs are used.

Exemplary nucleic acid sequences that can encode one or more molecules that bind a tissue-specific antigen described herein that can be included in a construct described herein are as follows.

anti-ECAD antibody heavy chain (SEQ ID NO: 18)
GAGGTGCAGCTGGTGGAGTCTGGGGGAGGCTTGGTACAGCCTGGGGGGTCCC

TGAGACTCTCCTGTGCAGCCTCTGGATTCACCTTCAGTAGCTATGGCATGCACT

GGGTCCGCCAGGCTCCAGGGAAGGGGCTGGAGTGGGTTGCATACATTACTACT

AGAAGTAGTACCATATACTACGCAGACTCTGTGAAGGGCCGATTCACCATCTCC

AGAGACAATGCCAAGAACTCACTGTATCTGCAAATGAACAGCCTGAGAGCCG

AGGACACGGCTGTGTATTACTGTACTAGAGAACCCCTAACTGGATACTATGCTA

TGGACTACTGGGGTCAAGGAACCTCAGTCACCGTCTCCTCAG anti-ECAD antibody heavy chain (SEQ ID NO: 19)
CAGATCCTGTTGGTGCAGTCTGGACCTGAGCTGAAGAAGCCTGGAGAGACAG

TCAAGATCTCCTGCAAGGCTTCTAATTATACCTTCACAGACTATGGAATGCACT

GGGTGAAGCAGGCTCCAGGAAAGGGTTTAAAGTGGATGGGCTGGATAAACCC

CAAGACTGGTGTGGCATCATATGCAGATGACTTCAAGGGAAGATTTGCCTTCTC

-continued

TTTGGAAACCTCTGCCAGCACTGCCTATTTGCAGATCAACAACCTCGAAAATG

AGGACACGTCTATATATTTCTGTGCTAGATTTTTTGACTACTGGGGCCAAGGCA

CCACTCTCACAGTCTCCTCA anti-ECAD antibody light chain (SEQ ID NO: 20)
GATGTTGTGATGACTCAGTCTCCACTCTCCCTGCCCGTCACCCTTGGACAGCC

GGCCTCCATCTCCTGCAGGTCTAGTCAAAGCATCGTACACAGTGATGGAAACA

CCTACTTGGAATGGTATCAGCAGAGGCCAGGCCAATCTCCAAGGCGCCTAATTT

ATAAGGTTTCTAACCGGTTCTCTGGGGTCCCAGACAGATTCAGCGGCAGTGGG

TCAGGCACTGATTTCACACTGAAAATCAGCAGGGTGGAGGCTGAGGATGTTG

GGGTTATTACTGCTTTCAAGGTTCACATGCTCCGTGGACGTTCGGTGGAGGCA

CCAAGGTGGAAATCAAAC anti-ECAD antibody light chain (SEQ ID NO: 21)
GATATTGTGCTGACACAGTCTCCACTCTCCCTGCTTGTCAGTCTTGGAGATCAA

GCCTCCATCTCTTGCAGATCTAGTCAGAGCCTTGTACACAGTAATGGAAACACC

TATTTACATTGGTATCTGCAGAAGCCAGGCCAGTCTCCAAACCTCCTGATCTTC

AAAGTTTCCAACCGATTTTCTGGGGTCCCAGACAGGTTCAGTGGCAGTGGATC

AGGGACAGATTTCACACTCAGGATCAGCAGAGTGGAGGCTGAGGATCTGGGA

GTTTATTTCTGCTCTCAAACTACACATGTGTGGACGTTCGGTGGAGGCACCAA

GCTGGAAATCAAA anti-ECAD scFv clone 5 (SEQ ID NO: 59; light chain followed by linker in bold/underlined followed by heavy chain)
CAGGCTGTGGTGACCCAGGAGCCCTCATTGACTGTGTCCCCAGGAGGGACAG

TCACTCTCACCTGTGGCTCCAGCACTGGAGCTGTCACCAGTGGTCATTATCCC

CACTGGTTCCAGCAGAGGCCTGGCCAGGCCCCCAAGTCACTGATTTATGATAT

AAGGAGCAAATACTCCTCAACACCTGCCCGGTTCTCAGGCTCCCTCCTTGGGG

GCAAAGCTGCCCTGACAGTGTCAGGTGTGCAGCCTGAGGACGAGGCTGAATA

TTACTGCCTGCTCTACTATGGTGGTGCTCAGGTGTTCGGCGGGGGGACCAAGC

TGACCGTCCTAGGTGAGGGTAAATCTTCCGGATCTGGTTCCGAATCCAAA

GCTAGCGAGGTGCAGCTGGTGGAGTCTGGGGCTGAGGTGAAGAAGCCTGGG

GCCTCAGTGAAGGTCTCCTGCAAGGCTTCTGGATACATGTTCACCGGCTACTT

TCTGCACTGGGTGCGACAGGCCCCTGGACAAGGGCTTGAGTGGATGGGATGG

ATCAACCCTAACAGTGGTGACACAAACTATCCACAGAAATTTCAGGGCAGGG

TCACCATGACCAGGGACACGTCCATCACCACAGCCTACATGGAACTGAGCAG

GCTGACTTCCAACGACACGGCCATGTACTATTGTGCGAGGAGGGCTATTTCTC

TGGTTCGGGGAATTATTAGCAACCAGTTCGACCCCTGGGGCCAGGGAACCCT

GGTCACCGTCTCCTCA anti-ECAD scFv clone 6 (SEQ ID NO: 60; light chain followed by linker in bold/underlined followed by heavy chain)
CTGCCTGTGCTGACTCAGCCACCCTCAGCGTCTGGGACCCCCGGGCAGAGGG

TCACCATCTCTTGTTCTGGAAGCAGCTCCAACATCGGAAGTAATTATGTCTAC

TGGTACCAGCAACTCCCAGGAACGGCCCCCAAACTCCTCATCTATAGGAATA

ATCAGCGGCCCTCAGGGGTCCCTGACCGATTCTCTGGCTCCAAGTCTGGCACC

TCAGCCTCCCTGGCCATCAGTGGGCTCCAGTCTGAGGATGAGGCTGATTATTA

TTGTGCATCATGGGATACCAGCCTGCGTGCCTGGGTGTTCGGCGGAGGGACC

-continued

AAGCTGACCGTCCTAGGTGAGGGTAAATCTTCCGGATCTGGTTCCGAATC

CAAAGCTAGCGAGGTGCAGCTGGTGCAGTCTGGGGGAGGCTTGGTACAGCC

TGGGGGGTCCCTGAGACTCTCCTGTGCAGCCTCTGGATTCACCTTCAGTAGCT

ATAGCATGAACTGGGTCCGCCAGGCTCCAGGGAAGGGGCTGGAGTGGGTTTC

ATACATTAGTAGTAGTAGTAGTACCATATACTACGTAGACTCTGTGAAGGGC

CGATTCACCATCTCCAGAGACAACGCCAAGAACTCACTGTATCTGCAAATGG

ACAGCCTGAGAGCCGAGGACACGGCTGTGTATTACTGTGCGAGAGGAGGTCG

GGTGTTAGTGGGAGCTCTATTTGACTACTGGGGCCAGGGAACCCTGGTCACC

GTCTCCTCA anti-ECAD scFv clone 7 (SEQ ID NO: 61; heavy chain followed by linker in bold/underlined followed by light chain)

GAGGTGCAGCTGGTGGAGTCTGGGACTGATGTGAAGAAGCCTGGGGCCTCAG

TGACGGTCTCCTGCAAGGCTTCTGGATACACCTTCACCGCCTACTATATCCAC

TGGGTGCGACAGGCCCCTGGACAAGGGCTTGAGTGGATGGGATGGATCAACC

CTTACAGTGGTGCCTCAAACTATGCACAGAAGTTTCTGGGCCGGGTCACCATG

ACCAGGGACACGTCCACCAACACAGTCTACATGCAGTTGAGCAGTCTGAGGG

CCTCGGACACCGCCATGTATTACTGTGCGAAAGCGGCTTGTGGTAGTAACGG

CTGCTATATGAGGGAGTTTGACTACTGGGGCCAGGGCACCCTGGTCACCGTCT

CCTCAAGCGAGGGTAAATCTTCCGGATCTGGTTCCGAATCCAAAGCTAGC

GATATTGTGATGACTCAGTCTCCACTCTCCCTGCCCGTCACCCTTGGACAGCC

GGCCTCCATCTCCTGCAGGTCTAGTCAAAGTCTCGTATACAGTGATGGAAACA

CCTACTTGAATTGGTTTCAGCAGAGGCCAGGCCAATCTCCAAGGCGCCTAATT

TATAAGGTTTCTAACCGGGACTCTGGGGTCCCAGACAGATTCAGCGGCAGTG

GGTCAGGCACTGATTTCACACTGAAAATCAGCAGGGTGGAGGCTGAGGATGT

TGGGATTTATTACTGCATGCAAGGTACATACTGGCCGGGCGCTTTTGGCCAGG

GGACCAAGGTGGACATCAAA anti-ECAD scFv clone 14 (SEQ ID NO: 62; light chain followed by linker in bold/underlined followed by heavy chain)

TCTTCTGAGCTGACTCAGGACCCTGCTGTGTCTGTGGCCTTGGGACAGACAGT

CAGGATCACATGCCAAGGAGACAGCCTCAGAAGCTATTATGCGAGCTGGTAC

CAGCAGAAGCCAGGACAGGCCCCTGTACTTGTCATCTATGGTAAAAACAACC

GGCCCTCAGGGATCCCAGACCGATTCTCTGGCTCCAGCTCAGGAAACACAGC

TTCCTTGACCATCACTGGGGCTCAGGCGGAAGATGAGGCTGACTATTACTGTA

ACTCCCGGGACAGCAGTGGTAACCCGGTATTCGGCGGAGGGACCAAGCTCAC

CGTCCTAGGTGAGGGTAAATCTTCCGGATCTGGTTCCGAATCCAAAGCTA

GCGAGGTGCAGCTGGTGCAGTCTGGGGGAGGCTTGGTCAAGCCTGGAGGGTC

CCTGAGACTCTCCTGTGCAGCCTCTGGATTCACCTTCAGTGACTACTACATGA

GCTGGATCCGCCAGGCTCCAGGGAAGGGGCTGGAGTGGGTTTCATACATTAG

TAGTAGTGGTAGTACCATATACTACGCAGACTCTGTGAAGGGCCGATTCACC

ATCTCCAGGGACAACGCCAAGAACTCACTGTATCTGCAAATGAACAGCCTGA

GAGCCGAGGACACGGCCGTGTATTACTGTGCGAGAGCCCAACGGCAGTGGGG

GGCCTTTGACTACTGGGGCCAGGGCACCCTGGTCACCGTCTCCTCA

-continued

```
anti-MOG antibody heavy chain (SEQ ID NO: 22)
GAGGTGAAGCTGCACGAGAGCGGCGCAGGTCTGGTGAAGCCCGGCGCCAGC

GTGGAGATCAGCTGCAAGGCCACCGGCTACACCTTCAGCAGCTTCTGGATCGA

GTGGGTGAAGCAGAGACCCGGCCACGGCCTGGAGTGGATCGGCGAGATCCTG

CCCGGCAGAGGCAGAACCAACTACAACGAGAAGTTCAAGGGCAAGGCCACC

TTCACCGCCGAGACCAGCAGCAACACCGCCTACATGCAGCTGAGCAGCCTGA

CCAGCGAGGACAGCGCCGTGTACTACTGCGCCACCGGCAACACCATGGTGAA

CATGCCCTACTGGGGCCAGGGCACCACCGTGACCGTGAGCAGC

anti-MOG antibody light chain (SEQ ID NO: 23)
GATATTGAACTGACCCAGAGTCCCAGTAGCCTGGCCGTGAGTGCCGGCGAGA

AAGTGACCATGAGCTGCAAAAGCAGCCAGAGCCTGCTGAACAGCGGCAACCA

GAAAAACTACCTGGCCTGGTACCAGCAGAAACCCGGCCTGCCTCCTAAGCTGC

TGATCTACGGCGCCAGCACCAGAGAAAGCGGCGTGCCCGATAGATTCACCGGC

TCTGGCTCTGGCACCGACTTCACCCTGACCATCAGCAGCGTGCAGGCCGAAG

ACCTGGCtGTcTACTACTGCCAGAACGACCACAGCTACCCCCTGACCTTCGGCG

CCGGCACCAAGCTGGAGATCAAG

anti-HER2 antibody heavy chain (SEQ ID NO: 24)
GAGGTTCAGCTGGTGGAGTCTGGCGGTGGCCTGGTGCAGCCCGGGGGCTCTC

TCCGTTTGTCCTGTGCAGCTTCTGGCTTCAACATTAAAGACACCTATATCCACT

GGGTGCGTCAGGCTCCGGGTAAGGGCCTGGAGTGGGTTGCAAGGATTTATCCT

ACGAATGGTTATACTCGTTATGCCGATAGCGTCAAGGGCCGTTTCACTATAAGC

GCAGACACTTCGAAAAACACAGCCTACCTCCAGATGAACAGCCTGCGTGCTG

AGGACACTGCCGTCTATTATTGTAGCAGATGGGGTGGGGACGGCTTCTATGCTA

TGGACTACTGGGGTCAAGGTACACTAGTCACCGTCAGCAGCGCTAGCACCAA

GGGCACCACGACGCCAGCGCCGCGACCACCAACACCGGCGCCCACCATCGCG

TCGCAGCCCCTGTCCCTGCGCCCAGAGGCGTGCCGGCCAGCGGCGGGGGGCG

CAGTGCACACGAGGGGGCTGGACTTCGCCTGTGAT

anti-HER2 antibody light chain (SEQ ID NO: 25)
GATATCCAGATGACCCAGTCCCCGAGCTCCCTGTCCGCCTCTGTGGGCGATAG

GGTCACTATCACCTGCCGTGCCAGTCAGGATGTGAATACTGCTGTAGCCTGGTA

TCAACAGAAACCCGGAAAGGCCCCGAAACTGCTGATTTACTCGGCATCCTTCC

TCTACTCTGGAGTCCCTTCTCGCTTCTCTGGTTCCCGCTCTGGGACGGATTTCA

CTCTGACCATCAGCTCCCTGCAGCCGGAAGACTTCGCAACTTATTACTGTCAG

CAACACTATACTACTCCTCCGACGTTCGGACAGGGTACCAAGGTGGAGATCAA

ACGTACCGTGGCGGCGCCA
```

A CAR described herein (e.g., a CAR-ECAD, a CAR-MOG, or a CAR-HER2) also can include one or more additional components. Examples of additional components that can be included in a CAR include, without limitation, a leader sequence (e.g., a CD8 leader sequence), a hinge (e.g., a CD8 hinge and a CD28 hinge), a transmembrane domain (e.g., CD8 transmembrane domain and a CD28 transmembrane domain), a co-stimulatory signaling domain (e.g., that may increase immunosuppression such as a TLR3 signaling domain and/or a TLR4 signaling domain), a Toll/interleukin-1 receptor/resistance (TIR) interaction sequence (e.g., a TLR3 TIR-interaction domain and/or a TLR4 TIR-interaction domain), a TLR intracellular domain (e.g., a TLR intracellular linker), and a TLR transmembrane domain (e.g., a TLR 3 transmembrane domain and/or a TLR4 transmembrane domain). In some cases, nucleic acid encoding a component of a construct encoding a CAR can be separated from nucleic acid encoding another component using one or more linkers. Nucleic acids in a construct encoding a CAR can be present in any appropriate order. In some cases, a CAR can be designed to include a scFv that is in a light chain to heavy chain orientation or in a heavy chain to light chain orientation using any appropriate linker between the chains. For example, constructs encoding a CHD1-CAR can be generated in a light to heavy chain orientation of the scFv or in a heavy to light chain orientation of the scFv. In some cases, a CAR can be designed to include a scFv that is in a light chain to heavy chain orientation or in a heavy chain to light chain orientation without a linker between the chains. Exemplary nucleic acid sequences that can encode one or more additional components that can be included in a CAR that can be included in a construct described herein include, without limitation, those that encode the following amino acid sequences:

```
CD8 leader sequence (SEQ ID NO: 26)
MALPVTALLLPLALLLHAARP

Linker (SEQ ID NO: 27)
GGGGSGGGGSGGGGS

CD8 hinge (SEQ ID NO: 28)
TTTPAPRPPTPAPTIASQPLSLRPEACRPAAGGAVHTRGLDFACD

CD28 hinge (SEQ ID NO: 29)
LEPKSCDKTHTCPPCPDPK

TLR long (long peptide derived from toll like
receptor; SEQ ID NO: 46)
NDFACTCEHQSFLQWIKDQRQLLVEVERMECATPSDKQGMPVLSLNITCQ

MNKTI

TLR short (short peptide derived from toll like
receptor; SEQ ID NO: 47)
MNKTI

CD8 transmembrane domain (SEQ ID NO: 30)
IYIWAPLAGTCGVLLLSLVITLYC

CD28 transmembrane domain (SEQ ID NO: 31)
FWVLVVVGGVLACYSLLVTVAFIIFWV

TLR4 transmembrane domain (SEQ ID NO: 48)
IGVSVLSVLVVSVVAVLVY

CD28 signaling domain (SEQ ID NO: 32)
RSKRSRLLHSDYMNMTPRRPGPTRKHYQPYAPPRDFAAYRS

CD3zeta signaling domain (SEQ ID NO: 33)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

4-1BB (CD137) signaling domain (SEQ ID NO: 34)
KRGRKKLLYIFKQPFMRPVQTTQEEDGCSCRFPEEEEGGCEL

TLR3 signaling domain (SEQ ID NO: 35)
FEYAAYIIHAYKDKDWVWEHFSSMEKEDQSLKFCLEERDFEAGVFELEAI

VNSIKRSRKIIFVITHHLLKDPLCKRFKVHHAVQQAIEQNLDSIILVFLE

EIPDYKLNHALCLRRGMFKSHCILNWPVQKERIGAFRHKLQVALGSKNSV

H

TLR4 signaling domain (SEQ ID NO: 36)
NIYDAFVIYSSQDEDWVRNELVKNLEEGVPPFQLCLHYRDFIPGVAIAAN

IIHEGFHKSRKVIVVVSQHFIQSRWCIFEYEIAQTWQFLSSRAGIIFIVL

QKVEKTLLRQQVELYRLLSRNTYLEWEDSVLGRHIFWRRLRKALLDGKSW

NPEGTVGTGCNWQEATSI

TLR4 intracellular domain (SEQ ID NO: 49)
KFYFHLMLLAGCIKYGRGENIYDAFVIYSSQDEDWVRNELVKNLEEGVPP

FQLCLHYRDFIPGVAIAANIIHEGFHKSRKVIVVVSQHFIQSRWCIFEYE
```

-continued

```
IAQTWQFLSSRAGIIFIVLQKVEKTLLRQQVELYRLLSRNTYLEWEDSVL

GRHIFWRRLRKALLDGKSWNPEGTVGTGCNWQEATSI
```

In some cases, additional components that can be included in a CAR and can be included in a construct described herein can have a sequence that deviates from a polypeptide sequence set forth in any one of SEQ ID NOs:26-36 and 46-49, sometimes referred to as a variant sequence. For example, an additional component that can be included in a CAR and can be encoded by a nucleic acid sequence that can be included in a construct described herein can have at least 80% sequence identity to any one of SEQ ID NOs:26-36 and 46-49. In some embodiments, an additional component that can be included in a CAR and can be encoded by a nucleic acid sequence that and can be included in a construct described herein can have at least 85% sequence identity, 90% sequence identity, 95% sequence identity, or at least 99% sequence identity to any one of SEQ ID NOs:26-36 and 46-49. Percent sequence identity is calculated by determining the number of matched positions in aligned polypeptide sequences, dividing the number of matched positions by the total number of aligned amino acids, respectively, and multiplying by 100. A matched position refers to a position in which identical amino acids occur at the same position in aligned sequences. The total number of aligned amino acids refers to the minimum number of amino acids in an additional component that can be included in a CAR and can be encoded by a nucleic acid sequence that can be included in a construct described herein that are necessary to align the second sequence, and does not include alignment (e.g., forced alignment) with other sequences. For example, when an additional component that can be included in a CAR and can be encoded by a nucleic acid sequence that can be included in a construct described herein is a signaling domain, the total number of aligned amino acids can exclude any transmembrane domain. The total number of aligned amino acids may correspond to the entire amino acid segment of an additional component that can be included in a CAR and can be encoded by a nucleic acid sequence that can be included in a construct described herein or may correspond to fragments of the amino acid segment of an additional component that can be included in a CAR and can be encoded by a nucleic acid sequence that can be included in a construct described herein. Sequences can be aligned using the algorithm described by Altschul et al. (*Nucleic Acids Res.,* 25:3389-3402 (1997)) as incorporated into BLAST (basic local alignment search tool) programs, available at ncbi.nlm.nih.gov on the World Wide Web. BLAST searches or alignments can be performed to determine percent sequence identity using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between an amino acid segment that can bind a tissue-specific antigen described herein and can be encoded by a nucleic acid sequence that can be included in a construct described herein and another sequence, the default parameters of the respective programs are used.

Exemplary nucleic acid sequences for some additional components that can be included in a CAR and can be included in a construct described herein are as follows.

CD8 leader sequence
(SEQ ID NO: 37)
ATGGCCTTACCAGTGACCGCCTTGCTCCTGCCGCTGGCCTTGCTGCTCCA

CGCCGCCAGGCCG

Linker
(SEQ ID NO: 38)
GGTGGAGGTGGTTCGGGAGGTGGAGGTAGCGGAGGTGGTGGATCT

Linker
(SEQ ID NO: 50)
GGTGGAGGTGGTTCGGGAGGTGGAGGTAGCGGAGGTGGTGGAAGC

CD8 hinge
(SEQ ID NO: 39)
ACCACTACCCCTGCACCGCGACCACCAACACCGGCGCCCACCATTGCGTC

GCAGCCTCTGTCCCTGCGCCCAGAAGCATGCCGTCCAGCAGCAGGTGGTG

CAGTTCATACTCGTGGTCTGGATTTCGCCTGTGAT

CD28 hinge
(SEQ ID NO: 40)
CTCGAGCCCAAATCTTGTGACAAAACTCACACATGCCCACCGTGCCCGGA

TCCCAAA

TLR long
(SEQ ID NO: 51)
AACGACTTCGCCTGCACCTGCGAGCACCAGAGCTTCCTGCAGTGGATCAA

GGACCAGAGGCAGCTGCTGGTGGAGGTGGAGAGGATGGAGTGCGCCACCC

CCAGCGACAAGCAGGGCATGCCCGTGCTGAGCCTGAACATCACCTGCCAG

ATGAACAAGACCATC

TLR short
(SEQ ID NO: 52)
ATGAACAAGACCATC

CD8 transmembrane domain
(SEQ ID NO: 41)
ATCTACATCTGGGCGCCCTTGGCCGGGACTTGTGGGGTCCTTCTCCTGTC

ACTGGTTATCACCCTTTACTGC

CD28 transmembrane domain
(SEQ ID NO: 42)
TTTTGGGTGCTGGTGGTGGTTGGTGGAGTCCTGGCTTGCTATAGCTTGCT

AGTAACAGTGGCCTTTATTATTTTCTGGGTG

TLR4 transmembrane domain
(SEQ ID NO: 53)
ATTGGGGTGTCTGTCCTAAGCGTGCTGGTTGTTTCCGTGGTTGCCGTTCT

GGTATAT

CD28 signaling domain
(SEQ ID NO: 43)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

CD3zeta signaling domain
(SEQ ID NO: 44)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

-continued

AGGGGCACGATGGCCTTTACCAGGGTCTCAGTACAGCCACCAAGGACACC

TACGACGCCCTTCACATGCAGGCCCTGCCCCCTCGC 4-1BB (CD137) signaling domain
(SEQ ID NO: 45)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

TLR4 intracellular domain
(SEQ ID NO: 54)
AAGTTCTATTTCCATCTGATGCTTCTCGCTGGCTGCATAAAGTACGGGAG

GGGGGAGAATATATATGACGCTTTCGTGATCTACTCGAGCCAGGATGAGG

ACTGGGTTCGCAACGAGCTAGTCAAGAATCTTGAAGAGGGCGTGCCTCCT

TTCCAGCTCTGTCTGCATTACCGCGATTTTATTCCTGGGGTGGCCATCGC

GGCCAACATCATCCACGAGGGCTTCCATAAATCCAGAAAAGTGATTGTCG

TTGTGAGCCAGCATTTCATCCAGTCCAGGTGGTGCATTTTCGAATATGAG

ATAGCCCAGACCTGGCAGTTTCTTAGCAGTCGGGCTGGGATTATTTTTAT

CGTGCTGCAGAAGGTTGAAAAGACCCTTTTGCGGCAACAGGTGGAACTGT

ACCGATTATTATCCCGTAACACTTACTTGGAATGGGAAGACTCAGTTCTC

GGACGCCACATTTTCTGGCGCCGGCTCAGGAAGGCCCTGCTGGATGGTAA

ATCCTGGAACCCCGAGGGGACAGTGGGGACCGGATGTAACTGGCAAGAGG

CAACAAGTATA

In some cases, a nucleic acid construct encoding a CAR-ECAD described herein can be designed to encode a CD8 leader sequence, an anti-ECAD antibody (e.g., a hSC10.17 antibody) heavy chain, a linker, an anti-ECAD antibody (e.g., a hSC10.17 antibody) light chain, a CD8 hinge, a CD8 transmembrane domain, and a CD3zeta signaling domain. For example, a nucleic acid construct encoding a CAR-ECAD can be designed to encode a CD8 leader including the amino acid sequence set forth in SEQ ID NO:26, a hSC10.17 heavy chain including the amino acid sequence set forth in SEQ ID NO:11, a linker including the amino acid sequence set forth in SEQ ID NO:27, a hSC10.17 light chain including the amino acid sequence set forth in SEQ ID NO:12, a CD8 hinge including the amino acid sequence set forth in SEQ ID NO:28, a CD8 transmembrane domain including the amino acid sequence set forth in SEQ ID NO:30, and a CD3zeta signaling domain including the amino acid sequence set forth in SEQ ID NO:33.

In some cases, a nucleic acid construct encoding a CAR-MOG described herein can be designed to encode a CD8 leader sequence, an anti-MOG antibody (e.g., a 8-18C5 antibody) heavy chain, a linker, an anti-MOG antibody (e.g., a 8-18C5 antibody) light chain, a CD8 hinge, a CD28 transmembrane domain, and a CD3zeta signaling domain. For example, a nucleic acid construct encoding a CAR-MOG can be designed to encode a CD8 leader including the amino acid sequence set forth in SEQ ID NO:26, a 8-18C5 heavy chain including an amino acid sequence set forth SEQ ID NO:14, a linker including the amino acid sequence set forth in SEQ ID NO:27, a 8-18C5 light chain including the amino acid sequence set forth in SEQ ID NO:15, a CD8 hinge including the amino acid sequence set forth in SEQ ID NO:28, a CD8 transmembrane domain including the amino acid sequence set forth in SEQ ID NO:30, and a CD3zeta signaling domain including the amino acid sequence set forth in SEQ ID NO:33.

In some cases, a nucleic acid construct encoding a CAR-HER2 described herein can be designed to encode a CD8 leader sequence, an anti-HER2 antibody (e.g., 4D5) heavy chain, a linker, an anti-HER2 antibody (e.g., 4D5) light chain, a CD8 hinge, a CD28 transmembrane domain, a 4-1BB signaling domain, and a CD3zeta signaling domain. For example, a nucleic acid construct encoding a CAR-HER2 can be designed to encode a CD8 leader including the amino acid sequence set forth in SEQ ID NO:26, a 4D5 heavy chain including the amino acid sequence set forth in SEQ ID NO:16, a linker including the amino acid sequence set forth in SEQ ID NO:27, a 4D5 light chain including the amino acid sequence set forth in SEQ ID NO:17, a CD28 hinge including the amino acid sequence set forth in SEQ ID NO:29, a CD8 transmembrane domain including the amino acid sequence set forth in SEQ ID NO:30, a 4-1BB signaling domain including the amino acid sequence set forth in SEQ ID NO:34, and a CD3zeta signaling domain including the amino acid sequence set forth in SEQ ID NO:33.

In some cases, a nucleic acid construct encoding a CAR-ECAD described herein, a CAR-MOG described herein, or a CAR-HER2 described herein can be designed to encode (a1) an anti-ECAD antibody (e.g., a hSC10.17 antibody) heavy chain, a linker, an anti-ECAD antibody (e.g., a hSC10.17 antibody) light chain, (a2) an anti-MOG antibody (e.g., a 8-18C5 antibody) heavy chain, a linker, an anti-MOG antibody (e.g., a 8-18C5 antibody) light chain, or (a3) an anti-HER2 antibody (e.g., 4D5) heavy chain, a linker, an anti-HER2 antibody (e.g., 4D5) light chain followed by (b) a CD8 hinge, (c) a TLR4 transmembrane domain, and (d) a TLR4 signaling domain or a TLR4 intracellular domain.

In some cases, a nucleic acid construct encoding a CAR-ECAD described herein, a CAR-MOG described herein, or a CAR-HER2 described herein can be designed to encode (a1) an anti-ECAD antibody (e.g., a hSC10.17 antibody) heavy chain, a linker, an anti-ECAD antibody (e.g., a hSC10.17 antibody) light chain, (a2) an anti-MOG antibody (e.g., a 8-18C5 antibody) heavy chain, a linker, an anti-MOG antibody (e.g., a 8-18C5 antibody) light chain, or (a3) an anti-HER2 antibody (e.g., 4D5) heavy chain, a linker, an anti-HER2 antibody (e.g., 4D5) light chain followed by (b) a CD8 hinge, (c) a TLR4 transmembrane domain, (d) a TLR4 signaling domain or a TLR4 intracellular domain, and (e) a CD3zeta signaling domain.

In some cases, a nucleic acid construct encoding a CAR-ECAD described herein, a CAR-MOG described herein, or a CAR-HER2 described herein can be designed to encode (a1) an anti-ECAD antibody (e.g., a hSC10.17 antibody) heavy chain, a linker, an anti-ECAD antibody (e.g., a hSC10.17 antibody) light chain, (a2) an anti-MOG antibody (e.g., a 8-18C5 antibody) heavy chain, a linker, an anti-MOG antibody (e.g., a 8-18C5 antibody) light chain, or (a3) an anti-HER2 antibody (e.g., 4D5) heavy chain, a linker, an anti-HER2 antibody (e.g., 4D5) light chain followed by (b) a linker such as a linker encoded by SEQ ID NO:50, (c) a TLR4 transmembrane domain, and (d) a TLR4 signaling domain or a TLR4 intracellular domain.

In some cases, a nucleic acid construct encoding a CAR-ECAD described herein, a CAR-MOG described herein, or a CAR-HER2 described herein can be designed to encode (a1) an anti-ECAD antibody (e.g., a hSC10.17 antibody) heavy chain, a linker, an anti-ECAD antibody (e.g., a hSC10.17 antibody) light chain, (a2) an anti-MOG antibody (e.g., a 8-18C5 antibody) heavy chain, a linker, an anti-MOG antibody (e.g., a 8-18C5 antibody) light chain, or (a3) an anti-HER2 antibody (e.g., 4D5) heavy chain, a linker, an anti-HER2 antibody (e.g., 4D5) light chain followed by (b) an TLR long, (c) a TLR4 transmembrane domain, and (d) a TLR4 signaling domain or a TLR4 intracellular domain.

In some cases, a nucleic acid construct encoding a CAR-ECAD described herein, a CAR-MOG described herein, or a CAR-HER2 described herein can be designed to encode (a1) an anti-ECAD antibody (e.g., a hSC10.17 antibody) heavy chain, a linker, an anti-ECAD antibody (e.g., a hSC10.17 antibody) light chain, (a2) an anti-MOG antibody (e.g., a 8-18C5 antibody) heavy chain, a linker, an anti-MOG antibody (e.g., a 8-18C5 antibody) light chain, or (a3) an anti-HER2 antibody (e.g., 4D5) heavy chain, a linker, an anti-HER2 antibody (e.g., 4D5) light chain followed by (b) an TLR short, (c) a TLR4 transmembrane domain, (d) a TLR4 signaling domain or a TLR4 intracellular domain, and (e) a CD3zeta signaling domain.

In some cases, a nucleic acid construct encoding a CAR-ECAD described herein, a CAR-MOG described herein, or a CAR-HER2 described herein can be designed to encode (a1) an anti-ECAD antibody (e.g., a hSC10.17 antibody) heavy chain, a linker, an anti-ECAD antibody (e.g., a hSC10.17 antibody) light chain, (a2) an anti-MOG antibody (e.g., a 8-18C5 antibody) heavy chain, a linker, an anti-MOG antibody (e.g., a 8-18C5 antibody) light chain, or (a3) an anti-HER2 antibody (e.g., 4D5) heavy chain, a linker, an anti-HER2 antibody (e.g., 4D5) light chain followed by (b) a CD28 hinge, (c) a CD28 transmembrane domain, and (d) a CD28 signaling domain.

In some cases, a nucleic acid construct encoding a CAR-ECAD described herein, a CAR-MOG described herein, or a CAR-HER2 described herein can be designed to encode (a1) an anti-ECAD antibody (e.g., a hSC10.17 antibody) heavy chain, a linker, an anti-ECAD antibody (e.g., a hSC10.17 antibody) light chain, (a2) an anti-MOG antibody (e.g., a 8-18C5 antibody) heavy chain, a linker, an anti-MOG antibody (e.g., a 8-18C5 antibody) light chain, or (a3) an anti-HER2 antibody (e.g., 4D5) heavy chain, a linker, an anti-HER2 antibody (e.g., 4D5) light chain followed by (b) a CD28 hinge, (c) a CD28 transmembrane domain, (d) a CD28 signaling domain, and (e) a CD3zeta signaling domain.

In cases where a MSC designed to express an antigen receptor (e.g., a CAR) capable of binding (e.g., specifically binding) to a tissue-specific antigen is also designed to express a polypeptide that can promote differentiation into a tissue specific cell, the MSC can include one or more nucleic acids encoding a polypeptide that can promote differentiation into a tissue specific cell. Nucleic acid that can encode a polypeptide that can promote tissue specific cell differentiation can encode any polypeptide that can promote a MSC to differentiate into any type of tissue specific cell. For example, a MSC can be designed to include one or more nucleic acids encoding a polypeptide that can promote cardiac cell differentiation. A polypeptide that can promote cardiac differentiation can promote differentiation into any appropriate type of cardiac cell (e.g., cardiomyocytes). Examples of polypeptides that can promote cardiac cell differentiation and can be included in a MSC as described herein include, without limitation, a GATA4 polypeptide, a MEF2C polypeptide, a TBX5 polypeptide, a ERRG polypeptide, and a MESP1 polypeptide. For example, a MSC can be designed to include one or more nucleic acids encoding a polypeptide that can promote neural differentiation. A polypeptide that can promote neural differentiation can promote differentiation into any appropriate type of neuron (e.g., sensory neurons, motor neurons, interneurons, oligodendrocytes, astrocytes, and glial cells). Examples of polypeptides that can promote neural differentiation and can be included in a MSC as described herein include, without limitation, a Oct3/4 polypeptide, a Klf4 polypeptide, a Sox2 polypeptide, a Glis1 polypeptide, a c□Myc polypeptide, a BMP4 polypeptide, a WNT polypeptide, a FGF2 polypeptide, a SHH polypeptide, a Sox11 polypeptide, a Sox2 polypeptide, a Sox3 polypeptide, a Zic1 polypeptide, a Zic2 polypeptide, a Irx1 polypeptide, a Irx2 polypeptide, a Irx3 polypeptide, a FoxD4 polypeptide, a MKx2.5 polypeptide, and a cTnT polypeptide.

This document also provides materials and methods for treating mammals (e.g., humans) having, or at risk of developing, a disease or disorder characterized by inflammation and/or degeneration of a tissue. For example, one or more MSCs expressing a CAR targeting a tissue-specific antigen and, optionally, expressing a polypeptide that can promote differentiation of the MSC and/or one or more resident progenitor cells into a tissue specific cell (e.g., a composition containing one or more MSCs expressing a CAR targeting a tissue-specific antigen and, optionally, expressing a polypeptide that can promote differentiation of the MSC and/or one or more resident progenitor cells into a tissue specific cell) can be administered (e.g., by adoptive transfer) to a mammal having, or at risk of developing, a disease or disorder characterized by inflammation and/or degeneration of a tissue to reduce the severity of the inflammation of the targeted tissue within the mammal. Any appropriate method can be used to identify a mammal as having or as being at risk of developing an inflammatory disease or condition and/or as having, or as being at risk of developing, a degenerative disease. For example, imaging techniques (e.g., ultrasound, computerized tomography (CT) scanning), laboratory tests (e.g., blood tests for inflammatory markers such as erythrocyte sedimentation rate (ESR), C-reactive protein (CRP), and/or plasma viscosity (PV)) can be used to identify a mammal as having or as being at risk of developing an inflammatory disease or condition and/or as having, or as being at risk of developing, a degenerative disease. Once identified as having (or as being at risk of developing) an inflammatory disease or condition and/or as having (or as being at risk of developing) a degenerative disease, one or more MSCs expressing a CAR targeting a tissue-specific antigen and, optionally, expressing a polypeptide that can promote differentiation of the MSC and/or one or more resident progenitor cells into a tissue specific cell can be administered to the mammal (e.g., a human) in need thereof (e.g., a human having, or at risk of developing, a disease or disorder characterized by inflammation and/or degeneration of a tissue expressing a tissue-specific antigen) as described herein to reduce the inflammation of a tissue by, for example, 10, 20, 30, 40, 50, 60, 70, 80, 90, 95, or more percent. For example, one or more MSCs expressing a polypeptide that can promote a MSC to differentiate into any type of tissue specific cell (e.g., a cardiac cell or a neuron) can be administered (e.g., by adoptive transfer) to a mammal (e.g., a human) having (or at risk of developing) a degenerative heart disease to treat that degenerative heart disease within the mammal. Any appropriate method can be used to identify a mammal as having or as being at risk of developing a degenerative disease. For example, imaging techniques (e.g., ultrasound, computerized tomography (CT) scanning), and/or laboratory tests (e.g., blood tests for genetic markers) can be used to identify a mammal as having or as being at risk of developing a degenerative disease. Once identified as having (or as being at risk of developing) a degenerative disease, one or more MSCs expressing a polypeptide that can promote a MSC to differentiate into any type of tissue specific cell can be administered to the mammal (e.g., a human) in need thereof (e.g., a human having, or at risk of developing, a degenerative disease) as described herein to increase the number of tissue specific cells in a tissue by, for example, 10, 20, 30, 40, 50, 60, 70, 80, 90, 95, or more percent.

Any appropriate mammal having, or at risk of developing, a disease or disorder characterized by inflammation and/or degeneration of a tissue can be treated as described herein. Examples of mammals that can have a disease or disorder characterized by inflammation and/or degeneration of a tissue and can be treated as described herein include, without limitation, humans, non-human primates such as monkeys, dogs, cats, horses, cows, pigs, sheep, mice, and rats. For example, one or more MSCs expressing a CAR targeting a tissue-specific antigen and, optionally, expressing a polypeptide that can promote differentiation of the MSC and/or one or more resident progenitor cells into a tissue specific cell (e.g., a composition containing one or more MSCs expressing a CAR targeting a tissue-specific antigen and, optionally, expressing a polypeptide that can promote differentiation of the MSC and/or one or more resident progenitor cells into a tissue specific cell) can be administered (e.g., by adoptive transfer) to humans having, or at risk of developing, a disease or disorder characterized by inflammation and/or degeneration of a tissue to treat the human.

In some cases, the materials and methods for treating mammals (e.g., humans) having, or at risk of developing, a disease or disorder characterized by inflammation and/or degeneration of a tissue can be used to treat a mammal (e.g., a human) having, or at risk of developing, a disease or disorder characterized by inflammation and/or degeneration of an epithelial tissue. Examples of diseases and disorders characterized by inflammation and/or degeneration of an epithelial tissue include, without limitation, an IBD such as colitis (e.g., characterized by inflammation of colon cells and/or rectal cells), hepatitis (e.g., characterized by inflammation of liver cells), cholangitis (e.g., characterized by inflammation of bile duct cells), dermatitis (e.g., severe dermatitis characterized by inflammation of skin cells), mucositis (e.g., severe mucositis characterized by inflammation of mucous membranes lining the digestive tract), colonic fistula, graft versus host disease, and inflammatory pneumonitis (e.g., characterized by inflammation of lung cells). When treating a mammal having (or at risk of developing) colitis, the colitis can be any type of colitis (e.g., ulcerative colitis, Crohn's colitis, diversion colitis, ischemic colitis, infectious colitis, fulminant colitis, collagenous colitis, chemical colitis, microscopic colitis, lymphocytic colitis, and atypical colitis).

In some cases, a mammal can be identified as having, or as being at risk of developing, a disease or disorder characterized by inflammation and/or degeneration of an epithelial tissue (e.g., an IBD such as colitis). Any appropriate method can be used to identify a mammal as having, or as being at risk of developing, a disease or disorder characterized by inflammation and/or degeneration of an epithelial tissue. For example, blood tests (e.g., for anemia or signs of infection), laboratory tests, (e.g., for white blood cells in a mammal's stool), imaging techniques (e.g., colonoscopy, flexible sigmoidoscopy, x-ray, CT scanning, CT enterography, and magnetic resonance (MR) enterography), biopsies, skin biopsy, and/or liver function tests can be used to identify a mammal as having, or as being at risk of developing, a disease or disorder characterized by inflammation of an epithelial tissue such as colitis. Once identified as having (or as being at risk of developing) a disease or disorder characterized by inflammation and/or degeneration of an epithelial tissue, the mammal can be administered (e.g., by adoptive transfer) or instructed to self-administer one or more MSCs described herein (e.g., MSCs expressing a CAR targeting an epithelial-specific antigen and, optionally, expressing a polypeptide that can promote differentiation of the MSC and/or one or more resident progenitor cells into a tissue specific cell) to treat the mammal (e.g., to reduce or eliminate inflammation of one or more epithelial tissues within the mammal).

When treating a mammal having (or at risk of developing) a disease or disorder characterized by inflammation and/or degeneration of an epithelial tissue (e.g., an IBD such as colitis) as described herein (e.g., by administering one or more MSCs expressing a CAR targeting an epithelial-specific antigen and, optionally, expressing a polypeptide that can promote differentiation into a tissue specific cell), the one or more MSCs expressing a CAR targeting an epithelial-specific antigen and, optionally, expressing a polypeptide that can promote differentiation of the MSC and/or one or more resident progenitor cells into a tissue specific cell can be effective to reduce the severity of the disease or disorder characterized by inflammation and/or degeneration of an epithelial tissue in the mammal. In cases where the disease or disorder characterized by inflammation and/or degeneration of an epithelial tissue is colitis, reducing the severity of colitis in a mammal can include reducing or eliminating one or more symptoms of colitis (e.g., diarrhea, abdominal pain and cramping, rectal pain, rectal bleeding, urgency to defecate, inability to defecate despite urgency, weight loss, fatigue, fever, jaundice, liver failure, abnormal liver tests, respiratory distress, skin erythema, and/or desquamation). For example, one or more MSCs expressing a CAR targeting an epithelial-specific antigen and, optionally, expressing a polypeptide that can promote differentiation of the MSC and/or one or more resident progenitor cells into a tissue specific cell can be administered to a mammal (e.g., a human) in need thereof (e.g., a human having, or at risk of developing, colitis) as described herein to reduce the severity of one or more symptoms of colitis by, for example, 10, 20, 30, 40, 50, 60, 70, 80, 90, 95, or more percent.

In some cases, one or more MSCs expressing a CAR targeting an epithelial-specific antigen and, optionally, expressing a polypeptide that can promote differentiation into a tissue specific cell (e.g., a composition containing one or more MSCs expressing a CAR targeting an epithelial-specific antigen and, optionally, expressing a polypeptide that can promote differentiation of the MSC and/or one or more resident progenitor cells into a tissue specific cell) can be the sole active ingredient for treating a mammal having (or at risk of developing) a disease or disorder characterized by inflammation and/or degeneration of an epithelial tissue (e.g., an IBD such as colitis) as described herein (e.g., by administering one or more MSCs expressing a CAR targeting an epithelial-specific antigen and, optionally, expressing a polypeptide that can promote differentiation of the MSC and/or one or more resident progenitor cells into a tissue specific cell).

In some cases, one or more MSCs expressing a CAR targeting an epithelial-specific antigen and, optionally, expressing a polypeptide that can promote differentiation of the MSC and/or one or more resident progenitor cells into a tissue specific cell (e.g., a composition containing one or more MSCs expressing a CAR targeting an epithelial-specific antigen and, optionally, expressing a polypeptide that can promote differentiation of the MSC and/or one or more resident progenitor cells into a tissue specific cell) can be administered in combination with one or more additional therapeutic agents (e.g., therapeutic agents that can be used to treat a mammal having or at risk of developing a disease or disorder characterized by inflammation and/or degeneration of an epithelial tissue and therapeutic agents that can be used for treating inflammation of an epithelial tissue within a mammal). For example, a mammal having (or at risk of developing) a disease or disorder characterized by inflammation and/or degeneration of an epithelial tissue (e.g., an IBD such as colitis) also can be treated with one or more additional therapeutic agents. In some cases, a therapeutic agent can be an anti-inflammatory. In some cases, a therapeutic agent can be an immunosuppressant. In some cases, a therapeutic agent can be a T cell such as a T cell expressing a CAR (a CAR-T cell). Examples of therapeutic agents that can be used in combination with one or more MSCs expressing a CAR targeting an epithelial-specific antigen and, optionally, expressing a polypeptide that can promote differentiation of the MSC and/or one or more resident progenitor cells into a tissue specific cell described herein include, without limitation, a CAR-T cell (e.g., a CART19 cell) 5-aminosalicylates (e.g., sulfasalazine, mesalamine, balsalazide, and olsalazine), corticosteroids (e.g., prednisone and methylprednisolone), azathioprine, mercaptopurine, cyclosporine, infliximab, adalimumab, golimumab, vedolizumab, antibiotics, anti-diarrheal medications (e.g., loperamide), pain relievers (e.g., acetaminophen), and iron supplements. In some cases, one or more MSCs expressing a CAR targeting an epithelial-specific antigen and, optionally, expressing a polypeptide that can promote differentiation of the MSC and/or one or more resident progenitor cells into a tissue specific cell can be administered at substantially the same time as one or more additional therapeutic agents that can be used for treating inflammation of an epithelial tissue within a mammal. For example, a composition including one or more MSCs expressing a CAR targeting an epithelial-specific antigen and, optionally, expressing a polypeptide that can promote differentiation of the MSC and/or one or more resident progenitor cells into a tissue specific cell also can include one or more additional therapeutic agents that can be used for treating inflammation of an epithelial tissue within a mammal. In some cases, one or more MSCs expressing a CAR targeting an epithelial-specific antigen and, optionally, expressing a polypeptide that can promote differentiation of the MSC and/or one or more resident progenitor cells into a tissue specific cell can be administered first, and the one or more additional therapeutic agents administered second, or vice versa.

In some cases, the materials and methods for treating mammals (e.g., humans) having, or at risk of developing, a disease or disorder characterized by inflammation and/or degeneration of a tissue can be used to treat a mammal (e.g., a human) having, or at risk of developing, a disease or disorder characterized by inflammation and/or degeneration of a neural tissue. Examples of diseases and disorders characterized by inflammation and/or degeneration of a neural tissue include, without limitation, multiple sclerosis (e.g., characterized by inflammation of neurons in the brain and/or spinal cord), encephalomyelitis such as immune mediated encephalomyelitis (e.g., characterized by inflammation of the CNS), and paraneoplastic encephalitis (e.g., characterized by multifocal inflammation of the CNS). When treating a mammal having, or at risk of developing, immune mediated encephalomyelitis, the immune mediated encephalomyelitis can be any type of immune mediated encephalomyelitis (e.g., acute disseminated encephalomyelitis (ADEM), and paraneoplastic encephalitis).

In some cases, a mammal can be identified as having, or as being at risk of developing, a disease or disorder characterized by inflammation and/or degeneration of a neural tissue (e.g., multiple sclerosis or immune mediated encephalomyelitis). Any appropriate method can be used to identify a mammal as having (or as being at risk of developing) a disease or disorder characterized by inflammation and/or degeneration of a neural tissue. For example, laboratory tests such as blood tests and lumbar punctures (e.g., to check for biomarkers associated with a particular disease or disorder characterized by inflammation and/or degeneration of a neural tissue such as multiple sclerosis, and to check for the presence of antibodies associated with a particular disease or disorder characterized by inflammation and/or degeneration of a neural tissue such as anti-MOG autoantibodies), imaging techniques (e.g., magnetic resonance imaging (MRI); to check for the presence of lesions on the brain and/or spinal cord), spinal fluid analysis for protein levels, and/or cell counts for special proteins can be used to identify a mammal as having, or as being at risk of developing, a disease or disorder characterized by inflammation and/or degeneration of a neural tissue such as multiple sclerosis or immune mediated encephalomyelitis. Once identified as having (or as being at risk of developing) a disease or disorder characterized by inflammation and/or degeneration of a neural tissue, the mammal can be administered (e.g., by adoptive transfer) or instructed to self-administer one or more MSCs described herein (e.g., MSCs expressing a CAR targeting a neural-specific antigen and, optionally, expressing a polypeptide that can promote differentiation of the MSC and/or one or more resident progenitor cells into a neuron) to treat the mammal (e.g., to reduce or eliminate inflammation of one or more neural tissues within the mammal and/or to regenerate neural tissues within the mammal).

When treating a mammal having (or at risk of developing) a disease or disorder characterized by inflammation and/or degeneration of a neural tissue (e.g., multiple sclerosis or immune mediated encephalomyelitis) as described herein (e.g., by administering one or more MSCs expressing a CAR targeting a neural-specific antigen and, optionally, expressing a polypeptide that can promote differentiation of the MSC and/or one or more resident progenitor cells into a neuron), the one or more MSCs expressing a CAR targeting a neural-specific antigen and, optionally, expressing a polypeptide that can promote differentiation of the MSC and/or one or more resident progenitor cells into a neuron can be effective to reduce the severity of the disease or disorder characterized by inflammation and/or degeneration of a neural tissue in the mammal. In cases where the disease or disorder characterized by inflammation and/or degeneration of a neural tissue is multiple sclerosis, reducing the severity of multiple sclerosis in a mammal can include reducing or eliminating one or more symptoms of multiple sclerosis (e.g., numbness or weakness in one or more limbs, electric-shock sensations (e.g., that occur with certain neck movements, especially bending the neck forward), tremor, lack of coordination, unsteady gait, partial or complete loss of vision, prolonged double vision, blurry vision, slurred speech, fatigue, dizziness, tingling or pain in parts of the body, problems with sexual function, problems with bowel function, and/or problems with bladder function) and/or one or more complications associate with multiple sclerosis (e.g., muscle stiffness, muscle spasms, paralysis, forgetfulness, mood swings, depression, epilepsy, focal weakness, and/or vision defects). For example, one or more MSCs expressing a CAR targeting a neural-specific antigen and, optionally, expressing a polypeptide that can promote differentiation of the MSC and/or one or more resident progenitor cells into a neuron can be administered to a mammal (e.g., a human) in need thereof (e.g., a human having, or at risk of developing, a disease or disorder characterized by inflammation and/or degeneration of a neural tissue) as described herein to reduce the severity of one or more symptoms of a disease or disorder characterized by inflammation and/or degeneration of a neural tissue and/or one or more complications associated with a disease or disorder characterized by inflammation and/or degeneration of a neural tissue by, for example, 10, 20, 30, 40, 50, 60, 70, 80, 90, 95, or more percent.

In some cases, one or more MSCs expressing a CAR targeting a neural-specific antigen and, optionally, expressing a polypeptide that can promote differentiation of the MSC and/or one or more resident progenitor cells into a neuron (e.g., a composition containing one or more MSCs expressing one or more neural-specific antigen and, optionally, expressing a polypeptide that can promote differentiation of the MSC and/or one or more resident progenitor cells into a neuron) can be the sole active ingredient for treating a mammal having (or at risk of developing) a disease or disorder characterized by inflammation and/or degeneration of a neural tissue (e.g., multiple sclerosis or immune mediated encephalomyelitis) as described herein (e.g., by administering one or more MSCs expressing a CAR targeting a neural-specific antigen and, optionally, expressing a polypeptide that can promote differentiation of the MSC and/or one or more resident progenitor cells into a neuron).

In some cases, one or more MSCs expressing a CAR targeting a neural-specific antigen and, optionally, expressing a polypeptide that can promote differentiation of the MSC and/or one or more resident progenitor cells into a neuron (e.g., a composition containing one or more MSCs expressing a CAR targeting a neural-specific antigen and, optionally, expressing a polypeptide that can promote differentiation of the MSC and/or one or more resident progenitor cells into a neuron) can be administered in combination with one or more additional therapeutic agents (e.g., therapeutic agents that can be used to treat a mammal having or at risk of developing a disease or disorder characterized by inflammation and/or degeneration of a neural tissue and therapeutic agents that can be used for treating inflammation of a neural tissue within a mammal). For example, a mammal having (or at risk of developing) a disease or disorder characterized by inflammation and/or degeneration of a neural tissue (e.g., multiple sclerosis or immune mediated encephalomyelitis) also can be treated with one or more additional therapeutic agents. Examples of therapeutic agents that can be used in combination with one or more MSCs expressing a CAR targeting a neural-specific antigen and, optionally, expressing a polypeptide that can promote differentiation of the MSC and/or one or more resident progenitor cells into a neuron described herein include, without limitation, corticosteroids (e.g., prednisone and methylprednisolone), ocrelizumab, beta interferons, glatiramer acetate, fingolimod, dimethyl fumarate, teriflunomide, siponimod, natalizumab, alemtuzumab, mitoxantrone, baclofen, tizanidine, amantadine, modafinil, methylphenidate, dalfampridine, and immunoglobulins. In some cases, one or more MSCs expressing a CAR targeting a neural-specific antigen and, optionally, expressing a polypeptide that can promote differentiation of the MSC and/or one or more resident progenitor cells into a neuron can be administered at substantially the same time as one or more additional therapeutic agents that can be used for treating inflammation of a neural tissue within a mammal. For example, a composition including one or more MSCs expressing a CAR targeting a neural-specific antigen and, optionally, expressing a polypeptide that can promote differentiation of the MSC and/or one or more resident progenitor cells into a neuron also can include one or more additional therapeutic agents that can be used for treating inflammation of a neural tissue within a mammal. In some cases, one or more MSCs expressing a CAR targeting a neural-specific antigen and, optionally, expressing a polypeptide that can promote differentiation of the MSC and/or one or more resident progenitor cells into a neuron can be administered first, and the one or more additional therapeutic agents administered second, or vice versa.

In some cases, the materials and methods for treating mammals (e.g., humans) having, or at risk of developing, a disease or disorder characterized by inflammation and/or degeneration of a tissue can be used to treat a mammal (e.g., a human) having, or at risk of developing, a disease or disorder characterized by inflammation and/or degeneration of a cardiac tissue. Examples of diseases and disorders characterized by inflammation and/or degeneration of a cardiac tissue include, without limitation, myocarditis (e.g., characterized by inflammation of cardiomyocytes), endocarditis (e.g., characterized by inflammation of endocardium cells), and cardiac failure.

In some cases, a mammal can be identified as having, or as being at risk of developing, a disease or disorder characterized by inflammation and/or degeneration of a cardiac tissue (e.g., myocarditis). Any appropriate method can be used to identify a mammal as having, or as being at risk of developing, a disease or disorder characterized by inflammation and/or degeneration of a cardiac tissue. For example, electrocardiogram (ECG; e.g., to detect abnormal rhythms), chest X-ray, MRI (e.g., cardiac MRI), echocardiogram, laboratory tests (e.g., blood tests to measure white and red blood cell counts, and/or levels of certain enzymes that indicate damage to heart muscle, and detect antibodies) can be used to identify a mammal as having, or as being at risk of developing, a disease or disorder characterized by inflammation and/or degeneration of a cardiac tissue such as myocarditis. Once identified as having (or as being at risk of developing) a disease or disorder characterized by inflammation and/or degeneration of a cardiac tissue, the mammal can be administered (e.g., by adoptive transfer) or instructed to self-administer one or more MSCs described herein (e.g., MSCs expressing a CAR targeting a cardiac-specific antigen and, optionally, expressing a polypeptide that can promote differentiation of the MSC and/or one or more resident progenitor cells into a cardiac cell) to treat the mammal (e.g., to reduce or eliminate inflammation of one or more cardiac tissues within the mammal).

When treating a mammal having (or at risk of developing) a disease or disorder characterized by inflammation and/or degeneration of a cardiac tissue (e.g., myocarditis) as described herein (e.g., by administering one or more MSCs expressing a CAR targeting a cardiac-specific antigen and, optionally, expressing a polypeptide that can promote differentiation of the MSC and/or one or more resident progenitor cells into a cardiac cell), the one or more MSCs expressing a CAR targeting a cardiac-specific antigen and, optionally, expressing a polypeptide that can promote differentiation of the MSC and/or one or more resident progenitor cells into a cardiac cell can be effective to reduce the severity of the disease or disorder characterized by inflammation and/or degeneration of a cardiac tissue in the mammal. In cases where the disease or disorder characterized by inflammation and/or degeneration of an epithelial tissue is myocarditis, reducing the severity of myocarditis in a mammal can include reducing or eliminating one or more symptoms of myocarditis (e.g., chest pain, arrhythmias, shortness of breath, fluid retention (e.g., with swelling of legs, ankles, and feet), fatigue, headache, body aches, joint pain, fever, a sore throat, diarrhea, fainting, and/or rapid breathing). For example, one or more MSCs expressing a CAR targeting a cardiac-specific antigen and, optionally, expressing a polypeptide that can promote differentiation of the MSC and/or one or more resident progenitor cells into a cardiac cell can be administered to a mammal (e.g., a human) in need thereof (e.g., a human having, or at risk of developing, myocarditis) as described herein to reduce the severity of one or more symptoms of myocarditis by, for example, 10, 20, 30, 40, 50, 60, 70, 80, 90, 95, or more percent.

In some cases, one or more MSCs expressing a CAR targeting a cardiac-specific antigen and, optionally, expressing a polypeptide that can promote differentiation of the MSC and/or one or more resident progenitor cells into a cardiac cell (e.g., a composition containing one or more MSCs expressing a CAR targeting a cardiac-specific antigen and, optionally, expressing a polypeptide that can promote differentiation of the MSC and/or one or more resident progenitor cells into a cardiac cell) can be the sole active ingredient for treating a mammal having (or at risk of developing) a disease or disorder characterized by inflammation and/or degeneration of a cardiac tissue (e.g., myocarditis) as described herein (e.g., by administering one or more MSCs expressing a CAR targeting a cardiac-specific antigen and, optionally, expressing a polypeptide that can promote differentiation of the MSC and/or one or more resident progenitor cells into a cardiac cell).

In some cases, one or more MSCs expressing a CAR targeting a cardiac-specific antigen and, optionally, expressing a polypeptide that can promote differentiation of the MSC and/or one or more resident progenitor cells into a cardiac cell (e.g., a composition containing one or more MSCs expressing a CAR targeting a cardiac-specific antigen and, optionally, expressing a polypeptide that can promote differentiation of the MSC and/or one or more resident progenitor cells into a cardiac cell) can be administered in combination with one or more additional therapeutic agents (e.g., therapeutic agents that can be used to treat a mammal having or at risk of developing a disease or disorder characterized by inflammation and/or degeneration of a cardiac tissue and therapeutic agents that can be used for treating inflammation of a cardiac tissue within a mammal). For example, a mammal having (or at risk of developing) a disease or disorder characterized by inflammation and/or degeneration of a cardiac tissue (e.g., myocarditis) also can be treated with one or more additional therapeutic agents. In some cases, a therapeutic agent can be an anti-inflammatory. In some cases, a therapeutic agent can be an immunosuppressant. In some cases, a therapeutic agent can be an angiotensin-converting enzyme (ACE) inhibitor. In some cases, a therapeutic agent can be an angiotensin II receptor blocker (ARB). Examples of therapeutic agents that can be used in combination with one or more MSCs expressing a CAR targeting a cardiac-specific antigen and, optionally, expressing a polypeptide that can promote differentiation of the MSC and/or one or more resident progenitor cells into a cardiac cell described herein include, without limitation, enalapril, captopril, lisinopril, ramipril, losartan, valsartan, metoprolol, bisoprolol, and carvedilol. In some cases, one or more MSCs expressing a CAR targeting a cardiac-specific antigen and, optionally, expressing a polypeptide that can promote differentiation of the MSC and/or one or more resident progenitor cells into a cardiac cell can be administered at substantially the same time as one or more additional therapeutic agents that can be used for treating inflammation of a cardiac tissue within a mammal. For example, a composition including one or more MSCs expressing a CAR targeting a cardiac-specific antigen and, optionally, expressing a polypeptide that can promote differentiation of the MSC and/or one or more resident progenitor cells into a cardiac cell also can include one or more additional therapeutic agents that can be used for treating inflammation of a cardiac tissue within a mammal. In some cases, one or more MSCs expressing a CAR targeting a cardiac-specific antigen and, optionally, expressing a polypeptide that can promote differentiation of the MSC and/or one or more resident progenitor cells into a cardiac cell can be administered first, and the one or more additional therapeutic agents administered second, or vice versa.

Any appropriate method can be used to administer one or more MSCs expressing a CAR targeting a tissue-specific antigen and, optionally, expressing a polypeptide that can promote differentiation of the MSC and/or one or more resident progenitor cells into a tissue specific cell (e.g., a composition containing one or more MSCs expressing a CAR targeting a tissue-specific antigen such as an epithelial-specific antigen, a neural-specific antigen, or a cardiac-specific antigen and, optionally, expressing a polypeptide that can promote differentiation of the MSC and/or one or more resident progenitor cells into a tissue specific cell such as a cardiac cell or a neuron) to a mammal (e.g., a human) in need thereof (e.g., a human having, or at risk of developing, a disease or disorder characterized by inflammation and/or degeneration of a tissue expressing a tissue-specific antigen). Examples of methods of administering MSCs described herein to a mammal can include, without limitation, injection (e.g., intravenous, intradermal, intramuscular, or subcutaneous injection). For example, a composition including one or more MSCs expressing a CAR targeting a tissue-specific antigen and, optionally, expressing a polypeptide that can promote differentiation of the MSC and/or one or more resident progenitor cells into a tissue specific cell can be administered to a human by intravenous injection.

This document also provides kits containing one or more materials described herein. In some cases, a kit can include one or more MSCs expressing a CAR targeting a tissue-specific antigen and, optionally, expressing a polypeptide that can promote differentiation of the MSC and/or one or more resident progenitor cells into a tissue specific cell (e.g., a composition containing one or more MSCs expressing a CAR targeting a tissue-specific antigen such as an epithelial-specific antigen, a neural-specific antigen, or a cardiac-specific antigen and, optionally, expressing a polypeptide that can promote differentiation of the MSC and/or one or more resident progenitor cells into a tissue specific cell such as a cardiac cell or a neuron). For example, one or more MSCs expressing a CAR targeting a tissue-specific antigen and, optionally, expressing a polypeptide that can promote differentiation of the MSC and/or one or more resident progenitor cells into a tissue specific cell (e.g., a composition containing one or more MSCs expressing a CAR targeting a tissue-specific antigen such as an epithelial-specific antigen, a neural-specific antigen, or a cardiac-specific antigen and, optionally, expressing a polypeptide that can promote differentiation of the MSC and/or one or more resident progenitor cells into a tissue specific cell such as a cardiac cell or a neuron) can be combined with packaging material to form a kit. For example, one or more constructs (e.g., nucleic acid constructs) described herein (e.g., encoding a CAR that can bind a tissue-specific antigen such as an epithelial-specific antigen, a neural-specific antigen, or a cardiac-specific antigen) can be combined with packaging material to form a kit. The packaging material included in such a kit typically contains instructions or a label describing how the composition can be used, for example, in an adoptive transfer to treat a mammal having, or at risk of developing, a disease or disorder characterized by inflammation and/or degeneration of a tissue as described herein. In some cases, materials provided in kits described herein can be used for treating mammals (e.g., humans) having, or at risk of developing, a disease or disorder characterized by inflammation and/or degeneration of a tissue as described herein. In some cases, the packaging material included in such a kit can contain instructions and/or a label describing how a composition described herein can be used. For example, a kit can contain instructions and/or a label describing how a composition described herein can be used to express one or more CARs in MSCs to engineer the MSCs to express CARs that bind one or more epithelial-specific antigens (e.g., CAR-ECAD, CAR-MOG, or CAR-HER2). In some cases, the packaging material included in such a kit can contain instructions and/or a label describing how the engineered MSCs described herein can be used. For example, the packaging material included in such a kit can contain instructions and/or a label describing how the engineered MSCs described herein can be used in adoptive transfer to treat a mammal having, or at risk of developing, a disease or disorder characterized by inflammation and/or degeneration of a tissue as described herein. In some cases, a kit (e.g., a kit containing instructions and/or a label describing how the engineered MSCs described herein can be used in adoptive transfer) can include materials for use in an adoptive transfer procedure.

The invention will be further described in the following examples, which do not limit the scope of the invention described in the claims.

EXAMPLES

Example 1: Engineered CAR-MSCs for Immunomodulation

To determine if MSCs expressing CARs could reduce inflammation in a target cell population, MSCs expressing CARs targeting CD19 (MSC-CAR19s) were engineered.

Figure 1:
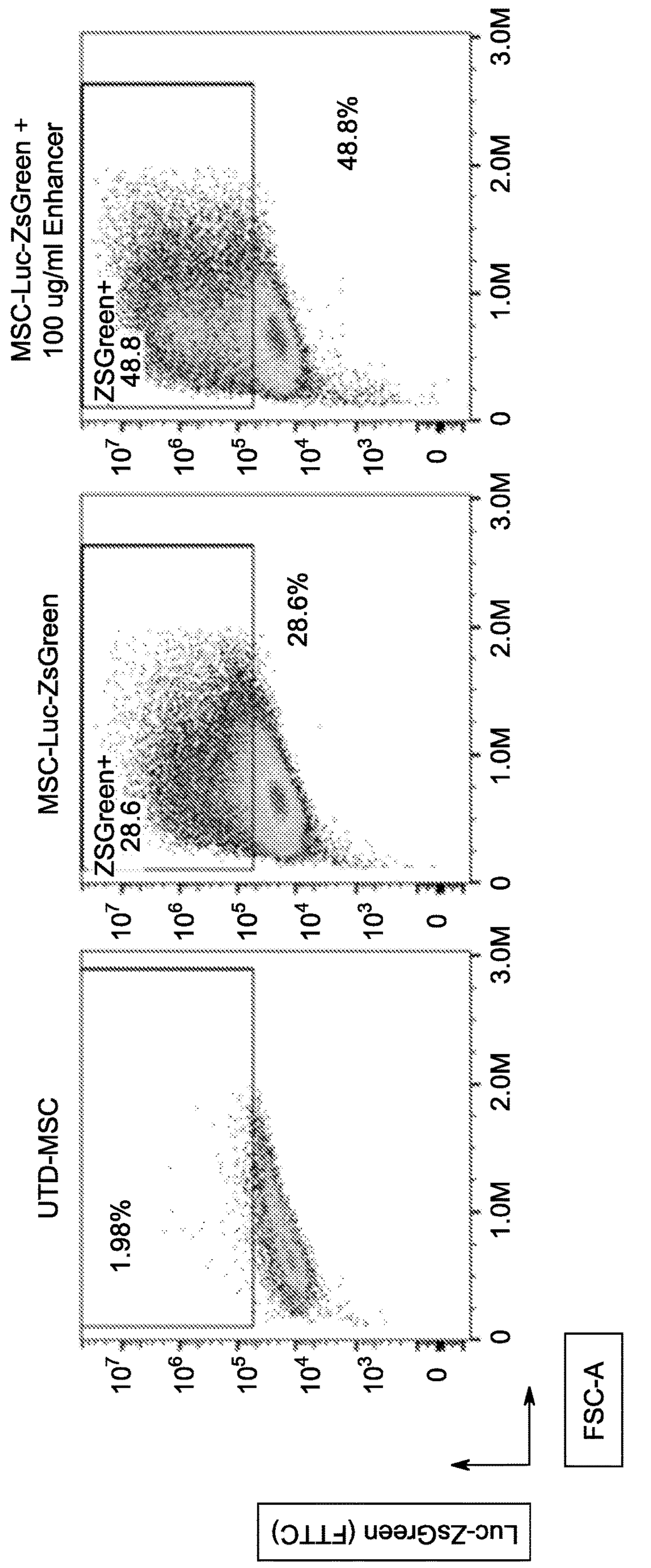
FIG. 1. Enhanced Lentiviral Transduction of MSCs.

Adipose derived-mesenchymal stem cells (100-Biotr-0024) were passaged into 3 wells of a 6 well plate (100 k each). One group was left as an untransduced (UTD) negative control. The second well was transduced with Luciferase-ZsGreen lentivirus (~MOI 3). The third group was transduced with the same MOI and lentivirus but with 100 μg/ml of a protamine sulfate solution transduction "enhancer PLUS" system. The efficiency of transduction increased >20% upon use of our "enhancer PLUS" (FIG. 1).

MSCs were transduced with CD19-CAR lentivirus (VSV-G pseudo-typed) to generate MSC-CAR19.

Figure 2:
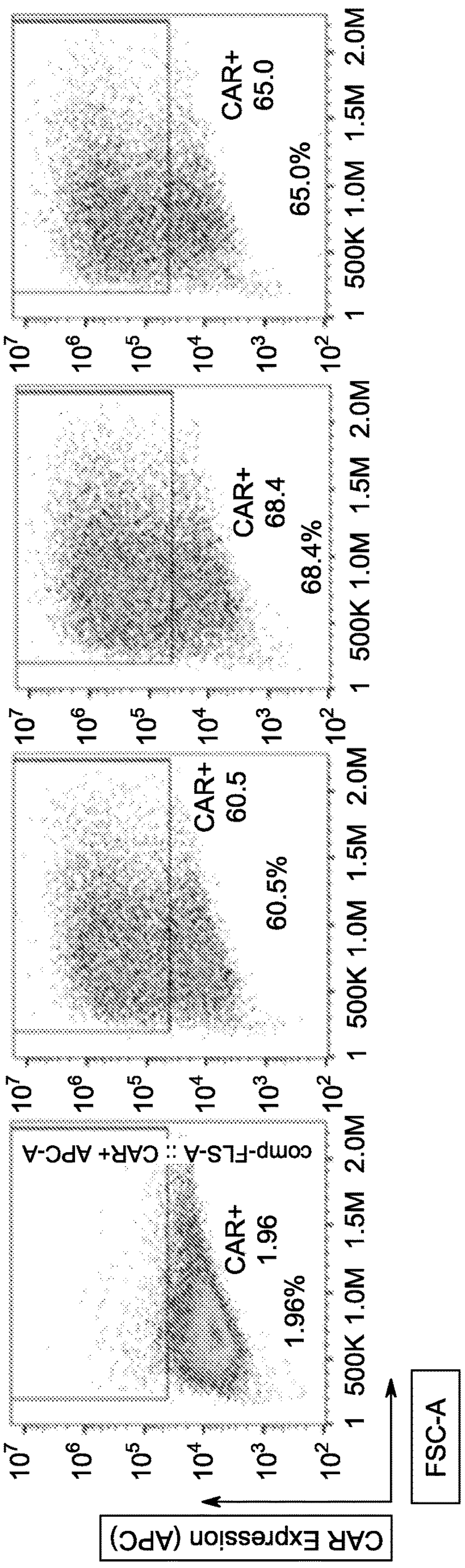
FIG. 2. MSC expression of CAR19 (MSC19).

Adipose derived-mesenchymal stem cells (100-Biotr-0024) were passaged into 4 wells of a 6 well plate (100 k each). One group was left as an untransduced (UTD) negative control. The second well was transduced with our GMP-grade, pan-VSV, CD19 recognizing-Chimeric Antigen Receptor (CAR19) lentivirus (~MOI 3). The third group was transduced with the same MOI and lentivirus in addition to 50 μg/ml Enhancer PLUS. The fourth group is identical to the third but 100 μg/ml of enhancer PLUS was used. The efficiency of transduction increased upon use of enhancer PLUS (FIG. 2).

Figure 3:
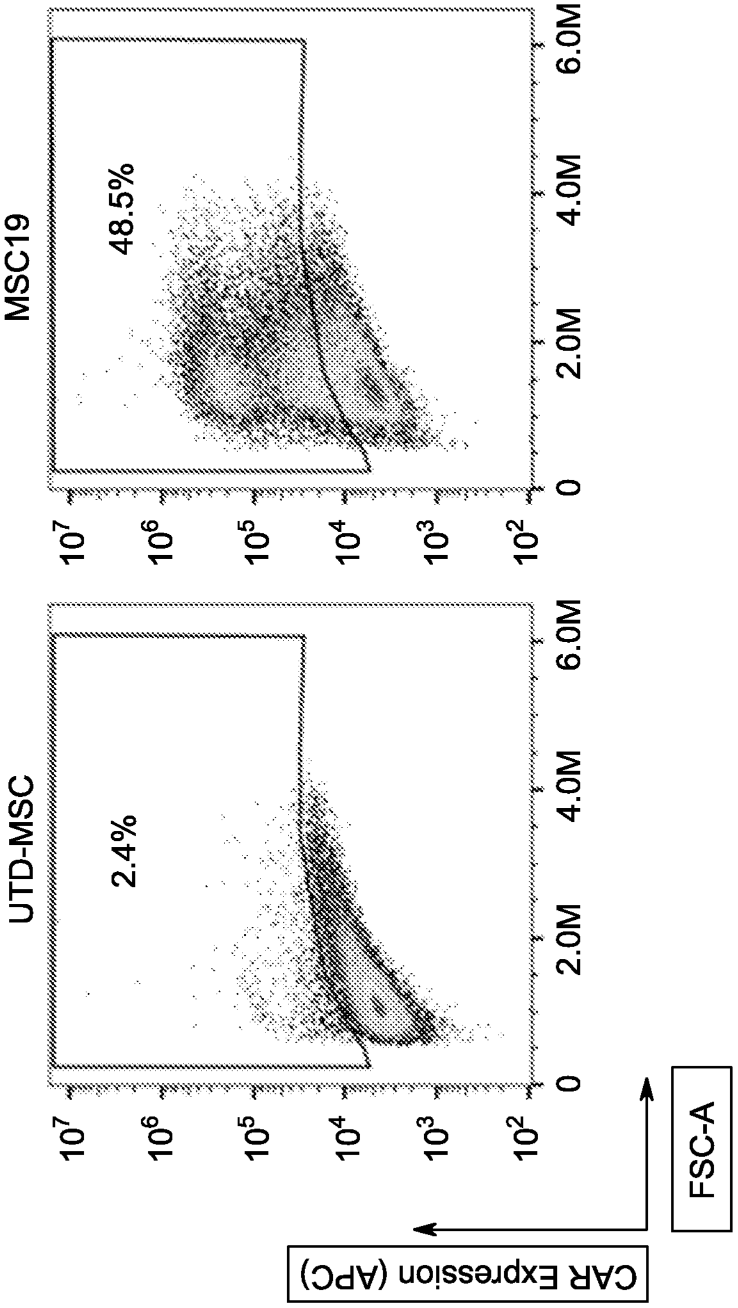
FIG. 3. Stability of MSC-CAR19 expression after passage 10+.

Adipose derived-mesenchymal stem cells (100-Biotr-0024) were taken from culture after consecutive 10+ passages and probed for surface expression of CAR19. As displayed above, 48.5% of the CAR19 transduced culture retained CAR19 expression, a loss of 20% since transduction (FIG. 3).

Figure 4A:
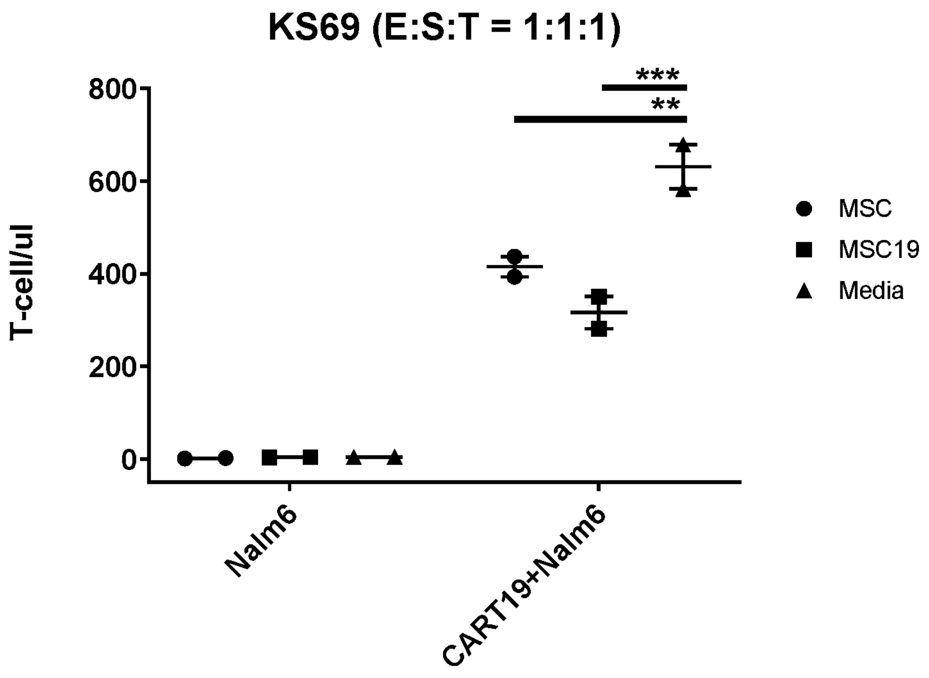
FIGS. 4A-4B. A. MSC suppression of antigen specific CAR-T cell proliferation. B. MSC suppression of antigen specific CAR-T cell proliferation.
Figure 4B:
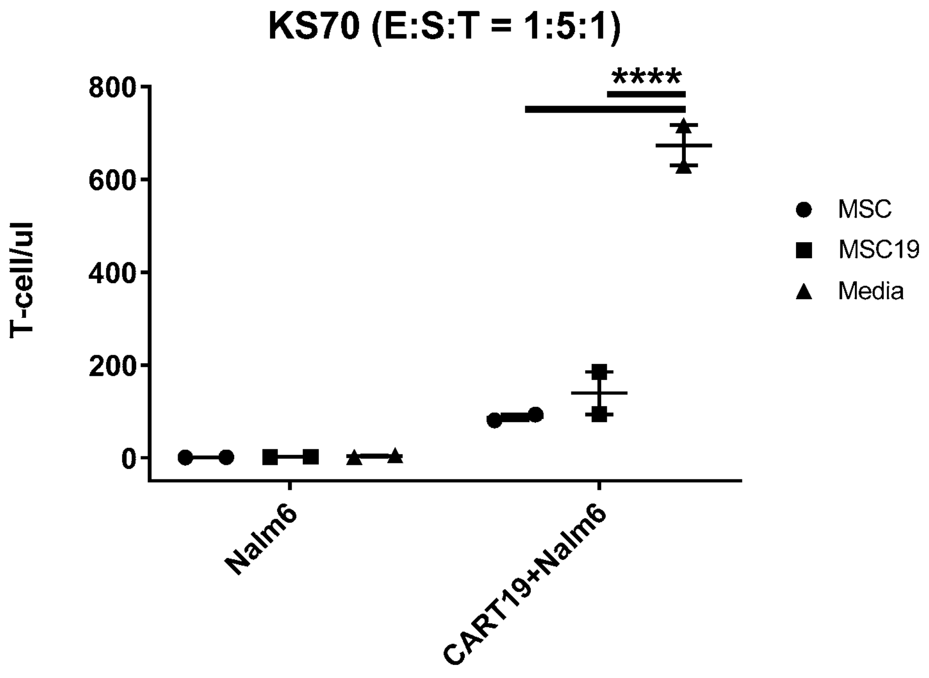

Adipose derived-mesenchymal stem cells (100-Biotr-0024), when engineered to express CAR19, suppress CART-cell proliferation. T-Cell proliferation can be further suppressed by increasing the ratio of MSC:T-cell (FIGS. 4A and 4B).

Figure 5:
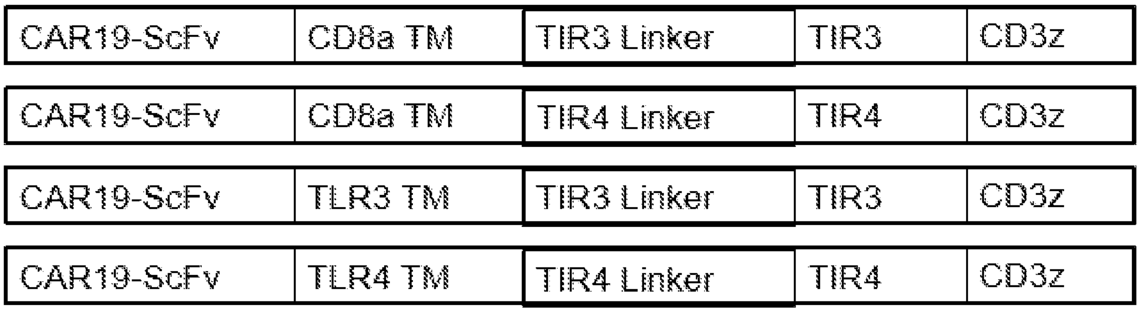
FIG. 5. Schematic representations of nucleic acid constructs encoding exemplary CAR19s.

Designer constructs for the enhancement of MSC trafficking, persistence, and efficacy for immunomodulation are shown in FIG. 5.

Example 2: Engineered CAR-MSCs for Immunomodulation of Epithelial Tissues

MSCs that can target epithelial tissues were designed by engineering MSCs to express CARs targeting ECAD (MSC-CAR-ECADs).

A nucleic acid sequence (SEQ ID NO:1) encoding an exemplary CAR-ECAD is shown in FIG. 12A. An amino acid sequence (SEQ ID NO:2) of an exemplary CAR-ECAD is shown in FIG. 12B.

MSCs were transduced with E-cadherin CAR lentivirus (VSV-G pseudo-typed) to generate MSC-CAR-ECAD. A second generation CAR construct including a TLR3 signaling domain and/or a TLR4 signaling domain was used.

Figure 6:
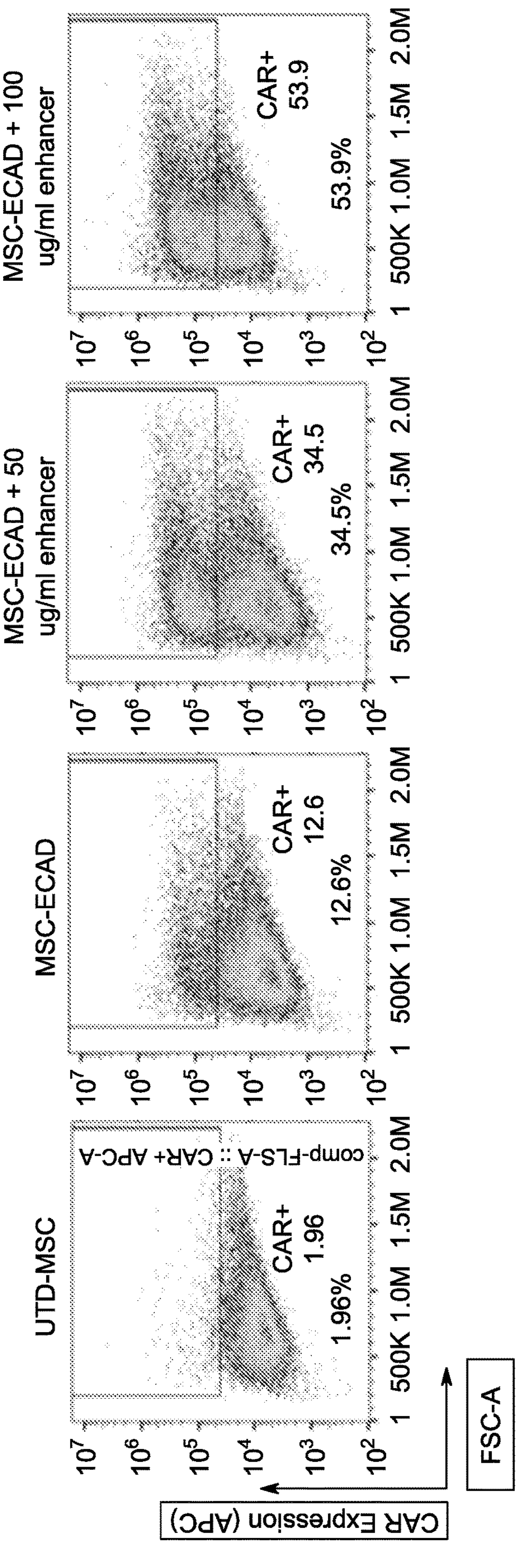
FIG. 6. MSC expression of CAR-ECAD.

Adipose derived-mesenchymal stem cells (100-Biotr-0024) were passaged into 4 wells of a 6 well plate (100 k each). One group was left as a, untransduced (UTD) negative control. The second well was transduced with our GMP-grade, pan-VSV, ECAD recognizing-Chimeric Antigen Receptor (CAR-ECAD) lentivirus (~MOI 3). The third group was transduced with the same MOI and lentivirus in addition to 50 μg/ml Enhancer PLUS. The fourth group is identical to the third but 100 μg/ml of enhancer PLUS was used. The efficiency of transduction increased in an enhancer PLUS concentration dependent manner (FIG. 6).

WT-MSCs significantly reduced the proliferative capacity of stimulated T-cells but not stimulated CART cells. When T cells were stimulated with nonspecific stimulus (PMA/IONO) and cultures in the presence of MSCs, proliferation was significantly inhibited. However, WT-MSCs were ineffective in suppressing CAR specific T-cell proliferation when activated through their antigen. When CART19 are activated through the CAR (through a co-culture with CD19+ cell line NALM6), in the presence of MSCs, antigen specific proliferation was not inhibited (FIG. 5 and FIG. 6). Thus, adipose derived-mesenchymal stem cells suppress naïve and CD3×CD28 T-cell proliferation but do not suppress CART-cell proliferation.

Figure 7:
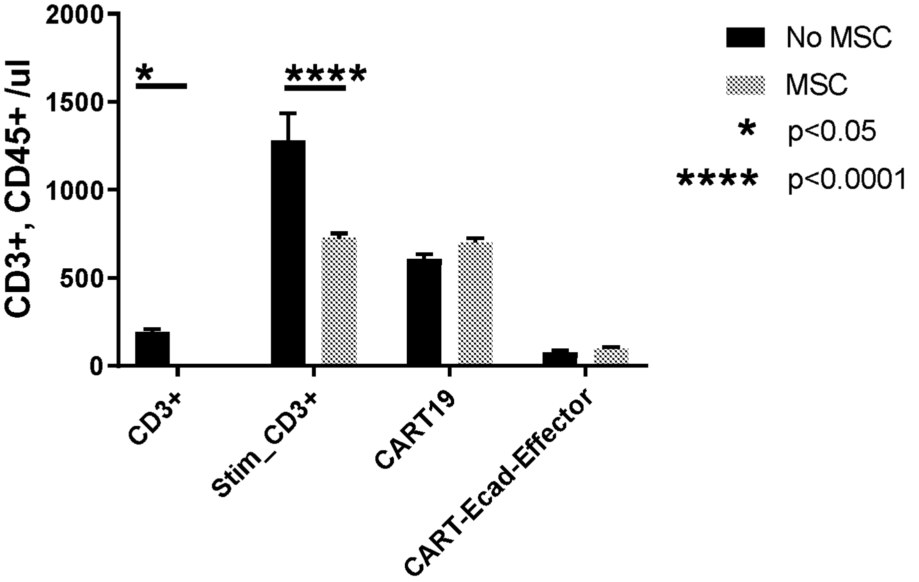
FIG. 7. MSCs suppress T cell proliferation but not CAR-T cell proliferation.
Figure 8:
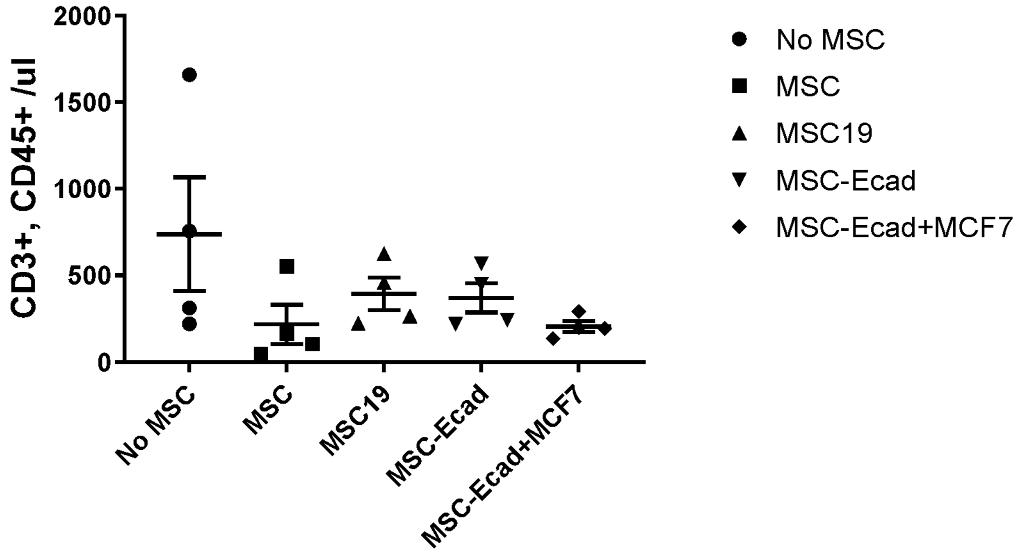
FIG. 8. MSC-CAR mediated suppression of T-cell proliferation.
Figure 9A:
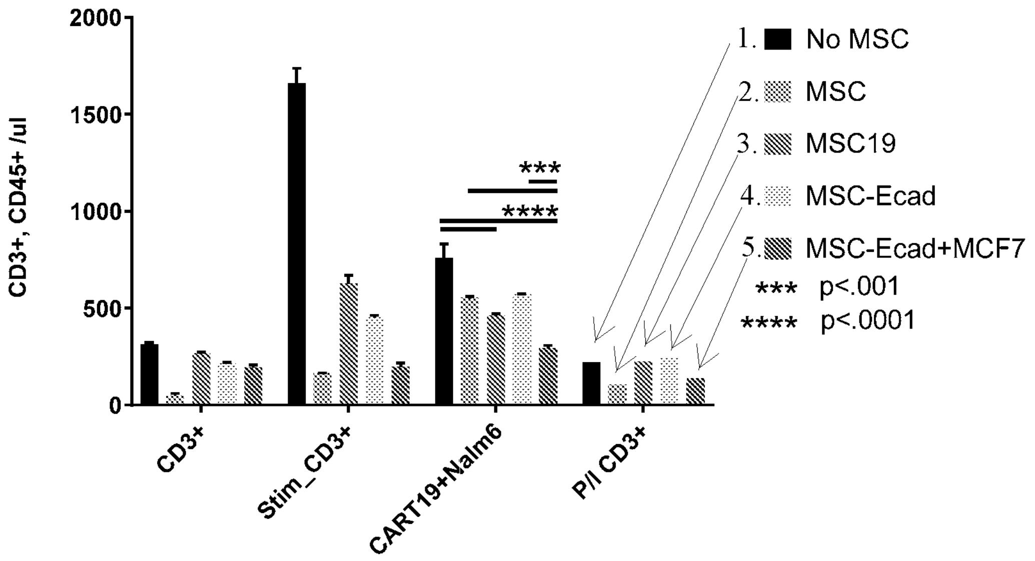
FIGS. 9A-9B. A. MSC-CAR mediated suppression of activated T-cell and CART-cells. B. Suppression of antigen-specific CAR-T proliferation by CART19+NALM6.
Figure 9B:
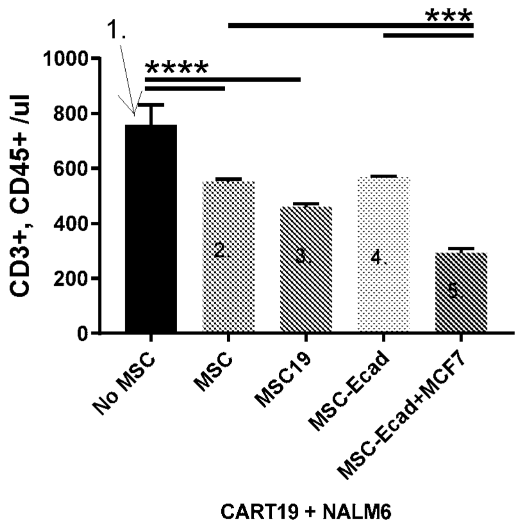
Figure 10A:
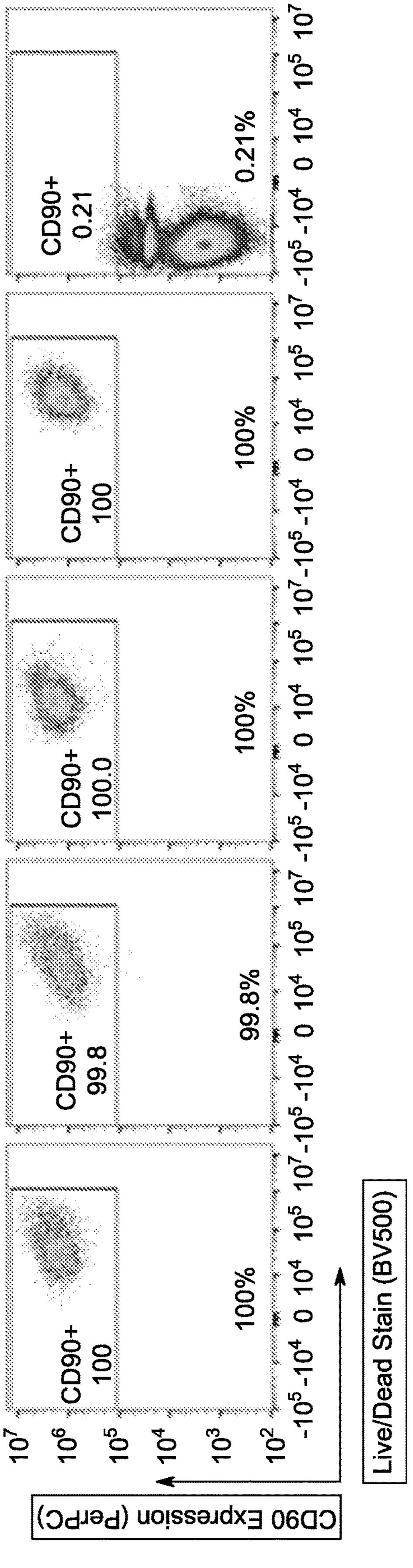
FIGS. 10A-10G. Stemness retention of MSCs. A. Flow cytometry analysis of CD90. B. Flow cytometry analysis of CD105. C. Flow cytometry analysis of CD73. D. Flow cytometry analysis of CD34. E. Flow cytometry analysis of CD45. F. Flow cytometry analysis of HLA-DR. G. Flow cytometry analysis of CD14.
Figure 10B:
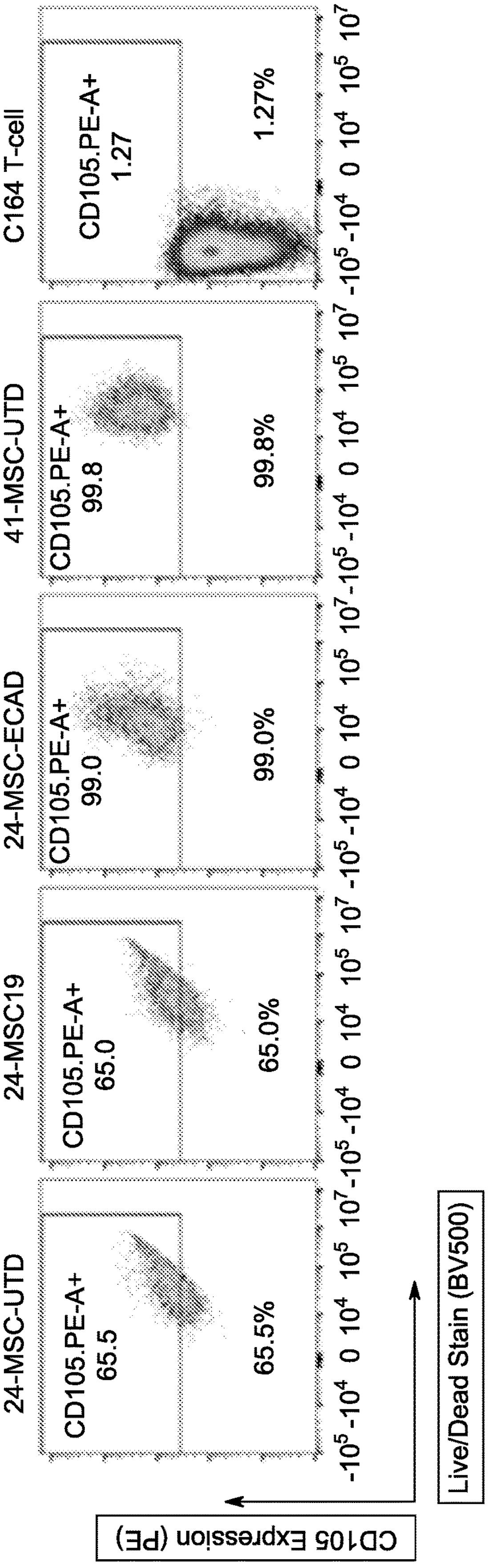
Figure 10C:
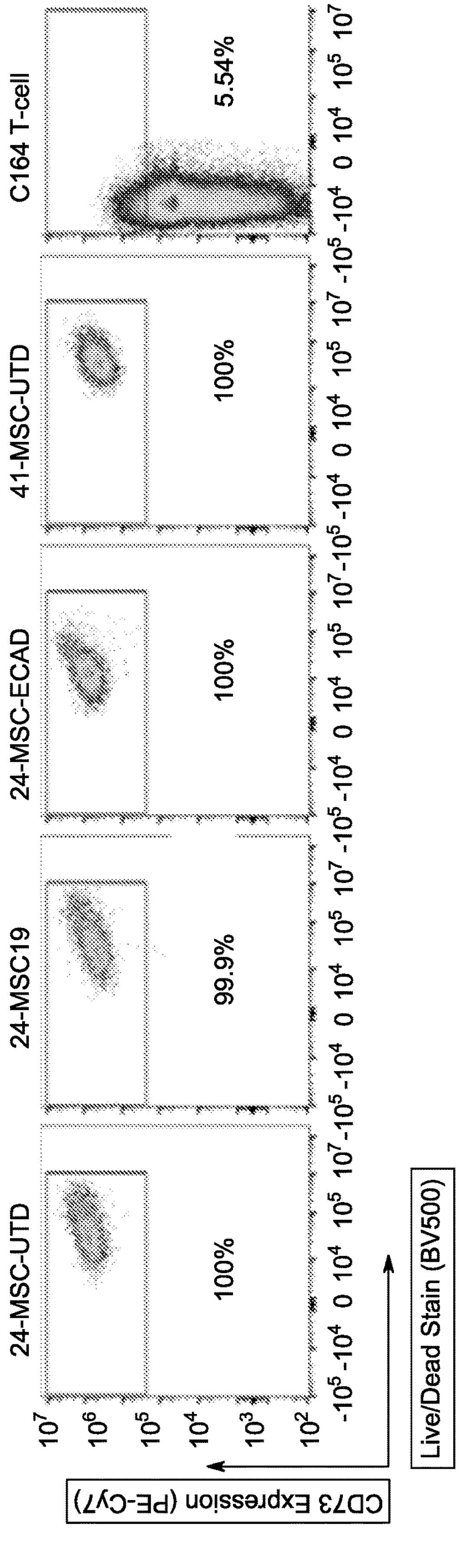
Figure 10D:
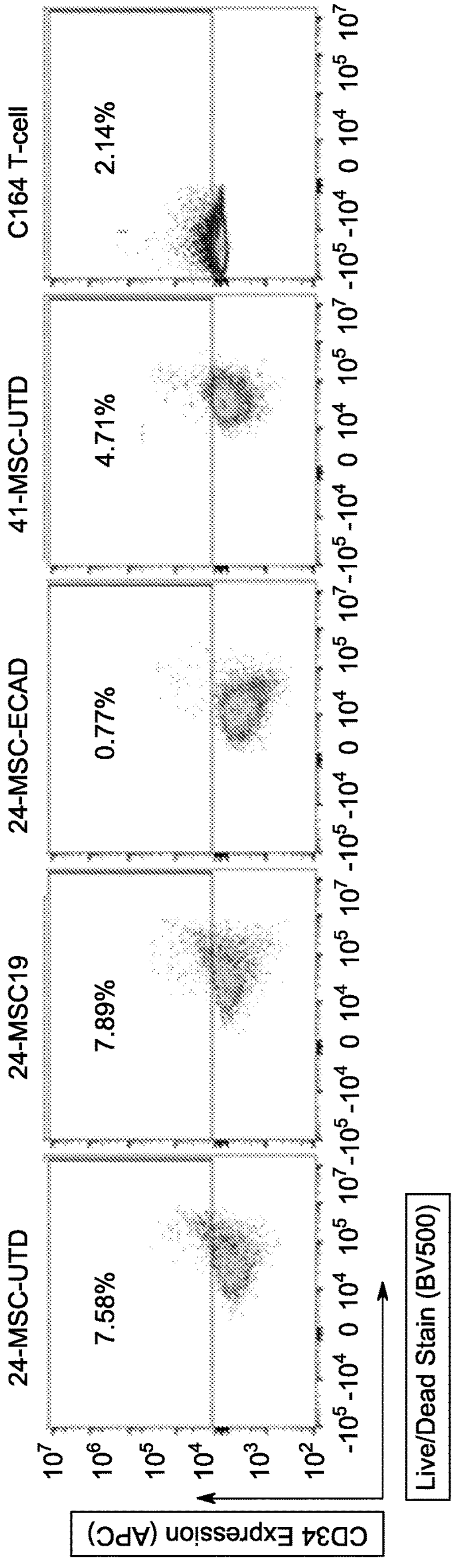
Figure 10E:
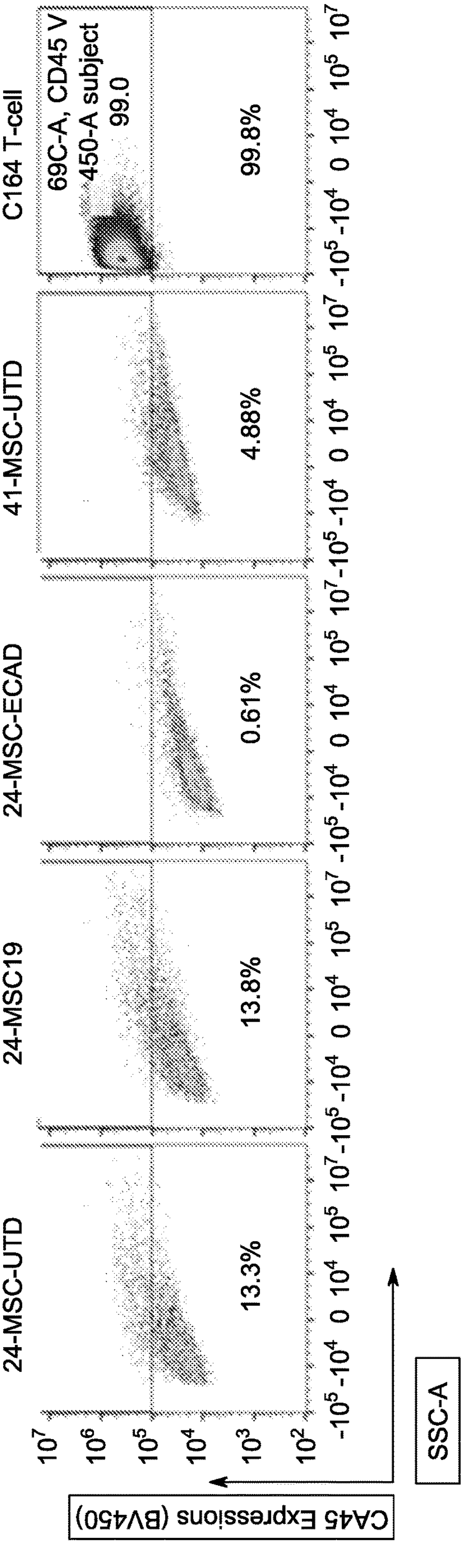
Figure 10F:
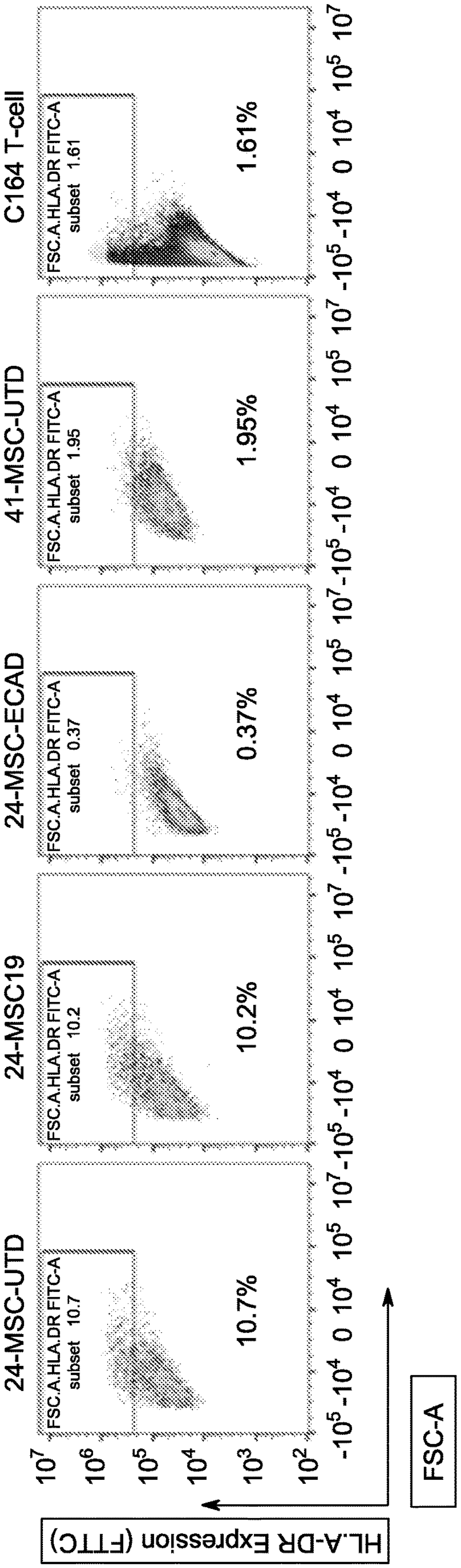
Figure 10G:
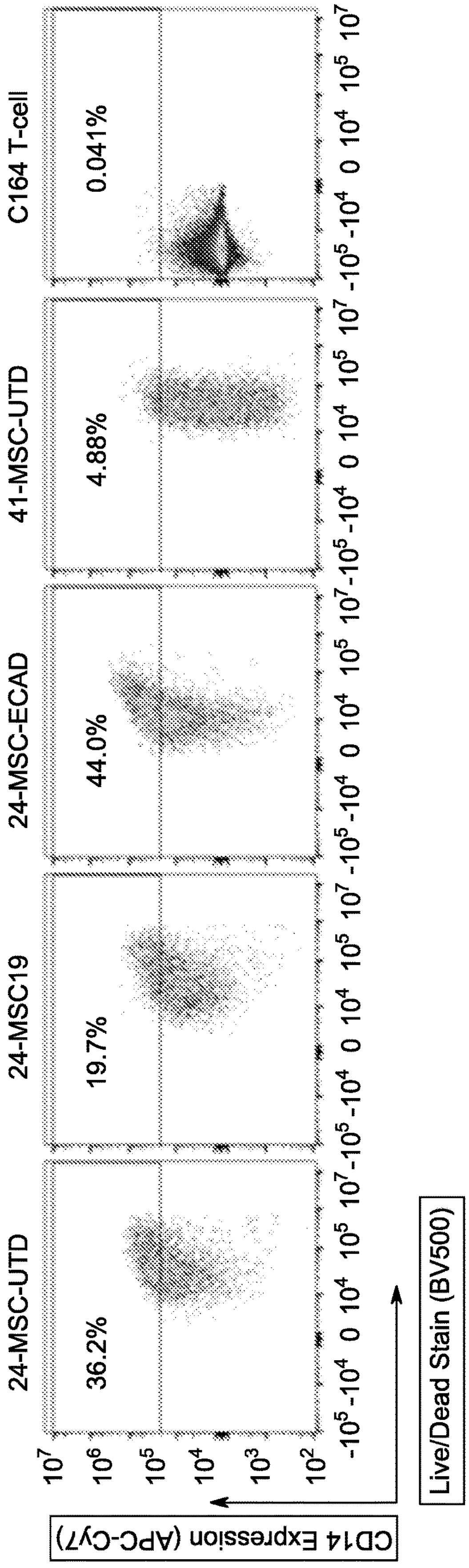

MSC-CAR cells exhibit more profound immunosuppressive effect when stimulated through the CAR, compared to wild type MSC or unstimulated MSCs. CD3+ T cells, stimulated CD3+ cells, or stimulated CART19 (stimulated through the CAR) were cultured in media alone, with wild type MSC, with MSCCAR19, with MSC-CAR-ECAD, or with MSC-CAR-ECAD with MCF-7 (ECAD expressing cell line). All conditions with MSC inhibited T cell proliferation. Stimulated MSC-CAR inhibited CAR-T cell proliferation more profoundly in the presence of their target antigens. MSC-CAR-ECAD inhibition of CART19 proliferation was more profound in the presence of MFC-7 cell line, compared to MSC-CAR-ECAD inhibition of CART19 proliferation in the absence of MCF-7 cell line (FIGS. 7A and 7B). Thus, adipose derived-mesenchymal stem cells, when engineered to express CAR-ECAD, suppress CART-cell proliferation in an antigen dependent manner.

Flow cytometry was used to confirm the MSC phenotype (FIGS. 10A, 10B, 10C, and 10D). MSCs that maintain stemness should be $CD90^{+}$, $CD105^{+}$, $CD73^{+}$, $CD34^{-}$, $CD45^{-}$, $CD19^{-}$, $CD14^{-}$, $HLA\text{-}DR^{-}$.

Example 3: Engineered CAR-MSCs for Immunomodulation of the Central Nervous System MSCs that can target neural tissues were designed by engineering MSCs to express CARs targeting MOG (MSC-CAR-MOGs).

Lentiviruses encoding CAR-MOGs were transduced into MSCs. Expression of CAR-MOGs in the MSCs was determined by comparison with an untransduced (UTD) MSC population. Transduction was performed with or without protamine sulfate solution (~70 μg/ml) for enhancement of transduction efficiency. CAR-MOGs were expressed on the surface of ~78% mesenchymal stem cells with specificity towards MOG (FIG. 11).

Nucleic acid sequences (SEQ ID NO:3, SEQ ID NO:5, and SEQ ID NO:7) encoding an exemplary CAR-MOG are shown in FIGS. 13A, 13C, and 13E. Amino acid sequences (SEQ ID NO:4, SEQ ID NO:6, and SEQ ID NO:8) of exemplary CAR-MOGs are shown in FIGS. 13B, 13D, and 13F.

Example 4: Engineered CAR-MSCs for Immunomodulation of Cardiac Tissue

MSCs that can target cardiac tissues were designed by engineering MSCs to express CARs targeting HER2 (MSC-CAR-HER2s).

A nucleic acid sequence (SEQ ID NO:9) encoding an exemplary CAR-HER2 is shown in FIG. 14A. An amino acid sequence (SEQ ID NO:10) of an exemplary CAR-HER2 is shown in FIG. 14B.

Example 5: Transduction Efficiency of MSC-CAR19

Lentivirus transduction of MSCs with CAR19 vectors result in a transduction efficiency of 60% compared to untransduced MSCs (FIG. 15A).

Example 6: MSCs Retain their Sternness after Lentiviral Transduction with a CAR Vector Flow cytometric analysis of MSC-CAR19, two days after their transduction with the CAR lentivirus, indicate their sternness, which was comparable to untransduced MSCs (MSC-UTD). MSC-CAR19 continued to express CD105, CD90, CD73, and lack expression of CD34, CD45, HLA-DR, and CD14 (FIG. 15B).

Example 7: MSC-CAR19 Inhibits T Cell Proliferation in the Presence of $CD19^{+}$ Targets, Indicating Antigen Specific Stimulation of MSC-CAR19

T cells were stimulated with CD3/CD28 beads, and 24 hours later were co-cultured with untransduced MSC (MSC- UTD), or MSC-CAR19 (CD28 containing CAR19, K122), or MSC-CAR19 (CD137 containing CAR19, K002), or with no MSCs. The K002 CAR, which targets CD19, was designed to have single chain antibody targeting CD19, derived from FMC63, followed by a CD8 hinge, followed by a CD8 transmembrane domain, followed by a 4-1BB (CD137) signaling domain. The amino acid sequence of K002 was as follows: MALPVTALLLPLALLLHAARPDIQMTQTTSSLSASLGDRVTISCRASQDISKYLN WYQQKPDGTVKLLIYHTSRLHSGVPSRFSGSGSGTDYSLTISNLEQEDIATYFCQQ GNTLPYTFGGGTKLEITGGGGSGGGGSGGGGSEVKLQESGPGLVAPSQSLSVTCT VSGVSLPDYGVSWIRQPPRKGLEWLGVIWGSETTYYNSALKSRLTIIKDNSKSQV FLKMNSLQTDDTAIYYCAKHYYYGGSYAMDYWGQGTSVTVSSTTTPAPRPPTP APTIASQPLSLRPEACRPAAGGAVHTRGLDFACDIYIWAPLAGTCGVLLLSLVITL YCKRGRKKLLYIFKQPFMRPVQTTQEEDGCSCRFPEEEEGGCELRVKFSRSADAP AYKQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR (SEQ ID NO:63). The K122 CAR, which targets CD19, was designed to have single chain antibody targeting CD19, derived from FMC63, followed by a CD28 hinge, followed by a CD28 transmembrane domain, followed by a CD28 signaling domain. The amino acid sequence of K122 was as follows:

```
                                           (SEQ ID NO: 64)
MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITGGGGSGGGGSGGGGSEVKLQES

GPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAM

DYWGQGTSVTVSSLEPKSCDKTHTCPPCPDPKFWVLVVVGGVLACYSLLV

TVAFIIFWVRSKRSRLLHSDYMNMTPRRPGPTRKHYQPYAPPRDFAAYRS

RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.
```

Figure 16:
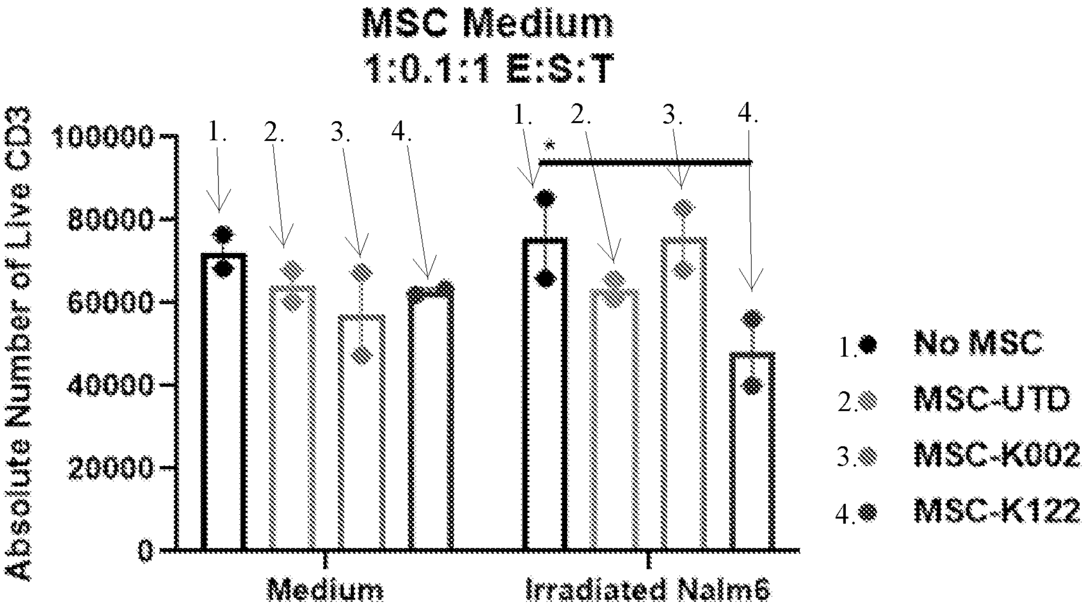
FIG. 16 is a graph plotting the absolute number of live CD3 cells after 5 days of stimulation with CD3/CD28 beads, following co-culture with untransduced MSC (MSC-UTD), or MSC-CAR19 (CD28 containing CAR19, K122), or MSC-CAR19 (CD137 containing CAR19, K002), or with no MSCs. T cells are activated with CD3/CD28 beads and then co-cultured with different MSC conditions either in medium alone, or in the presence of irradiated $CD19^+$ cells as a strategy to stimulate MSC-CAR19 through the CAR. Proliferation of CD3 is inhibited in the presence of MSC-CAR19 (containing CD28 signaling domain), but not in the presence of MSC-CAR19 (containing CD137 signaling domain), or un-transduced MSCs. T cells, MSCs, and NALM6 cells were cultured at ratio of 1:0.1:1 E (T cells (effectors):MSCs (suppressors):T (tumor). This demonstrates that MSC-CAR cells are able to suppress T cell proliferation when MSC-CAR cells contain a CD28 signaling domain and when the MSCs are activated through the CAR upon antigen specific stimulation. * represents p value≤0.05.

T cells and MSCs were co-cultured either in medium alone, or in the presence of irradiated $CD19^+$ cells as a strategy to stimulate MSC-CAR19 through the CAR. Proliferation of CD3 was inhibited in the presence of MSC-CAR19 (containing CD28 signaling domain), but not in the presence of MSC-CAR19 (containing CD137 signaling domain), or un-transduced MSCs, and in the presence of irradiated $CD19^+$ cells, but not in the absence of $CD19^+$ cells (FIG. 16). T cells, MSCs, and NALM6 cells were cultured at ratio of 1:0.1:1 E (T cells (effectors):MSCs (suppressors):T (tumor). These results indicate that MSC-CARs were able to suppress T cell proliferation upon antigen specific stimulation, when the CAR contained a CD28 signaling domain Example 8: Incorporation of CD28 Signaling Enhances the Proliferation of MSC-CAR19

MSC-CAR19 cells with different stimulatory domains were co-cultured with or without the irradiated $CD19^+$ cell line NALM6 and MSC growth was monitored. The incorporation of CD28 signaling domain resulted in enhanced proliferation of MSC-CAR19 compared to MSC-UTD or MSC-CAR19 that incorporated CD137 stimulatory domain. On the other hand, the proliferation of MSC-CAR19 cells that incorporate TLR4 signaling was suppressed. These results demonstrate that CD28 and TLR4 signaling are involved in proliferation of MSC-CAR upon antigen specific stimulation. The K142 CAR, which targets CD19, was designed to have single chain antibody targeting CD19, derived from FMC63, followed by a CD8 hinge, followed by a TLR4 transmembrane domain, followed by a TLR4 signaling domain. The amino acid sequence of K142 was as follows:

```
                                           (SEQ ID NO: 65)
MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITGGGGSGGGGSGGGGSEVKLQES

GPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAM

DYWGQGTSVTVSSTTTPAPRPPTPAPTIASQPLSLRPEACRPAAGGAVHT

RGLDFACDIGVSVLSVLVVSVVAVLVYKFYFHLMLLAGCIKYGRGENIYD

AFVIYSSQDEDWVRNELVKNLEEGVPPFQLCLHYRDFIPGVAIAANIIHE

GFHKSRKVIVVVSQHFIQSRWCIFEYEIAQTWQFLSSRAGIIFIVLQKVE

KTLLRQQVELYRLLSRNTYLEWEDSVLGRHIFWRRLRKALLDGKSWNPEG

TVGTGCNWQEATSI.
```

Figure 17:
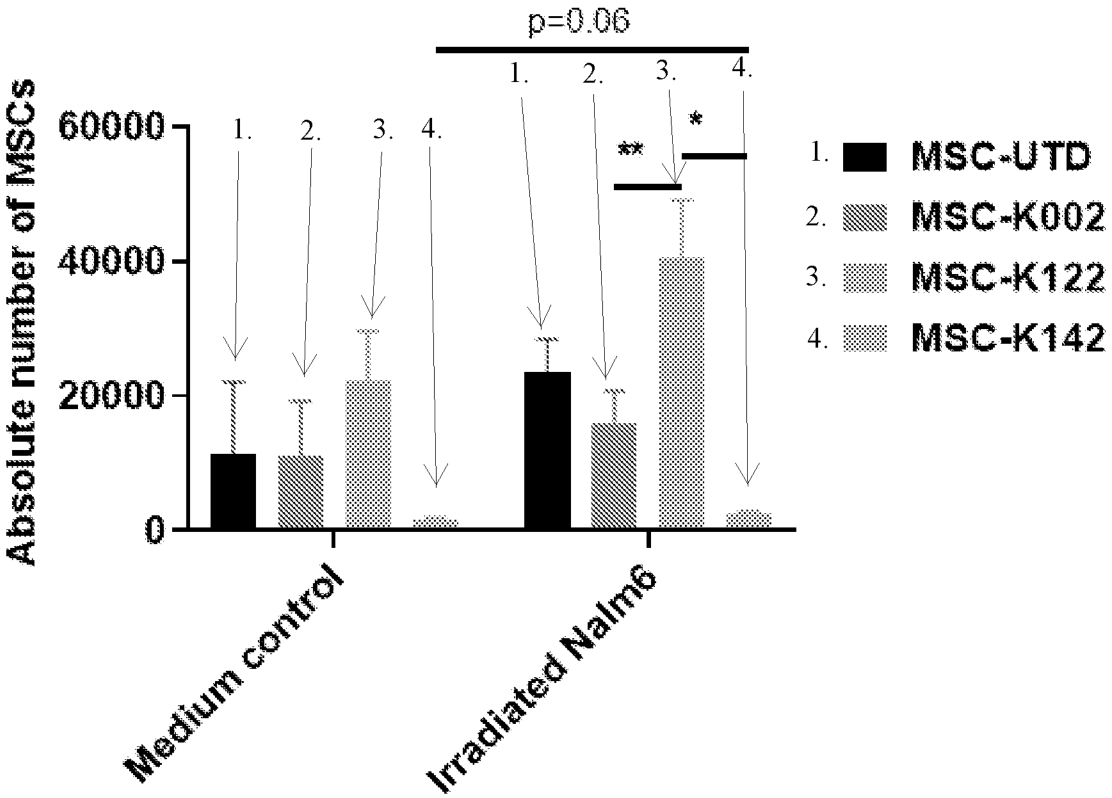
FIG. 17 is a graph plotting the absolute number of live MSC cells after 5 days of co-culture of untransduced MSC (MSC-UTD), or MSC-CAR19 (TLR4 containing CAR19, K142), or MSC-CAR19 (CD137 containing CAR19, K002), or MSC-CAR19 (CD28 containing CAR19, K122), with or without the irradiated $CD19^+$ NALM6 cells. Proliferation of MSC-CAR19 containing CD28 is enhanced in the presence but not in the absence of irradiated $CD19^+$ cells, suggesting antigen specific stimulation of MSC-CAR19 and signaling through CD28. Similarly, proliferation of MSC-CAR19 containing TLR4 is decreased in the presence but not in the absence of irradiated $CD19^+$ cells, suggesting antigen specific stimulation of MSC-CAR19 and signaling through CD28. * represents P≤0.05; ** represents P≤0.01.

T cells and MSCs were co-cultured either in medium alone, or in the presence of irradiated $CD19^+$ cells as a strategy to stimulate MSC-CAR19 through the CAR. Proliferation of CD3 was inhibited in the presence of MSC-CAR19 (containing TLR4 signaling domain), but not in the presence of MSC-CAR19 (containing CD137 signaling domain), or un-transduced MSCs, and in the presence of irradiated $CD19^+$ cells, but not in the absence of $CD19^+$ cells (FIG. 17). T cells, MSCs, and NALM6 cells were cultured at ratio of 1:0.1:1 E (T cells (effectors):MSCs (suppressors):T (tumor). These results indicate that MSC-CARs were able to suppress T cell proliferation upon antigen specific stimulation, when the CAR contained TLR4 stimulatory molecule.

Example 9: MSC-CAR19 Inhibits T Cell Proliferation in the Presence of $CD19^+$ Targets, Indicating Antigen Specific Stimulation of MSC-CAR19

Figure 18:
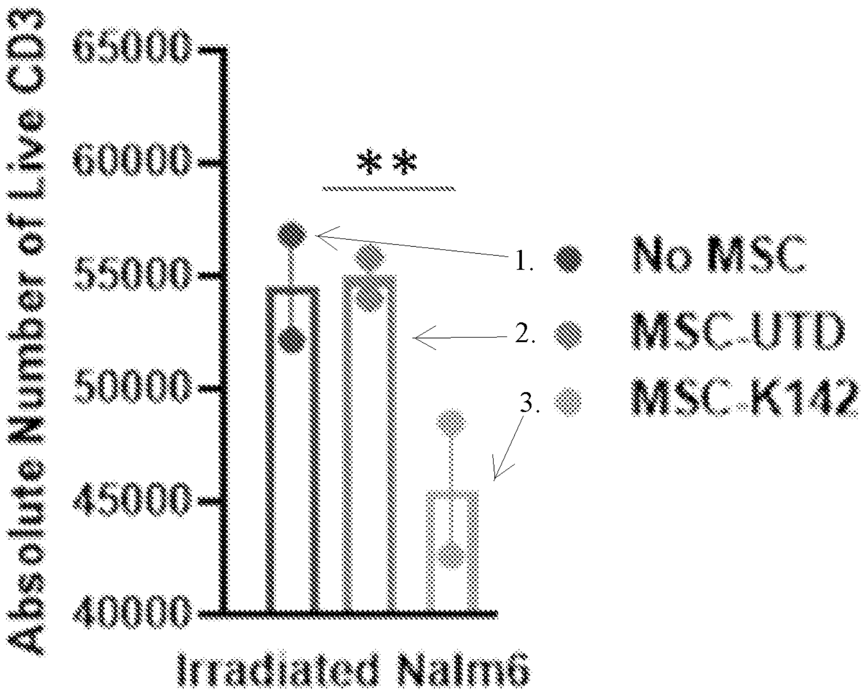
FIG. 18 is a graph plotting the absolute number of live CD3 cells after 5 days of stimulation with CD3/CD28 beads, following co-culture with untransduced MSC (MSC-UTD), or MSC-CAR19 (TLR4 containing CAR19, K142), or with no MSCs. T cells are activated with CD3/CD28 beads and then co-cultured with different MSC conditions either in medium alone, or in the presence of irradiated $CD19^+$ cells as a strategy to stimulate MSC-CAR19 through the CAR. Proliferation of CD3 is inhibited in the presence of MSC-CAR19 (containing TLR4 signaling domain, K142), but not in the presence of un-transduced MSCs. T cells, MSCs, and NALM6 cells were cultured at ratio of 1:0.1:1 E (T cells (effectors):MSCs (suppressors):T (tumor). This demonstrates that MSC-CAR cells are able to suppress T cell proliferation when MSC-CAR cells contain a TLR4 signaling domain and when the MSCs are activated through the CAR upon antigen specific stimulation. ** represents P≤0.01.

T cells were stimulated with CD3/CD28 beads, and 24 hours later were co-cultured with untransduced MSC (MSC-UTD), or MSC-CAR19 (TLR4 containing CAR19, K142), or with no MSCs, and in the presence of irradiated $CD19^+$ cells as a strategy to stimulate MSC-CAR19 through the CAR. Proliferation of CD3 was inhibited in the presence of MSC-CAR19 (containing TLR4 signaling domain), but not in the presence of un-transduced MSCs (FIG. 18). T cells, MSCs, and NALM6 cells were cultured at ratio of 1:0.1:1 E (T cells (effectors):MSCs (suppressors):T (tumor). These results indicate that MSC-CARs were able to suppress T cell proliferation upon antigen specific stimulation, when the CAR contained TLR4 stimulatory molecule.

Example 10: Antigen Specific Stimulation of MSC-CARs Containing CD28 Signaling Molecule Enhances their Proliferation Un-transduced MSC (MSC-UTD), MSC-CAR19 (CD28 containing CAR19, K122), MSC-CAR19 (CD137 containing CAR19, K002), or MSC-CAR19 (TLR4 containing CAR19, K142) were co-cultured with the irradiated CD19$^+$ cell line NALM6 at 1:1 ratio. The absolute number of MSCs was counted by flow cytometry using absolute counts on days 3 and 5. Antigen specific stimulation of MSC-CAR19 (containing CD28) led to increased MSC proliferation (FIGS. 19A and 19B). These results demonstrate that CD28 signaling via a CAR contributes to MSC-CAR growth.

Figure 20:
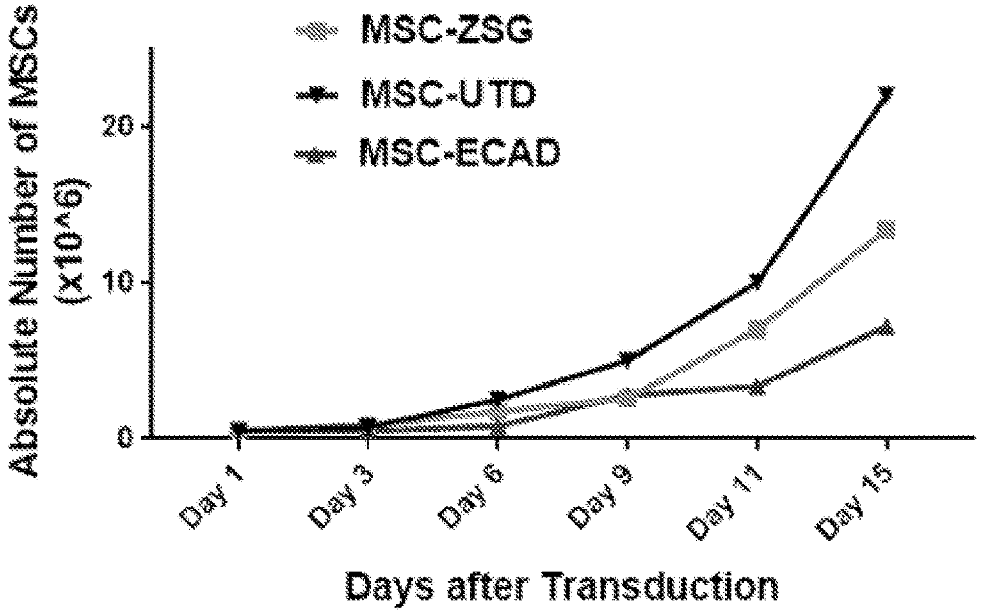
FIG. 20 is a graph plotting the absolute number of MSCs in cultures following their transduction with CAR-MSC-E-cadherin or with control GFP (MSC-ZSG).

Example 11: Lentiviral Transduction of MSCs with CAR Results in Reduced Proliferation MSCs were transduced with CAR lentiviruses or GFP lentiviruses on day 1 and followed in culture for 15 days. Transduction with CAR-Ecadherin resulted in reduced expansion compared to untransduced MSCs or MSCs transduced with GFP lentivirus (FIG. 20).

Example 12: MSC-CAR Exert their Suppressive Abilities Through Cell to Cell Contact Mediated and Soluble Factor Mediated Mechanisms T cells were first stimulated with CD3/CD28 beads at 1:3 (T cell to bead) ratio. 24 hours later, they were cultured with MSCs and CD19$^+$ cells (to stimulate MSC-CARs), either in direct contact or in transwell experiments. A co-culture with MSC-CAR19 (containing CD28 stimulatory domain) with activated T cells, and CD19$^+$ cells led to inhibition of T cell proliferation both when cells were in direct contact or not in direct contact in a trans-well experiment (FIG. 21). These results demonstrate that MSC-CAR exert their suppressive functions through both direct, cell to cell contact and through secretion of soluble inhibitory factors/cytokines.

Example 13: MSC-CAR Suppress T Cell Proliferation Upon Antigen Specific Stimulation T cells were first stimulated with CD3/CD28 beads at a 1:3 ratio. 24 hours later, T cells were cultured with untransduced MSCs, or MSC-CAR19 (CD28 containing CAR19, K122) at higher E:S:T ratio with NALM6, or T cells were cultured with NALM6 alone as a control for allogeneic effect. The addition of irradiated CD19$^+$ cells was to stimulate MSC-CAR19 through the CAR. Proliferation of CD3 was inhibited in the presence of MSC-CAR19 (containing CD28 signaling domain), but not in the presence of untransduced MSCs (FIG. 22). T cells, MSCs, and NALM6 cells were cultured at ratio of 1:1:1 E (T cells (effectors): MSCs (suppressors):T (tumor).

Example 14: MSC-CAR-E-Cadherin Cells Suppress T Cell Proliferation Upon Antigen Specific Stimulation at Low E:T Ratios T cells were first stimulated with CD3/CD28 beads at 1:3 ratio. 24 hours later, activated T cells were cultured with untransduced MSC (MSC-UTD, FIG. 23A), or MSC-CAR-E-cadherin (CD28 containing CAR-E-cadherin, FIG. 23B), in the presence or absence of the E-cadherin$^+$ cell line MCF-7, at different effector:suppressor (E:S) ratios. The co-culture of MSC-CAR-E-cadherin with T cells resulted in suppression of their antigen specific proliferation in the presence of the E-cadherin$^+$ cell line MCF-7, at low effector: suppressor ratios. These results demonstrate that antigen specific stimulation of MSC-CAR-E-cadherin containing a CD28 signaling domain results in enhanced suppressive ability of T cells.

Example 15: Designing CAR Constructs Targeting E-Cadherin Using scFvs

Four scFvs, clones 5, 6, 7, and 14, were identified as having binding affinity for human E-CAD. Three of these (clones 6, 7, and 14) were used to design CARs targeting E-CAD.

The K128-CAR, which targets human E-CAD, was designed to have a single chain antibody derived from clone 14, followed by a CD28 hinge, followed by a CD28 transmembrane domain, followed by a CD28 signaling domain. The amino acid sequence of K128-CAR was as follows:
MALPVTALLLPLALLLHAARPEVQLVQSGG-
GLVKPGGS-LRLSCAASGFTFSDYYMSWIRQAPGK-
GLEWVSYISSSGSTIYYADSVKGRFTISRD NAKNS-
LYLQMNSLRAEDTAVYYCARAQRQWGAFDYW-
GQGTLVTVSSEGKSSG SGSESKASSSELTQD-
PAVSVALGQTVRITCQGDSLRSYYAS-
WYQQKPGQAPVLVI YGKNNRPSGIPDRFSGSSSGN-
TASLTITGAQAEDEADYYCNSRDSSGNPVFGGGT
KLTVLGLEPKSCDKTHTCPPCPDPKFWVLVVVGGV-
LACYSLLVTVAFIIFWVRSK RSRLLHSDYMNMT-
PRRPGPTRKHYQPYAPPRDFAAYRSRVKFSRSADA-
PAYKQG
QNQLYNELNLGRREEYDVLDKRR-
GRDPEMGGKPRRKNPQEGLYNELQKDKMA EAYSEI-
GMKGERRRGKGHDGLYQGLSTATKDTY-
DALHMQALPPR (SEQ ID NO:66). The K129-CAR, which targets human E-CAD, was designed to have a single chain antibody derived from clone 6, followed by a CD28 hinge, followed by a CD28 transmembrane domain, followed by a CD28 signaling domain. The amino acid sequence of K129-CAR was as follows: MALPVT-ALLL-
PLALLLHAARPEVQLVQSGGGLVQPGGSLRLS-
CAASGFTFSSYSMNWVRQ APGKGLEWVSYIS-
SSSSTIYYVDSVKGRFTISRDNAKNSLYLQMDSLRAE-
DTAVY
YCARG-
GRVLVGALFDYWGQGTLVTVSSEGKSSGSGS-
ESKASLPVLTQPPSASGTP GQRVTISCSGSSSNIG-
SNYVYWYQQLPGTAPKLLIYRNNQRPSGVPD-
RFSGSKSGT SASLAISGLQSEDEADYYCASWDTSL-
RAWVFGGGTKLTVLGLEPKSCDKTHTCP
PCPDPKFWVLVVVGGVLACYSLLVTVAFIIFWVR-
SKRSRLLHSDYMNMTPRRPG PTRKHYQPYAPPRD-
FAAYRSRVKFSRSADAPAYKQGQNQLYNELNLGR-
REEYD
VLDKRRGRDPEMGGKPRRKNPQEGLYNELQKDK-
MAEAYSEIGMKGERRRGKG HDGLYQGLSTATKDTY-
DALHMQALPPR (SEQ ID NO:67). The K130-CAR, which targets human E-CAD, was designed to have a single chain antibody derived from clone 7, followed by a CD28 hinge, followed by a CD28 transmembrane domain, followed by a CD28 signaling domain. The amino acid sequence of K130-CAR was as follows:

(SEQ ID NO: 70)

MALPVTALLLPLALLLHAARPE-VQLVESGTDVKKPGASVTVSCKASGYT

FTAYYIHWVRQAPGQGLEWMGWINPYSGASNYAQKFLGRVTMTRDTSTNT

VYMQLSSLRASDTAMYYCAKAACGSNGCYMREFDYWGQGTLVTVSSSEGK

SSGSGSESKASDIVMTQSPLSLPVTLGQPASISCRSSQSLVYSDGNTYLN

WFQQRPGQSPRRLIYKVSNRDSGVPDRFSGSGSGTDFTLKISRVEAEDVG

IYYCMQGTYWPGAFGQGTKVDIKLEPKSCDKTHTCPPCPDPKFWVLVVVG

GVLACYSLLVTVAFIIFWVRSKRSRLLHSDYMNMTPRRPGPTRKHYQPYA

PPRDFAAYRSRVKFSRSADAPAYKQGQNQLYNELNLGRREEYDVLDKRRG

RDPEMGGKPRRKNPQEGLYNELQKDKMAEAYSEIGMKGERRRGKGHDGLY

QGLSTATKDTYDALHMQALPPR.

T cells transduced with all three constructs exhibited potent killing against the luciferase/human E-cadherin$^+$ MCF-7 cells. T cells transduced with K129-CAR also exhibited potent killing against the luciferase/mouse E-cadherin$^+$ ID8 cells and luciferase/canine E-cadherin$^+$ MCDK cells. These results demonstrate that CARs targeting E-cadherin are functional and can be used as described herein to create MSCs having CARs targeting E-cadherin.

Example 16: Treating or Preventing Colitis

To create a mouse model for xenograft colitis, NSG mice are treated with PBMCs, and their weight is monitored over time. Mice develop colitis within about 30-40 days, associated with weight loss. At this time point, satellite mice are euthanized, and colon tissue is harvested and examined for the infiltration of lymphocytes. Mice are then treated with MSC-UTD, or different MSC-CAR-E-cadherin cells (derived from various scFv clones) and daily weight is monitored. Thirty days later, mice are euthanized, and T cell infiltration into the colon is measured by flow cytometry and compared between mice treated with MSC-UTD and MSC-CAR-E-cadherin to confirm the treatment of colitis.

Example 17: Treating a Human Having Colitis

A human is identified as having colitis and is administered MSC-CAR-E-cadherin cells at a dose of about 1 to about 2 million cells/kg of body weight intravenously or intra-arterially. A dose escalation is included with one dose given every 10 days. Patients are monitored clinically for improvement of symptoms of colitis.

Example 18: Treating Multiple Sclerosis

Using the experimental autoimmune encephalomyelitis (EAE) mouse model, the efficacy of MSC-CAR-MOG is confirmed. After neuro-encephalitis is established, mice are treated with MSC-CAR-MOG or MSC-UTD. Neurological status of the mice is monitored on daily basis, and mice are followed for survival.

Example 19: Treating a Human Having Multiple Sclerosis

A human is identified as having multiple sclerosis and is administered MSC-CAR-MOG at a dose of about 2 to about 10 million cells/kg of body weight. The cells are administered either intravenously or intraventricularly. A dose escalation is included, and multiple doses are administered, for example, every 10 days. Patients are monitored clinically for improvement of symptoms of multiple sclerosis.

Example 20: Treating Immune Mediated Encephalomyelitis

Using the experimental autoimmune encephalomyelitis (EAE) mouse model, the efficacy of MSC-CAR-MOG is confirmed. After neuro-encephalitis is established, mice are treated with MSC-CAR-MOG or MSC-UTD. Neurological status of the mice is monitored on daily basis, and mice are followed for survival.

Example 21: Treating a Human Having Immune Mediated Encephalomyelitis

A human is identified as having immune mediated encephalomyelitis and is administered MSC-CAR-MOG at a dose of about 2 to about 10 million cells/kg of body weight. Cells are administered either intravenously or intraventricularly. A dose escalation is included, and multiple doses are administered, for example, every 10 days. Patients are monitored clinically for improvement of symptoms of immune mediated encephalomyelitis.

Example 22: Treating Myocarditis

Using an experimental mouse myocarditis model, induced by infection with coxsackievirus B3, mice are treated with MSC-UTD or MSC-CAR-HER2. Mice are followed clinically and for survival. At the completion of the experiment, mice are euthanized, and infiltration of T cells into the heart is determined by flow cytometry.

Example 23: Treating a Human Having Myocarditis

A human is identified as having severe or life threatening myocarditis and is administered MSC-CAR-HER2 at a dose of about 2 to about 10 million cells/kg of body weight. Cells are administered either intravenously or via intra-cardiac route. A dose escalation is included, and multiple doses are administered, for example, every 10 days. Patients are monitored clinically for improvement of symptoms of myocarditis.

Example 24: MSC-CAR-E-Cadherin Suppresses T Cell Antitumor Activity and their Proliferation In Vivo NSG mice were engrafted with the luciferase$^+$/E-cadherin$^+$ MCF-7 cell line ($1\times10^6$ cells intravenously). One week later, bioluminescent imaging was performed to confirm engraftment. All mice were treated with E-cadherin CAR T cells ($2\times10^6$ cell), and mice were randomized to treatment with MSC-CAR-E-cadherin ($1\times10^6$), untransduced MSC (MSC-UTD) ($1\times10^6$), or no MSC control. Mice were followed with serial bioluminescent imaging to measure disease burden. Treatment with MSC-CAR-ECAD resulted in reduced anti-tumor activity of E-cadherin directed CAR T cells (FIG. 24A). Peripheral blood flow cytometry on day 7 post treatment with CAR T cells and CAR-MSC cells was performed. Treatment with MSC- CAR-E-Cadherin led to a trend to reduced T cell proliferation in vivo (FIG. 24B). These results demonstrate that MSC-CAR-E-CAD are able to suppress T cell effector functions in this xenograft model.

In another experiment, luciferase MSC-CAR-E-cadherin cells were generated and injected intraperitoneally into immunocompromised NSG mice. Serial bioluminescent imaging was performed to determine the persistence of MSC-CAR-E-cadherin. MSC-CAR-E-cadherin cells were found to persist in vivo for over 10 days (FIGS. 25A and 25B). These results demonstrate that MSC-CAR cells are able to persist in vivo, for example, within xenograft models.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having colitis, wherein said method comprises administering to said mammal a composition comprising mesenchymal stem cells (MSCs) comprising exogenous nucleic acid encoding a chimeric antigen receptor (CAR) targeting an antigen expressed within said mammal, wherein said MSCs express said CAR, wherein said antigen is E-cadherin (ECAD), cytokeratin, p-cadherin, or ALCAM, and wherein binding for said CAR to said antigen within said mammal results in suppression of an immune response within said mammal.

2. The method of claim 1, wherein said mammal is a human.

3. The method of claim 1, wherein said antigen is E-cadherin (ECAD).

* * * * *